(12) United States Patent
Puhler et al.

(10) Patent No.: US 12,351,847 B2
(45) Date of Patent: Jul. 8, 2025

(54) METHODS FOR THE IMPROVED FORMATION OF ACARBOSE

(71) Applicant: BAYER AKTIENGESELLSCHAFT, Leverkusen (DE)

(72) Inventors: Alfred Puhler, Bielefeld (DE); Jorn Kalinowski, Bielefeld (DE); Susanne Schneiker-Bekel, Halle (DE); Marcus Persicke, Bielefeld (DE); Lena Schaffert, Cologne (DE)

(*) Notice: Subject to any disclaimer, the term of this patent is extended or adjusted under 35 U.S.C. 154(b) by 526 days.

(21) Appl. No.: 17/769,001

(22) PCT Filed: Oct. 2, 2020

(86) PCT No.: PCT/EP2020/077688
§ 371 (c)(1),
(2) Date: Apr. 14, 2022

(87) PCT Pub. No.: WO2021/073900
PCT Pub. Date: Apr. 22, 2021

(65) Prior Publication Data
US 2023/0227879 A1  Jul. 20, 2023

(30) Foreign Application Priority Data
Oct. 16, 2019  (EP) .................... 19203693

(51) Int. Cl.
| | | |
|---|---|---|
| *C12P 19/26* | (2006.01) | |
| *C12N 9/12* | (2006.01) | |
| *C12N 9/88* | (2006.01) | |
| *C12N 15/52* | (2006.01) | |
| *C12N 15/76* | (2006.01) | |
| *C12R 1/045* | (2006.01) | |

(52) U.S. Cl.
CPC ............ *C12P 19/26* (2013.01); *C12N 9/1241* (2013.01); *C12N 9/88* (2013.01); *C12N 15/52* (2013.01); *C12N 15/76* (2013.01); *C12R 2001/045* (2021.05); *C12Y 207/07009* (2013.01); *C12Y 402/01046* (2013.01)

(58) Field of Classification Search
CPC ......... C12P 19/26; C12N 9/1241; C12N 9/88; C12N 15/52; C12N 15/76; C12N 15/74; C12R 2001/045; C12Y 207/07009; C12Y 402/01046; C07K 14/365
See application file for complete search history.

(56) References Cited

U.S. PATENT DOCUMENTS

| | | | |
|---|---|---|---|
| 6,031,004 | A | 2/2000 | Timmins et al. |
| 6,117,451 | A | 9/2000 | Kumar |
| 9,719,064 | B2 | 8/2017 | Selber et al. |
| 2006/0222709 | A1 | 10/2006 | Devane |
| 2010/0316711 | A1 | 12/2010 | Yamanouchi et al. |
| 2014/0287040 | A1 | 9/2014 | Joshi et al. |

FOREIGN PATENT DOCUMENTS

| | | |
|---|---|---|
| DE | 19860698 A1 | 7/2000 |
| EP | 2601209 B1 | 3/2017 |
| WO | 2004110422 A1 | 12/2004 |
| WO | 2007131930 A1 | 11/2007 |
| WO | 2009135951 A2 | 11/2009 |
| WO | 2012016960 A1 | 2/2012 |
| WO | 2013115742 A1 | 8/2013 |
| WO | 2013115745 A1 | 8/2013 |

OTHER PUBLICATIONS

Wang, Y-J et al. "Actinoplanes utahensis ZJB-08196 fed-batch fermentation at elevated osmolality for enhancing acarbose production", Bioresource Technology, vol. 103, Issue 1, 2012, pp. 337-342. (Year: 2012).*

Kosloff, M et al. "Sequence-similar, structure-dissimilar protein pairs in the PDB." Proteins. May 1, 2008;71(2):891-902. (Year: 2008).*

Gren, Tetiana, "Development and application of genetic engineering methods for *Actinoplanes* sp. SE50/110," Publication 29147923 [Doctoral dissertation], Bielefeld, Germany: University of Bielefeld; May 2017 (Year: 2017).*

Gruszecki W. and Strzalka; K., "Carotenoids as modulators of lipid membrane physical properties", Biochimica et Biophysica Acta, Elsevier, Dec. 16, 2004, 1740, 108-115.

Parenti Francesco and Coronelli; Carolina., "Members of the Genus *Actinoplanes* and Their Antibiotics", Annual Reviews in Microbiology, 1979, 33(1), 389-411.

Schwientek; P. et al, "The complete genome sequence of the acarbose producer *Actinoplanes* sp. SE50/110", BMC Genomics, BioMed Central, Mar. 23, 2012, 13(1), 1-18.

Selber; et al, "Actinoplanes utahensis derived protein, SEQ:14145", Database Geneseq, Mar. 29, 2012.

Wang; Y. et al, "Reconstruction and in silico analysis of an *Actinoplanes* sp. SE50/110 genome-scale metabolic model for acarbose production", Frontiers in microbiology, Jun. 25, 2015, vol. 6, pp. 1-14.

Wehmeier Uf and Piepersberg; W., "Biotechnology and molecular biology of the a-glucosidase inhibitor acarbose", Applied microbiology and biotechnology, Dec. 11, 2003, 63(6), 613-625.

Wendler; S. et al, "Carbon source dependent biosynthesis of acarviose metabolites in *Actinoplanes* sp. SE50/110", Journal of Biotechnology, Elsevier, Aug. 26, 2014, 191, 113-120.

(Continued)

*Primary Examiner* — Adam Weidner
*Assistant Examiner* — Dennis Ignatius Armato, Jr.

(57) ABSTRACT

The present invention relates to Actinomycetales strains for the improved formation of acarbose. Provided are Actinomycetales strains which are engineered to overexpress dTDP-D-glucose-4,6-dehydratase (AcbB) and/or uridyltransferase (GtaB). Also provided are Actinomycetales strains which are engineered to have a reduced or absent expression of the small carbohydrate binding protein (Cgt) and/or a reduced or absent expression of genes which are essential for carotenoid synthesis. Also provided are tools, methods and means to generate these strains.

2 Claims, 29 Drawing Sheets
Specification includes a Sequence Listing.

(56) References Cited

OTHER PUBLICATIONS

Wendler; S. et al, "Comparative proteome analysis of *Actinoplanes* sp. SE50/110 grown with maltose or glucose shows minor differences for acarbose biosynthesis proteins but major differences for saccharide transporters", Journal of Proteomics, Elsevier, Oct. 25, 2015, 131, 140-148.

Wendler; S. et al, "Comprehensive proteome analysis of *Actinoplanes* sp. SE50/110 highlighting the location of proteins encoded by the acarbose and the pyochelin biosynthesis gene cluster", Journal of proteomics, ScienceDirect, Jul. 1, 2015, 125, 1-16.

Wendler; S. et al, "The cytosolic and extracellular proteomes of *Actinoplanes* sp. SE50/110 led to the identification of gene products involved in acarbose metabolism", Journal of Biotechnology, ScienceDirect, Aug. 31, 2012, 167, 178-189.

Wolf; T. et al, "Genome improvement of the acarbose producer *Actinoplanes* sp. SE50/110 and annotation refinement based on RNA-seq analysis", Journal of Biotechnology, Elsevier, Apr. 17, 2017, 251, 112-123.

Xie; H. et al, "Comparative functional genomics of the acarbose producers reveals potential targets for metabolic engineering", Snythetic and systems biotechnology, KeAi, 2019, vol. 4 / Issue No. 1, 49-56.

Zhao; Q. et al, "Improving acarbose production and eliminating the by-product component C with an efficient genetic manipulation system of *Actinoplanes* sp. SE50/110", Synthetic and Systems Biotechnology, Elsevier, 2017, 2, 302-309.

Arndt et. al., Influence of binder properties on dry granules and tablets, Powder Technology, Elsevier, 2018, 337, 68-77.

Barot et. al., Devlopment of directly compressible metformin hydrochloride by the spray-drying technique, Acta Pharm, 2010, 60, 165-175.

Block et al., Pharmaceutical equivalence of metformin tablets with various binders, Journal of Basic and Applied Pharmaceutical Sciences, Revista de Ciencias Farmaceuticas Basica e Aplicada, 2008, vol. 29, No. 1, 29-35.

Herting et al., Comparison of Different Dry Binders for Roll Compaction/Dry Granulation, Pharmaceutical Development and Technology, Taylor & Francis, Oct. 2008, 525-532.

International Preliminary Report on Patentability in PCT Application No. PCT/EP2018/085501, Jul. 2, 2020.

International Search Report and Written Opinion from PCT Application No. PCT/EP2018/085501, May 24, 2019.

Joshi et al., Acarbose Plus Metformin Fixed-Dose Combination in the Management of Type 2 Diabetes, Expert Opinion on Pharmacotherapy, 2014, vol. 15 No. 11, 1611-1620.

Lakshman Et al., Application of Melt Granulation Technology to Enhance Tabletting Properties of Poorly Compactible High-Dose Drugs, Journal of Pharmaceutical Sciences, Wiley Online Library, 2011, vol. 100, No. 4, 1553-1565.

Mangal et al., Roll compaction/dry granulation: Suitability of different binders, International Journal of Pharmaceutics, Elsevier, 2016, 213-219.

Mohaptra Et al., Formulation, development and evaluation of patient friendly dosage forms of metformin, Part-II: Oral soft gel, Asian Journal of Pharmaceutics, Jul.-Sep. 2008, 172-176.

Takasaki et al., The importance of binder moisture content in Metformin HCL high-dose formulations prepared by moist aqueous granulation (MAG), Results in Pharma Sciences, Elsevier, 2015, 1-7.

Wang et al., Acarbose plus metformin fixed-dose combination outperforms acarbose monotherapy for type 2 diabetes, Diabetes Research and Clinical Practice, Elsevier, 2013, 16-24.

* cited by examiner

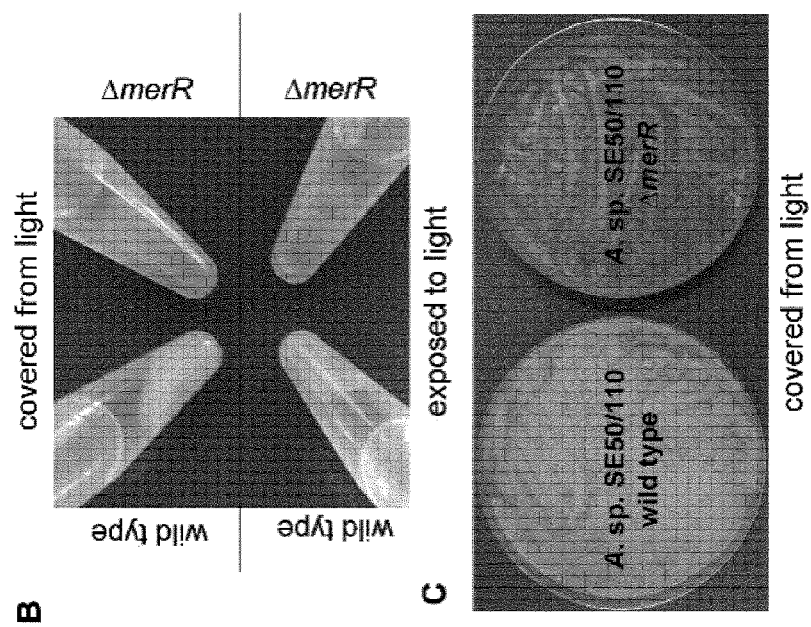
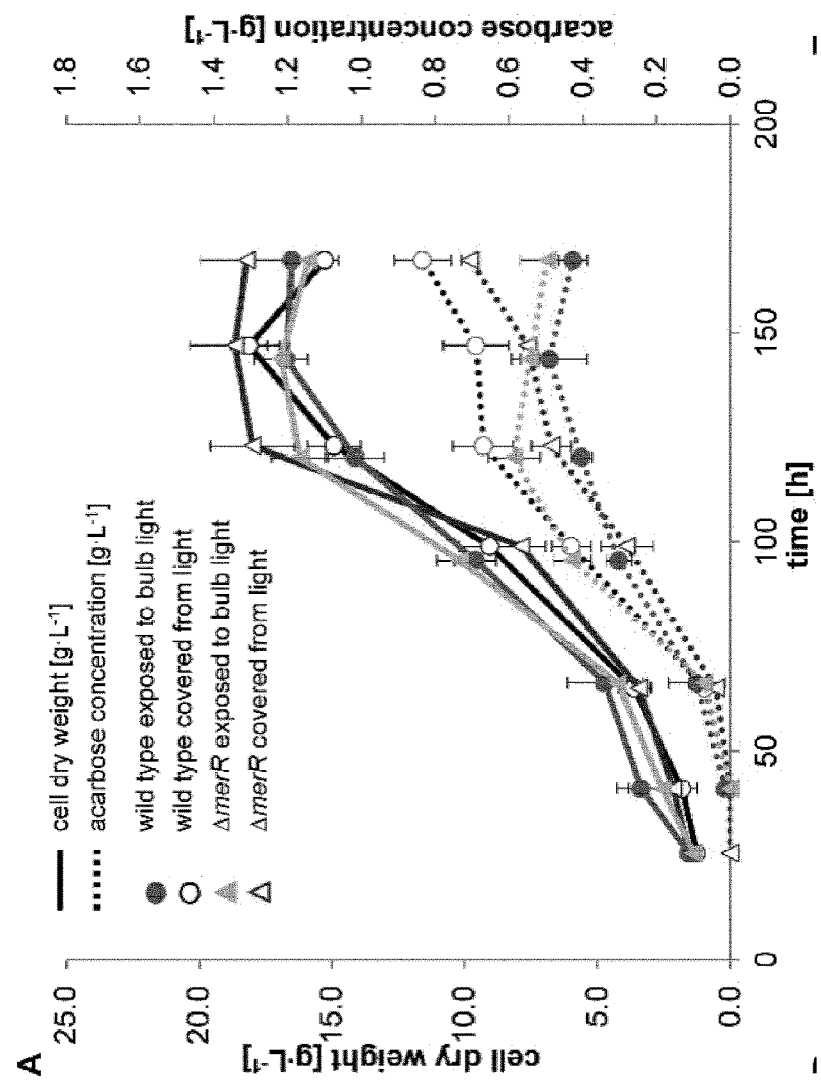
Fig. 24 a, b

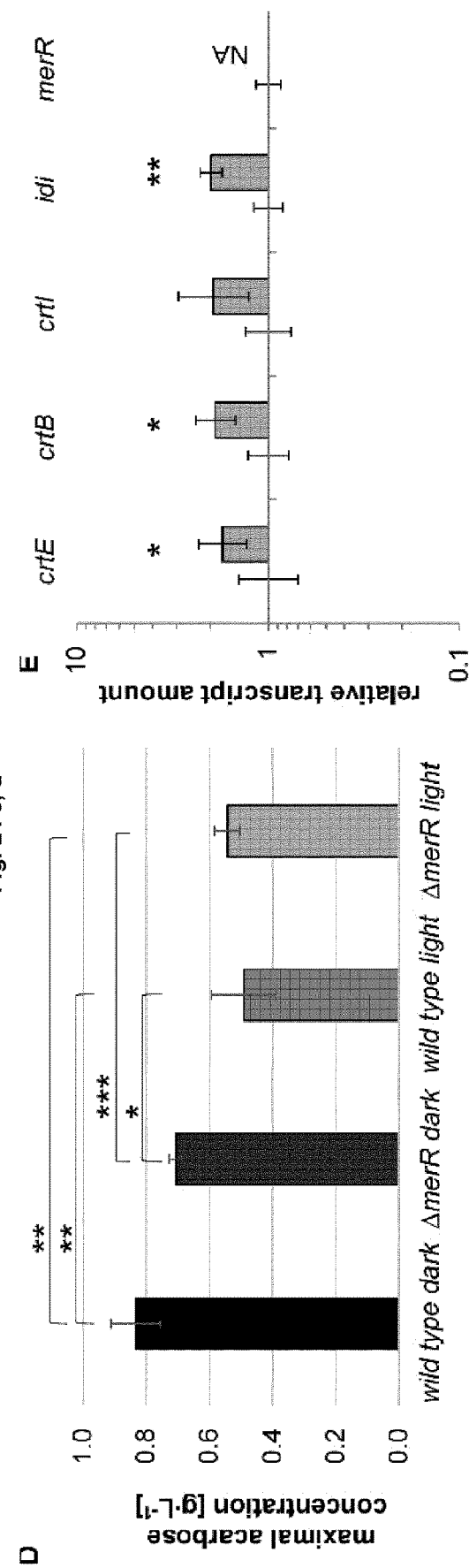
Fig. 24 c, d

METHODS FOR THE IMPROVED FORMATION OF ACARBOSE

FIELD OF THE DISCLOSURE

The present invention relates to Actinomycetales strains for the improved formation of acarbose. Provided are Actinomycetales strains which are engineered to overexpress dTDP-D-glucose-4,6-dehydratase (AcbB) and/or uridyltransferase (GtaB). Also provided are Actinomycetales strains which are engineered to have a reduced or absent expression of the small carbohydrate binding protein (Cgt) and/or a reduced or absent expression of genes which are essential for carotenoid synthesis. Also provided are tools, methods and means to generate these strains.

BACKGROUND

Acarbose

The therapeutic agent acarviosyl-maltose (acarbose) is used since 1990 in the medical treatment of diabetes mellitus (Wehmeier and Piepersberg 2004; Wehmeier 2004). It shall support the rigorous diet plan of patients and prevent sugar peaks when consuming high carb meals. After oral application acarbose inhibits intestinal α-glucosidases, which leads to a retarded release of monosaccharides from starch- and sucrose-containing diets. By this, acarbose helps to control the rate of absorption of monosaccharides into the blood system and leads to a decreased postprandial blood and serum sugar level, which are assumed to be crucial in the context of cardiovascular disease mortality.

INDUSTRIAL APPLICABILITY

Acarbose is known and marketed in Europe and China as Glucobay (Bayer AG), in North America as Precose (Bayer Pharmaceuticals), and in Canada as Prandase (Bayer AG). Being an important and highly demanded drug for the treatment of diabetes mellitus, there is a need to provide acarbose in high yields and high quality. As the incidence of type II diabetes is continuously increasing worldwide, optimization of product yields and quality is an issue of current concern.

Acarbose Production Strains

Acarbose is naturally produced by different Actinomycetales, like *Streptomyces coelicoflavus* ZG0656 (Geng et al. 2009), *Streptomyces glaucescens* GLA.O (Rockser and Wehmeier 2009; Ortseifen et al. 2015) and Actinoplanes sp. SE50/110 (reviewed by Wehmeier and Piepersberg 2004), of which the latter is the wild type of industrial producer strains (Ortseifen 2016; Mahmud et al. 1999). The genus Actinoplanes was first introduced by Couch (1950) as member of the family Micromonosporaceae, order Actinomycetales, phylum Actinobacteria. Actinoplanes sp. SE50/110 (ATCC 31044, CBS 674.73) is a slow-growing natural derivate of SE50 (ATCC 31042, CBS 961.70) (Frommer et al. 1973). SE50 was isolated in 1970 during a screening program by the Bayer AG from a soil sample close to a coffee plantation in Kenia (Frommer et al. 1972). SE50/110 produces approximately 1 g·L$^{-1}$ acarbose, when maltose is provided in the medium (Wendler et al. 2014). Further production strains have been engineered, as described for example in (EP2601209B1) and (CN103298828B).

For Actinoplanes sp. SE50/110 it was shown, that the biosynthesis of acarviosyl-sugars depends on the supply of carbon sources in the culturing medium (Wendler et al. 2014). Growing on glucose, acarviosyl-glucose was formed as the major compound, whereas mainly acarviosyl-maltose was formed, when growing on maltose (Wendler et al. 2014), and acarviosyl-maltotriose, when growing on maltotriose (Ortseifen 2016).

Due to its medical and industrial relevance as wild type of industrial acarbose producer strains, Actinoplanes sp. SE50/110 was extensively studied in the last years: The complete genome (Schwientek et al. 2012), transcriptome (Schwientek et al. 2013) and proteome (Wendler et al. 2015b; Wendler et al. 2015a; Wendler et al. 2013) were analyzed comprehensively. This led to a refined genome sequence and an improved annotation in 2017 (GenBank: LT827010.1) (Wolf et al. 2017b). Also, an intergeneric conjugation system (Gren et al. 2016) as well as advanced genome editing tools by use of CRISPR/Cas9 (Wolf et al. 2016) were established, allowing targeted genetic engineering. Still, a reliable expression system enabling medium to strong gene expression is missing for Actinoplanes sp. SE50/110. Since a suitable system for the medium strong overexpression of singular genes did not exist before, different strategies were tested and evaluated according to the current invention, which led to the development of a novel expression system called pSETT4.

Acarbose Biosynthesis

The biosynthetic pathway of acarbose is based on monofunctional enzymes catalyzing single steps (FIG. 1) (Wehmeier and Piepersberg 2009). According to the model of Zhang et al. (2002), the biosynthesis proceeds via the intermediate valienone-7P. In the refinement by Wehmeier (2003), the steps reduction and dehydration were changed leading to valiolol-7P as intermediate. As the order of steps is unknown, they are shown in brackets. The first step of acarbose biosynthesis, a cyclic reaction by AcbC to form 2-epi-5-epi-valiolone from sedo-heptulose-7P, is missing in this illustration. Although becoming a focus of research in the last decades, still, the acarbose biosynthetic pathway is not completely unraveled yet. Only the first three steps of biosynthesis were experimentally confirmed. AcbC (ACSP50_3607), the first enzyme of the acarbose biosynthesis, catalyzes a cyclic reaction to generate 2-epi-5-epi-valiolone from sedo heptulose 7P7P (Stratmann et al., 1999). Phosphorylation to 2-epi-5-epi-valiolone-7P is catalyzed by the kinase AcbM (ACSP50_3603) in presence of ATP (Zhang et al. 2002) and epimerization to 5-epi-valiolone-7P by the cofactor independent epimerase AcbO (ACSP50_3606) (Zhang et al. 2002; Zhang et al. 2003).

The remaining steps of the model base on protein homologies and functional predictions (Zhang et al. 2002), Wehmeier (2003), Wehmeier and Piepersberg (2004), Wehmeier and Piepersberg (2009) and Wendler et al. (2013): NADH-dependent (polyol) dehydrogenase/reductase AcbL (ACSP50_3604) and the cyclitol dehydrogenase/oxidoreductase AcbN (ACSP50_3605) have been suggested to catalyze reduction and 5,6 dehydration to 1-epi-valienol-7P. Phosphorylation to 1,7-diphospho-1-epi-valienol is assumed to be catalyzed by the 1-epi-valienol-7-phosphate-1-kinase AcbU (ACSP50_3595) and/or hydrolase AcbJ (ACSP50_3600). Nucleotidylation to NDP-1-epi-valienol-7P is possibly catalyzed by a GlgC-related NDP-polyol synthase AcbR (ACSP50_3597) (1-epi-valienol-1,7-bisphosphate-1-adenylyltransferase), and transfer of the activated intermediate to an activated amino sugar seems to be mediated by the glycosyltransferases AcbI (ACSP50_3599) and/or AcbS (ACSP50_3596) to generate acarviosine-7P. The activated amino sugar is supposed to be synthesized from D-glucose-1-phosphate in three steps (Wehmeier and Piepersberg 2004; Wehmeier and Piepersberg 2009; Zhang et al. 2002), which are: (i) nucleotidylation by the dTDP-glucose-synthase AcbA (ACSP50_3609) to dTDP-D-glucose, (ii) dehydration by dTDP-D-glucose-4,6-dehydratase AcbB (ACSP50_3608) to dTDP-4-keto-6-deoxy-D-glucose, and (iii) amination by a GabT-like aminotransferase AcbV (ACSP50_3594) to dTDP-4-amino-4,6-dideoxy-D-glucose (Diaz-Guardamino Uribe 2000; Zhang et al. 2019).

Glucose-1P is a branching metabolite displaying an important role in different pathways, like the glycogen metabolism, the galactose metabolism and—after conversion to glucose-6P—the glycolysis (Frey 1996; Purves 2006). UDP-glucose-1P uridyltransferase GtaB catalyzes the conversion of glucose-1P and UDP-glucose into each other.

Last, maltose is transferred in a one-step reaction (Hemker et al. 2001), potentially by AcbS. However Acbl or AcbJ have also been proposed to catalyze the transfer reaction (Wehmeier and Piepersberg 2004; Wendler et al. 2013). Another candidate for this reaction might be the amylomaltase AcbQ (ACSP50_3601).

In Actinoplanes sp. SE50/110, the biosynthesis genes are organized in the acarbose biosynthesis gene cluster (acb gene cluster), which was first identified in 1999 by Stratmann et al. and subsequently sequenced (GenBank: Y18523.4) (Stratmann et al. 1999; Thomas 2001). The cluster contains 22 genes (FIG. 2).

Beside of the already mentioned biosynthetic genes (acbCMOLNUJRSIVBA), the cluster encodes functions in extracellular starch degradation (AcbEZ, ACSP50_3610 and ACSP50_3590), transglycosylation (AcbD, ACSP50_3611) and in export of acarbose (AcbWXY, ACSP50_3591-3). Besides, an acarbose-7-kinase (AcbK, ACSP50_3602) and an intracellular amylomaltase (AcbQ) are encoded, which were assigned to a function within the carbophore (Wendler et al. 2015b; Schwientek et al. 2012; Wehmeier and Piepersberg 2009). The function of AcbP (ACSP50_3598), annotated as NTP-pyrophosphohydrolase, is unknown.

Actinoplanes Proteins with Possible Metabolic Relevance

The singular CBM-20 domain protein Cgt is one of the most strongly expressed genes in Actinoplanes sp. SE50/110 and in derived acarbose producer strains (Ortseifen 2016; Wendler et al. 2015a; Schwientek et al. 2013). It is secreted via the Sec-pathway according to SignalP-analysis (Almagro Armenteros et al. 2019) and makes up to 8% of the total secreted proteome of this organisms (data not shown). Cgt contains 149 amino acids and a CBM-20-domain of fold-family 1, functional group A, characterized by a β-sandwich structure (Schwientek et al. 2013; Guillén et al. 2010). Members of this family are described to bind starch (Guillén et al. 2010).

Methods for Gene Deletion in Actinoplanes

The establishment of an intergeneric conjugation system (Gren et al. 2016) and the CRISPR/Cas9 technique (Wolf et al. 2016), allow genome editing in Actinoplanes sp. SE50/110. In addition, according to the current invention the inventors have successfully established a novel deletion system by homologous recombination, which uses an integrase-free vector backbone and CodA for counter selection, like described by Zhao et al. (2017). By this, the genetic toolbox for Actinoplanes sp. SE50/110 could be further extended. As proof of principle the novel deletion system was successfully tested for deletion of the example gene cgt. Homologous recombination (HR) is a common process in Actinobacteria, which can be technically used to create deletion mutants by double crossover. Temperature-sensitive replicons, like the pSG5 replicon, can support and force this process. (Du et al. 2015; Garg and Parry 2010; Myronovskyy et al. 2009; Zhang and Parry 2007). Further methods exist in the art, e.g. CRISPR-Base Editing System for the exchange of single nucleotides, CRISPR-BEST according to Tong et al. 2019, CRISPRi/dCas9 according to Qi et al. 2013, RNA interference etc., Methods for Gene Overexpression in Actinoplanes Actinoplanes sp. SE50/110 has been extensively studied in the last decades. Appropriate expression systems are difficult to design, see Schaffert et al. (2019). The whole content of the publication and in particular the description of the expression systems and promoters for the genetic manipulation of Actinoplanes are included herein in their entirety.

Previous studies have shown successful expression of genes by use of pKC1139 in A. teichomyceticus (Horbal et al. 2012). However, the replicative pSG5-based vector pKC1139 (constructed by Bierman et al. (1992)) turned out to be unsuitable for expression of homologous genes in Actinoplanes sp. SE50/110, as unwanted vector integration by homologous recombination occurs, see Schaffert et al. (2019). This seems to be a favored process, putatively due to the high metabolic costs of vector replication. Without being bound by theory, a protein encoded by ACSP50_7170 in SE50/110, predicted as recombinase A (recA) might catalyze the recombination process. Interestingly, no homologue of recA was found in the genome of A. teichomyceticus. Presence of recA in a. sp. SE50/110 and lack in A. teichomyceticus provides a conclusive explanation, why HR-mediated vector-integration has not been reported for A. teichomyceticus before. A pSG5-based replicative expression system may therefore be implemented by deletion of the recombinase gene recA in Actinoplanes sp. SE50/110.

Other replicative Streptomyces-E. coli shuttle plasmids, like pKC1218, which is based on the SCP2*-replicon (Kieser et al. 2000), and pSOK101, which is based on the plJ101-replicon (Zotchev et al. 2000), did not give exconjugants with Actinoplanes sp. SE50/110 (Gren 2017). These replicons are probably unstable or inactive in SE50/110, which is in accordance with findings from the related species A. teichomyceticus (Horbal et al. 2012).

By use of integrative vector systems, a genetic duplication can be achieved by integration of the complete vector carrying an additional gene copy at a distinct genomic location. This process is mediated by phage integrases. Phage integrases catalyze the targeted and unidirectional recombination of two attachment sites: attP, which is localized on the plasmid, and attB, which is localized in the host chromosome (the Poele et al., 2008). After integration, the vector is flanked by the attachment site left (attL) and right (attR), which are derived from attP-attB-recombination (the Poele et al., 2008).

Four different integrative vectors have been described for Actinoplanes sp. SE50/110 (Gren et al. 2016): Two are based on the integration mechanism of the phage qC31 (pSET152 and plJ6902). The vectors pRT801/2 and pSOK804 are based on the integration mechanism of the phage qBT1 and of the VWB-phage. However, doubling of relative transcript amounts by use of the native promoters was not achieved, see Schaffert et al. (2019).

Evaluation of Homologous and Heterologous Promoters for Integrative Vectors

A method to evaluate homologous and heterologous promoters with regard to their strength is provided in Schaffert et al. (2019), which is incorporated herein in its entirety. In brief, the integrative qC31-based vector pSET152 was used for promoter screening in Actinoplanes sp. SE50/110 (Gren et al. 2016). The promoter strengths of 13 homologous and heterologous promoters were analyzed on protein level, and 12 of these were analyzed on transcript level (Table 1, FIG. 3).

TABLE 1

Constructs with the reporter gene gusA tested in a promoter screening experiment.

| | abbr. | origin of promoter | construct | source/comment |
|---|---|---|---|---|
| homologous | cgt | promoter of cgt (ACSP50_5024), annotated as small carbohydrate binding protein | pSETcgtPgusA | Schaffert et al. (2019) |
| | efp | promoter of efp (ACSP50_6465), annotated as the translation elongation factor P | pSETefpPgusA | Schaffert et al. (2019) |
| | 7457 | promoter of ACSP50_7457, annotated as hypothetical protein | pSET7457PgusA | Schaffert et al. (2019) |
| | katE | promoter of katE (ACSP50_3066), annotated as catalase hydroperoxidase (HP) II | pSETkatEPgusA | Schaffert et al. (2019) |
| | rpsJ | promoter of rpsJ (ACSP50_0690), annotated as 30S ribosomal protein S10 | pSETrpsJPgusA | Schaffert et al. (2019) |
| heterologous | tipA | promoter of tipA from S. lividans, annotated as HTH-type transcriptional activator (Chiu etal. 1999) | pSETGUS | Myronovskyi et al. (2011) |
| | moeE5 | promoter of moeE5 from S. ghananensis, a central moenomycin A biosynthetic gene encoding for a nucleotide sugar epimerase (Ostash et al. 2009) | pSETPmoeES | Horbal et al. (2013) and R. Makitrynskyy, Ivan Franko National University, Lviv, Ukraine |
| | apm | promoter of aac(3)IV from pCRISPomyces-2 (Cobb et al. 2015), an aminoglycoside 3-N-acetyltransferase, which mediates apramycin resistance | pSETaac(3)IVPgusA | Schaffert et al. (2019) |
| | cdaR | promoter of cdaR from S. coelicolor, encoding for a transcriptional regulator (proposed as activator of a calcium-dependent antibiotic CDA (McKenzie and Nodwell 2007; Ryding et al. 2002)) | pSETPcdaRgusA | Horbal etal. (2013) |
| | act | promoter of actII-4 from S. coelicolor, annotated as actinorhodin operon activator protein (Fernández-Moreno et al. 1991) | pSETactPgusA | Schaffert et al. (2019), using primers and design from Horbal et al. (2013) |
| | ermE* | promoter of ermE* from S. erythraea, annotated as 23S rRNA (adenine-N6)-dimethyltransferase mediating erythromycin resistance (Thompson et al. 1982) | pGUSPErmE | Schaffert et al. (2019), referring to Siegl et al. (2013); Bibb et al. (1994) |
| | gapDH | promoter of gapDH from Eggerthella lenta used on pCRISPomyces-2 (Cobb et al. 2015), annotated as type I glyceraldehyde-3-phosphate dehydrogenase | pSETgapDHPgusA | Schaffert et al. (2019) |
| | rpsL | promoter of rpsL from Xylanimonas cellulosilytica used on pCRISPomyces-2 (Cobb et al. 2015), annotated as ribosomal protein S12 | pSETrpsLPgusA | Schaffert et al. (2019) |
| | pGUS | no promoter | pGUS | Myronovskyi et al. (2011) |

Strategy

For the current invention, the acarviosyl-maltose metabolism was studied by gene deletion and overexpression, leading to a set of associated tools and methods to engineer strains for the improved production of acarbose. In order to improve the acarviose-synthesis, three different strategies were followed: (i) increasing of the gene dose of acb genes to enhance the flux through the acarbose biosynthesis, (ii) deployment of precursors of acarbose biosynthesis and (iii) reducing the metabolic burden (FIG. 4). Approaches of each of these related strategies surprisingly led to an improved acarbose formation: By overexpression of dTDP-D-glucose-4,6-dehydratase AcbB, the final acarbose concentration was significantly increased by approx. 50%. By overexpression of the uridyltransferase GtaB acarbose yields were improved by 8.5%, presumably because the supply of the precursor glucose-1P was improved. By functional deletion of the small carbohydrate binding protein Cgt, the acarbose formation was significantly enhanced by 8-16%, possibly because the metabolic burden is thereby reduced. The enhancement was robust over long time periods and in different cultivation settings. Furthermore, growth experiments of the wild type and a regulator mutant ΔmerR exposed to and hidden from light were conducted, revealing a negative influence of light-induced stress and carotenoid formation on the acarbose production. Consequently, the acarbose production can furthermore be improved by reducing the carotenoid formation.

BRIEF DESCRIPTION OF THE DRAWINGS

FIG. 21 and Table E12). The genes of the cluster encode a MerR-like transcriptional regulator (ACSP50_0145), an isopentenyl-diphosphate delta-isomerase (idi, ACSP50_0146), a phytoene dehydrogenase (crtI, ACSP50_0147), a polyprenyl synthetase (crtE, ACSP50_0148), a phytoene synthase (crtB, ACSP50_0149), a deoxyribodipyrimidine photo-lyase (ACSP50_0150) and a pyridine nucleotide-disulfide oxidoreductase (ACSP50_0151).

FIG. 24. Growth, acarbose and pigment formation of Actinoplanes sp. SE50/110 and the deletion mutant ΔmerR exposed to and covered from light. A. Cultivation of the wild type and the deletion mutant ΔmerR of Actinoplanes sp. SE50/110 in maltose minimal medium exposed to or covered from bulb light (22-44 ρE, 1 µE=µmol$_{photons}$ m$^2$ s$^{-1}$). Shown are the cell dry weights of at least four biological replicates and the acarbose concentration in the supernatant of three biological replicates. B. Pellets and supernatants at final cultivation time. C. Growth and pigment formation on solid media (SFM agar plates). D. Maximal acarbose concentrations (p-values of a two-sided t-test: wt dark vs. wt light: 0.003975, wt dark vs. ΔmerR dark: 0.09711, wt dark vs. ΔmerR light: 0.007043, ΔmerR dark vs. wt light: 0.02081, ΔmerR dark vs. ΔmerR light: 0.0002131). E. Relative transcript amounts of the genes crtE (ACSP50_0148), crtB (ACSP50_0149), crtI (ACSP50_0147), idi (ACSP50_0146) and merR (ACSP50_0145) in the deletion mutant compared to the wild type (set to a value of 1) when cultivated under dark conditions (p-values of a two-sided t-test: crtE: 0.04245, crtB: 0.01017, crtI: 0.07162, idi: 0.004366). Asterisks indicate the significance level: * p-value<a=5%, p-value<a=1%, *p-value<a=0.1%.

BRIEF DESCRIPTION OF THE SEQUENCE IDS

Figure 1:
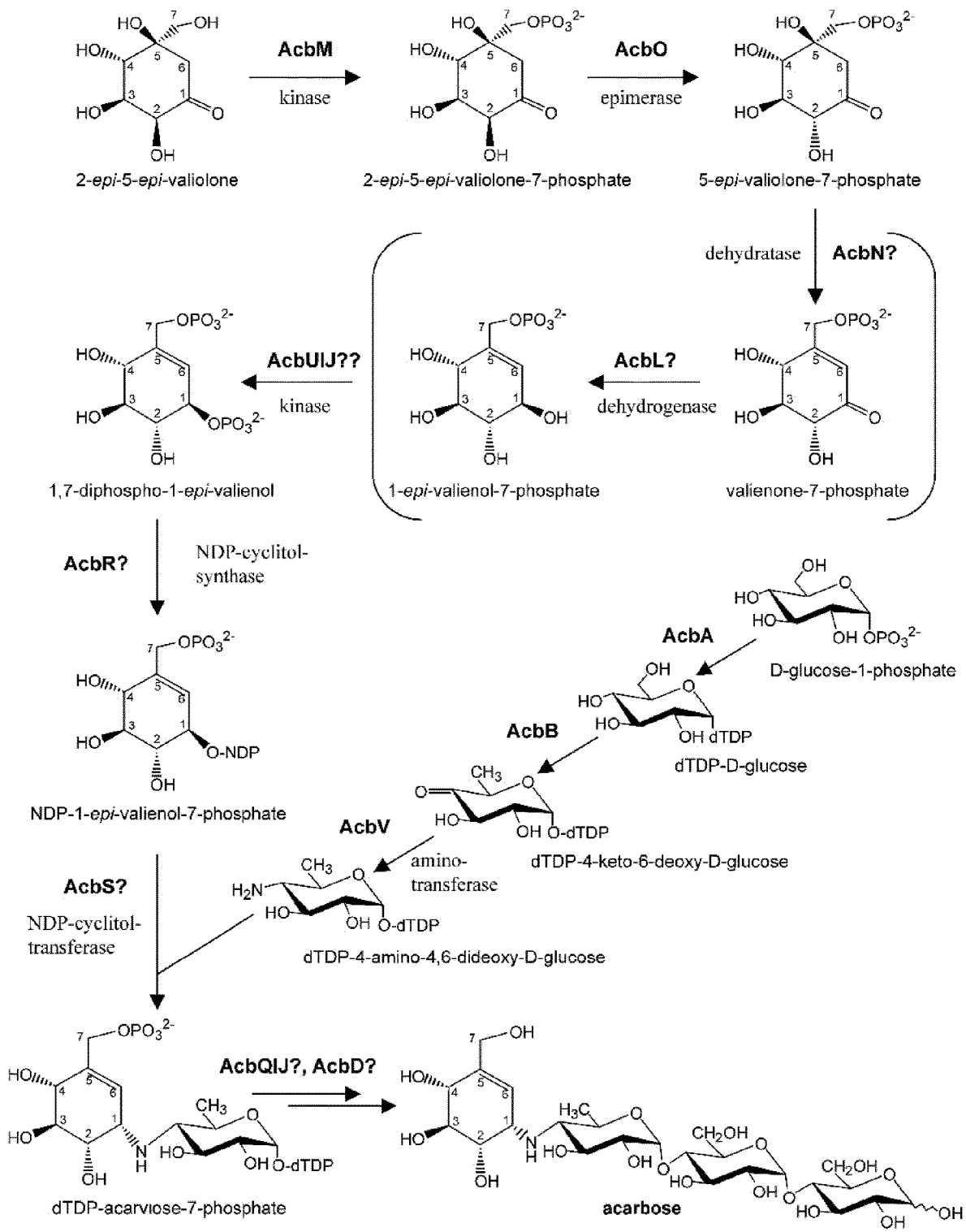
FIG. 1. Model of the biosynthesis of acarviosyl-maltose in Actinoplanes sp. SE50/110. Shown are the eleven steps of acarbose biosynthesis from 2-epi-5-epi-valiolone (Zhang (2002)).
Figure 2:
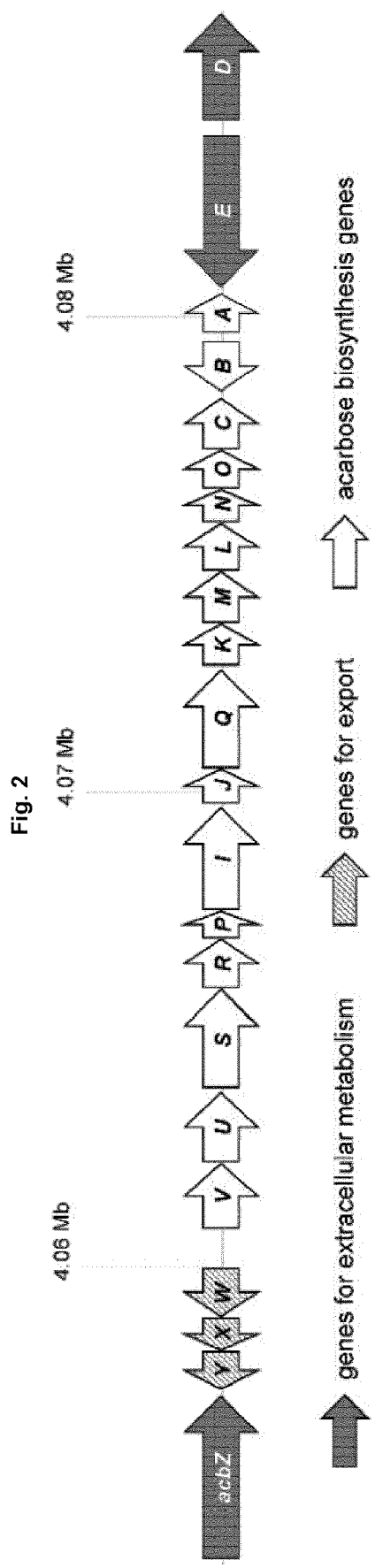
FIG. 2. The acarbose biosynthesis gene cluster and gene disposition in the genome of Actinoplanes sp. SE50/110 (GenBank: LT827010.1) (Schaffert, et al. 2019).

The Sequence Listing associated with this application is filed in electronic format and hereby incorporated by reference into the specification in its entirety.

| SEQ ID No. | Type | Name | Sequence |
|---|---|---|---|
| 1 | DNA | >acbA (ACSP50_3609) | GTGCGCGGAATATTGCTGGCCGGGGGAACCGGCTCACGGCTTCGACC<br>GGTGACCTGGGCGGTTTCCAAACAACTGATGCCGGTCTATGACAAACC<br>GATGATCTACTATCCGCTGGCCACGCTCGTCAGCTGCGGGATCCGGG<br>AGATCCTGGTCATCACGACCGAGACCGAGGCCGCCCAGTTCCAGCGG<br>TTGCTGGGTGACGGCTCGCAGTGGGGCCTGCGTCTGGAGTTCGCCGT<br>GCAGCAGCGCCCCGGGGGCATCGCCGAGGCCTTCCTCATCGGCGAG<br>GAGTTCCTGGCCGGTGGGCCGGTGGCGCTCATGCTCGGCGACAACCT<br>GCTGCACGGGGTGGACTTCCGCCCCTGCGTGCAGCGGGCACGCGAG<br>ACGGCCGGTGGGCACGTCTTCGGAGTGGCGGTGGCCGACCCGTCGG<br>CCTACGGGGTGGTCGAGTTCGACGCCGCCGGGCGGGTGCTGTCCATC<br>GAGGAGAAACCGGTCCGTCCCCGCTCGCCGTACGCGGTTCCCGGCTT<br>CTACCTCTACGACGCCGATGTGGTCGAGACGGCCCGGTCGCTGCGGC<br>CCAGCGCCCGCGGGGAGCTGGAGATCACCGAGGTCAACCAGGCCTA<br>CCTGCGGCGCGGCGCACTCTCGGTGACGCTGCTGGGTCGGGGCGCG<br>GTCTGGCTCGACACCGGCACCCTGGCCGACTGCATGCGCGCGGTCGA<br>CTACGTGCGCGCCATCGACGAGGGCCAGGGCATCAAGATCGGCTGTG<br>TGGAGGAGGCGGCCTGGCGGGCCGGTTTCCTCGACACCGCGCAGCT<br>GCGTGCCCTCGCCGAGCCGTTGATGAGCAGCGGCTACGGACAGTACC<br>TGCTGGCTCTGACCGGCGACGGGCTCAGCCGTACCCCGCAGTGGCC<br>GGCCTTGACCGCCGCCGCCGGGTGA |
| 2 | DNA | >acbB (ACSP50_3608) | ATGAAAATCTTGGTCACCGGCGGAGCCGGCTTTATCGGGTCCCATTTT<br>GTAACTTCCCTGATCAGTGGCGACATTGCCACACCACAACCCGTGACG<br>CAGGTTACGGTCGTCGACAAACTGGGTTACGGAGGCAATCTCAGAAAT<br>CTCGCCGAAGCGTCGGCGGACCCTCGTTTCAGCTTCGTTCGGGGCGA<br>CATCTGTGACGAAGGTCTAATCGAGGGGCTGATGGCGCGGCACGACA<br>CCGTGGCGCACTTCGCCGCCGAGACCCACGTCGACCGCTCGGTGGTC<br>GCCTCCGGCCCCTTCGTGGCCAGCAACCTGGTCGGCACTCAGGTGCT<br>ACTGGACGCCGCGCTACGCCACCATATCGGCCGCTTCCTGCATGTTTC<br>CACCGACGAGGTGTACGGGTCGATCGACACCGGCTCGTGGGCCGAG<br>GGCCATCCGCTGGCGCCCAACTCGCCGTACGCCGCGAGCAAAGCCG<br>GGTCCGACCTCCTCGCTCTGGCCTACCACCAGACGCACGGGATGGAC<br>GTCGTGGTGACCCGCTGCTCGAACAACTACGGGCCCCGGCAATTCCC<br>GGAGAAAATGATTCCGCTGTTCGTCACCCAGGCTGCTCGACGGGCTCG<br>ACGTACCGGTCTACGGCGACGGCCGCAACATCCGCGACTGGCTCCAC<br>GTCAGCGACCATTGCCGCGGTCTCGCCCTGGCCCTGGGTGCCGGCC<br>GGGCAGGCGAGGTCTATCACATCGGCGGTGGGTGGGAGGCGACGAA<br>TCTCGAATTGACCGAGATCCTCCTCGAGGCGTGCGGCGCCCCGGCTT<br>CGCGCATATCTTTCGTGACCGATCGCAAAGGTCACGACCGGCGCTATT<br>CTCTCGACTATTCGAAAATCGCCGGGGAACTCGGTTACCGGCCGCGG<br>GTCGATTTCACCGACGGCATCGCGGAAACGGTCGCGTGGTATCGCGC<br>CAACCGTTCCTGGTGGACCTGA |
| 3 | DNA | >acbC (ACSP50_3607) | GTGAGTGGTGTCGAGACGGTAGGGGTGCACGCGGATGCGCACCGCG<br>ACTCGTGGCAGGTGCGGGCCCAGAAGCAGATCACCTACGAGGTGCGC<br>TTCCGGGACGACGTGTTCGGGCTGGACTCCACCGACCTGCTGGAGGC |

| SEQ ID No. | Type | Name | Sequence |
|---|---|---|---|
| | | | CGGGGCGGACGGGGCCGGTTCACGGCGGCGGTTCGTGGTGGTGGAC<br>AGCGCCGTCGACGCCTTGTACGGGTCCCGGATCCGGGAGTACTTCAC<br>CCATCACGGCATCGATCATTCGATCCTGGTGATGCGGGTGGGCGAGA<br>CGGGTCAAGGACTTCGACACGGCGGGCCGCATCGTCGCCGCGATGGAC<br>GCCTTCGGACTGGCCCGCCGCCGGGAGCCGATGATCGTCGTCGGTG<br>GTGGGGTGCTGATGGACGTGGCCGGTCTGGTGGCCAGCCTCTACCGG<br>CGCGGCACGCCGTTCCTGCGGGTGCCGACGACACTGGTCGGACTGAT<br>CGACGCGGGTGTCGGCGCGAAGACCGGGGTCAACTTCAACGGCCACA<br>AGAACCGGCTGGGTACGTACGCCCCGGCTGATCTGACCCTGCTGGAC<br>CGCCGCTTCCTGGCCCACCCTGGACCGGCGCCACCTCAGCAACGGGCT<br>CGCCGAGATGCTCAAGATCGCGCTGATCAAGGATGCCGAGCTGTTCC<br>AGCTGCTGGAGCGGCACGGGCGGGTCCTGATCGAGGAACGGTTCCA<br>GGGCCGTACCGGAACCGGTGACCGGGCCGCCGTCCGGGCCCTGCGC<br>GCGGGCCACCCATGGCATGCTGGAGGAACTCGGCCCCAATCTGTGGGA<br>GAGCCGGCTGGAACGCAGTGTCGACTACGGGCACACGTTCAGCCCGA<br>CCATCGAGATGCGCGCGCTGCCGGCTCTGCTGCACGGCGAGGCCGT<br>GTGTGTGGACATGGCGCTGACCACGGTGCTGGCGTACCGGCGGGGT<br>CTGCTCGACGTCGCGCAGCGGGACCGGATCTTCGCGGTGATGACCGC<br>CCTGGGCCTGCCGACCTGGCATCCGCTGCTCACGCCGGAGGTGCTGG<br>AGGCGGCGTTGCAGGACACCGTCCGGCACCGGGACGGGTGGCAGCG<br>GCTGCCACTGCCGGTGGGGATCGGGGTGTCACGTTCGTCAACGACG<br>TGACGGCCGCCGAGCTGCAGGCCGCCGCTGATGCAGCACCGGCT<br>CGCCGAGGACGCCCTGCTGCTGCGCGCCTAG |
| 4 | DNA | >acbS<br>(ACSP50_<br>3596) | ATGCACATCATCGAGACGTACTTCGAATGCGGCGGCTTCGACCACCGG<br>TTCATCCAGGGCGGCACCTCGGTCTATCTCTGGCAGCTGTCGCGTGG<br>CCTGGCCGACCTGGGACACCGGGTCTCCATCGTCACACCGGCGCACG<br>GCCGCCTGGACGATCTGCGCCGGCTGCACGAGGTCGAGGACCTGCC<br>CGGCACCGACGAGTACGAACTGCCGCTGGTGCTCGACCCGCGCGTGT<br>GGGGCGAACGGTTCCCGGCCCAGATGGACATCGCCCTGCGGACCAC<br>CGCGCATCGGATCCGGCTGGCGGGCGTGGACCTGTACTTCCTCTCCA<br>ACGAACTGCTCGATCAGTTGCCGGACCGGTTCTATCCCCGTACGAGA<br>GCAAGGGGGTTGATCTGGTCTTCTTCAAGCCGCTCGCCTATCAGGTGG<br>CGGCCATCCGGTTCATCAGGTCGCACTTCGGTGACCAGCGCGCGATC<br>GTGCACGCACACGAGCCGTTCTACCACTACCTGATGCCGGCCGCCTT<br>CGCCGCGGACCCGGCCAAACACGTGGTCAGCACGGTGCAGAGCAACA<br>TGCCGATCAACAAGTCGGTGTACCGGGCCGAGGTGGCGCGGCTGCTC<br>GGCTTCCTCGGCGCCCCGAACGCGCTGCCCGCCGACGATCCGGCCG<br>GCAGCCGTTCGCCGCACACCGTGGCGATGAGCCAGTACCAGCAGCTG<br>ACCCACCTGCACTACGAATACCCGCCGGACCACGTGCGGGTCTACGA<br>CCTGGTGGCCGAGCACGCCGACCGGATCGACTTCCTGTCGCCGGGG<br>CACCGCGACTACTACACCTGCTTCGCCGACACCCCGTTCGCGCAGCT<br>GTTCGCCACCCTGCCGGTGTCGCGGACCGGTACGGCGCAACGCGGAC<br>AAGACGTTCGTCGGCGGCTGCGCCGTCGGTGACGAGTGGGTGACCG<br>GCGAGCTGCCCCCGGTCGACCGGGAGAAGGTGCTGGCCGGGCTCGG<br>CCTGGACCCGGACCTGCCGGCCTTCTACCACAACGCCCGGTACGCGG<br>TCAACCACAAGGGGCAGGTCGAGCTGATCCGGGCCGTCGACCGGGTG<br>CTGAGCGGCGGCGTGCGGGCCAGCTTCATCGTGCGCTGCCTCAGCGA<br>CGCCGGGATCGCCGACCCGCTCTTCCACGAGGTGGTGGCCCGCCAC<br>CCGGGCCGGGTGAATCTGGAGTGGCACCGGGTGCCGGAGGACCAGC<br>TGCGGGAGTACGCCCGAGCCGCGGACTTCTGTCTCTTCCCCGTCCAAG<br>TTCGAGATGGACACCTTCCTGATCGCCCAGGGTGAGGCCGATGGCTGC<br>CGGTGCGGTACCGATCGCCACCGCCCAGCTGGGGATGGCGCACTTCG<br>GTCACGTCGCCGACCCGCTGACCGGGCCGGACGCGGCGACGGCCAC<br>CGGATTCGCCGTCAACGCTCGTTCGCCGAGGACGATCCGCTGCTGG<br>TCCAGGGCCTGACCGAGCAGATCCGCCGGGCCGTCACGCTCTGGAAC<br>GAGCAGCCCGGCCAGTACCGCCGGTTGTCCGCCAACGCCGTCGCCC<br>GGGCCCGCGAGTTCACCTGGCGGCGGGCGGCCCAGGCGCACGAGGC<br>CGCGTTCGCCGGGGTGTGGGCCGGCCGTACCCCCCGCCTGCCGGTC<br>GGTGACCTGCTGCGGTTCGGCTGGTTCGACGAGCTGCCCGCGGACGC<br>CTGGACGCTGCACCGCGACGAGATCGCGGAGGTGGCCCTGGCCCAC<br>GGCGACGCCGACGCCTACCTGCGCTGCCGGCCCGACGACCTCGACG<br>CCCTGGCGGCACTCTTCGAGCGGGCCTGGGCCCGGGCCGACTTCCC<br>GGCCTGCGCGCGGACCGTAGAGCTGGCCGAGGAGCACCGGCAGGAG<br>CGGGTGCCGCAGTGGCGGGCCGGCTCGCCGGCCGCGGCCGCATC<br>GACCGCGACGGTCGGCTGCACTACCGTCCGCCGTCCGCCGAACGGG<br>TCGAACTGGTCTTGCCCGACCTGGCCGAACCCTGCGCGAACGGTC<br>ACCGTGACCGCGATGGCTCCGACCGGCGACACCTTCACCGGACAGCT<br>GCCGGCCGGAACCCGGCGTGCCGACCTGCTGCTCACCCTCAGTGACG<br>GCGCACCGTCTGGGACGAGGTGACGGCATGA |
| 5 | DNA | >acbW<br>(ACSP50_<br>3593) | ATGCCCGGGTACGCCCGGCATGCCCGGCCGGACGGCACGACCGGCA<br>TGATCGTCGCCGAGCACCTCAGCAAGCACTTCAAGCGCTACCGGCGC<br>GAGCCGGGTCTGCGGGGCAGCCTGCGAACCATGTTCTCGGCCCCGGTA<br>CGACGTGGTCCGGGCCGTCGACGACATCAGCTTCGAGGTCCCGTCCG |

| SEQ ID No. | Type | Name | Sequence |
|---|---|---|---|
| | | | GTGTCAAGATCGCCTACATCGGGGCGAACGGCGCGGGCAAGTCCACC<br>ACGATCAAACTCCTGACCGGCATCATGCGCCCGACCACCGGGCGGGT<br>CCGGGTCGACGGCCTCGACCCGCACCGGCAGCGCACCCGGGTCGCC<br>GGCCGGATCGGCGTGGTCTTCGGCCAGCGCAGCCAGCTCTGGTGGG<br>ATCTGCCGGTCCTCGACTCGTTCCGCATCCTGCGGCACGTCTACGAG<br>GTGCCGCAGGCGGTGTACGACCGGAACATGCGCCTGTTCCGGGACCG<br>GCTGGACCTCGGCGCCCTCGGCAACACCCCGGTCCGCCAGCTGAGC<br>CTGGGCCAGCGCATGCGGGCCGAGATCGCCGCCTCGCTGCTGCACG<br>ACCCGGCCGTGGTCTTCCTCGACGAACCCACCATCGGCCTGGACCTG<br>GTCCTCAAGCAGGCGGTCCGGGACCTGATCAACCACATCCACGCCGA<br>ACTGGGCACCACGGTCATGCTGACCAGCCACGACATCGGCGACATCA<br>CCAGCATCTGCGATCAGGCGCTGGTCGTGGACCGCGGGACGATCGTC<br>CACCAGGGAACGATGCGGGACCTGCTGCGGTCGGTGGACACCCGGG<br>CGGTCACCTTCGAGTACGCCGCCGGCAGCGTCTCCGAGGCCGCCGC<br>GCTGCGCATCATCACCGAAGGACTGCCCGAGGTGGACGCCACTCCGG<br>CCGAGTCCGGCCGGATCCGGGTCGAGTTCCCGGTGGACCGCTGGTC<br>GGCCCGGCAGGTGATCGCCTTCCTGCTGGACCGGTTCGACCTGAGCG<br>ACGTGCTGGTGCCGGACGCCGATCGGAGACTGCTGCGCCGCATC<br>TACGCCGGGTCGCGCCCGGAGCCGGTCACCGCCGGGGACGGCGCAT<br>GA |
| 6 | DNA | >acbX<br>(ACSP50_<br>3592) | ATGATCCGCGCCGCGCCGGTACGCGCCGTTCGCCCTCGCCGGACT<br>GCACGCCGTCACCCGTTACCGCTCGACCATCGTCCTGAGCGCACTCA<br>CGGCGGCTGCGGCCACCTCGTTGCAGGTGTTCCTGTGGCGAGCCGTC<br>TACGCCGGCGGACCGGCACCGGCCGGCCTCCCGTTCGCACAGCTCA<br>CCTCGTACATCGTGCTCGCGCAGGTGCTCGGGATGCTGCACACCAAC<br>CGGATCGACGAGATGATCGCCGGCGAGGTGTACCGCGGGGACATCG<br>CGGTCTCCCTGGTACGCCCGGCGAACTACGCGCTCAGCTGTCTGGCG<br>GTGAACCTGCCGACCGCCGCGCTCAGTGCGCTGCTGGCCGGCGCCC<br>CGGTGCTCGCCGGTTTCGCGATGTTCGCGTCGCTGCCCGCTCCCCCG<br>CCCGCCAACCTGCTGCTGTTCGCCGTCGCTGCTGCTCTCGGTGAT<br>CCTCGCCTTCGAGATCAACTTCCTGGTGGGTCTCGCCGCCTTCGTCAC<br>GACCAACACCTGGGGCATCCGTACGATCAAGAACGCGCTCGTCGCCT<br>TCCTGGCCGGCCAGGTCGTCCGCTCGCGCTGTTCCCGGACGGCGTG<br>GCCCGGCTGCTGCGGCTGCTGCCGTTCCAGGGCCTGATCGACAGCCC<br>GTTGCGGCTGCTCGGCGGCTACTCCGGCGGTTCCGGCGCCGCT<br>GCCATCCTCGGTGTCCAGGCGCTCTGGGCGGTACTGCTGTACGGCGT<br>GCTGGGCCCTGGCCTGGAACCGGTCGCTGCGCAGGGTGGAGGTGCTC<br>GGCGGATGA |
| 7 | DNA | >acbY<br>(ACSP50_<br>3591) | atgaccgtctccacgcgcgccggtacctgcgcctcacggcggtgctgtgcggggcgagcctgcaccg<br>gctcaccgcgtaccggatggacttcctcatcggggcggcagcttcgtcatccggatcgcctgccagatc<br>gccctgatcggggtgatcttccagtacgttccggcgctcggcggctggaccgccagcaggcgctgttcc<br>tgctcgggttctccctgctgccccgcgggctggaccggctcttcaccgaccagctgtggatcctggcctgg<br>cagctggtgcgcaccggcgacttcttccgctacctgatccggccggtgaaccgttctacgcgctgctgtc<br>cgaacggttcctctatccggacgggttcggggagctggccaccggcatcgccatcgtggtcaccgcggc<br>cgggacgatggacctgcaccgtgacagtggctgctgttgctgccctggtcctcggccggcgc<br>cctgatccacaccttcctcaaggcgttcctggcctccctgtcgttctggatgaccagcagcctcaacgtgat<br>ggtggccggtcaaccagctcagcgagttcaccgcgtacccgctcaacctctaccaccggtgctgcgcgg<br>ggtgctcacctgggctgctgccgttcgcgttcaccgcctacctaccggtgcgctacctgctcaccgggacg<br>ccgggccgctgctgtggatgctgccggtcaccacgctcaccgtcctgctggggtacggcaccttccggct<br>cgggctgcgcgctacgagatgcccggcagctga |
| 8 | DNA | >gtaB<br>galU<br>(ACSP50_<br>7820) | ATGACGACGAACGCGCAAGGGTCGGGCAAGCGCGCGGTGAAAGCAG<br>TGATTCCGGCGGCCGGCCTAGCCACGCGTTTCCTGCCTGCCACCAAA<br>GCCGTTCCGAAAGAGCTGCTGCCGGTCGTCGACCGGCCGGTCCTGCA<br>GTACATCGTCGAGGAGGCCGCCGCGGCCGGCATCACCGACGTGCTG<br>CTGGTGACCGGGCGTGGCAAGACCTCGATGGTCGACCACTTCGACCG<br>TCGCCCCGACGTGGAGCAGCGGCTGGAGGAGAAGGGCGACACCGAG<br>CGGCTCGCCGCCGTCCGGCGCACCAGTGAGCTGGCCGACATCTACAC<br>CTGCCGACAGGGGGAGCCGCTCGGCCTCGGCCATGCCGTCGGGACC<br>GCCGCCTCGCACGTCGGGGACAACCCGTTCGCGGTGCTGCTCGGGG<br>ACGAGTTCGTCGAGGAGGGCAGCCCGCTGCTGCCGACATGCTCGAC<br>CTGCAGGCCCGCACCGGCGGCATCGTGCTCGCCTTCATCGAGGTCAC<br>CCCGGAGGAGACGTCGCGCTACGGGATCGCCTCGGTGCGGGAGTCC<br>GACCTGGGCGAGGGCGTGGTCGAGGTGACCGGCCTGGTGGAGAAGC<br>CGTCGCCGGAGGAGGCGCCGAGCAACCTTGCCGTGGTGGGGCGGTA<br>CGTGCTGCCTGGCAGGATCTTCGAGACGATCGCCGGCACCAAGCCGG<br>GCAGCGGGGGCGAGATCCAGCTGACCGACGCGATGGCGACGCTGCT<br>GGCCGAGGGCACCCCGGTCACGGCATCGTCTACCGCGGTGTCCGG<br>TACGACACCGGCCAGCCGCTGGGCTACCTGCAGACCGTCGTCCAGCT<br>CGCCGGCTCAGCGTCCCGACCTGGGTGCCGAGTTCCGGGCCTGGCTCA<br>CCGACTTCGTCGGTGGTCAGAAGGGATGA |

| SEQ ID No. | Type | Name | Sequence |
|---|---|---|---|
| 9 | DNA | >cgt (ACSP50_5024) | ATGAATCGCACCACCGTTCGGGCCGGCGTGCTGGCCACCGCCCTGAT CAGCGGCGTGCTCGGGGTGGCCGGCCCGGCGCTCGCCGCCCCGGTC ACCGACGCGGCGCCGGTCGCCGCCGCCGGCACCGCCGTCGCGCCGA TCGCCGCGACCTTCAACGTGACCGCCGGGTTCACCAGCTGGGGTCAG AACGTCTACGTCGTCGGCAGCATCCCGGCGCTCGGCTCCTGGGACGT CTCCAAGGCGGTGCCGCTGACCACCACGAGCAGCGCCTTCCCGACCT GGACCGGGAGCGTGGCGCTGCCGGCGAACACGTACACCGAGTTCCA GTACGTGGTGAAGAACGCCGACGGCAGCGTCGCCCGCTGGGAGAAG GGTTTCCAGCAGAACCGCACCACGATCACCCCGCCGACCGGCACCTA CGTCACGCACGACACCTTCGGCGCGTACTGA |
| 10 | DNA | >crtI (ACSP50_0147) | ATGATGAAACCCCCCACCCCCTGGAGCCGCGGCGTGCGCACTGTTAC CGGACCCACCGATCGTGTCGTGATAGTGGGGGCCGGCCTGGCCGGC CTCTCCTGCGCCTTGCACCTGGCCGCAGCCGGGCGGCAGGTCACCGT CGTCGAGCGGGAGCCGGTGCCGGGCGGCCGCGCCGGGCGCCTCTC GGTCGGCGGATACGACTTCGACACCGGCCCGACCGTGCTGACCATGC CGGAACTGATCGCCGAGCCGCTCGCCGCGGTCGGCGAGAATCTCTCC GACTGGCTGGAGCTGACCCCGCTCGACCCGGCCTACCGGGCGTACTA CCCGGACGGCTCCACGCTGGACGTCCGCACCGACACCACCCGGATG GCGGCCGAGATCGCCCAGGTCTGCGGCGCCCCGCGAGGCCGACGGCT ACCTGCGGTTCGTCGACTACACCCCGGCGGTCTGGCAGCTGGAACGG GACCACTTCATCGACCGGAACCTGGACAGTCCGCTCGACCTGCTCAAC CTCAACCTGCTGAAGCTGCTCGGGATGGGCGCTTTCGGTCGCCTGCA GCCGAAGATCAACGAGTTCTTCCGCGATCCGCGGACCCAGCGGATCT TCTCCGTTCCAGGCGATGTACGCCGGTCTCGCCCCGCACGACGCGATG GCCATCTACGCGGTGATCGCCTACCTCGACTCGGTCGCCGGGGTGTA CTACCCCAAGGGCGGCATGCACGCCGTCCCCAAGGCGCTGGCCGGC GCCGCCGAGAAGCACGGGGTCACCTTCCGTTACGACACGACGGTCGA GCGGGTGCTCACCCAGCACGGCCGGGCGACCGGGGTGGTGACCGTC GGCGGGGACGTGATCGAGGCGGACACCGTCGTACTCAATCCCGACCT GCCCATCGCGTACCGCGACCTGCTGCCTGCCCGGAACAGCCGCAACC TGCGCTTTTCGCCCTCCTGCGTGGTACTCCACATCGGATCGTCACAGC GGTATTCGAAGATCGCACACCACAACATCCACTTTGGTACGACGTGGC GCCGCACCTTCGACGAAGTGATCAACCGTGGGCTGCTGATGAGCGAC CCGTCACTGCTGGTCACCAATCCCACGCACACCGACCCCTCTGCCGC GCCCGACGGCAAACAGACCTACTACGTGCTGGCGCCCGCCCCGAACC TCGTCTCCGGTCCGATGAACTGGCGCGGCGGCCTCGCCGAACGGTAT GCCGACGAGCTGCTGCGTACCCTGGAGCAGCGCGGCTACATCGGCTT CCCGGGACGGGGTCGAGGTCGAACGGATCATCACGCCGGCCGACTGG GCCGACGACGGGATGGCGGCCGGCACGCCGTTCGCCGCCGCGCACA CCTTCGCCCAGACCGGCCCGTTCCGGCGGCGAACCTGCACCCCACG CTGCCGAACGTGGTCTTCACCGGTTCGGGCACACAACCCGGGGTCGG CGTGCCGATGGTGCTCATCTCCGGGAAGCTGGCCGCGAGCCGGATCA CACAGGGAGCCTCATGA |
| 11 | DNA | >merR (ACSP50_0145) | GTGGCCGGTGAGGCGTTGAGCGCCGAGATCCCCACCTCGCCGGGCA GCTCGGTCGCCTCCTCGCACGACATCCCGGCCACAGCCGGTCCCGGC GCCGTCCGGACCGGCCCGGTGGCTGCCGCGCCCGGTGGCCCGAGCG ATACGCCCCTGACCGACGCGACAGCTGCCGCGTCGGGTGCCGCGGA CGACGCCTCCCGGGCCGCCTCGCCGGCGACCGCCACGGACGACGCCTCC CGCACCGGCCCGGCGACCGCCGCGACGGATTCTCCGGACGACGCCG TCCGGACCGGCGTGGCAGATGCCGCGCCGGCCGGGCGGGCGGGCG ATGTGGCGTTGAGTGCCGGGGCGGCCGCGGCGGCTGGGAGTGGC GGTCACGACCCTGCGCACCTGGCACCAGCGGTACGGGCTCGGGCCG AGCCGGCACGAGCCCGGACATCACCGGCGGTACACCGCCGAGGACA TGGACCGGCTGCAGGTGATGCAGCGGCTCACCACTCAGGGCGTGGC GCCCGCCGAGGCCGCCGCCTGGGCGCGGTCCAGGCCCCTCACCCCA CCGGGAGCCCGGCGCGGCGCTGTACGACCCCACCGCCGTGGCGTCGC CACCCACCCCGGCCGCTCCCGGACAGCCCCCGGTCGGCCCCGCCGG CCGGGGCACCCGCCCGACCCGCGGACCGGCCCCGGCCGCTCGCGG GCTGACCCCGGGCCGCGATGCGGCTCGACGTGCGCGGCATGCGCGAC ATCCTCTGCAGCACGCTGCACGACCGCGGCGTGATACCCGCCTGGAC CGAGGTGATGGTCCCGCTCTGGCCGCGATCGGCGACCGGTACGAG GCCACTCGGCGTTTCGTCGAGGTCGAACACCTGCTGTCGCGCGCCGT CACCGAAATCCTCGCCTCGGTCCCACACCCCGCCGGCTCTCCCCGGG TGCTGCTCGCCGCCGCCGACGAGGAACAGCACACACTGCCCCTGGAG GCCCTGGCCGCCGCCCTGGCCGAGGGAGGCGTGCCGAGCCGTCTGT TCGGCGCCCGGGTGCCGTCACAGGCCCTGCTGGACGCCATCGCCCG CACCGGCCCGGCTGCCGTCGTGCTCTGGTCGCAGCGCCCGGCCACC GGCATCGTCACCCAGCTGACCCGGGTCCGCGACATCCCGACCCGCC GCTGGTCATCGCCGCCGCCGGCCCCGGCTGGCCGCATGACCTGCCTT CCGGGATCACCCGCCTGACCGGCCTCACCGAGGCCGTCCACCTGCTC GCCACGGTCTAG |

| SEQ ID No. | Type | Name | Sequence |
|---|---|---|---|
| 12 | PRT | >AcbA (ACSP50_3609) | MRGILLAGGTGSRLRPVTWAVSKQLMPVYDKPMIYYPLATLVSCGIREILVI TTETEAAQFQRLLGDGSQWGLRLEFAVQQRPGGIAEAFLIGEEFLAGGPV ALMLGDNLLHGVDFRPCVQRARETAGGHVFGVAVADPSAYGVVEFDAAG RVLSIEEKPVRPRSPYAVPGFYLYDADVVETARSLRPSARGELEITEVNQA YLRRGALSVTLLGRGAVWLDTGTLADCMRAVDYVRAIDEGQGIKIGCVEE AAWRAGFLDTAQLRALAEPLMSSGYGQYLLALTGDGLSRTPQWPALTAA AG |
| 13 | PRT | >AcbB (ACSP50_3608) | MKILVTGGAGFIGSHFVTSLISGDIATPQPVTQVTVVDKLGYGGNLRNLAEA SADPRFSFVRGDICDEGLIEGLMARHDTVAHFAAETHVDRSVVASGPFVA SNLVGTQVLLDAALRHHIGRFLHVSTDEVYGSIDTGSWAEGHPLAPNSPY AASKAGSDLLALAYHQTHGMDVVVTRCSNNYGPRQFPEKMIPLFVTRLLD GLDVPVYGDGRNIRDWLHVSDHCRGLALALGAGRAGEVYHIGGGWEATN LELTEILLEACGPASRISFVTDRKGHDRRYSLDYSKIAGELGYRPRVDFTD GIAETVAWYRANRSWWT |
| 14 | PRT | >AcbC (ACSP50_3607) | MSGVETVGVHADAHRDSWQVRAQKQITYEVRFRDDVFGLDSTDLLEAGA DGAGSRRRFVVVDSAVDALYGSRIREYFTHHGIDHSILVMRVGETVKDFD TAGRIVAAMDAFGLARRREPMIVVGGGVLMDVAGLVASLYRRGTPFLRVP TTLVGLIDAGVGAKTGVNFNGHKNRLGTYAPADLTLLDRRPFLATLDRRHLS NGLAEMLKIALIKDAELFQLLERHGRVLIEERFQGRTGTGDRAAVRALRAA THGMLEEELGPNLWESRLERSVDYGHTFSPTIEMRALPALLHGEAVCVDMA LTTVLAYRRGLLDVAQRDRIFAVMTALGLPTWHPLLTPEVLEAALQDTVRH RDGWQRLPLPVGIGGVTFVNDVTAAELQAAALMQHRLAEDALLLRA |
| 15 | PRT | >AcbS (ACSP50_3596) | MHIIETYFECGGFDHRFIQGGTSVYLWQLSRGLADLGHRVSIVTPAHGRLD DLRRLHEVEDLPGTDEYELPLVLDPRVWGERFPAQMDIALRTTAHRIRLAG VDLYFLSNELLDQLPDRFYPPYESKGVDLVFFKPLAYQVAAIRFIRSHFGD QRAIVHAHEPFYHYLMPAAFAADPAKHVVSTVQSNMPINKSVYRAEVARL LGFLGAPNALPADDPAGSRSPHTVAMSQYQQLTHLHYEYPPDHVRVYDL VAEHADRIDFLSPGHRDYYTCFADTPFAQLFATLPVSRTVRRNADKTFVG GCAVGDEWVTGELPPVDREKVLAGLGLDPDLPAFYHNARYAVNHKGQVE LIRAVDRVLSGGVRASFIVRCLSDAGIADPLFHEVVARHPGRVNLEWHRVP EDQLREYARAADFCLFPSKFEMDTFLIAQGEAMAAGAVPIATAQLGMAHF GHVADPLTGPDAATATGFAVNRSFAEDDPLLVQGLTEQIRRAVTLWNEQP GQYRRLSANAVARAREFTWRRAAQAHEAAFAGVWAGRTPRLPVGDLLR FGWFDELPADAWTLHRDEIAEVALAHGDADAYLRCRPDDLDALAALFERA WARADFPACARTVELAEEHRQERVPQWRARLAGRGRIDRDGRLHYRPP SAERVELVLPDLAEPLRGTVTVTAMAPTGDTFTGQLPAGTRRADLLLTLSD GRTVWDEVTA |
| 16 | PRT | >AcbW (ACSP50_3593) | MPGYARHARPDGTTGMIVAEHLSKHFKRYRREPGLRGSLRTMFSARYDV VRAVDDISFEVPSGVKIAYIGANGAGKSTTIKLLTGIMRPTTGRVRVDGLDP HRQRTRVAGRIGVVFGQRSQLWWDLPVLDSFRILRHVYEVPQAVYDRNM RLFRDRLDLGALGNTPVRQLSGQRMRAEIAASLLHDPAVVFLDEPTIGLD LVLKQAVRDLINHIHAELGTTVMLTSHDIGDITSICDQALVVDRGTIVHQGT MRDLLRSVDTRAVTFEYAAGSVSEAAALRIITEGLPEVDATPAESGRIRVEF PVDRWSARQVIAFLLDRFDLSDVLVPDADLETLLRRIYAGSRPEPVTAGDG A |
| 17 | PRT | >AcbX (ACSP50_3592) | MIRAARRYAPFALAGLHAVTRYRSTIVLSALTAAAATSLQVFLWRAVYAGG PAPAGLPFAQLTSYIVLAQVLGMLHTNRIDEMIAGEVYRGDIAVSLVRPANY ALSCLAVNLPTAALSALLAGAPVLAGFAMFASLPAPPPANLLLFAVALLLSVI LAFEINFLVGLAAFVTTNTWGIRTIKNALVAFLAGQWPLALFPDGVARLLRL LPFQGLIDSPLRLLLGGYSGGSGAAAILGVQALWAVLLYGVLALAWNRSLR RVEVLGG |
| 18 | PRT | >AcbY (ACSP50_3591) | MTVSTARRYLRLTAVLCGASLHRLTAYRMDFLIGAASFVIRIACQIALIGVIF QYVPALGGWTRQQALFLLGFSLLPRGLDRLFTDQLWILAWQLVRTGDFR YLIRPVNPFYALLSERFLYPDGFGELATGIAIVVTAAGTMDLHLTVAQWLLL LPLVLGGALIHTFLKAFLASLSFWMTSSLNVMVAVNQLSEFTAYPLNLYHP VLRGVLTWVLPFAFTAYLPVRYLLTGDAGPLLWMLPVTTLTVLLGYGTFRL GLRRYEMPGS |
| 19 | PRT | >GtaB GalU (ACSP50_7820) | MTTNAQGSGKRAVKAVIPAAGLATRFLPATKAVPKELLPWDRPVLQYIVE EAAAAGITDVLLVTGRGKTSMVDHFDRRPDVEQRLEEKGDTERLAAVRRT SELADIYTCRQGEPLGLGHAVGTAASHVGDNPFAVLLGDEFVEEGSPLLP DMLDLQARTGGIVLAFIEVTPEETSRYGIASVRESDLGEGWEVTGLVEKP SPEEAPSNLAVVGRYVLPGRIFETIAGTKPGSGGEIQLTDAMATLLAEGTP VHGIVYRGVRYDTGQPLGYLQTWQLAAQRPDLGAEFRAWLTDFVGGQK G |
| 20 | PRT | >Cgt (ACSP50: 5024) | MNRTTVRAGVLATALISGVLGVAGPALAAPVTDAAPVAAAGTAVAPIAATF NVTAGFTSWGQNVYVVGSIPALGSWDVSKAVPLTTTSSAFPTWTGSVALP ANTYTEFQYVVKNADGSVARWEKGFQQNRTTITPPTGTYVTHDTFGAY |

| SEQ ID No. | Type | Name | Sequence |
|---|---|---|---|
| 21 | PRT | >CrtI (ACSP50_0147) | MMKPPTPWSRGVRTVTGPTDRVVIVGAGLAGLSCALHLAAAGRQVTVVE REPVPGGRAGRLSVGGYDFDTGPTVLTMPELIAEPLAAVGENLSDWLELT PLDPAYRAYYPDGSTLDVRTDTTRMAAEIAQVCGAREADGYLRFVDYTRR LWQLERDHFIDRNLDSPLDLLNLNLLKLLGMGAFGRLQPKINEFFRDPRTQ RIFSFQAMYAGLAPHDAMAIYAVIAYLDSVAGVYYPKGGMHAVPKALAGA AEKHGVTFRYDTTVERVLTQHGRATGWTVGGDVIEADTWLNPDLPIAYR DLLPARNSRNLRFSPSCVVLHIGSSQRYSKIAHHNIHFGTTWRRTFDEVIN RGLLMSDPSLLVTNPTHTDPSAAPDGKQTYYVLAPAPNLVSGPMNWRGG LAERYADELLRTLEQRGYIGFRDGVEVERIITPADWADDGMAAGTPFAAA HTFAQTGPFRPANLHPTLPNVVFTGSGTQPGVGVPMVLISGKLAASRITQ GAS |
| 22 | PRT | >MerR (ACSP50_0145) | MAGEALSAEIPTSPGSSVASSHDIPATAGPGAVRTGPVAAAPGGPSDTPL TDATAAASGAADDASRARPATATDDASRTGPATAATDSPDDAVRTGVAD AAPAGRAGDVALSAGAAARRLGVAVTTLRTWHQRYGLGPSRHEPGHHR RYTAEDMDRLQVMQRLTTQGVAPAEAAAWARSRPLTPPEPGAALYDPTA VASPPTPAAPGQPPVGPAGRGTRPTRGPAPAARGLTRAAMRLDVRGMR DILCSTLHDRGVIPAWTEVMVPALAAIGDRYEATRRFVEVEHLLSRAVTEIL ASVPHPAGSPRVLLAAADEEQHTLPLEALAAALAEGGVPSRLFGARVPSQ ALLDAIARTGPAAVVLWSQRPATGIVTQLTRVRDIPHPPLVIAAAGPGWPH DLPSGITRLTGLTEAVHLLATV |
| 23 | DNA | >dxs (ACSP50_7096) | ATGAGCGACTCCCCTTCGACCCCGGCCGGCCTGCTGGCGAGCGTCAC CGGTCCCGGTGCTCTCAAGCGACTGTCCGCGGAGCAGCTGACCCTGC TCGCGGCCGAGATCCGGACTTCCTCGTGGCCAAGGTGTCGAAGACC GGGGGGGCACCTCGGACCGAACCTGGGCGTGGTCGAGATGACCCTCG CCATGCACCGGGTCTTCGACTCGCCGCGCGACAAGATCCTCTTCGACA CCGGCCACCAGGCGTACGTGCACAAGATCGTCACCGGCCGGCAGGAC GGTTTCGACCTGCTCCGCCAGCGGGGTGGCCTGACCGGCTACCCGAG CCAGGCGGAGAGCGAGCACGACCTCATCGAGAACTCGCACGCCTCCA CCGCGTTGTCCTACGCCGACGGCCTGGCCAAGGCGTTCGCGCTGCGC GGCGAGGACCGGCACGTGGTGGCCGTGGTCGGCGACGGCGCGCTCA CCGGCGGCATGTGCTGGGAGGCGCTCAACAACATCGCCGCCACGAAG AACAGGCTGGTCATCGTCGTCAACGACAACGGTCGGTCGTACGCGCC GACGATCGGCGCCTGGCCGACCACCTCTCCACGCTGCGGCTCAACC CCGGCTACGAGAAGGTGCTCGACCTGGTCAAGGACGCGCTCGGCTCG ACCCCGCTGGTCGGAAAGCCGGTCTTCGAGGTGCTGCACGCGGTCAA GCGCGGGATCAAGGACGCGGTCAGCCCGCAGCCGATGTTCGAGGAC CTCGGCCTGAAGTACATCGGGCCGGTCGACGGTCACGACCAGCAGGC GATGGAGTCCGCGCTGCGCCGGGCCAAGGGGGTTCAACGCGCCGGTG ATCGTGCACGCGGTGACCCGCAAGGGCTACGGCTACCGTCCCGCCGA GCAGGACGAGGCGGACTGCCTGCACGGCCCGGGCGCCTTCGACCCG CAGACCGGCGCGCTCACCGCCAAGCCGTCGCTCAAGTGGACCAAGGT CTTCGCCGAGGAGCTGGTGAAGATCGCCGACGAACGCCCCGACGTGG TGGGCATCACGGCCGCCATGGCCGAGCCGACCGGCATCGCCGCTCTC GCCAAGAAGTACCCCGACCGGGCGTACGACGTGGGCATCGCCGAGCA GCACGCCGCGACCAGCGCCGCGGGCCTGGCGATGGGCGGCCTGCAC CCGGTGGTGGCCGGTCTACGCCACCTTCCTGAACCGCGCTTTCGACCA GGTGCTGCTGGACGTCGCGATGCATCGGCTGCCGGTGACCTTCGTGC TGGACCGGGCCGGCATCACCGGGCCGGACGGCCCCAGCCACTACGG CATCTGGGACATGAGTGTCTTCGGCGCCGTCCCCGGCCTGCGCATCG CCGCCCCGCGGGACGCCGCCACCCTGCGCGAGGAACTGCGCGAGGC GGTCGCGGTCGACGACGGCCCGACCATCGTGCGGTTCCCGACCGGT GCGGTCGCCGCGGACACCCCGGCGGTGCGCGGGTCGGTCAGGTCG ACGTGCTGCGCGAGGCGGAGAAGAAGGACATCCTGCTGGTCGCGGTC GGCTCGTTCGTCGGCCTCGGGCTGACGCCGCCGAGCGGCTCGCCG AGCAGGGGTACGGCGTGACCGTGGTCGACCCGCGCTGGGTGCGCCC GGTGCCGATCGAGCTGACCGGCCTGGCCGCCCAGCACCGCCTGGTG GTGACCCTGGAGGACGGGATCCGCGCCGGTGGTGTCGGTGACGCGG TGGCCGCCGCGCTGCGCGACGCCGGGGTGCACGTGCCGCTGCGCGA TTTCGGCGTGCCGGCCGGTTTCCACCCGCACGGCACCCGGGCCGAGA TCCTCGCCTCGCTGGGTCTGACCGCGCAGGACGTCGCGCGGGACGT GACCGGCTGGGTGTCCGGCCTGGACGCCGGCACGTCGGTGGCGGCC CCGGCGATCTGA |
| 24 | DNA | >ispG (ACSP50_7248) | GTGACCGCGATCAGTCTCGGAATGCCGGCCGTCCCCCCGCCGCCGCT GGCCCCGCGCCGCCAGAGCCGGCAGATCAACGTCGGAGGAGTCCTG GTCGGCGGGGGCGCCCCGGTCAGCGTCCAGTCGATGACCACCACCC TCACCTCCGACGTCAACGCGACCCTGCAGCAGATCGCCGAGCTGACC GCGGCCGGCTGCCAGATCGTCCGGGTCGCCGTGCCGTCCCAGGACG ACGTCGAGGCGCTGCCGGCGATCGCCAAGAAGTCGCAGATCCCGGTG ATCGCCGACATCCACTTCCAGCCCAAGTACGTGTTCGCCGCGATCGAC GCGGGCTGCGCGGCGGTCCGGGTCAATCCGGGCAACATCCGCCAGT TCGACGACAAGGTCAAGGAGATCGCCCGGGCCGCGTCCGACGCCGG |

| SEQ ID No. | Type | Name | Sequence |
|---|---|---|---|
| | | | CGTGCCGATCCGGATCGGGGTCAACGCCGGCTCGCTCGACAAGCGG<br>CTTCTCGAGAAATACGGCAAGGCCACCGCCGAGGCGCTGGTGGAGTC<br>GGCGCTCTGGGAGTGCTCGCTGTTCGAGGAGCACGGTTTCCGGGACA<br>TCAAGATCTCGGTCAAACACAACGATCCGGTCGTGATGATCCGCGCCT<br>ACCGTCAGCTCGCCGAGCAGTGCGACTACCCGCTGCACCTGGGCGTG<br>ACCGAGGCCGGGCCGGCCTTCCAGGGCACGATCAAGTCGGCGGTGG<br>CGTTCGGCGCGCTGCTCGCCGAGGGATCGGCGACACCATCCGGGT<br>CTCGCTGTCCGCCGCCGGTCGAGGAGATCAAGGTCGGGCAGCAG<br>ATCCTGGAGTCGCTCGGCCTGCGCGAACGCGGCCTGGAGATCGTCTC<br>CTGCCCGTCCTGCGGGCGGGCCCAGGTCGACGTCTACACGCTGGCC<br>GAGCAGGTGACCGCGGCGCTCGACGGGTTCCCGGTGCCGCTGCGAG<br>TGGCCGTGATGGGCTGCGTCGTGAACGGGCCCGGGGAGGCTCGCGA<br>GGCCGACCTCGGGGTCGCCTCCGGCAACGGCAAGGGGCAGATCTTC<br>GTCAAGGGCAAGGTGATCAAGACGGTGCCGGAGGCGGTGATCGTCGA<br>GACGCTGGTCGAGGAGGCGCTGCGGCTCGCCGACGAGATGGGCGCG<br>GAGCTGCCCGACGAGCTGCGCGAGCTGCTGCCCGGTCCCACGGTCA<br>CCGTGCACTAG |
| 25 | DNA | >dxr<br>(ACSP50_<br>7250) | ATGCGTGAGCTTGTGCTGCTGGGGTCGACCGGGTCCATCGGCACCCA<br>GGCCATCGATATCGTCCGGCGCAACCCGGAGCTGTTCCGGGTGGTCG<br>CGATCGGGGCCGGGGGTGGCAACGTCGCGTTGCTCGGCGCAGGC<br>GCTGGAGCTGGGCGTCGAGGTGGTCGGGGTGGCCCGGGCCTCGGTC<br>GTGCAGGATCTGCAGCTGGCCTTCTACGCCGAGGCGCAGAAGCGTGG<br>CTGGTCGTCCGGCGACTTCAAACTGCCGAAGATCGTGGCCGGGCCGG<br>ACGCGATGACCGAGCTGGCCCCGCTGGCCGTGTGACGTCGTTCTCAAC<br>GGGGTGGTCGGCAGCCTCGGCCTGCGCCGACCCCTGGCCGCTCTGG<br>AGTCCGGGCGGATCCTTGCGCTGGCCAACAAGGAGTCGCTGGTCGCC<br>GGCGGCCCGCTGGTCCGGCGGATCGCCAAGGACGGGCAGATCGTCC<br>CGGTCGACTCGGAGCATTCGGCGCTGGCCCAGTGCCTGCGCGGCGG<br>GCGGGCCGCGGAGGTGCGCCGGCTGGTGCTGACCGCCAGCGGGGG<br>AGCCTTCCGCGGGCGGCGGCGCGGAGCTGACGAACGTCACCCCC<br>GAGGAGGCGCTCAAGCACCCGACCTGGGACATGGGGCCGGTCGTCA<br>CGATCAACTCGGCGACCATGGTGAACAAGGCGCTGGAAGTGATCGAG<br>GCGCACGAGCTGTTCGGCGTGCCGTACGACGACATCGCGGTGATGGT<br>GCACCCGCAGTCGGTGCTGCATTCGCTGGTCGAGTTCACCGACGGCT<br>CGACGCTGGCCCAGGCCAGCCCGCCGGACATGCGGCTGCCGATCGC<br>GCTGGCGCTGGCCTGGCCGGACCGGGTGCCGGGGGCGGCCGCCGC<br>GGTGGACTGGACGCTGGCCGCACAACTGGGAGCTGCGACCGCTGGAC<br>GACGAGGCGTTCCCGGCGGTCGAGCTGGCCAAGGCGGCCGGCCGGT<br>ACGGTCGCTGCCGTCCGGCGATCTTCAACGCCGCCAACGAGGAGTGT<br>GTGGCCGCTTTCGCCGCCGGTCGGCTACCTTTCTTGGGCATCGTCGA<br>CACCCTGGAACGGGTGCTCGCGGCGGCCCCGGATTTCGCGGAGCCG<br>AGTACCGTCGATGACGTGCTGGCCGCAGAATCCTGGGCGCGTGCCCA<br>GGCACAGCGGACGATCGCGACTGTGGCTGAAGGAGCCTGA |
| 26 | DNA | >ispH<br>(ACSP50_<br>7707) | GTGTTGCTCGCCAAGCCGCGTGGTTACTGCGCCGGTGTCGACCGCGC<br>CGTGCAGACCGTCGAGGAGGCGCTGAAACTCTACGGCGCCCCGGTCT<br>ACGTGCGTAAGCAGATCGTGCACAACAAGCACGTGGTCAGCACGCTG<br>GAGGCCCGCGGCGCGATCTTCGTCGAGGAGAACTACGAGGTGCCCGA<br>GGGCGCCACCGTGGTGTTCTCCGCGCACGGCGTCGCCCCGAGGTG<br>CACGACCAGGCCCGCGAGCGCCGGCTCAAGGCGGATCGACGCGACCT<br>GCCCGCTGGTCACCAAGGTGCACCACGAGGCGAAACGGTTCGCCGCC<br>GAGGACTACGACATCCTGCTGATCGGTCACGGAGGGGCACGAGGAGGT<br>CATCGGCACCTCCGGCGAGGCCCCGGCGCACATCCAGCTCGTCGACG<br>GCCCCGACGACGTGGCGAACGTCGTCGTCCGCGACCCGGCCAAGGT<br>CGTCTGGCTGTCGCAGACCACGCTGTCGGTGGACGAGACGATGGAGA<br>CGGTGGCCCGGCTCAAGACCCGGCTGCCGCTGCTGCAGTCGCCGCC<br>CAGCGACGACATCTGCTACGCCACCTCGAACCGGCAGCACGTGATCA<br>AGGAGATCGCGCCGAGTGCGACGTGGTGATCGTGGTCGGCTCGACC<br>AACTCGTCGAACTCGGTCCGCCTGGTCGAGGTCGCCCTCGGTGCCGG<br>CGCCCGGGCCGGTCACCTCGTCGACTACGCCGCCGAGATCCAGGAC<br>GAGTGGCTGGCCGGCGCCACCACGGTCGGTGTCTCCTCCGGCGCCA<br>GCGTGCCGGACGAGCTGGTGATGGAGGTGCTGGCGCACCTCGCGGA<br>GCGTGGCTTCGGCGAGGTCACCGAGTTCACCACGGCCGAGGAGCGG<br>CTCACCTTCTCCCTCCCGCAGGAGCTCCGCAAGGACATGAAGGCCGC<br>CGAGGCGGCCCGGGCCGCTGCCGCCGGCTGA |
| 27 | DNA | >ispE<br>(ACSP50_<br>7802) | ATGACCGAGGCGTGGGGTCCGGACGACGACGAGCCGCGCCCGTACA<br>GCGGGCCCGGTCAAGGTCCGCGTGCCGGCCAAAATCAACCTGCACCTC<br>GCGGTCGGCCCGCTGCGACCCGACGGGTACCACGAGCTGAACACCGT<br>CTACCACGCCATCTCGCTGTTCGACGAGATCACCGCCCGGCACGGCG<br>ACACCCTCACCCTCACCATGGAGGGCGAGGGCACCGGCGACCTCGCC<br>CTCGACGAGACCAACCTGATCATCCGCGCCGCCCGCGCCCTGGCCGC<br>CCGCGCCCCGCTCCCCGCCTACGCCCGGCTGCACCTGCGCAAGAGC<br>ATCCCGCTCGCCGGCGGCCTGGCCGGCGGCAGCGCCGACGCCGCCG |

-continued

| SEQ ID No. | Type | Name | Sequence |
|---|---|---|---|
| | | | CCACCCTGATCGCCTGCGACCTGCTCTGGGGCCTCGGCATGAGCCGC<br>GACGAGCTCGCCGAGGTCGGCGCCCAACTCGGCTCCGACATCCCCTT<br>CCTGCTGCACGGCGGCACCGCCCTCGGCACCGGCCACGGCGAGGCG<br>GTCAGCCCCATCCTGGCCCGCCCCACCACCTGGCACTGGACCGTCGC<br>CATCGCCGACGGCGGCTGGCCACCCCCGCCGTCTACCGCGAGCTC<br>GACACCCTGCGCGCCGGCACCTGGCCACCCACTCCGCTCGGCAGCG<br>CCGACACCCTGATGGCCGCCCTGCGCCAGCGCAACCCGGAAATCCTC<br>GGCGCCGCCCTCGGCAACGACCTGCAACCGGCCGCCCTCGCCCTGC<br>GCCCCCAGCTCGCCGACGTGCTCAAAGCCGGCACCGAGGCCGGCGC<br>CCTCGCCGGCCTCGTCTCCGGCTCCGGCCCCACCTGCGTCTTCCTCG<br>CCGCCGACGCCACACACGCCCAGGAGATCGCCGACAGCCTCACCGAA<br>GCCGGCGTCTGCCGGGCCGCGGTCACCGCCCGCGGACCCCAGCCCG<br>GCGCGCGGGTAATCTAG |
| 28 | DNA | >ispF (ACSP50_8046) | GTGATCATTCCGCGGGTGGGTATCGGCACGGACGTGCACGCATTCGA<br>CGCTGACCGGGCCTGCTGGGTGGCCGGGCTGGAGTGGCCGGGGGAG<br>CCGGGGCTGGCCGGGCACTCGGACGCGGACGTGGTGGCCCACGCGG<br>CCTGTGACGCGCTGCTGTCGGCGGCCGGGCTCGGGGATCTGGGGGG<br>CAACTTCGGGACGAGCCGGCCGGAGTGGGCCGGGGCAGCCGGGGTC<br>ACGCTGCTCGCCGAGACGGCGCGGCTGGTCCGGGCGGCCGGGTTCG<br>CGATCGGCAACGTGTCGGTGCAGGTGATCGGGAACCGGCCGAAGATC<br>GGGAAGCGGCGGGCCGAGGCCGAGAAGGTGCTCTCCGCGGCGGTGG<br>GGGCGCCGGTCACCGTGTCCGGGACCACATCCGACGGGCTGGGGCT<br>CACCGGGCGTGGTGAGGGGCTGGCCGGAGTCGCGGTGGCGATGGTC<br>TACACGGAGAACGCTCTTCCGGCCTGA |
| 29 | DNA | >ispD (ACSP50_8047) | GTGATCGCCGACCGCGACGTGACCGCGCAGCTCAATGCTCGCGGTGA<br>CGTCGCGGTCGTCGTTCCGGCGGCGGGGGCGGGTCTCCGGCTCGGC<br>CCGGGCGGCCCGAAAGCTCTGCGTCTGCTCGACGGCGAGCCGCTGC<br>TCGTGCACGCGGTCCGGCGGTTGGCCGCGGCCGCGCCGGTCCGCAT<br>GATCGTGGTGGCCGCTCCGCCCGCCGAGGTCGACGCGGTGTCCGCG<br>CTCCTCGCCCCGGTGGCCCCGGTCACCGTCGTGCCCGGCGGCGCCG<br>AACGCCAGGAATCGGTCGCCGCGGCACTCGCGGTCGTTCCGCCGGAC<br>GTTCCGATCGTTCTGGTCCACGACGCGGCTCGATGCTCACCCCGCC<br>CTCGGTTACGGAGCGTGTCGCCGCCGCTGTCCGGGACGGTGCCGAC<br>GCGGTGATCCCGGTCCTGCCGGTCGTCGACACGATCAAAGAGGTCGC<br>GGCCGATGCCACCGTTCTCGGCACGGTCGACCGTTCCGTGCTGCGTG<br>CGGTACAGACTCCGCAAGGCTTCCGCGCCTCGGTGCTGCGCGCCGCT<br>CACCGGGCCGCCGCCGACTCACACACCGACGACGCCGGTGCCGTCG<br>AGAAGCTCGGCATCCCGGTCCTGTGCGTCCCGGGCTCCGACCTCGCG<br>CTCAAGATCACCCGGCCGATCGATCTGGCGCTCGCCACGCACCTCCT<br>GGCCCTGCCGGACCCGGACGCCCCTACCGCCTGA |
| 30 | DNA | >idi (ACSP50_0146) | ATGAGCAGCATCGGTCACCTCAACCGTGAAGATCATCTCGTCGAGCTC<br>GTCAACGAGGAGGGGCAGCCGCTCGGGTCGGCCACCGTCTCCGACG<br>CCCACCTCTCGCCGGGTGCGCTGCACCGGGCCTTCTCGGTCTTCCTC<br>ACCGACGATGAGGGCCGGGTGCTGCTCCAGCAGCGGGCCGCGGCCA<br>AAACCCGCTTCCCGCTCCGCTGGGGCAACACCTGCTGCGGCCACCCC<br>GCGCCCGGCGAGCCGGTCACGGTCGCCGCGGCGCGGCGTCTCACCG<br>AGGAATTGGCGGTACGTGACGTCACGCTGACCGAGATCGGCGTGTAC<br>ACCTACCGCGCGACCGACCCGGTCACCGGCCGGGTGGAGCACGAATA<br>CGACCACGTGCTGATCGGCGCCCTGCCGGACGGCGTCGTGCCACACC<br>CCGATCCGGCGGAGATCGCCACGCTGCGCTGGGCCTCGCTGCCCGG<br>GCTGCGCACCGGGTTGACGGAGTCCCCCGAGCTGTACGCGCCCTGG<br>CTCCCCGGGGTGTTCGAGATTCTCACGGAGCGGTCGGGTGTCCTTTC<br>CACGGAGCGGTCGGGTGGCCGGTGA |
| 31 | DNA | >crtE IdsA (ACSP50_0148) | GTGGCCAATGACACCCTCGAGGGAAATCGCCTTGCCGCGATACCCCG<br>GCAGTCCGTCTCTCACACTGGGCTGGTCGGTGCAGTCGAGGGGACAC<br>TCGCCGACTTCCTCGCCTCCCAGATCGCCTCTCTCGACGCCGTCGACC<br>CATCGCTCGGTGGCTTCGGCCGCACCGCCCGTGACCTGGTGATGGCC<br>GGCGGCAAACGGCTGCGGCCGACGTTCGCGTACTGGGCTGGCGCG<br>GCGTCGCCGGGCCGGCCGCGGACGCCGAGACGCTGCTGCCCGCGCT<br>CGGCGCGCTGGAGCTGATGCACACCTTCGCGCTCGTCACGACGACG<br>TGATGGACGACTCGTCCACCCGCCGCGGCCGGCCACCGCCCACCG<br>GATCTTCGCGGCCCAGCACGGCGGCCGGTTCGGCACGTCGGCCGCG<br>ATCCTGGTCGGCGACCTCTGCCTGGTCTGGGCCGACCAGCTGTTGGC<br>CCGCACCCCGGTGCCGGCGGCCACCCTGCTTGCAGTCCGCGCGCATT<br>ACGACCGGATGCGGATCGAGGCGGTCGCCGGGCAGTATCTGGACGTC<br>CTCGGTGAGACCGATCCGGCGTCCTGGTCGGTGGAGCGCGCACTGCT<br>GGTCGCCCGGCACAAGACCGCCAGCTACACCGTGCAGCGGCCGCTC<br>GACTTCGGCCTGGCCCTGGCCGGGGTCGAGGACGTGGAGGTCGCCG<br>AGGCGTACCGGACCTACGGCATCGCCGTCGGCGAGGCCTTCCAGCTG<br>CGCGACGACCTGCTCGGTGTCTACGGCGACCCGGCGGTGACCGGCA<br>AACCGGTCAGCGACGACCTGCGCACCGGCAAACCGACCGCACTGCTG |

| SEQ ID No. | Type | Name | Sequence |
|---|---|---|---|
| | | | ATGCTGGCCCGTCGGATGGCCACCCCCGGCCAGCTGGCCGAGCTGG<br>AGTCGGCGGAGATCGAGCGCAAGGCGCAGGTCGTCGCCGAGACCGG<br>CGCCCCGGCCCGGGTCGAGGAGATGATCCGTGCCCGGGTCACCGAA<br>GGACTGACCGCGCTGGCCTCGGCGCCGATCGACGCCGAGGCCCGTG<br>CCACCCTGATCGAGCTGGCCACCGTGGCGACGCAGCGCCCGGCATGA |
| 32 | DNA | >crtB (ACSP50_0149) | ATGGAAACCGATCTGGCCGCCGCCTATGAGCGGTGCCGTGAGCTACA<br>CCGAGAGCACGGACGCACGTACTACCTGGCGACCCGGTTACTACCGG<br>CCTGGAAGCGCCGGCATGTGCACGCTCTGTATGGATTCACCCGGTTC<br>GCCGACGAGATCGTCGACCGCACCGAGGCGCAACCACCCGCCGAGC<br>GCGCCGCCGAGCTGGCCACCTGGTCCGCCGGATTCCTCGCCGGACT<br>GCGCGGCGAGCCGGTCGACGACCCGCTGCTCCCGGCCGTGCTGCAC<br>ACCATCGCGGTCTTCGGGCTCGACCTGGAGGACTTCGCGAAGTTCCT<br>GCGCAGCATGGAGATGGACCTCACCGTCACCGGCTACCGCACCTACG<br>ACGACCTGCTCGACTACATGGAGGGCTCGGCCGCCGTGATCGGCACC<br>ATGATGCTGCCGATCCTGGGCTCCACCGACCCGGCCGCCGCCCGCGA<br>ACCGGCCCGCCAGCTCGGCTTCGCCTTCCAGCTCACCAACTTCATCCG<br>GGACGTCGCCGAGGACCTCGCGCGGGACCGGATCTACCTGCCCGAG<br>GAGCACCTCGCCGAGTTCGGTGTGACCCGCGCCGACCTGGCCGCCG<br>GCGTCGCCACCCCGGCGATCCGCGCGCTCATCCGGGCCGAGGTGGA<br>CCGCGCCCGTGAGCACTACGCGGCCGCCGCCCCGGCATCCCGCTG<br>CTCGAACGCACCTCGCAGGCCTGCATGCGGACCGCCTTCCAGCTGTA<br>CGGCGGGATCCTGGACGAGATCGAGGCGGCCGACTACGACGTGTTCG<br>CCCCGGCGGGTCACGGTGCCGAACCGGCGCCGGGCCGCGGTCGCCGT<br>CCGCAGCCTGCTCACCCGGCCCGGCACCCCGGTCGAACTGGCGGCC<br>TGA |
| 33 | DNA | >ACSP50_0150 | ATGGGCGCCCGCGTCGCGCTGTTCACCCGCGACCTGCGGATCCACGA<br>CAACCCGCTGCTCAGCGGGCCCGACCCGGTGGTGCCGCTGTTCGTCC<br>TCGACCCACGGCTGAGCGGCCTCTCGGCCAACCGCAGCCGCTTTCTC<br>CACCAGAGCCTGGCCGACCTGCGGAACAGTCTCCGCGAGCGTGGCG<br>CCGACCTGGTGATCCGGGAGGGCGACCCGGTGGCCGAGACCATCGC<br>GGTCGCCTCCGAGGTGGACGCGTCGACGATCACGGTGGCCGCCGAC<br>GTGACCGGTTACGCCCAGCGGCGCGAGCGGCCGGCTGCGGGACGAGC<br>GATTCCGGGTGAAGACGGTGCCGAGCGTCACGGTGCTGCCGCCGGT<br>ACGGTCCGGCCGGGCGGGGAGGCGAGTCGTACCGCGTGTTCACGC<br>CGTACTTCAAAGCCTGGGAGAAAGCTGGGTGGCGCGCACCCTCCGCA<br>ACGCCGGGGAAGGTCGCGATGCCGGCCGGCATCGCGCCGGGAAGGC<br>TCCCCGAGATGCCCGCCGGCGACTCACCGGACGCCGTCGCCGGTGG<br>CGAGACCGAGGGCCGCCGCCGGCTCCAGGCCTGGCAGAAAGAAATG<br>GCGCGGTACGCCGAGGACCACGACGACATGGCCGCCGACAACACCA<br>GCCGGCTCAGCGCCTACCTCCGGTTCGGCTGCCTGTCGCCGCTCGAA<br>CTGGCGCTGGCCGCGAAAGCCGACGACTCTCCCGGCGCCCAGGCCT<br>ACCTGCGGCAACTGTGCTGGCGGGACTTCTACTACCAGGTCACCGCG<br>ACCTTCCCGGAGATCTCCACCCGGCCGCTGCGGGAGAAGGCGGACCA<br>GAACTGGCGATACGACGACGACGCGCTGCGTCACTGGCAGGACGGCC<br>TGACCGGGGTGCCGATCGTCGACGCCGGCATGCGCAGCTCCGCGC<br>GGAGGGCTGGATGCACAACCGGGCCCGGCTGATCACCGCCGCGTTC<br>CTCACCCAAAACCTGGGCATCGACTGGCGGCCCGGGCTGCAATGGTT<br>CTTCCGCTGGCTGCTCGACGGCGACGTGCCGAACAACTCCGGCAACT<br>GGCAGTGGACCGCCGGCACCGGCAACGACACCCGGCCCTATCGCAG<br>GTTCAATCCCATTCGCCAAGCGCAGCGATTCGATGCGCAGGGCGTGTA<br>CGTTCGGCGCTACGTACCGGAGTTGAAAGACATCGACGGTGTCACGG<br>TGCATCAGCCGTGGCGACTGCCGGAATCGGTACGCCGCGGGCTCGAC<br>TATCCCGGACCGTTGGAGTCACATCGGGACGAGGCGGTCTGGCTGCG<br>CGACTGA |
| 34 | DNA | >ACSP50_0151 | ATGTCTGAAGCGCGGCAAGTGGACGTGGTGGTCGTCGGGCTCGGTGT<br>CGGCGGCGAGGAGGTCGCCGGTCGCCTGGCCGTCGCGCGGCCTGAG<br>CGTGATCGGCGTCGAACACCGACTGGTCGGTGGCGAATGCCCGTACT<br>GGGGATGCATCCCCACCAAGATCATGGTCCGCGCCGGGAACGCGCTG<br>GCCGAGGCCCGCCGGATCCCCGGCCTCGCCGGGACGTCCACGGTGC<br>GGGCCGACTGGGCGCCGGTCGCCAAACGGATCCGCGACGAGGCCAC<br>CGACGACTGGAACGACAAGGTCGCCGTCGAGCGGTTCACCGGTAAGG<br>CGGAACGTTCGTCCGGGGCACGGCCGAACTGACCGGTCCCGGTCA<br>GGTCCGGGTCGGGGACCAGGAATTCGCCGCTTCGCGCGGCGTGGTC<br>ATCGCCACCGGCACCGCCGCTGTGGTCCCACCCATCGAGGGCCTGTC<br>CGGTACGCCGTTCTGGACGAACCGTGAGGCCGTGGAAGCGGCGGCC<br>CTGCCCGCATCGATGCTGGTGCTCGGCGGCGGGGCGATCGGGTGCG<br>AGCTGGCCCAGGCGTACGCCCGGTTCGGCGTGCAGGTGACGGTCATC<br>GAGGGCTCACCCCGGGTGCTGGCCATGGAGGAACGGAGTCGTCCG<br>AGGTGGCGGCCGCCGCCCTGACCGCCGACGGGGTCCGGATCGTCAC<br>CGGGGTGCGCGCGCAGAAGGTCGCCCACGACGACGGGTTCCACGTG<br>ACCCTCTCCGACGGCAGCGTGCTGGCCGGCGAGAAGCTGCTGGTCGC<br>GACCGGGCGGGCGGCCCGGCTCGGCGGGCTCGGGCTGGACCGGGT |

-continued

| SEQ ID No. | Type | Name | Sequence |
|---|---|---|---|
| | | | GGGGCTGGACCCGTCGGCTCGATTCCTGGCCACCGATGACCGGCTGC<br>GCGCCGGCGAGGGCATCTGGGCGGTGGGGGACGTGACCGGGAACG<br>GGGCGTTCACCCACATGGCGATGTACGAGGCGGACATCGCGGTGCGG<br>GACATCCTGGGGCAGGGCGGCCCGGGAGCCGACTACCGGGCGCGGC<br>CGCGGGTGACCTTCCTCGACCCGGAGATCGGGGCGGTGGGGATGAC<br>CGAGCAGCAGGCCCGGGACGCCGGCCTCGAGGTGCGGGTGGGGTAC<br>GTGCCGCTGAACCAGACCTCGCGAGGGTTCATCCACGGGCCGGGGAA<br>CGAGGGATTCCTCAAACTTGTCGCGGACGGGGAGCGGGGAGTGCTGG<br>TCGGCGGGACGACCGCCGGGCAGTCCGGTGGCGAGATGATCGGGGC<br>GGTGGCGGTGGCGGTGCACGCCGAGGTGCCGGTGTCGACGTTGCTC<br>AGCCAGATCTGGGCGTACCCGACGTTTCATCGGGGGCTGGGGCAGGC<br>GCTTCAGTCGCTGGCCTGA |
| 35 | DNA | >ACSP50_<br>1631 | GTGAGCGAACCCGTCATCACCGAACCGGCTGCCTGGATCAACCTGCC<br>CGACCTGTCCGAGAGGCTGGACGTGTCGATCAGCAAGGTGCACCAGA<br>TGATCAGAGACGGCGACCTGCTCGCGGTCCGCCGCGACGGCATCCGC<br>GTGGTGCCCGCCGAACTGGTGGCCAACGCCACCGTCCTCAAGCATCT<br>GCCCGGTGTGCTGAACGTGCTCCGCGACGCCGGGTACAACGACGAAG<br>AGGCCTTCCGGTGGCTCTACGCCGAGGACGCCGAGGTCGGCGGCAG<br>CGCCGCGATCGCGCTCGGCGGTCAGCAGGCGCGCGAGATCAAGCGC<br>CGCGCGCAGGCCCTCGGCTTCTGA |
| 36 | DNA | >ACSP50_<br>1632 | ATGAGGCATTTGTCGTACGTCGCGGTGCTGGCCGGATGCCTGGCCGG<br>GGCGCTGTGGCTGGAACCGATCCTGCGGGTCAACGTGCTGCGCCGGT<br>GGCGTCGGCTGCTGCTGGCCGTGCTGCCGATGGCGGTCGTCTTCACC<br>CTGTGGGACCTGGCGGCGATCGCGGCCGGCCACTGGCACTTCGACC<br>CGGCCCAGATCACCGGCGTCTACCTCGGCGGCGGGCTGCCCCTCGA<br>CGAGGTGCTGTTCTTCCTGGTGGTGCCGGTCTGCGCGATCCTCGGCT<br>TCGAGGCCGTGCGGGCCGTGCTGCGACGTCCGGCGGGGACGAGTG<br>A |
| 37 | DNA | >ACSP50_<br>1633 | GTGACCTACACCACCGCTGCGGTGCTCGGCGTGCTGGCCGCCCTCAC<br>GCTCGACGTGCTGATCCTGCGGACCCGGCTCGTCGGGCGACTGGTGT<br>TCTGGGCCACGTACCCCATCATCTTCGTCTTTCAGTTGATCTCGAACG<br>GCATTCTGACCGGGCGCGACATCGTGATGTACGACCCGGCCGCGATC<br>CTCGGCCCGCGGCTCGTCCACGCCCCGGTCGAGGACCTGCTGTTCGG<br>TTTCGCCCTGGTGCTCGGCACGCTGTCGCTGTGGGTGGCGCTGGGCC<br>GGCGCGGCATCAGCGCACCCCGCGAGCCGGGTCTAGACGGACCGA<br>CGAGTAG |
| 38 | DNA | >crtE<br>fps2<br>(ACSP50_<br>1634) | GTGACGAACTCCCCGCTCGACGAGGCCGGTCTGCGGTCGCGTGTCGA<br>CAAGGCGCTGACCGTGTTCCTGGCCGGGCAGCGTGACCGGCTGCTG<br>GCGATCGACCCGGCGCTGGCCGAGATGTTCCGCCACGGTCTCCGAGTT<br>CGTGCTGGGCGGCGGGAAGCGGCTGCCGGCCGGCATTCGCCTACTGG<br>GGTTTCCGCGGGGCCGGCGGCGCCGACTCGGACGCCGTGGTGGCGG<br>CCGTCGCCGCGCTGGAGCTGGTGCAGGCCAGCGCGCTGATCCACGA<br>CGATCTGATGGACCGCTCGGACACCCGGCGCGGGGTGCCGTCGGTG<br>CACCGTCGGTTCGAGAAACTGCACGCCGGCGAGGGCTGGCGGGGCA<br>GCGCGGCCGGGTTCGGCGACTGCGCCGCGGTGCTGCTCGGCGACCT<br>GGCCCTGGTCTGGTCGGACGAGCTGCTGCACACCTCGGGGATGGCG<br>GTGGCCGACGTGCAACGGGCCCGCCCGATCTTCGACGGGGATGCGCA<br>CCGAGGTGACCGTCGGGCAGTACCTGGACGTGCTCACCCAGGCGACC<br>GGCGACACGTCGCTGGAGCGGGCCGGCAAGGTGGCCGTCTACAAGG<br>CCGCGAAATACACCGTGGAGCGTCCGCTGCTGCTGGGCGCGGCGCT<br>GGCCGGAGCGGCCCCCGGGGTGCACGCGGCGTACTCGGCGTTCGGC<br>CTGCCGCTGGGCGAGGCGTTCCAGCTGCGCGACGACGTGCTGGGCG<br>TGTTCGGCGACCCGGAGCGGACCGGCAAGCGCGGCCGGCGACGACCT<br>GCGCGAGGGCAAGCGCACCTATCTGGTCGCGGCCGCCTTCGGCGCG<br>CTGGACGCGGCCGGGCGGGCCGAACTGGACGCCGCGCTCGGCGACC<br>CCGGCCTGGACGAGGCCGGGGTGGCCCGGCTGCGCACGGTCATCCG<br>GGACAGCGGTGCGCTGGCCGCGACCGAGGCCCGGATCGACGAGCTG<br>ATGACCGCGTCGATCGGCGCGCTGGACGCGGCACCCGATCGATCAGGA<br>CGCCCGGGAGGTGCTGCGCCGGCTGGCCGACGCGGCTACTCGTCGG<br>TCCGTCTAG |
| 39 | DNA | >ACS<br>P50_1<br>635 | GTGTCTCTCGGACTTCCCTCCCGGCTGCCCGGCACCCCGTCGATCGG<br>CGACCTGGTCCGCGGCGCGGCGCCGACGTTCTCCTTCGAGTTCTTCC<br>CGCCGAAGACACCGGACGGGGAGCGGCTGCTCTGGCAGGCCATCCG<br>GGAGCTGGAGTCGCTGCGCGCCCAGCTTCGTCTCGATCACCTACGGG<br>CCGGCGGCACCACCCGGGAGAACACGGTCGCGGTCACCGAGCGGGT<br>CGCCACCGAGACCACGCTGCTGCCGCTGGCCCACCTCACCGCGGTCG<br>ACCACTCAGTGCCGACCTGCGCAACGTGATCGGCCGGCTGGCCGGC<br>GCCGGGATCCGCAACGTGCTGGCGCTGCGCGGCGACCCGCCGGGCG<br>ACCCGATGGGCAGTGGGTCCGGCACCCGGACGGCGTCGGTTACGC<br>CGACGAGCTGGTCCGGCTGATCCGCGAGTCCGGCGACTTCAGCGTCG |

| SEQ ID No. | Type | Name | Sequence |
|---|---|---|---|
| | | | GGGTGGCCGCCTTCCCGCACAAACACCCCGGTCGGCCGGCGTCAA GGACGACACCCGCAACTTCGTCCGCAAGTGCCGGGCCGGTGCCGACT ACGCGATCACCCAGATGTTCTTCGACGCCGACGAATATCTGCGGCTGC GCGACCGGGTGGTGGCCGCCGGCTGTCACACCCCGATCGTGGCCGG CGTGATGCCGGTGACCCGGATGGCCACCATCGCGCGCTCCACCCAGC TCTCCGGCGCGCCCTTCCCGCCGGCGCTGCTGCGCGACTTCGAGCG GGTCGCCGGCGACGACGCGGCGGTGCGCGAGCTGGGCATCGAGACG TGCGCGGCGATGTGCGCCCGGTTGCTGCGGGAGGGTGTGCCGGGCA TCCACTTCATCACCATGAACCGGTCCACCGCCACCCGCGAGGTCTGG CAGCGGCTGGCCCCCGCGGAAGTCGCCGCGTCGGCGTGA |
| 40 | DNA | >ACSP50_<br>1650 | GTGCAGCTGCAACAACTCCGGTACTTCCTGGCGGTGGTGGAGACCCG GCATTTCACCCAAGCAGCGGACATTCTGGGCGTCTCGCAACCTACCTT GAGTAAGCAGATTCACACCCTTGAGATGTCACTCGGAGCCCCGCTGTT CGAGCGGATGCGCGGTGCGGTGACCCTGACCGTCGCCGGCGAGACA TTGCTGCCGATGGCCCAGCGGATCGTCGCCGACGCCGACGCGGCCC GCGACGCCGTGCAGGACATCGTCGGTCTGCGCCGCGGCGAGGTGCG CCTGGGTGCCACCCCGAGCCTGTGCTCCTCGCTGGTCCCGGCCGTGT TGCGCACCTTCCGCGCCGACCACCCGGGGGTCAAGCTGCACATCAGT GAGGGCAGCTCGCACGACCTGACCGCCGGCCTGCTGGCGCACACCC TGGATCTGGCCCTGATCGTGCAGCCCGAGCACGGCGTCGATCCGGCC CTGGTGGCCATCGAGCTGCTGCGCGAGAGCTGGTGGTGGCCTCGGT CGCGGCCGGCCCGCCGCCCACCGTGGGCCGCCAACTGGAGCTCTCC GAGCTGCGCCACACCCCGATGGTGATGTTCCGCGAGGGCTACGACAT CCGTGAGGTCACCCTGCACGCCTGCGAGCGGGCCGGCTTCGCGCCG AAGTTCGCGGTCGAGGGTGGTGAGATGGACGCGGTGCTCGCCTTCGT CGAGGCCGGCCTCGGGGTCGCCCTGGTGCCCAGCATGGTGCTCGCC AACCGGCCGCTGCTGCGGGCCACCCCGCTCGCGCCGCCGGGGATGC GCCGGACCATCGCGCTCGCCCAGCGCCGTGCCGCGGTGCTGCCGCA TGCCGCGGCCGCGCTGCGTGAGGTGGTGCTCGACCACATCGGCTCG GGCCGGCTGCCGTTCGGCGTGCGCGCCCTGGAGAGACCGTCCACTTA G |
| 41 | DNA | >ACSP50_<br>1651 | ATGGGCGAGTTCCACGACCCGCGACTCGTCGAGGTCTACGACGCCGA ATGTCCCTGGGGCTGGGACGACGACTTCTTCATGGCCGTGCTCGCCG AACGCTCCGCGCACCGGGTCGCCGACCTGGGGTGCGGCACCGGCCG GCTGGCCATCGCGATGGCCGCGGCCGGGCACGAGGTGATCGCGATC GACCCGGCGCCGGCCGCCCTGGCCGCGGCCGCCGCAAGCCGGGC GGCACCCGGGTGCGCTGGCTGCAGGGCTCGGCCGAGCGGCTCGCCC CGCGCTCGCTCGACGCCGCGTTCATGACCGGTCACGTCGCCCAGTCC TTCGTCGACGACGAGGAATGGGACACCGTGCTCCGCGGGCTGCGCCG GGCGCTGGTCCCGGAGGGACGGCTGGTCTTCGACAGCCGGGACCCG GACGACCGGCCGTGGCAGCAGTGGAACCCGCAGGATTCGTGGCGCA CCGTGGTGCTCGACGACGGGAGGGTGGTGGAGGCGTGGAGCGAGGC CGAGCAGGTCGGGCTGAACACCGTGCGCGTCACCGGGCGCTACCGG TTCGCCGACGGAGGGGAACTGGCGAACTCGGCCGACCCTGCGTTTCCG GACCGAGCCGGAGCTGCGCGACTCACTGCGCGAGGCGGGCTTCCGG GTCGAGCGGATCTACGGCGGCTGGGGCGCGAGCCGGTGGGTCTGA GCGGCGACGGCGAGTTCATCGTGATCGCGGTCGCGACGCCCCGGCT GATGTCCTGA |
| 42 | DNA | >ACSP50_<br>1652 | ATGCCCGAGAACGAGTGGCCCGACGACCCCCGCCCGCCCGACCAGG GCGAGTGGAGCCAGCCGCATCACGAGCCGCCACCCGGCCGTGGCCG CGCCCTGCTGGCCGCCGCGGTGGTGGTGCTGGTCCTGCTGGCCGCC GGCGGCATCGCGCTGGCGTCTGATGAGCAGCCGCGGCGCTACGCCGG TGGCGCAGCCCACCGCGCCCGCCCCGACGCCACCGCGCAGACCGC GCCACCCTGCCCACAGCCGCGCCTGCGGGTCGCCGCCGCGCCGGAG ATCGCCCCGGTGATCCAGCAGGCCGCCGCCGCACTCAGCCAGCCCG GCCAGCGCTGCTCCGAGGTGCTGGTGCAGGCCGCCGAGCCGGGCGC CGCGCTGACCGGCAAGCCGGACGTCTGGGTGCCGTCCAGCAGCGTG TGGCTGGCCCTGGCCAAAAGCGCGGCGACGTCTACACCACGCAGGG CGCGTCGCTGGCCTGGTCGCCGCTGGTGATCGCCGGGCCGGAGTCG ATCGCCAGCCTGTTCGCGCCGAACGGGGTCACCTCCTGGTCCGGCCT GGTCAGGGCACCATCCAGAAACGGGTGCCGGCGGTCGGCGATGCCC GATCCGACGCTGACCACGACCGGACTGCTCAGCGTCTACGCGGTGGG CCAGGCCACGGTCAAGGCCAACCCGGACGCCGGGATCGCCCAGTTG CAGGCGCTCACCCTGCGCAGCCGGCTGGAGAACGCGGCCGCCGACC CGGCGGAACTGTTCGCGCAGATGGGCAAGCAGACCGACGCGGCCAC GGCGATCTACCAGGTCGGGGTCTTCCCGACCACCGAGCAGCAGCTGC TGACCTATCAGAAGAGTCAGCACGACGTCCGGCTGTCCGGCTCGGCG CCCGCCGACGGCCAGATGACGCCGACTATCCGTACGCGGTCCGCAA GGGCGCCCCGGCCGACCTGGTCGAGAGCCTTCGCGAGGCGATCACC CCGGACGCGCTGACGACGGCCGGATTCCGGGCCACCGCGACCAAGA ACGCGCTGCGCCTGCCGGCCCCGGCCGTGCTCGCCGGGGCGGCCCG GCAGTGGTCGGCGTACAAGTCGGTGGCCTTCCAGGTGCTGCTGCTGA |

| SEQ ID No. | Type | Name | Sequence |
|---|---|---|---|
| | | | TCGACGCGTCCGGCTCGATGAACGAGAAGATCACCGACCGGGCCGGC<br>CGCAGCGTCACCAAGGCCGCGCTGCTGCGCGAGTCCGGGACCAGCG<br>CGGCCCAGCTCTTCGGTGACGACACCAGCCTCGGCCTGTGGTTCTTC<br>GGCACCCCGACGGCGGACAGCCCGGCGCACACCGAGGAGGTGCCGT<br>TCGGCCCGGTCATCGCCACCGTCGACGGCAAGAGCCGCCGTGACCTG<br>CTGGCCGCCAAGATCGGCGAGTACCGGCCGGTGGCGAACGCCGGGA<br>CCCCGCTCTACCAGAGCGTGCTGGACGGCGTCGCCGAGATGCGCGG<br>CCGGGCCAAGCCGGACACGGCGACCGTGGTGGTGGTCCTCACCGAC<br>GGCTCGGACGGCGGCACGAAGTACCGGATGTCCAACGCGGACTTCCT<br>GAAGAAGCTGACCGCCGGTGCCGACCCCGCCAAGCCGGTGCCGGTG<br>ATCGCCGTCGGTTACGGCCCGGCCGCGAACGCCACCGCCCTGCAGG<br>CCATGGCCAAGGCCACCGGTGCCAGGCGGTCACCGTCAAGAACCCG<br>GCCGACCTGGCCGCCGGCATCGCCCAGGCCTTCCTCGCCGCACACAC<br>CCACTAG |
| 43 | DNA | >crtD<br>(ACSP50_<br>1653) | ATGAGCGACATCGTGGTGGTCGGGGCTGGGGTCGGCGGGCTGGCCG<br>CGGCGATCCGGCTGGCCGAGGCGGGGCATCGGGTCAGCATCCATGA<br>GCGGTCCGGCGTGGTCGGCGGCAAGCTGGCGGCATACAGAGAGGGAC<br>GGCTACCGGTTCGACACCGGCCCCAGCCTGCTCACCCTGCCGGACGT<br>GTTCACCGGCCTCGGTCTGGACCTGCGCCCGGAGCCGCTGGACCCG<br>GTGGTGCGGCACTTCTTCCCGGACGGCACGGTGCTGGACTCGTCGTC<br>GGACCACGAGACCTTCCTGGCCCGGATACACCGACGCGCTGGGCGGT<br>GCCGCGGCGCGCGACTGGGACCGGTTCTGGCGCCGTGCCGAGCGGA<br>TCTGGCACGCCTCCTGGGAGTCGGTGCTGCGCCGCCCGGTGACCGC<br>GGCGTCGCTGGCCCGGCTGTCCTGGCGGCTCGGTGACCTGGCCGCG<br>ATCGCTCCCGGCCGGTCACTGCGGTCGCTGGGCCGCCGCTATCTGCG<br>CGACCCGCGGCTGCGGATGCTGCTGGACCGCTATGCGACGTATTCGG<br>GCGCGGATCCGCGGCGGGCGCCGGCGGCGCTGGCCGCGATCCCCTA<br>CGCCGAGCTGGCGTTCGGCGGGTGGTATCTGCGGGTGGGCTGGTC<br>ACCCTCGCGGAGGCGCTGCTGCCCCGATGCGAGAAACTGGGCGTACG<br>GGTGCATCTGCACTCACCGGTCGCCTCGATCGCCACGACCGGCGCCC<br>GGGTGTCCGGGGTCCGGCTGGGGACGGGACCCGCCTCGCGGCGG<br>ACGTCGTCGTCTCCAACGTGGACGCCGTCACGCTCTACCGGGATCTG<br>CTGCCCAGTCCGAAACCGCTGGCCCGCCTCGCCGACCGGAGCCTGG<br>CCGGATTCGTGCTGCTCGCGGTGCGGGGCGAGACTCCGCGGCT<br>GGCGCACCACAACGTGTTCTTCCCGCGGGACTACGACGCCGAGTTCG<br>ACGCGGTCTTCGGGGGGCCGGGCGGCGGGCGCGGCCGGCCGGCG<br>ACCCGACCGTCTTCGTCACCCGGGCCGCGGATCCGGCGGTGCGCCC<br>GGCCGGCGACGAGGCGTGGTTCGTGCTGGTCAACGCGGCGCCACAC<br>GGCACCTCGTGGTCCACCGTGGACTGGCTGCGGGGCGGGGCTGGCCG<br>ACGCGTACCGGGATCGGGTCCTCGAGGTCCTGGCGGGGCGCGGTCT<br>CGACGTACGCGATCGGCTGATCTTCGCCGAGACCGGACCCCGGCGG<br>ATCTGGCGGCGTCGGCCGCAGCGCGGGCGGAGCGATCTACGGCAC<br>CGCCGGCGGCCTGGTCCGGCCGGCGAACCGCGCGCCGGTCGACGG<br>GTTGTTCCTGGTCGGCGGCTCGACGCATCCCGGCGGCGGGCTGCCG<br>ATGGTCACCCTCTCCGCCGAGATCGTCGCGGGCATGATCGGATCGAA<br>CTGA |
| 44 | DNA | >cruC<br>(ACSP50_<br>1654) | ATGATCGTCGCCTGGCTGATCCTGCCGCCGCTGCTGCTGATCACCGC<br>ACACACCGCCGTCAACGCGCTGCTGCTGCGCCGCCCGCGCCGGGCG<br>GCGACCAGCACCGAACGGGTCGCCGTCCTGCTCCCGCTGCGCGACG<br>AGGCCACCCGGGTCACCCCGTGCCTGCGCGCCCTGCTCGCCCAGCG<br>CGGCGTCGCCGATCTCACCGTGCACGTGCTCGACGACGGCTCCACCG<br>ACGGCACCGCGGACGTGGTCCGGGCGGTCGCCGGCGACCGGGTCCG<br>GCTGCACACCGGCACTCCGCCGCCGCCCGGCTGGCTCGGCAAACCG<br>GCCGCCTGCCAACGGCTCGCCGACCTGGCCGGGGACGTGGACGTGC<br>TGGTCTTCGTCGACGCCGACGTGGTGCTCGCGCCGGACGCGGTGGC<br>CGGGGCCGTCGATCTGCTGCGCCGGGCCGGAGCGGACCTGCTCAGC<br>CCGTACCCGAAGATCGTCGGTGCCGGCCGGCTGGTCCAGCCGCTGCT<br>GCAGTGGTCCTGGCTGAGTTTCCTGCCACTGCGCGCGATGGAACGCT<br>CGGCGCGGCCGTCGCTGGCCGCCGCCGGTGGCCAGTGGCTGGTGCT<br>GGACCGGGCCGGTTACCGGCGAGCCGGTGGCCACGCCGCGGTGCGC<br>GGCGAGATCCTGGAGGACATCGCGCTGGCCCGCGCGGTCAAACGGG<br>CCGGCGGCGGATCGCCCTGGCCGACGGTTCCGGCCTGGCCACCTG<br>CCGGATGTACGAGTCCTGGGACGAGCTCGCCGACGGATACGCCAAT<br>CGCTGTGGGCGTCATTGGGGTCCGCGGCCGGCGCGACCGCCGTCAC<br>GCTCCTGCTGATTCTGCTGTACGTGGTGCCACCCCTGCTGGCGCCCTT<br>CGCCCCGCTTCCGGCGGTGCTCGGCTACCTGCTCGGCGTGACCGGC<br>CGGATGATCGCCGCCAGGGCCACCGGCGGCGCGTCCTGCCCGGCA<br>CGCTGGCCCATCCGGTCTCCATCGTCCTGTTCGGCTACCTGATCGCCC<br>GCTCCTTCCGGCTGCGCCGGGCCGGCCGCCTGGCCTGGCGCGGCCG<br>CCCGGTGCCCTGA |

| SEQ ID No. | Type | Name | Sequence |
|---|---|---|---|
| 45 | DNA | >cruF (ACSP50_ 1655) | GTGTCTCCCCGTCATCTGCCCTGGGGCCTGCTCGGGGCGCTCGTGCT CGCCCAGATCTGCTATCCGCTCACCGAGGGTGACACCCGGGCCGGGC TGACCGTGCTCACCGTGCTGCTCGGCGTCGCGTTCTCGCTGAGCCAC GCGCTGCTCACCCGGGGCCCCCGGGCGCTCACGGCGCTGCTGTCGA CCGCCACCCTGGGCGGGTTCGCGGTGGAGGCGATCGGGGTGGCCAC CGGTTTCCCGTTCGGTTCCTACGAGTACTCCGGGCGTCTCGGTCCGC GCCTGCTCGGCGTACCGCTGATCATCCCGCTGGCCTGGACCTGGATG GCCTGGCCGGCCTGGCTCGCCGCGCTGCGGGTGACCCGGCGGCGGC TCCCCCGGATCCTGGTCGCCGGGGCCGGCCTGGCCGCCTGGGACGT CTTCCTCGACCCGCAGATGGTCGCCGAGGACTACTGGCGGTGGCGGC ACCCGGTGCCCGCGCTGCCCGGCGTGCCCGGTGTGCCGCTCGGCAA CTACCTGGGCTGGCTCGGCTTCGCGCTGCTGCTGATGACCGCGCTGG CCGCCGTCGCCGCCGGCCGCGACCGGCCGCTGTCCGCCGACCG GCCGGCGCTCGCCCTGTGGATCTGGACGTACGCCTCGTCGGTGCTCG CCCACGCCGTCTTCCTGTCGCTGCCGGCGTCCGCGGCGTGGGGCGC GCTGATCATGGGCGCCGCGGTCCTCCCGCTGCTCGCCCGGCTGCGC GCACCCGCATGA |
| 46 | DNA | >ACSP50_ 1656 | ATGAGGCTTGTGGCGTGGCAGCCGGACGACCTGCTGCGGCGGCTCG ACGACGTGGTCGGGGTCTACGGCGAGGCGATGGGCTACCGCCAGGA GCTGCTGCAGACCCGCCGGGGATACATCGGGTCGCACGTGCGCCGG CCCGGGTTCCGGGCGGTGGCCACGCTGACCACCGAGGGCCGGCTGA TGGGCTTCGGATACGGCTACACCTCCGCCGCCGGCCAGTGGTGGCAC GACCAGGTCCGGTTCGCTCTCGGCGAGGACGACCGCCGGCAGTGGC TGACCGACTGCTTCGAGGTGGTCGAGCTGCACGTGCGCCCGGCCGCG CAGGGCCACGGGGTGGGCGCCCGGCAGCTGCGCGCGCTGCTGGCCA TGGCCAAAGGCCGCACCGTGCTGCTGTCCACTCCGGAGGCCGACGAG CAGGCGTCCCGCGCCTGGCGGCTGTACCGGCGGTACGGCTTCGCCG ACGTGCTGCGGCACTTCTACTTCCCGGGTGACGAGCGGGCCTTCGCG GTCCTCGGCCGCGAGCTGCCGCTGGCCGAGCGTCCGCTCGAGGACG CACCGGGCATCGCCGGCGCCTGA |
| 47 | DNA | >ACSP50_ 1657 | ATGACGCACGTCGCCCTGCACGTCTGGCGGGTGCCGCGCAGCGCCG TCGGCTCGGCCATGCTGCGCATGGCCTTCGCGCGGCGCCATCTGGCC GGTCTGCGGTTCGGCAAGTTCCTCGGCACCGGCACCGGCACCGGCTT CGGTCCCGGCGACACCGATCTCACCCGGTGGGCGGCGATCACGGTCA GTGATGCGCCGTACGTTTCCCCGTCTGGGAGCGGATCGCCGTCAAC GGCGCCCGGATCGATCTGGAGCCACTGATCAGCCGGGGCACCTGGG CCGGCCGTACCCCGTTCGAGCCCACCGGCCGCCGCCCGGACGGTCC GGTGCTCGCGCTCACCCGGGCCCGGCTGCGGCCGGCTCGCGCGCTG ACCTTCTGGCGGGCGGTCCCGGCGGTGGTGCGCGAGGTGCACCGGG CGCCCGGGCTGCTCGCCCGGTTCGGCGTCGGCGAGGCGCCGATCGG CTGGCAGGGCACCGTCACCGTGTGGCGGGACGCGGCGGATCTCGTC GCGTTCGCGTACCGTCAGCCGGAGCATCGCGCGGCGATCGCCCGGA CCCCGGCCGACCGCTGGTACGCCGAGGAGTTGTTCGCCCGGTTCGCG GTGCTCGGGATCAGCGGTGACCGGTCCGTGCTGGGCTGGACCGCCG ACGAAGGGGAACGGGCGGAAGCATGA |
| 48 | DNA | >ACSP50_ 1658 | ATGACACAGACCATCGTGATCACCGGGGCCAGCTCCGGGGTCGGGCT GGCCGCCGCCGAGCAGCTCGCCGCCCGCGGTGACGAGGTGGTGCTG GTCGGCCGCGACCCGGGCCGGCTCGACGCGGCCGTGCAGCGGGTCC GGGAGGCCGGCGGCGGCCGCGCGCCCGGCACTTCCGGGCCGACTT CGAACGGCTCGACGACGTGCGGGAGCTCGCCGCCGGGCTGCTGGCC GAGCTGCCCCGGATCGACGTGCTGGCCAACAACGCCGGCGGGATCAT CAAGCGGCCCCGGCAGACGGTGGACGGCCACGAGGCCACCATCCAG GGCAACCACCTGGCCCCGTTCCTGCTCACCCACCTGCTGCGGGAGCG GCTGACCGGGGCCGGGTGGTGAACACCGCCTCGGCGGCACACGTG CAGGGCCGGCCCGGCACCCGGTTCACCGACGACCCGGAAGTCGTACA GTCCGTGGCGCTCCTACGGGGCGAGCAAGGCGGCCAACATCCTGTTC GCCGCCGAGGCCGCCCGCCGCTGGCCGGACGTGTGCAGCGTCTCGT TCCACCCCGGTGTGGTGCGCACCAACTTCGGGGAGGGCCGGCTGATC CGGCTGTTCTACCGGTACGCGCCCGGCCTGGTCACCCCGGAGGCCG CCGGCGAGCTGCTGACCTGGCTGTGCACCACCCCGGCCGGGAGCT GGAGAACGGCGCCTACTACGTCAAGCGTCAGGTGACCCGGCCGGCC GCGCACGCCCGCGACCCGCGGCTGGCCGCCGAGTTGTGGGACGCCA GCCTGACCGCGACCGGCCTCGCCGGATGA |
| 49 | DNA | >crtE (ACSP50_ 3873) | GTGATCGACGACTTCCTCAGCGCGCAACGCGACGTGCTGGCCGAGGT CAGCGACGACTGCGCGCCGCTGGAACGCTACGTGGCCGACCTGATGG GCGGCGGCAAACGACTCCGGCCGGCGTTCTGCTACTGGGCGTGGCG GGCGGCCGGCGCCCCCGACGGCCCGGGCATCGTGGCGGCCGCGAC ATCCCTGGAGTTCCTGCAGGCCGCCGCGCTGATCCACGACGACATCA TGGACGATTCGGACACCCGTCGCGGCGCCCCGGCGGTGCACCGCAG ACTGGCGGCCCTGCACTCCGGCGGCCGCTGGGCCGGGGACGCCGAC |

| SEQ ID No. | Type | Name | Sequence |
|---|---|---|---|
| | | | CACTTCGGGCTGTCCGCCGCCGTGCTCGCCGGCGACCTGTGCCTGAC<br>CTGGAGCGACGCGTTGTATTCGGGCAGCGGCCTGCACCCGTCCGCGC<br>TGGCCCGGGGCCGGCCGGTCTTCGACCGGATGCGCACCCAGCTGAT<br>GGGCGGCCAGTATCTGGACCTGCTGGACCAGGCGCGGCCGTCCCGG<br>GGCGGCGTCGACCGGGCGCGCGGGTGGTGCACTTCAAGAGCGCCA<br>AGTACACCGTCGAACATCCGCTGCTGCTCGGCGCCCGGCTCGCCGGC<br>GCGGACGACGATCTGCTCGCCCGGTTGTCCGCGTTCGGTCTGCCGCT<br>GGGCGAGGCGTTCCAGCTGCGCGACGACCTGCTCGGGGTCTTCGGC<br>GACGCGGCGCAGACCGGCAAACCCACCGGCGACGACCTGCGCGAGG<br>GAAAGCGCACCACGCTGGTCATCCTGGCCGCGGACCGCGCCACCGCA<br>CCCCAGCAGGCCGCCCTCACCGCGCTGCTCGGCGATCGCGGCCTGA<br>CCGGGGCCGGCGTCGACACCCTCCGGCAGATCATCGTGGACACCGGT<br>GCCCGGGCCGAGGTCGAGCGGATGATCGAGCAACTGCTGGCGACGA<br>GTCTCGGCGTGCTCAGCGGCACGCCCGTCGACGAGGCGGCCCGCTC<br>GGTGCTGCTCGCCCTCGCCGAGGCGGCGACCGCCCGCAGCTCCTGA |
| 50 | DNA | >ACSP50_<br>1950 | ATGGTGAGCACAGTGATCGCCTCGGGGCCCACCGGCCTGGGCACCTC<br>CGCGGCCCGTCTCTTCGGTCGGGTGGACCGGGACGAGCCGGAGCTC<br>TTCTGCCCGGCGCCGCTGCGCGACGACCGGGCGCTGGGGGAGCGGG<br>TCAACGACGCCGTGGTCCAGTGGGCCGAGAAGGCCGGCATCTACCCC<br>GGCCGGCTGGACAAGCTGCGCGGGGCGAACTTCGGCCGCTTCATGAT<br>GCTCGCCCACCCGGCCACCAGCGATCCCGACCGGCTGCTCGCCGCG<br>ACGAAGTGTCTGGTCGCCGAGTGGGCGGCGGACGACTACTACGTCGA<br>CGAGGTGTCCCTGGGCGCGGATCCGATGGTGGTCGGCTCGCGGCTG<br>GCCAACCTCTACTCGGTGGTCGACCCGGCCTCGCTGACCCCGCGCTA<br>TCAGGCCGACTTCGAGAAGCATCACCGCCTGCAGCCGATCTCGGTGG<br>CGTTCCGCACCGCGATGGAACACCTGGCCGAGTACGCCTCGGTCACC<br>CAACTGGCCCGGTTCCAGCACCAGATGGCCGATCCTGTTCGTCGCCTG<br>GTCGCAGGAGGCCGACTGGCACGCCAACCGGCGCACCCCGCCGGTC<br>TGGGAGTATCTGGTGCAGCGGCACCTGAACAGCTATCTGCCGCCGAT<br>GATCCTGGTCGACGTGCTGGCCGGGTACGAGCTGTCGCCGGCCGAGT<br>TCTTCGATCCGGGTCCGCGCGGCGTTCACCACCGCAGGCAACGCC<br>GCCGTGCTGGTCAACGACCTCTACTCGGGCAGGAACGAGTCCGAGAC<br>CGATCACAACCTGCCGACCGTGCTGGTGTCCGGGGAGCGGCTCACGC<br>CGCGGGCCGCGGTCCGGCGCACCGTGGAGATCCACAACGAGTTGAT<br>GCACACCTTCGTGACCTCGGCCGCGTCGTTGAGCGCGTCCGGCTCGC<br>CGCAGCTGCGCCGGTTTCTCGCGGACACCTGGGCCTGGCTGGGCGG<br>AAGTCGCGAGTGGCACGCCACGAGCGGCCGCTACCACTCATCCAACT<br>GA |
| 51 | DNA | >ACSP50_<br>5522 | ATGACGACCACCGCACCGACTCCCGCCCACCTCGCCGGCAACTTCGC<br>GCCCGTCACCGGGGAGACCACCACGCTCGACCTGCCGGTCACCGGC<br>GCCGTCCCGGCCGAACTGACCGGGTGGTATCTGCGCAACGGGCCCAA<br>CCCCCACCACGGGACCTCGGCGCACTGGTTTCTCGGCGACGGCATGG<br>TGCACGCGTCCGCCTCGATCACGGCCGGGCCACCTGGTACCGCAAC<br>CGCTGGGTGCGGACCCGGGTGCTGACCGACGACGCCCGCGCCTACG<br>GCCCGGACGGCACCCGCGACCTCACCGCCGGCCCGGCGAACACCAA<br>CGTCGTGCGCCACGGCGGACGACTGCTGGCGCTGGTCGAGTCCGCG<br>CTTCCGTACGAGATCACCACCGACCTGGAGACCGTCGGCCCCTACGA<br>CTTCGGCGGCCGCCTGCACACCCCGATGACCGCCCACCCCAAGGTCT<br>GTCCCACCACCGGGGAGATGCACTTCTTCGGCTACGGGGACTCGAG<br>CCGCCCTACCTCACCTACCACCGCGCCGGCGCGGACGGCCGGCTGT<br>CGCTCAGCCGCCCGATCGACGTCCCCGCGCACACGATGATGCACGAC<br>TTCAGCCTCACCGCGGCCCACGTGATCTTCATGGACCTGCCGGTGCT<br>GTTCAGCCTGGACGGGGCGCGGACCGGCGGCATGCCGTACCGGTGG<br>GACGACACCTACCAGGCGCGCCTGGGCGTGCTGCGGCGCGACGCCC<br>CGCAGGGGGAGGTCCGCTGGTACACCATCGATCCCGGATACGTCTTC<br>CACACCCTGAACGCCCACGACGACGGCGACCGGATCGTCATGCACGT<br>CGTCCGCCACGAGCACGCGTACCGCCGGGGCAGCCCGCCGCCGCA<br>CCGGACCTCTGGCGCTGGACCATCGACCAGCGCACCGGCCGGGTCG<br>CCGAGGAACGGCTGGACGACGAAGCGGTCGAGTTCCCCCGCATCGAC<br>GATCGGCGCACCGGGCAGCCGGCCCGTTACGGCTTCGCCGTGACCG<br>ACAACGTTCCCGCCGGCTCGCCGACGTCAGCGCCGTCATCCGCTAC<br>GACCTGCACACCGGCTCGACCACCCGGCACCGCCTGCCGACCGGGC<br>AGGTACCCGGGGAGGCGGTCTTCGTGCCGGCCGGCGGCGCCCCCGC<br>CGGATCGGCCGACGGCTGGCTGCTGACGTTCGCCTACGACCCGGGG<br>CGCGACGCCAGCGATCTGATCATCATCGACGCCACCGACCTCGCCGC<br>CCCGCCGCTGGCCCGGATCCACCTGCCGCACCGGGTGCCGTTCGGC<br>TTCCACGGCAACTGGCTGCCCGACCACGACCGCGCAGAATAG |
| 52 | PRT | >Dxs<br>(ACSP50_<br>7096) | MSDSPSTPAGLLASVTGPGALKRLSAEQLTLLAAEIRDFLVAKVSKTGGHL<br>GPNLGVVEMTLAMHRVFDSPRDKILFDTGHQAYVHKIVTGRQDGFDLLRQ<br>RGGLTGYPSQAESEHDLIENSHASTALSYADGLAKAFALRGEDRHWAVV<br>GDGALTGGMCWEALNNIAATKNRLVIWNDNGRSYAPTIGGLADHLSTLRL<br>NPGYEKVLDLVKDALGSTPLVGKPVFEVLHAVKRGIKDAVSPQPMFEDLG |

| SEQ ID No. | Type | Name | Sequence |
|---|---|---|---|
| | | | LKYIGPVDGHDQQAMESALRRAKGFNAPVIVHAVTRKGYGYRPAEQDEA<br>DCLHGPGAFDPQTGALTAKPSLKWTKVFAEELVKIADERPDVVGITAAMA<br>EPTGIAALAKKYPDRAYDVGIAEQHAATSAAGLAMGGLHPVVAVYATFLNR<br>AFDQVLLDVAMHRLPVTFVLDRAGITGPDGPSHYGIWDMSVFGAVPGLRI<br>AAPRDAATLREELREAVAVDDGPTIVRFPTGAVAADTPAVRRVGQVDVLR<br>EAEKKDILLVAVGSFVGLGLDAAERLAEQGYGVTVVDPRWVRPVPIELTGL<br>AAQHRLWTLEDGIRAGGVGDAVAAALRDAGVHVPLRDFGVPAGFHPHG<br>TRAEILASLGLTAQDVARDVTGWVSGLDAGTSVAAPAI |
| 53 | PRT | >lspG<br>(ACSP50_<br>7248) | MTAISLGMPAVPPPPLAPRRQSRQINVGGVLVGGGAPVSVQSMTTTLTSD<br>VNATLQQIAELTAAGCQIVRVAVPSQDDVEALPAIAKKSQIPVIADIHFQPKY<br>VFAAIDAGCAAVRVNPGNIRQFDDKVKEIARAASDAGVPIRIGVNAGSLDK<br>RLLEKYGKATAEALVESALWECSLFEEHGFRDIKISVKHNDPVVMIRAYRQ<br>LAEQCDYPLHLGVTEAGPAFQGTIKSAVAFGALLAEGIGDTIRVSLSAPPVE<br>EIKVGQQILESLGLRERGLEIVSCPSCGRAQVDVYTLAEQVTAALDGFPVP<br>LRVAVMGCVVNGPEAREADLGVASGNGKGQIFVKGKVIKTVPEAVIVET<br>LVEEALRLADEMGAELPDELRELLPGPTVTVH |
| 54 | PRT | >Dxr<br>(ACSP50_<br>7250) | MRELVLLGSTGSIGTQAIDIVRRNPELFRVVAIGAGGGNVALLAAQALELGV<br>EVVGVARASVVQDLQLAFYAEAQKRGWSSGDFKLPKIVAGPDAMTELAR<br>WPCDVVLNGVVGSLGLAPTLAALESGRILALANKESLVAGGPLVRRIAKDG<br>QIVPVDSEHSALAQCLRGGRAAEVRRLVLTASGGAFRGRRRAELTNVTPE<br>EALKHPTWDMGPWTINSATMVNKALEVIEAHELFGVPYDDIAVMHPQS<br>VLHSLVEFTDGSTLAQASPPDMRLPIALALAWPDRVPGAAAAVDWTLAHN<br>WELRPLDDEAFPAVELAKAAGRYGRCRPAIFNAANEECVAAFAAGRLPFL<br>GIVDTLERVLAAAPDFAEPSTVDDVLAAESWARAQAQRTIATVAEGA |
| 55 | PRT | >lspH<br>(ACSP50_<br>7707) | MLLAKPRGYCAGVDRAVQTVEEALKLYGAPVYVRKQIVHNKHVVSTLEAR<br>GAIFVEENYEVPEGATWFSAHGVAPEVHDQARERRLKAIDATCPLVTKVH<br>HEAKRFAAEDYDILLIGHEGHEEVIGTSGEAPAHIQLVDGPDDVANWVRD<br>PAKVVWLSQTTLSVDETMETVARLKTRLPLLQSPPSDDICYATSNRQHVIK<br>EIAPECDVVIVVGSTNSSNSVRLVEVALGAGARAGHLVDYAAEIQDEWLAG<br>ATTVGVSSGASVPDELVMEVLAHLAERGFGEVTEFTTAEERLTFSLPQEL<br>RKDMKAAEEAARAAAAG |
| 56 | PRT | >lspE<br>(ACSP50_<br>7802) | MTEAWGPDDDEPRPYSGPVKVRVPAKINLHLAVGPLRPDGYHELNTVYH<br>AISLFDEITARHGDTLTLTMEGEGTGDLALDETNLIIRAARALAARARVPAY<br>ARLHLRKSIPLAGGLAGGSADAAATLIACDLLWGLGMSRDELAEVGAQLG<br>SDIPFLLHGGTALGTGHGEAVSPILARPTTWHWTVAIADGGLATPAVYREL<br>DTLRAGTWPPTPLGSADTLMAALRQRNPEILGAALGNDLQPAALALRPQL<br>ADVLKAGTEAGALAGLVSGSGPTCVFLAADATHAQEIADSLTEAGVCRAA<br>VTARGPQPGARVI |
| 57 | PRT | >lspF<br>(ACSP50_<br>8046) | MIIPRVGIGTDVHAFDADRACWVAGLEWPGEPGLAGHSDADVVAHAACD<br>ALLSAAGLGDLGGNFGTSRPEWAGAAGVTLLAETARLVRAAGFAIGNVSV<br>QVIGNRPKIGKRRAEAEKVLSAAVGAPVTVSGTTSDGLGLTGRGEGLAGV<br>AVAMVYTENALPA |
| 58 | PRT | >lspD<br>(ACSP50_<br>8047) | MIADRDVTAQLNARGDVAVVVPAAGAGLRLGPGGPKALRLLDGEPLLVHA<br>VRRLAAAAPVRMIVVAAPPAEVDAVSALLAPVAPVTWPGGAERQESVAA<br>ALAVVPPDVPIVLVHDAARCLTPPSVTERVAAAVRDGADAVIPVLPVVDTIK<br>EVAADATVLGTVDRSVLRAVQTPQGFRASVLRAAHRAAADSHTDDAGAV<br>EKLGIPVLCVPGSDLALKITRPIDLALATHLLALPDPDAPTA |
| 59 | PRT | >ldi<br>(ACSP50_<br>0146) | MSSIGHLNREDHLVELVNEEGQPLGSATVSDAHLSPGALHRAFSVFLTDD<br>EGRVLLQQRAAAKTRFPLRWGNTCCGHPAPGEPVTVAAARRLTEELAVR<br>DVTLTEIGVYTYRATDPVTGRVEHEYDHVLIGALPDGVVPHPDPAEIATLR<br>WASLPGLRTGLTESPELYAPWLPGVFEILTERSGVLSTERSGGR |
| 60 | PRT | >CrtE<br>ldsA<br>(ACSP50_<br>0148) | MANDTLEGNRLAAIPRQSVSHTGLVGAVEGTLADFLASQIASLDAVDPSLG<br>GFGRTARDLVMAGGKRLRPTFAYWGWRGVAGPAADAETLLPALGALELM<br>HTFALVHDDVMDDSSTRRGRPTAHRIFAAQHGGRFGTSAAILVGDLCLVW<br>ADQLLARTPVPAATLLAVRAHYDRMRIEAVAGQYLDVLGETDPASWSVER<br>ALLVARHKTASYTVQRPLDFGLALAGVEDVEVAEAYRTYGIAVGEAFQLRD<br>DLLGVYGDPAVTGKPVSDDLRTGKPTALLMLARRMATPGQLAELESAEIE<br>RKAQWAETGAPARVEEMIRARVTEGLTALASAPIDAEARATLIELATVATQ<br>RPA |
| 61 | PRT | >CrtB<br>(ACSP50_<br>0149) | METDLAAAYERCRELHREHGRTYYLATRLLPAWKRRHVALYGFTRFAD<br>EIVDRTEAQPPAERAAELATWSAGFLAGLRGEPVDDPLLPAVLHTIAVFGL<br>DLEDFAKFLRSMEMDLTVTGYRTYDDLLDYMEGSAAVIGTMMLPILGSTD<br>PAAAREPARQLGFAFQLTNFIRDVAEDLARDRIYLPEEHLAEFGVTRADLA<br>AGVATPAIRALIRAEVDRAREHYAAAAPGIPLLERTSQACMRTAFQLYGGIL<br>DEIEAADYDVFARRVTVPNRRRAAVAVRSLLTRPGTPVELAA |

| SEQ ID No. | Type | Name | Sequence |
|---|---|---|---|
| 62 | PRT | >ACSP50_0150 | MGARVALFTRDLRIHDNPLLSGPDPVVPLFVLDPRLSGLSANRSRFLHQSL ADLRNSLRERGADLVIREGDPVAETIAVASEVDASTITVAADVTGYAQRRE RRLRDERFRVKTVPSVTVLPPGTVRPGGGGESYRVFTPYFKAWEKAGWR APSATPGKVAMPAGIAPGRLPEMPAGDSPDAVAGGETEGRRRLQAWQK EMARYAEDHDDMAADNTSRLSAYLRFGCLSPLELALAAKADDSPGAQAYL RQLCWRDFYYQVTATFPEISTRPLREKADQNWRYDDDALRHWQDGLTG VPIVDAGMRQLRAEGWMHNRARLITAAFLTKHLGIDWRPGLQWFFRWLL DGDVPNNSGNWQWTAGTGNDTRPYRRFNPIRQAQRFDAQGVYVRRYVP ELKDIDGVTVHQPWRLPESVRRGLDYPGPLESHRDEAVWLRD |
| 63 | PRT | >ACSP50_0151 | MSEARQVDVVVVGLGVGGEEVAGRLAAAGLSVIGVEHRLVGGECPYWG CIPTKIMVRAGNALAEARRIPGLAGTSTVRADWAPVAKRIRDEATDDWND KVAVERFTGKGGTFVRGTAELTGPGQVRVGDQEFAASRGVVIATGTAAV VPPIEGLSGTPFWTNREAVEAAALPASMLVLGGGAIGCELAQAYARFGVQ VTVIEGSPRVLAMEEPESSEVAAAALTADGVRIVTGVRAQKVAHDDGFHV TLSDGSVLAGEKLLVATGRAARLGGLGLDRVGLDPSARFLATDDRLRAGE GIWAVGDVTGNGAFTHMAMYEADIAVRDILGQGGPGADYRARPRVTFLD PEIGAVGMTEQQARDAGLEVRGYVPLNQTSRGFIHGPGNEGFLKLVAD GERGVLVGGTTAGQSGGEMIGAVAVAVHAEVPVSTLLSQIWAYPTFHRGL GQALQSLA |
| 64 | PRT | >ACSP50_1631 | MSEPVITEPAAWINLPDLSERLDVSISKVHQMIRDGDLLAVRRDGIRVVPAE LVANATVLKHLPGVLNVLRDAGYNDEEAFRWLYAEDAEVGGSAAIALGGQ QAREIKRRAQALGF |
| 65 | PRT | >ACSP50_1632 | MRHLSYVAVLAGCLAGALWLEPILRVNVLRRWRRLLLAVLPMAVVFTLWD LAAIAAGHWHFDPAQITGVYLGGGLPLDEVLFFLVVPVCAILGFEAVRAVLR RPAGDE |
| 66 | PRT | >ACSP50_1633 | MTYTTAAVLGVLAALTLDVLILRTRLVGRLVFWATYPIIFVFQLISNGILTGRD IVMYDPAAILGPRLVHAPVEDLLFGFALVLGTLSLWVALGRRGIQRTPRAG SRRTDE |
| 67 | PRT | >CrtEfps2 (ACSP50_1634) | MTNSPLDEAGLRSRVDKALTVFLAGQRDRLLAIDPALAEMSATVSEFVLG GGKRLRPAFAYWGFRGAGGADSDAVVAAVAALELVQASALIHDDLMDRS DTRRGVPSVHRRFEKLHAGEGWRGSAAGFGDCAAVLLGDLALVWSDELL HTSGMAVADVQRARPIFDGMRTEVTVGQYLDVLTQATGDTSLERAGKVA VYKAAKYTVERPLLLGAALAGAAPGVHAAYSAFGLPLGEAFQLRDDVLGV FGDPERTGKPAGDDLREGKRTYLVAAAFGALDAAGRAELDAALGDPGLD EAGVARLRTVIRDSGALAATEARIDELMTASIGALDAAPIDQDAREVLRRLA DAATRRSV |
| 68 | PRT | >ACSP50_1635 | MSLGLPSRLPGTPSIGDLVRGAAPTFSFEFFPPKTPDGERLLWQAIRELES LRPSFVSITYGAGGTTRETTVAVTERVATETTLLPLAHLTAVDHSVADLRN VIGRLAGAGIRNVLALRGDPPGDPMGEWVRHPDGVGYADELVRLIRESGD FSVGVAAFPHKHPRSAGVKDDTRNFVRKCRAGADYAITQMFFDADEYLRL RDRVVAAGCHTPIVAGVMPVTRMATIARSTQLSGAPFPPPALLRDFERVAG DDAAVRELGIETCAAMCARLLREGVPGIHFITMNRSTATREVWQRLAPAE VAASA |
| 69 | PRT | >ACSP50_1650 | MQLQQLRYFLAWETRHFTQAADILGVSQPTLSKQIHTLEMSLGAPLFERM RGAVTLTVAGETLLPMAQRIVADADAARDAVQDIVGLRRGEVRLGATPSL CSSLVPAVLRTFRADHPGVKLHISEGSSHDLTAGLLAHTLDLALIVQPEHG VDPALVAIELLRESLVVASVAAGPPPTVGRQLELSELRHTPMVMFREGYDI REVTLHACERAGFAPKFAVEGGEMDAVLAFVEAGLGVALVPSMVLANRPL LRATPLAPPGMRRTIALAQRRAAVLPHAAAALREVVLDHIGSGRLPFGVRA LERPST |
| 70 | PRT | >ACSP50_1651 | MGEFHDPRLVEVYDAECPWGWDDDFFMAVLAERSAHRVADLGCGTGRL AIAMAAAGHEVIAIDPAPAALAAARRKPGGTRVRWLQGSAERLAPRSLDA AFMTGHVAQSFVDDEEWDTVLRGLRRALVPEGRLVFDSRDPDDRPWQQ WNPQDSWRTVVLDDGRVVEAWSEAEQVGLNTVRVTGRYRFADGGELAN SATLRFRTEPELRDSLREAGFRVERIYGGWGREPVGLSGDGEFIVIAVATP RLMS |
| 71 | PRT | >ACSP50_1652 | MPENEWPDDPRPPDQGEWSQPHHEPPPGRGRALLAAAVVVLVLLAAGGI AWRLMSSRGATPVAQPTAPAPTPTAQTAPPCPQPRLRVAAAPEIAPVIQQ AAAALSQPGQRCSEVLVQAAEPGAALTGKPDVWVPSSSVWLALAKSRGD VYTTQGASLAWSPLVIAGPESIASLFAPNGVTSWSGLVQGTIQKRVPAVR MPDPTLTTTGLLSVYAVGQATVKANPDAGIAQLQALTLRSRLENAAADPAE LFAQMGKQTDAATAIYQVGVFPTTEQQLLTYQKSQHDVRLSGSAPADGQI DADYPYAVRKGAPADLVESLREAITPDALTTAGFRATATKNALRLPAPAVL AGAARQWSAYKSVAFQVLLLIDASGSMNEKITDRAGRSVTKAALLRESGT SAAQLFGDDTSLGLWFFGTPTADSPAHTEEVPFGPVIATVDGKSRRDLLA AKIGEYRPVANAGTPLYQSVLDGVAEMRGRAKPDTATWVVLTDGSDGG |

| SEQ ID No. | Type | Name | Sequence |
|---|---|---|---|
| | | | TKYRMSNADFLKKLTAGADPAKPVPVIAVGYGPAANATALQAMAKATGGQ AVTVKNPADLAAGIAQAFLAAHTH |
| 72 | PRT | >CrtD (ACSP50_1653) | MSDIVWGAGVGGLAAAIRLAEAGHRVSIHERSGWGGKLAAYERDGYRF DTGPSLLTLPDVFTGLGLDLRPEPLDPVVRHFFPDGTVLDSSSDHETFLAR ITDALGGAAARDWDRFWRRAERIWHASWESVLRRPVTAASLARLSWRLG DLAAIAPGRSLRSLGRRYLRDPRLRMLLDRYATYSGADPRRAPAALAAIPY AELAFGGWYLPGGLVTLAEALLARCEKLGVRVHLHSPVASIATTGARVSG VRLGDGTRLAADVVVSNVDAVTLYRDLLPSPKPLARLADRSLAGFVLLLAV RGETPRLAHHNVFFPRDYDAEFDAVFGGPGRRARPAGDPTVFVTRAADP AVRPAGDEAWFVLVNAAPHGTSWSTVDWLRAGLADAYRDRVLEVLAGR GLDVRDRLIFAETRTPADLAASAAAPGGAIYGTAGGLVRPANRAPVDGLFL VGGSTHPGGGLPMVTLSAEIVAGMIGSN |
| 73 | PRT | >CruC (ACSP50_1654) | MIVAWLILPPLLLITAHTAVNALLLRRPRRAATSTERVAVLLPLRDEATRVTP CLRALLAQRGVADLTVHVLDDGSTDGTADVVRAVAGDRVRLHTGTPPPP GWLGKPAACQRLADLAGDVDVLVFVDADWLAPDAVAGAVDLLRRAGAD LLSPYPKIVGAGRLVQPLLQWSWLSFLPLRAMERSARPSLAAAGGQWLVL DRAGYRRAGGHAAVRGEILEDIALARAVKRAGGRIALADGSGLATCRMYE SWDELADGYAKSLWASLGSAAGATAVTLLLILLYVVPPLLAPFAPLPAVLG YLLGVTGRMIAARATGGRVLPGTLAHPVSIVLFGYLIARSFRLRRAGRLAW RGRPVP |
| 74 | PRT | >CruF (ACSP50_1655) | MSPRHLPWGLLGALVLAQICYPLTEGDTRAGLTVLTVLLGVAFSLSHALLT RGPRALTALLSTATLGGFAVEAIGVATGFPFGSYEYSGRLGPRLLGVPLIIP LAWTWMAWPAWLAALRVTRRRLPRILVAGAGLAAWDVFLDPQMVAEDY WRWRHPVPALPGVPGVPLGNYLGWLGFALLLMTALAAVAGRAADRPLSA DRPALALWIWTYASSVLAHAVFLSLPASAAWGALIMGAAVLPLLARLRAPA |
| 75 | PRT | >ACSP50_1656 | MRLVAWQPDDLLRRLDDVVGVYGEAMGYRQELLQTRRGYIGSHVRRPG FRAVATLTTEGRLMGFGYGYTSAAGQWWHDQVRFALGEDDRRQWLTDC FEVVELHVRPAAQGHGVGARQLRALLAMAKGRTVLLSTPEADEQASRAW RLYRRYGFADVLRHFYFPGDERAFAVLGRELPLAERPLEDAPGIAGA |
| 76 | PRT | >ACSP50_1657 | MTHVALHVWRVPRSAVGSAMLRMAFARRHLAGLRFGKFLGTGTGTGFG PGDTDLTRWAAITVSDAPVRFPVWERIAVNGARIDLEPLISRGTWAGRTPF EPTGRRPDGPVLALTRARLRPARALTFWRAVPAVVREVHRAPGLLARFGV GEAPIGWQGTVTVWRDAADLVAFAYRQPEHRAAIARTPADRWYAEELFA RFAVLGISGDRSVLGWTADEGERAEA |
| 77 | PRT | >ACSP50_1658 | MTQTIVITGASSGVGLAAAEQLAARGDEVVLVGRDPGRLDAAVQRVREAG GGRAPRHFRADFERLDDVRELAAGLLAELPRIDVLANNAGGIIKRPRQTVD GHEATIQGNHLAPFLLTHLLRERLTGGRWNTASAAHVQGRPGTRFTDDP KSYSPWRSYGASKAANILFAAEAARRWPDVCSVSFHPGVVRTNFGEGRLI RLFYRYAPGLVTPEAAGELLTWLCTTPAGELENGAYYVKRQVTRPAAHAR DPRLAAELWDASLTATGLAG |
| 78 | PRT | >CrtE (ACSP50_3873) | MIDDFLSAQRDVLAEVSDDCAPLERYVADLMGGGKRLRPAFCYWAWRAA GAPDGPIVAAATSLEFLQAAALIHDDIMDDSDTRRGAPAVHRRLAALHSG GRWAGDADHFGLSAAVLAGDLCLTWSDALYSGSGLHPSALARGRPVFDR MRTQLMGGQYLDLLDQARPSRGGVDRARRVVHFKSAKYTVEHPLLLGAR LAGADDDLLARLSAFGLPLGEAFQLRDDLLGVFGDAAQTGKPTGDDLREG KRTTLVILAADRATAPQQAALTALLGDRGLTGAGVDTLRQIIVDTGARAEVE RMIEQLLATSLGVLSGTPVDEAARSVLLALAEAATARSS |
| 79 | PRT | >ACSP50_1950 | MVSTVIASGPTGLGTSAARLFGRVDRDEPELFCPAPLRDDRALGERVNDA WQWAEKAGIYPGRLDKLRGANFGRFMMLAHPATSDPDRLLAATKCLVAE WAADDYYVDEVSLGADPMVVGSRLANLYSVVDPASLTPRYQADFEKHHR LQPISVAFRTAMEHLAEYASVTQLARFQHQMAILFVAWSQEADWHANRRT PPVWEYLVQRHLNSYLPPMILVDVLAGYELSPAEFFDPRVRAAFTTAGNA AVLVNDLYSGRNESETDHNLPTVLVSGERLTPRAAVRRTVEIHNELMHTFV TSAASLSASGSPQLRRFLADTWAWLGGSREWHATSGRYHSSN |
| 80 | PRT | >ACSP50_5522 | MTTTAPTPAHLAGNFAPVTGETTTLDLPVTGAVPAELTGWYLRNGPNPHH GTSAHWFLGDGMVHGVRLDHGRATWYRNRWVRTRVLTDDARAYGPDG TRDLTAGPANTNVVRHGGRLLALVESALPYEITTDLETVGPYDFGGRLHTP MTAHPKVCPTTGEMHFFGYGGLEPPYLTYHRAGADGRLSLSRPIDVWRT MMHDFSLTAAHVIFMDLPVLFSLDGARTGGMPYRWDDTYQARLGVLRRD APQGEVRWYTIDPGYVFHTLNAHDDGDRIVMHVVRHEHAYRPGQPAAAP DLWRWTIDQRTGRVAEERLDDEAVEFPRIDDRRTGQPARYGFAVTDNVP RRLADVSAVIRYDLHTGSTTRHRLPTGQVPGEAVFVPAGGAPAGSADGW LLTFAYDPGRDASDLIIIDATDLAAPPLARIHLPHRVPFGFHGNWLPDHDRA E |

| SEQ ID No. | Type | Name | Sequence |
|---|---|---|---|
| 81 | DNA | >tipA promoter | atccctagaacgtccgggcttgcacctcacgtcacgtgaggaggcagcgtggacggcgtggtaccaag cttattggcactagtcgagcaacggaggtattccg |
| 82 | DNA | >gapDH promoter | gtactggccgatgctgggagaagcgcgctgctgtacggcgcgcaccgggtgcggagcccctcggcga gcggtgtgaaacttctgtgaatggccgttcggttgcttttttttatacggctgccagataaggcttgcagcat ctggccggctaccgctatgatcggggcgttcctgcaattcttagtgcgagtatctgaaaggggatacgc |
| 83 | DNA | >lacZ? promoter and gene | taatgtgagttagctcactcattaggcaccccaggctttacactttatgcttccggctcgtatgttgtgtgga attgtgagcggataacaatttcacacaggaaacagctatgacatgattacgaattcgatatcgcgcggcc gcggatcctctagagtcgacctgcagcccaagcttggcactggccgtcgttttacaacgtcgtgactggg aaaaccctggcgttacccaacttaatcgccttgcagcacatccccctttcgccagctggcgtaatagcga agaggcccgcaccgatcgcccttcccaacagttgcgcagcctgaatggcgaatggcgcctgatgcggt attttctccttacgcatctgtgcggtatttcacaccgcataaattccccaatgtcaagcacttccggaatcggg agcgcggccgatgcaaagtgccgataacaataa |
| 84 | DNA | >T4 terminator | aagctttatgcttgtaaaccgttttgtgaaaaaattttaaaataaaaaggggacctctagggtccccaatt aattagtaatataatctattaaaggtcattcaaaaggtcatcca |
| 85 | DNA | >PhiC 31 integrase gene | gtggacacgtacgcgggtgcttacgaccgtcagtcgcgcgagcgcgagaattcgagcgcagcaagcc cagcgacacagcgtagcgccaacgaagacaaggcggccgaccttcagcgcgaagtcgagcgcgac ggggccggttcaggttcgtcgggcatttcagcgaagcgccgggcacgtcggcgttcgggacggcgga gcgcccggagttcgaacgcatcctgaacgaatgccgcgccgggcggctcaacatgatcattgtctatga cgtgtcgcgcttctcgcgcctgaaggtcatgacgcgcattccgattgtctcggaattgctcgccctgggcgt gacgattgtttccactcaggaaggcgtcttccggcagggaaacgtcatgaccgattcacctgattatgc ggctcgacgcgtcgcacaaagaatctcgctgaagtcggcgaagattctcgacacgaagaaccttcag cgcgaattgggcgggtacgtcggcgggaaggcgccttacggcttcgagcttgtttcggagacgaagga gatcacgcgcaacgccgaatggtcaatgtcgtcatcaacaagcttgcgcactcgaccactcccttac cggacccttcgagttcgagcccgacgtaatccggtggtggtggcgtgagatcaagacgcacaaacacc ttcccttcaagccgggcagtcaagccgccattcaccccggcagcatcacgggcgctttgtaagcgcatgg acgctgacgccgtgccgaccccggggcgagacgattcggaagaagaaccgcttcaagccgcctgggacc cggcaaccgttatgcgaatcctcgggacccgcgtattgcgggcttcgccgctgaggtgatctacaagaa gaagccggacggcacgccgaccacgaagattgagggttaccgcattcagcgcgacccgatcacgctc cggccggtcgagcttgattgcggaccgatcatcgagcccgctgagtggtatgagcttcaggcgtggttgg acggcaggggcgcggcaagggcgttccccggggcaagccattctgtccgcgcatggacaagctgta ctgcgagtgtggcgccgtcatgacttcgaagcgcggggaagaatcgatcaaggactcttaccgctgccg tcgccggaaggtggtcgacccgtccgcacctgggcagcacgaaggcacgtgcaacgtcagcatggcg gcactcgacaagttcgttgcggaacgcatcttcaacaagatcaggcacgccgaaggcgacgaagaga cgttggcgcttctgtgggaagcgcccgacgcttcggcaagctcactgaggcgcctgagaagagcggc gaacgggcgaaccttgttgcggagcgcgccgacgcccttgaaacgcccttgaagagctgtacgaagacc gcgcggcaggcgcgtacgacggacccgttggcaggaagcacttccggaagcaacaggcagcgctg acgctccggcagcaaggggcggaagagcggcttgccgaacttgaagccgccgaagccccgaagctt cccctttgaccaatggttccccgaagacgccgctgacccgaccggccctaagtcgtggtggggcg cgcgtcagtagacgacaagcgcgtgttcgtcgggctcttcgtagacaagatcgttgtcacgaagtcgact acgggcaggggcagggaacgcccatcgagaagcgcgcttcgatcacgtgggcgaagccgccgac cgacgacgacgaagacgacgcccaggacggcacggaagacgtagcggcgtag |
| 86 | DNA | >PhiC 31 attachment site | cccaggtcagaagcggttttcgggagtagtgccccaactggggtaacctttgagttctctcagttgggggc gtagggtcgccgacatgacacaagggggtt |
| 87 | DNA | >incP | ccggccagcctcgcagagcaggattcccgttgagcaccgccaggtgcgaataagggacagtgaaga aggaacacccgctcgcgggtgggcctacttcacctatcctgccc |
| 88 | DNA | >traJ | atggctgatgaaaccaagccaaccaggaagggcagcccacctatcaaggtgtactgcctccagacg aacgaagagcgattgaggaaaaggcggcggcggccggcatgagcctgtcggcctacctgctggccgt cggcagggctacaaaatcacgggcgtcgtggactatgagcacgtccgcgagctggcccgcatcaat ggcgacctgggccgcctgggcggcctgctgaaactctggctcaccgacgacccgcgcacggcgcggt tcggtgatgccacgatcctcgccctgctggcgaagatcgaagagaagcaggacgagcttggcaaggtc atgatgggcgtggtccgcccgagggcagagccatga |
| 89 | DNA | >ColE 1/pMB 1/pBR 322/ pUC ori | ttgagatcctttttttctgcgcgtaatctgctgcttgcaaacaaaaaaaccaccgctaccagcggtggtttgtt tgccgcagttaccaactttcttccgaaggtaactggcttcagcagagcgcagataccaaatact gttcttctagtgtagccgtagttaggccaccacttcaagaactctgtagcaccgcctacatacctcgctctgc taatcctgttaccagtggctgctgccagtggcgataagtcgtgtcttaccgggttggactcaagacgatagt taccggataaggcgcagcggtcgggctgaacggggggttcgtgcacacagcccagcttggagcgaac gacctacaccgaactgagatacctacagcgtgagctatgagaaagcgccacgcttcccgaagggaga aaggcggacaggtatccggtaagcggcagggtcggaacaggagagcgcacgagggagcttccagg gggaaacgcctggtatctttatagtcctgtcgggtttcgccacctctgacttgagcgtcgatttttgtgatgct cgtcagggggcggagcctatggaaa |
| 90 | DNA | >aac(3) IV | gtgcaatacgaatggcgaaaagccgagctcatcggtcagcttctcaaccttggggttaccccggcggt gtgctgctggtccacagctccttccgtagcgtccggcccctcgaagatgggccacttggactgatcgagg ccctgcgtgctgcgctgggtccggaggacgctcgtcatgccctcgtggtcaggtctggacgacgagc |

| SEQ ID No. | Type | Name | Sequence |
|---|---|---|---|
| | | | cgttcgatcctgccacgtcgcccgttacaccggaccttggagttgtctctgacacattctggcgcctgccaa atgtaaagcgcagcgcccatccatttgcctttgcggcagcggggccacaggcagagcagatcatctctg atccattgcccctgccacctcactcgcctgcaagcccggtcgcccgtgtccatgaactcgatgggcaggt acttctcctcggcgtgggacacgatgccaacacgacgctgcatcttgccgagttgatggcaaaggttccct atggggtgccgagacactgcaccattcttcaggatggcaagttggtacgcgtcgattatctcgagaatga ccactgctgtgagcgctttgccttggcggacaggtggctcaaggagaagagccttcagaaggaaggtcc agtcggtcatgcctttgctcggttgatccgctcccgcgacattgtggcgacagccctgggtcaactgggcc gagatccgttgatcttcctgcatccgccagaggcgggatgcgaagaatgcgatgccgctcgccagtcga ttggctga |
| 91 | DNA | >cgt promoter | GCCCGGCCCTGTCGAGCTGACGGCTGTCCCGCGGCCTCGTCATCGGT GCTGTCGAGCAGGCTGTCGCCTGGTAGGAAGATTGCCATGGTCCAGA TGGACCCCCTCAGCGCACGTCCCGATGGACGACGTTCCGTCTTGTCG ACGACTCCGAGCCGCCCGACCCACCGGGCCTGAGCGCGCCCGATCA CGGCTCCCCGGCCTGACGGGTTCTGCACCTCCGGCGGCTTTCCCGAG GACGGCGTGGTGGTCGGTGACGGCTGCTGGACCTCCTCCGGTGGGC AAGCGTTTCGGTGAGGTGGGCAGCCCGGCTGCGGGCACATCGGGGG CGGAGAGACGCTTAGGTTTATTGCAAGTTCTTTCTTCGGTGGCGCGGC GTGTCATCAGCAGCCGATTGTGGCATTCTGGTGACGCATTGACGCAGG TCACAGATTTGTTGGGATAGGCAACGAACAATTCCTAAATCGCCTATTC GGACAAATAGGCTTGACCTGACGACGCTGTCCCACCACTGTGGATGAC GCCTACCGCGCAAGTTCTGGAAGTACTTGCAATCAGCGGTGAGGATCA TCAAAGGGGACTGTC |
| 92 | DNA | >efp promoter | TGGAGCACATCTGCCGGTAGACCCGATTCGCCCTCACCAGCGAATCG CCGGTAAAGTGGTTCGGTCAACGATTCGAGTCAAGATCAAGGCAGGAC ATGGCTTCCACCAACGACCT |
| 93 | DNA | >rpsJ promoter | ATTGCGGGTTGTCGCCGGTGAGAGCCGGTGACAACCCCCACCGGTGA CCCCGATTAGCAATGCTGCGTTCAATCGGGCATACTAGTCAGGTTGCG TCCGCGCGGGTGGGTGGCTGGCGTTCGTCAGCGCCCACCCTCGC CGGGTGTCCGGGTGTGTTTCCAGCCGCCCGGCGCCCTCAGATCCCCG CGATCGCGTTCGTCCCCGGCAAGATCGGGGATGGAGGCCGAAAGCTG AGTGCCCAGCACTCTGTGACGAGGCGCGACACGCCCGACCGCGGGG GTCGGACAACGCAGGATCAACGGTCCTGCGGGCATGTGGGGGCCACC GCCTCCGCACGTAGCGGCATCGAGAGAAGGAAACAGAAGCCACC |
| 94 | DNA | >katE promoter | ATCTCGGGCTCGGTAGGCATCAGGCACTCGTTTCGTCGGGCTCTCGT GACAGTGACCTTGATACTGGAGGGGTACGACAAAACCGGGACCGCCA CCGACGTCCGGACCGACCCGATCGTCGGCCACGAACAGGGCCGGAT GGTCGTCGTGACGCGTCCGCGAGACGCCGTCCGGGCCGGGCCGATG CTCGGCCGGACCGTTTGCCGGGGTTCATGCGGGGTATCCGCCATCCG ATCACATACCCTTATCGAGGAGTTTGTCCGG |
| 95 | DNA | >moeE5 promoter | AGGGCGCCACCAGCTGGAGCCCCATCCCCGCGGGGACCAGGAGGGC GAGCAGCGCCACGGCGGTCCGTTCACCGCGCAGGTAGCGGACAAAC GTGGAGAGATGCCGCAACGGACTGTCTGCCAACGCGCCCCTCCCCCG TTCGCCCGGCGGCGAGCGGCCAGCATAAAGTCCTGTGCGCCTCCTTG TGAATGACGCCTCGTCAACGGCGGCCGGAGCACGCCCTTTCTGCGGG AAGCCGATAGCGGACGCCGCTCCGGGAGGGGGCGAAGCACACCATT GCTCGTGATTGACGCATGCTGTTAGACTCCCCACGTCTCTTGGTCGG ACATGCGTTTCTCAACGCCGAAAGCCTGGTCAACCGCACTTTCGGCAC CGCACAGTCCCACGGCGTCCGAGCGGTCGCGCGAGTCGGCCCGGTC GAGCCAGAGGCAGCCACACGAACGTGCACCGCAATGCACCGCCTTGA TC |
| 96 | DNA | >apm promoter | CTCTGCTGAAGCCAGTTACCTTCGGAAAAAGAGTTGGTAGCTCTTGAT CCGGCAAACAAACCACCGCTGGTAGCGGTGGTTTTTTTGTTTGCAAGC AGCAGATTACGCGCAGAAAAAAAGGATCTCAAGAAGATCCTTTGATCTT TTCTACGGGGTCTGACGCTCAGTGGAACGAAAACTCACGTTAAGGGAT TTTGGTCATGAGATTATCAAAAAGGATCTTCACCTAGATCCTTTTGGTTC ATGTGCAGCTCCATCAGCAAAAGGGGATGATAAGTTTATCACCACCGA CTATTTGCAACAGTGCCGTTGATCGTGCTATGATCGACTGAGC |
| 97 | DNA | >cdaR promoter | GGGCCCCCCCTCGAGGTCGACGGTATCGATAAGCTTGATTTTTCTGGA CAACCTGGACGCCGAGACCTCGGCGGCGACCCTCGCGCTGTTCCTCA CGGCCCTGTGGGCGCTGGCCGTCATCGCCCGCCCCTACACCTGGTGG CGCGTGCTGCTGGTGCTGACCATGGCGGTGGGCTTCGCCGTGGTGCT GGTGGTGCCCTACCTCCAGGAGTTCTTCCAGCTGAAGCTGGTCGGCG TCACCGGCCGTGGGCGGCGGTCGCCTGTCGGCGGTCGCCGGGCT GGTGCTGGAGTTGGTGTGGGCACGTATGCGGCGTCGTCTCGACGCCG ACTGAGCCCACCGGGCGGTCGACCCCCGTACCGCCCGGTGAAGAGG AGGGGACGCCCGGTCCGTGCCGGGCGTCCCCTCCGTCTTTGTGCGCC CCCGCCGACCGGAACGGCACGATCCGGCCAAACCTGCGCAGCGGT GCGGCCGGAGGAGCCGCTTCCGGGCCGTTCGACGGGCGGCCCGCCA |

| SEQ ID No. | Type | Name | Sequence |
|---|---|---|---|
| | | | CGGGACCGGAACGAGCCCCGGCATCCGCCGCCACCAGCGGATTTCAC<br>ATTCCTTACGCAATCGGCGGCGAGAGCGACCGGCAGGTAACCTCGGG<br>GCTGAATCCAGGCCATCGGGGAATAGCAAACGGCGCACTGACGAAAG<br>CAAGGGCAGAGACCTGCCGAAAGTTGAGTGTTGGATTCAAAGAAGATC<br>CGTATTATTCCGACTGCAGGCAGGGGGGAGCCGGCTACGAAGGAAAA<br>GTTCCGCAGGTCAGATTGGGCCGGGTCGCAGGCAGCGCCGCACCGG<br>CAACCACGACCGCGACTTTCGTCGACGCACCCCCTCGCACCGCCGCC<br>CGGCCACCGGTCCGGGCGCACGACCCGAAGGGAAGTGAGGCTCACG<br>CACGGACCAGCAGCTCCTGACGCAGCGACCCGGACCCGGAGGTGAG<br>TGACATGACGACGAGGCCCCGACCAGCGGTGAACCCTGCTGACCCGG<br>CCGTAACGAAGTCTTCATGCCCGTGGCACCCGACGGCTTCGGAGAGT<br>TTCGGCACGCAGACATCAGCACAACTTGACGCGGGGGTATCAAGAGG<br>TCATGGATCTTCGGTACC |
| 98 | DNA | >ermE*<br>promoter | GCGGTTGATCGGCGATCGCAGGTGCACGCGGTCGATCTTGACGGCTG<br>GCGAGAGGTGCGGGGAGGATCTGACCGACGCGGTCCACACGTGGCA<br>CCG<br>CGATGCTGTTGTGGGCACAATCGTGCCGGTTGGTAGGATCCAGCGAG<br>CA |
| 99 | DNA | >rpsL<br>promoter | TGAGCACGTCCGCGAGCTGGCCCTGCAGGCGGAAGTCAGGTAGACAC<br>GACTTCCGCTAGTCCTTGCAAGGTCTGCTGACGTGAGGCGGGCGGT<br>CGTTTTTGACCGCCCTGCCTTCGTCATGTAGGCTCGCTCGCTGTGCCT<br>GGCGTGTCATCAGACGCCCAGGTCCCGGTGCCGTGAGGCCCGGGCC<br>ATCGAGCCGGTGGTACGTGGCTGCGGTCCCCTTGTGAGGGCTGCGCG<br>CCGTGTGCTGTCCGGCGCGCACAGCCTTGAATCCACCCGCGGGGGCC<br>GGCCGGTCTCCGTGAGCTCG AGTAGACGACGGAGACGTA |
| 100 | DNA | >ACSP50_<br>1949 | GTGGCGACTCCCACGCAGTCCGAGATCCGCGAGGAAGAGCACGAAGA<br>GCAGCGGCAGAGCCTGAGCACGGCGGCGGCCCGCAACCTCACGACC<br>ACCACCAAGACCGCGCCGCAGATGCAGGAGATCACTTCGCGATGGCT<br>GCTCCGTAAGCTTCCCTGGGTTCAGGTCGCCGGTGGGGCGTATCGGG<br>TGAACCGGCGGATGACTTATCGGATCGGCGACGGCCGGCTGAGCTTC<br>ACCAACGTCGGTGCGCAGGTCCGGGTCGTCCCGGCCGAGCTGCGGG<br>AACTCTCGGTGCTCAGCGAGTTCGACGACGCGGACGTGCTGGCCGCC<br>ATGGCCGACAAGTTCGTGCAGCAGGAGTACCAGCCCGGTCAGGTGAT<br>CGTCGAGTTCGGCTCGGTCGCCGACCACGTGTACGTGATCGCGCACG<br>GCAAGGTGAACAAGGTCGGCGTCGGCAACTACGGCGACCCGGTCAAC<br>CTGGGGGTGCTCGCCGACGGGGAGGCGTTCGGCGAGAAGTCGCTCA<br>CCGACGAGGAGCGGATCTGGGACTACACCGCCAAGGCGATGACCGC<br>GGTGACCCTGCTGGCCATGCCGCGCTCGGCGTTCACCGCGCTGCTCG<br>GCCAGAGTGACCACCTGCGCACGCACGTCGAGCAGTTCCGGGCCAAG<br>AACCGCCGGCCGCAGAACAAGCACGGCGAGGCGGAGATCTCGGTGG<br>CCGCCGGGCACACCGGCGAACCGAAGCTGGACGGCACGTACGTCGA<br>CTACGAGCTGACGCCGCGCGAATACGAGCTGAGCGTCGCGCAGACCG<br>TGCTGCGCGTGCACACCCGGGTCGCCGACCTCTACAACGAGCCGATG<br>AACCAGGTGGAGCAGCAGCTCCGGCTGACCGTCGAGGCGCTGCGCG<br>AGCGTCAGGAATACGAAATGATCAACAACCGCGAGTTCGGCCTGCTGC<br>ACAACGCCGACCTGCGGCAGCGCATCCACACCCGGGGCGGCCCGCC<br>CACCCCGGACGACCTCGACGAGCTGCTCAGCATGCGGCGCGGCACCA<br>GGATGTTCGTGGCCCACCCGCAGGCGGTCGCGCGTTCGGCCGGGA<br>GTGCACCAAGCGGGGCATCTATCACCGATGCTGGAACAGGACGGCG<br>GCACCTTCCTGTCCTGGCGCGGGTCCCGATCCTGCCGTGCGGCAAG<br>ATCCCGGTGACCGAGACGCACACCACCTCGATCCTGGCGATGCGCAC<br>CGGGGAGAGCGACCAGGGTGTGGTCGGGCTGCACCAGACCGGGATC<br>CCGGACGAGTACGAGCCGAGCCTGTCCGTGCGGTTCATGGGGATCAG<br>CGAGCAGGCGATCATGTCGTACCTGGTGAGCGCGTACTACTCGGCCG<br>CGGTGCTGGTGCCGGACGCGCTGGGCATCCTGGACCACGTCGAGCT<br>GTCCCACTGA |
| 101 | DNA | >ACSP50_<br>1951 | ATGACAAGTGCTGTTGCTTCGCCACTGCGGACCGACTTCGAGCGCTCG<br>GTCGCCAGCTACTGGAACACCAACCGGGCCGACCCGGTCAACCTGCG<br>CCTCGGCGAGGTCGACGGGCTGTACCACCACCACTACGGCGTCGGCG<br>AGCCCGACCTCAGCGTGCTGGACGGCCCGGCCGACACCCGCGAGCA<br>GCGGATCATCGCCGAGCTGCACCGGCTGGAGAACGCCCAGGCCGAC<br>CTGCTGCTCGACCACCTCGGCCCGATCCGGCGGGCGACGCGCTGCT<br>CGACGGCGGGTCCGGCCGCGGCGGCACCAGCATCATGGCCAACGCG<br>CGGTTCGGCTGCCGGGTCGACGGGGTGTCCATCTCGGAATACCAGGT<br>GGGTTTCGCCAACGAGCAGGCCGCTCAGCGCGGCGTCGCCGACAGG<br>GTGCGCTTCCACTTCCGCAACATGCTGGACTCCGGATTCGCGACCGG<br>GTCACGGCAGGCGATCTGGACGAACGAGACGACGATGTACGTCGACC<br>TGTTCGACCTGTACGCGGAGTTCGCCCGGATGCTCGGCTTCGGCGG<br>CGCTACGTGTGCATCACCGGTTGCGCCAACGACGTGACCGGCCGGCG<br>CTCCAAGGCGGTCAACAGGATCAACGAGCACTACACCTGTGACATCCA<br>CCCGCGCAGCGACTACTTCAAGGCGCTCGCCGCCCACGATCTCGTGC |

| SEQ ID No. | Type | Name | Sequence |
|---|---|---|---|
| | | | CGATCGCCGTCACCGACCTGACCGCGGCCACCATCCCGTACTGGGAG<br>CTGCGCGCCCGGTCCGAGGTGGCGACCGGGATCGAACAGGCTTTCCT<br>CACGGCGTACTCAGAAGGCAGTTTCCACTACCTTCTGATCGCCGCCGA<br>TCGGGTCTGA |
| 102 | DNA | >ACSP50_1952 | ATGGCCCTGCCGATCGAGGACTACGCGATCATCGCCGACACCCAGAC<br>CGCGGCCCTGGTCGGTCGCAACGGATCGATCGACTGGCTCTGCGTGC<br>CCCGCTTCGACTCCGGCGCGATCTTCGCGGCGCTGCTCGGCGAGGC<br>GGAGAACGGCCACTGGACCATCGCACCCGTCCGGCGAGGTGGTCACCA<br>CCCGCCGCCGCTACCGGGACGACACGCTGGTGTTGGAGACGGAGTTC<br>GAGACGGCCGGCGGCGTCGCCCGGTTGATCGACTTCATGCCGCCGC<br>GCACCGACTCGCCGTCCGTCATCCGGATCGTCGAGGGCGTCCGCGG<br>GCAGGTGGACTTCGGCATGGAGCTGCGGCTGCGCTTCGACTATGGAC<br>ACGTCGTGCCATGGGTCTACCGCGAGGGTGGGGCGCTCGTCGCGGT<br>CGCCGGTCCGGACGCGGCCTGGTTGCGCACCGACGTGCCGACCCGG<br>GGCGAGAATCTGACCACCAAAGCCGATTTCCGGGTACGGGCGGGGA<br>ACGCGCCGCCTTCACCCTGACCTGGCGCCCGTCGCATCTGCCCTCGC<br>CCGCCCCGCTGGACCCGGCCCACGAGCTCGGCGTGACCGAGGGGTTA<br>CTGGCGCGGCTGGGTGTCCGCCTGACGTACGAGGGGGAGTGGCGG<br>GACGCCGTCGTCCGATCGCTGCTCACTCTGAAAGCCCTCACCTACGCA<br>CCCACCGGCGGCATTGTCGCGGCCGCCACCACCAGCCTCCCGGAGAA<br>ACTCGGCGGCGTCCAACTGGGACTACCGCTTCTGCTGGCTCCGCG<br>ACGCACCATCACCCTGCAGTCGCTGCTCTTCTCCGGTTTCCAGAGTG<br>AGGCGATCGCCTGGCGCAAATGGCTGCTGCGCGCGATCGCCGGCAAC<br>CCCGCCGAGCTGCAGATCATGTACGGCGTCGCCGGCGAACGCCGCCT<br>CGACGAGTATCTGGCCGACTGGCTCACCGGCTACGACGGCAACCCGG<br>TCCGGATCGGCAACGCCGCCGCCGAGCAGTTCCAGTTGGACGTGTAC<br>GGCGAGGTGATGGACGCCCTGCATCAGGGCCGCCGGGCCGGCCTCA<br>AAGCCGACGACCCGTCCTGGGGCCTGCAGGTCAAACTGATGGAGTTC<br>GTCGAGGAGCACTGGCAGGACCCGGACGAGGGCATCTGGGAGGTCC<br>GCGGCGGCCCCCGCCAGTTCACCCCACTCCAAACTGATGGCCTGGGTC<br>GCCGCCGACCGCGCCGTCAAGGCCGTCGAGGAGTTCGGCCTGGACG<br>GCCCCGCCGACCGCTGGCGCCGCCTGCGCGACGAGATCCGTCAGGA<br>CATCCTGGACAAGGGTTACGACCCGGTCCGCAAGACCTTCACCCAGTA<br>CTACGGCTCCGATGAGCTCGACGCCGCGATGCTGATGGTCCCCCTGG<br>TCGGCTTCCTCCCCGGGGATGACGAACGCGTCGCCGGCACGGTCGCC<br>GCCATCGAGCAACACCTGCTGGTCGACGGTTTCGTCCAGCGGTACAC<br>CCAACATCCGGACGCCGACGTCGACGGCCCTTCCCCCGGGCGAGGGC<br>GCGTTCCTGGCCTGCACGTTCTGGCTGGCCGACAACTACGCGCTGAT<br>GGGTCGCCACGACGAGGCCCGGGAGACGTTCGCCCGCCTGCTGGCC<br>CTGCGCAACGACGTGGGTCTGCTCGCCGAGGAGTACGACACCACCAC<br>CGGCCGCCTGGTCGGCAACTTCCCTCAGGCCTTCAGTCACGTCCCGC<br>TGATCGACACGCCCCGACCTTGACCAGCGCGCTGGCGCCGACCGA<br>GGCCCCGGGCCTCGGAGGGCCTCAGGTAG |
| 103 | DNA | >ACSP50_1953 | atgcgtacggtgattcgtgggatcgtggtgttggcgctggtggccggggggtggcgccggcatggtggggc<br>ccgccggagcggcgccggcggtgacgttcaagaactgcactgagctgaacaagaagtacaagcacg<br>gggtcggcaagcggggcgccgaggacagggtgagcgggtccaccaagccggtcaccaccttctccgt<br>gaacaacgatctctatgcggcgaacaagaggctggaccgtgacaaggacgggatcgcctgcgagaa<br>gcggtga |
| 104 | PRT | >ACSP50_1949 | MATPTQSEIREEEHEEQRQSLSTAAARNLTTTKTAPQMQEITSRWLLRKL<br>PWVQVAGGAYRVNRRMTYRIGDGRLSFTNVGAQVRVVPAELRELSVLSE<br>FDDADVLAAMADKFVQQEYQPGQVIVEFGSVADHVYVIAHGKVNKVGVG<br>NYGDPVNLGVLADGEAFGEKSLTDEERIWDYTAKAMTAVTLLAMPRSAFT<br>ALLGQSDHLRTHVEQFRAKNRRPQNKHGEAEISVAAGHTGEPKLDGTYV<br>DYELTPREYELSVAQTVLRVHTRVADLYNEPMNQVEQQLRLTVEALRERQ<br>EYEMINNREFGLLHNADLRQRIHTRGGPPTPDDLDELLSMRRGTRMFVAH<br>PQAVAAFGRECTKRGIYPPMLEQDGGTFLSWRGVPILPCGKIPVTETHTTS<br>ILAMRTGESDQGVVGLHQTGIPDEYEPSLSVRFMGISEQAIMSYLVSAYYS<br>AAVLVPDALGILDHVELSH |
| 105 | PRT | >ACSP50_1951 | MTSAVASPLRTDFERSVASYWNTNRADPVNLRLGEVDGLYHHHYGVGEP<br>DLSVLDGPADTREQRIIAELHRLENAQADLLLDHLGPIRPGDALLDGGSGR<br>GGTSIMANARFGCRVDGVSISEYQVGFANEQAAQRGVADRVRFHFRNML<br>DSGFATGSRQAIWTNETTMYVDLFDLYAEFARMLGFGGRYVCITGCANDV<br>TGRRSKAVNRINEHYTCDIHPRSDYFKALAAHDLVPIAVTDLTAATIPYWEL<br>RARSEVATGIEQAFLTAYSEGSFHYLLIAADRV |
| 106 | PRT | >ACSP50_1952 | MALPIEDYAIIADTQTAALVGRNGSIDWLCVPRFDSGAIFAALLGEAENGH<br>WTIAPSGEVVTTRRRYRDDTLVLETEFETAGGVARLIDFMPPRTDSPSVIRI<br>VEGVRGQVDFGMELRLRFDYGHVVPWVYREGGALVAVAGPDAAWLRTD<br>VPTRGENLTTKADFRVRAGERAAFTLTWRPSHLPSPAPLDPAHELGVTEG<br>YWRGWVSACTYEGEWRDAVRSLLTLKALTYAPTGGIVAAATTSLPEKLG<br>GVRNWDYRFCWLRDATITLQSLLFSGFQSEAIAWRKWLLRAIAGNPAELQI |

| SEQ ID No. | Type | Name | Sequence |
|---|---|---|---|
| | | | MYGVAGERRLDEYLADWLTGYDGNPVRIGNAAAEQFQLDVYGEVMDALH<br>QGRRAGLKADDPSWGLQVKLMEFVEEHWQDPDEGIWEVRGGPRQFTHS<br>KLMAWVAADRAVKAVEEFGLDGPADRWRRLRDEIRQDILDKGYDPVRKT<br>FTQYYGSDELDAAMLMVPLVGFLPGDDERVAGTVAAIEQHLLVDGFVQRY<br>TQHPDADVDGLPPGEGAFLACTFWLADNYALMGRHDEARETFARLLALR<br>NDVGLLAEEYDTTTGRLVGNFPQAFSHVPLIDTARTLTSALAPTEARASEG<br>LR |
| 107 | PRT | >ACSP50_<br>1953 | MRTVIRGIVVLALVAGGGAGMVGPAGAAPAVTFKNCTELNKKYKHGVGKR<br>GAEDRVSGSTKPVTTFSVNNDLYAANKRLDRDKDGIACEKR |
| 108 | DNA | >anti-<br>sense<br>1 (put.<br>Anti-<br>sense<br>promoters) | CACTCATTAGGCACCCCAGGCTTTACACTTTATGCTTCCGGCTCGTATG<br>TTGTGTGG |
| 109 | DNA | >anti-<br>sense<br>2 (put.<br>Anti-<br>sense<br>promoters) | ACGCGGTCGAACACGCGGTGGTACATGTCCAGCCACGCGCACTGGTA<br>CTCTTCGGAC |
| 110 | DNA | >pSET<br>T4gap | aagcgcggggaagaatcgatcaaggactcttaccgctgccgtcgccggaaggtggtcgacccgtccg<br>cacctgggcagcacgaaggcacgtgcaacgtcagcatggcggcactcgacaagttcgttgcggaacg<br>catcttcaacaagatcaggcacgccgaaggcgacgaagagacgttggcgcttctgtgggaagccgcc<br>cgacgcttcggcaagctcactgaggcgcctgagaagagcggcgaacgggcgaaccttgttgcggagc<br>gcgccgacgccctgaacgcccttgaagacgccgctgtacgaagaccgcgcggcaggcgcgtacgacggac<br>ccgttggcaggaagcacttccggaagcaacaggcagcgctgacgctccggcagcaagggcggaa<br>gagcggcttgccgaacttgaagccgccgaagccccgaagcttccccttgaccaatggttccccgaaga<br>cgccgacgctgacccgaccggccctaagtcgtggtggggcgcgcgtcagtagacgacaagcgcgtg<br>ttcgtcgggctcttcgtagacaagatcgttgtcacgaagtcgactacgggcaggggcagggaacgccc<br>atcgagaagcgcgcttcgatcacgtgggcgaagccgccgaccgacgacgaagacgacgccca<br>ggacggcacggaagacgtagcggcgtagcgagacacccgggaagcctgatctacgtctgtcagaaa<br>gtttctgatcgaaaagttcgacagcgtctccgacctgatgcagctctcgcagggcgaagaatctcgtgctttt<br>cagcttcgatgtaggagggcgtggatatgtcctgcgggtaaatagctgcgccgatggttCTCTGTCG<br>TCGCTGACGTCTGTAGTCTAGCCTCATTATGATTGTACGCTATTCAGGG<br>ATTGACTGATACCGGAAGACATCTCAAATGAAGTGGTCAAGCTTTATGC<br>TTGTAAACCGTTTTGTGAAAAAATTTTTAAAATAAAAAGGGGACCTCTA<br>GGGTCCCCAATTAATTAGTAATATAATCTATTAAAGGTCATTCAAAAGGT<br>CATCCAAGCTTGGCTGTTTTGGCGGATGAGAGAAGATTTTCAGCCTGA<br>TACAGATTAAATCAGAACGCAGAAGCGGTCTGATAAAACAGAATTTGCC<br>TGGCGGCAGTAGCGCGGTGGTCCCACCTGACCCCATGCCGAACTCAG<br>AAGTGAAACGCCGTAGCGCCGATGGTAGTGTGGCCCATGCGAGAGTA<br>CATATGGTACTGGCCGATGCTGGGAGAAGCGCGCTGCTGTACGGCGC<br>GCACCGGGTGCGGAGCCCCTCGGCGAGCGGTGTGAAACTTCTGTGAA<br>TGGCCTGTTCGGTTGCTTTTTTTATACGGCTGCCAGATAAGGCTTGCAG<br>CATCTGGGCGGCTACCGCTATGATCGGGGCGTTCCTGCAATTCTTAGT<br>GCGAGTATCTGAAAGGGGATACGCATGGTACCGAGACCTTATGTTGAT<br>CGGCACTTTGCATCGGCCGCGCTCCCGATTCCGGAAGTGCTTGACATT<br>GGGGAATTTATGCGGTGTGAAATACCGCACAGATGCGTAAGGAGAAAA<br>TACCGCATCAGGCGCCATTCGCCATTCAGGCTGCGCAACTGTTGGGAA<br>GGGCGATCGGTGCGGGCCTCTTCGCTATTACGCCAGCTGGCGAAAGG<br>GGGATGTGCTCAAGGCGATTAAGTTGGGTAACGCCAGGGTTTTCCCA<br>GTCACGACGTTGTAAAACGACGGCCAGTGCCAAGCTTGGGCTGCAGG<br>TCGACTCTAGAGGATCCGGCCGCGCGCGATATCGAATTCGTAATCA<br>TGTCATAGCTGTTTCCTGTGTGAAATTGTTATCCGCTCACAATTCCACA<br>CAACATACGAGCCGGAAGCATAAAGTGTAAAGCCTGGGGTGCCTAATG<br>AGTGAGCTAACTCACATTAATTGCGTTGCGCGGTCTCGGCGTTTCGTG<br>CCGCGTGATTTTCCGCCAAAAACTTTAACGAACGTTCGTTATAATGGTG<br>TCATGACCTTCACGACGAAGTACTAAAATTGGCCCGAATCATCAGCTAA<br>GCTTTATGCTTGTAAACCGTTTTGTGAAAAAATTTTTAAAATAAAAAAGG<br>GGACCTCTAGGGTCCCCAATTAATTAGTAATATAATCTATTAAAGGTCA<br>TTCAAAAGGTCATCCACCTCACTTCGGTGAATCGAAGCGCGGCATCAG<br>GGTTACTTTTTGGATACCTGAGACATTCGTCGCTTCCGGGTATGCGCT<br>CTATGTGACGGTCTTTTGGCGCACAAATGCTCAGCACCATTTAAATTAG<br>ACCGACTCCAGATCTGTAAGGTCCAACAAAACCCATCGTAGTCCTTAG<br>ACTTGGCACACTTACACCTGCAGTGGATGACCTTTTGAATGACCTTTAA<br>TAGATTATATTACTAATTAATTGGGGACCCTAGAGGTCCCCTTTTTTATT<br>TTAAAAATTTTTTCACAAAACGGTTTACAAGCATAAAGCTTGCCACGCA<br>GACGACAGCCCACGCTGACCGATCTACCTGAACGGCGACCATCTGTG<br>TGGTACTGGGGCGGAGAGATAACTACGGTGCCGCTTACCGGgctcactca<br>aaggcggtaatacggttatccacagaatcaggggataacgcaggaaagaacatgtgagcaaaaggc |

| SEQ ID No. | Type | Name | Sequence |
|---|---|---|---|
| | | | cagcaaaaggccaggaaccgtaaaaaggccgcgttgctggcgttttccataggctccgccccctgac<br>gagcatcacaaaaatcgacgctcaagtcagaggtggcgaaacccgacaggactataaagataccag<br>gcgtttccccctggaagctccctcgtgcgctctcctgttccgaccctgccgcttaccggatacctgtccgcctt<br>tctcccttcgggaagcgtggcgctttctcatagctcacgctgtaggtatctcagttcggtgtaggtcgttcgct<br>ccaagctgggctgtgtgcacgaaccccccgttcagcccgaccgctgcgccttatccggtaactatcgtctt<br>gagtccaacccggtaagacacgacttatcgccactggcagcagccactggtaacaggattagcagag<br>cgaggtatgtaggcggtgctacagagttcttgaagtggtggcctaactacggctacactagaagaacagt<br>atttggtatctgcgctctgctgaagccagttaccttcggaaaaagagttggtagctcttgatccggcaaaca<br>aaccaccgctggtagcggtggtttttttgtttgcaagcagcagattacgcgcagaaaaaaaggatctcaa<br>gaagatcctttgatcttttctacggggtctgacgctcagtggaacgaaaactcacgttaagggattttggtca<br>tgagattatcaaaaaggatcttcacctagatccttttggttcatgtgcagctccatcagcaaaaggggatga<br>taagtttatcaccaccgactatttgcaacagtgccgttgatcgtgctatgatcgactgatgtcatcagcggtg<br>gagtgcaatgtcgtgcaatacgaatggcgaaaagccgagctcatcggtcagcttctcaaccttgggtta<br>ccccggcggtgtgctgctggtccacagctccttccgtagcgtccggcccctcgaagatgggccacttgg<br>actgatcgaggccctgcgtgctgcgctgggtccggagggacgctcgtcatgccctcgtggtcaggtctg<br>gacgacgagccgttcgatcctgccacgtcgcccgttacaccggacctggagttgtctctgacacattctg<br>gcgcctgccaaatgtaaagcgcagcgcccatccatttgcctttgcggcagcggggccacaggcagagc<br>agatcatctctgatccattgccccctgccacctcactcgcctgcaagcccggtcgcccgtgtccatgaactc<br>gatgggcaggtacttctcctcggcgtgggacacgatgccaacacgacgctgcatcttgccgagttgatgg<br>caaaggttccctatgggtgccgagacactgcaccattcttcaggatggcaagttggtacgcgtcgattat<br>ctcgagaatgaccactgctgtgagcgctttgccttggcggacaggtggctcaaggagaagagccttcag<br>aaggaaggtccagtcggtcatgcctttgctcggttgatccgctcccgcgacattgtggcgacagccctgg<br>gtcaactgggccgagatccgttgatcttcctgcatccgccagaggcgggatgcgaagaatgcgatgccg<br>ctcgccagtcgattggctgagctcatgagcggagaacgagatgacgtggaggggcaaggtcgcgctg<br>attgctggggcaacacgtggagcggatcggggattgtctttcttcagctcgctgatatatgctgacgctca<br>atgccgtttggcctccgactaacgaaaatcccgcatttggacggctgatccgattggcacggcggacgg<br>cgaatggcggagcagacgctcgtccggggcaatgagatatgaaaaagcctgaactcaccgcgacgt<br>atcgggccctggccagctagctagagtcgacctgcaggtccccggggatcggtcttgccttgctcgtcggt<br>gatgtacttcaccagctccgcgaagtcgctctcttcttgatggagcgcatggggacgtgcttggcaatcacgc<br>gcaccccccggccgttttagcggctaaaaaagtcatggctctgccctcgggcggaccacgcccatcatg<br>accttgccaagctcgtcctgcttctcttcgatcttcgccagcagggcgaggatcgtggcatcaccgaaccg<br>cgccgtgcgcgggtcgtcggtgagccagagtttcagcaggcagcccaggcggcccaggtcgccattga<br>tgcgggccagctcgcggacgtgctcatagtccacgacgcccgtgattttgtagccctggccgacggcca<br>gcaggtaggccgacaggctcatgccggccgccgccgccttttcctcaatcgctcttcgttcgtctggaagg<br>cagtacaccttgataggtgggctgcccttcctggttggtttcatcagccatccgcttgccctcatctg<br>ttacgccggcggtagccggccagcctcgcagagcaggattcccgttgagcaccgccaggtgcgaataag<br>ggacagtgaagaaggaacaccgctcgcgggtgggcctacttcacctatcctgcccggctgacgccgtt<br>ggatacaccaaggaaagtctacacgaaccctttggcaaaatcctgtatatcgtgcgaaaaaggatggat<br>ataccgaaaaaatcgctataatgaccccgaagcagggttatcgcgagggaaaagatccgtcgacctga<br>ggcatgcaagctctagcgattccagacgtcccgaaggcgtggcgcggcttccccgtgccggagcaatc<br>gccctgggtgggttacacgacgcccctctatggcccgtactgacggacacaccgaagccccggcggc<br>aaccctcagcggatgccccggggcttcacgttttcccaggtcagaagcggttttcgggagtagtgccca<br>actggggtaacctttgagttctctcagttgggggcgtacgatgcgcacacaagggggtttgtgacc<br>ggggtggacacgtacgcgggtgcttacgaccgtcagtcgcgcgagcgcgagaattcgagcgcagcaa<br>gcccagcgacacagcgtagcgccaacgaagacaaggcggccgaccttcagcgcgaagtcgagcgc<br>gacggggccggttcaggtcgtcgggcatttcagcgaagcgccgggcacgtcggcgttcgggacggc<br>ggagcgcccggagttcgaacgcatcctgaacgatgtcgcgggcggctcaacgatggcattgtct<br>atgacgtgtcgcgcttctcgcgcctgaaggtcatggacgcgattccgattgtctcggaattgctcgccctgg<br>gcgtgacgattgttttccactcaggaaggcgtcttccggcagggaaacgtcatggacctgattcacctgatt<br>atgcggctcgacgcgtcgcacaaagaatcttcgctgaagtcggcgaagattctcgacacgaagaaccttt<br>cagcgcgaatttgggcgggtacgtcggcgggaaggcgccttacggcttcgagcttgtttcggagacgaa<br>ggagatcacgcgcaacggccgaatggtcaatgtcgtcatcaacaagcttgcgcactcgaccactcccct<br>taccggacccttcgagttcgagcccgacgtaatccggtggtggtggcgtgagatcaagacgcacaaac<br>accttcccttcaagccgggcagtcaagccgccattcacccgggcagcatcacggggctttgtaagcgca<br>tggacgctgacgccgtgccgaccccggggcgagacgattgggaagaagaccgcttcaagcgcctggg<br>acccggcaaccgttatgcgaatcctttcgggacccgcgtattgcgggcttcgccgctgaggtgatctacaa<br>gaagaagccggacggcacgccgaccacgaagattgagggttaccgcattcagcgcgaccgatcac<br>gctccggccggtcgagcttgattgcggaccgatcatcgagcccgctgagtggtatgagcttcaggcgtgg<br>ttggacggcagggggcgcggcaaggggctttccggggggcaagccattctgtccgccatggacaagct<br>gtactgcgagtgtggcgccgtcatgacttcg |
| 111 | DNA | >pSET<br>T4tip | aagcgcggggaagaatcgatcaaggactcttaccgctgccgtcgccggaaggtggtcgaccccgtccg<br>cacctgggcagcacgaaggcacgtgcaacgtcagcatggcggcactcgacaagttcgttgcggaacg<br>catcttcaacaagatcaggcaccgcgaaggcgacgaagaagacgttggcgcttctgtgggaagccgcc<br>cgacgcttcggcaagctcactgaggcgcctgagaagagcggcgaacgggcgaaccttgttgcggagc<br>gcgccgacgccctgaacgcccttgaagagctgtacgaagaccgcgcggcaggcgcgtacgacggac<br>ccgttggcaggaagcacttccggaagcaacaggcagcgctgacgctccggcagcaagggcggaa<br>gagcggcttgccgaacttgaagccgccgaagcccgaagcttccccttgaccaatggttccccgaaga<br>cgccgacgctgacccgaccggccctaagtcgtggtggggcgcgcgtcagtagacgacaagcgcgtg<br>ttcgtcgggctcttcgtagacaagatcgttgtcgaccaagtcgactacgggcgggatgcactgccagggcc<br>atcgagaagcgcgcttcgatcacgtgggcgaagccgccgaccgacgacgacgaagacgacgccca<br>ggacggcacggaagacgtagcggcgtagcgagacacccgggaagcctgatctacgtctgtcgagaa<br>gtttctgatcgaaaagttcgacagcgtctccgacctgatgcagctctcgcagggcgaagaatctcgtgctttt<br>cagcttcgatgtaggagggcgtggatatgtcctgcgggtaaatagctgcgccgatggttCTCTGTCG<br>TCGCTGACGTCGTAGTCTAGCCTCATTATGATTGTACGCTATTCAGGG |

| SEQ ID No. | Type | Name | Sequence |
|---|---|---|---|
| | | | ATTGACTGATACCGGAAGACATCTCAAATGAAGTGGTCAAGCTTTATGC
TTGTAAACCGTTTTGTGAAAAAATTTTTAAAATAAAAAAGGGGACCTCTA
GGGTCCCCAATTAATTAGTAATATAATCTATTAAAGGTCATTCAAAAGGT
CATCCAAGCTTGGCTGTTTTGGCGGATGAGAGAAGATTTTCAGCCTGA
TACAGATTAAATCAGAACGCAGAAGCGGTCTGATAAAACAGAATTTGCC
TGGCGGCAGTAGCGCGGTGGTCCCACCTGACCCCATGCCGAACTCAG
AAGTGAAACGCCGTAGCGCCGATGGTAGTGTGGCCCATGCGAGAGTA
CAATCCCTAGAACGTCCGGGCTTGCACCTCACGTCACGTGAGGAGGC
AGCGTGGACGGCGTGGTACCAAGCTTATTGGCACTAGTCGAGCAACG
GAGGTATTCCGATGGTACCGAGACCTATGTTGATCGGCACTTTGCAT
CGGCCGCGCTCCCGATTCCGGAAGTGCTTGACATTGGGGAATTTATGC
GGTGTGAAATACCGCACAGATGCGTAAGGAGAAAATACCGCATCAGGC
GCCATTCGCCATTCAGGCTGCGCAACTGTTGGGAAGGGCGATCGGTG
CGGGCCTCTTCGCTATTACGCCAGCTGGCGAAAGGGGGATGTGCTGC
AAGGCGATTAAGTTGGGTAACGCCAGGGTTTTCCCAGTCACGACGTTG
TAAAACGACGGCCAGTGCCAAGCTTGGCTGCAGGTCGACTCTAGAG
GATCCGCGGCCGCGCGATATCGAATTCGTAATCATGTCATAGCTGT
TTCCTGTGTGAAATTGTTATCGCTCACAATTCCACACAACATACGAGC
CGGAAGCATAAAGTGTAAAGCCTGGGGTGCCTAATGAGTGAGCTAACT
CACATTAATTGCGTTGCGCGGTCTCGGCGTTTCGTGCCGCGTGATTTT
CCGCCAAAAACTTTAACGAACGTTCGTTATAATGGTGTCATGACCTTCA
CGACGAAGTACTAAAATTGGCCCGAATCATCAGCTAAGCTTTATGCTTG
TAAACCGTTTTGTGAAAAAATTTTTAAAATAAAAAAGGGGACCTCTAGG
GTCCCCAATTAATTAGTAATATAATCTATTAAAGGTCATTCAAAAGGTCA
TCCACCTCACTTCGGTGAATCGAAGCGCGGCATCAGGGTTACTTTTTG
GATACCTGAGACATTCGTCGCTTCCGGGTATGCGCTCTATGTGACGGT
CTTTTGGCGCACAAATGCTCAGCACCATTTAAATTAGACCGACTCCAGA
TCTGTAAGGTCCAACAAAACCCATCGTAGTCCTTAGACTTGGCACACTT
ACACCTGCAGTGGATGACCTTTTGAATGACCTTTAATAGATTATATTACT
AATTAATTGGGGACCCTAGAGGTCCCCTTTTTTATTTTAAAAATTTTTTC
ACAAAACGGTTTACAAGCATAAAGCTTGCCACGCAGACGACAGCCCAC
GCTGACCGATCTACCTGAACGGCGACCATCTGTGTGGTACTGGGGCG
GAGAGATAACTACGGTGCCGCTTACCGgctcactcaaaggcggtaatacggttatc
cacagaatcaggggataacgcaggaaagaacatgtgagcaaaaggccagcaaaaggccaggaac
cgtaaaaaggccgcgttgctggcgtttttccataggctccgcccccctgacgagcatcacaaaaatcgac
gctcaagtcagaggtggcgaaacccgacaggactataaagataccaggcgtttccccctggaagctcc
ctcgtgcgctctcctgttccgaccctgccgcttaccggatacctgtccgcctttctcccttcgggaagcgtgg
cgctttctcatagctcacgctgtaggtatctcagttcggtgtaggtcgttcgctccaagctgggctgtgtgcac
gaaccccccgttcagcccgaccgctgcgccttatccggtaactatcgtcttgagtccaacccggtaagac
acgacttatcgccactggcagcagccactggtaacaggattagcagagcgaggtatgtaggcggtgct
acagagttcttgaagtggtggcctaactacggctacactagaagaacagtatttggtatctgcgctctgctg
aagccagttaccttcggaaaaagagttggtagctcttgatccggcaaacaaaccaccgctggtagcggt
ggtttttttgtttgcaagcagcagattacgcgcagaaaaaaaggatctcaagaagatcctttgatcttttctac
ggggtctgacgctcagtggaacgaaaactcacgttaagggattttggtcatgagattatcaaaaaggatc
ttcacctagatccttttggttcatgtgcagctccatcagcaaaaggggatgataagtttatcaccaccgacta
tttgcaacagtgccgttgatcgtgctatgatcgactgatgtcatcagcggtggagtgcaatgtcgtgcaata
cgaatggcgaaaagccgagctcatcggtcagcttctcaaccttggggttacccccggcggtgtgctgctg
gtccacagctccttccgtagcgtccggcccctcgaagatgggccacttggactgatcgaggcctgcgtg
ctgcgctgggtccgggagggacgctcgtcatgccctcgtggtcaggtctggacgacgagccgttcgatcc
tgccacgtcgcccgttacaccggaccttggagttgtctctgacacattctggcgcctgccaaatgtaaagc
gcagcgcccatccatttgcctttgcggcagcggggccacaggcagagcagatcatctctgatccattgcc
cctgccacctcactcgcctgcaagccggtcgcccgtgtccatgaactcgatgggcaggtacttctcctcg
gcgtgggacacgatgccaacacgacgctgcatcttgccgagttgatggcaaaggttccctatggggtgc
cgagacactgcaccattcttcaggatggcaagttggtacgcgtcgattatctcgagaatgaccactgctgt
gagcgctttgccttggcggacaggtggctcaaggagaagagccttcagaaggaagttccagtcggtca
tgccttttgctcggttgatcgctcccgcgacattgtggcgacagccctgggtcaactgggccgagatccgtt
gatcttcctgcatccgccagaggcgggatgcgaagaatgcgatgccgctcgccagtcgattggctgagc
tcatgagcggagaacgagatgacgttggaggggcaaggtcgcgctgattgctggggcaacacgtgga
gcggatcggggattgtctttcttcagctcgctgatgatatgctgacgctcaatgccgtttggcctccgactaa
cgaaaatcccgcatttggacggctgatccgattggcacggcggacgcgaattggcggagcagacgct
cgtccggggcaatgagatatgaaaaagcctgaactcaccgcgacgtatcgggcctggccagctag
ctagagtcgacctgcaggtcccggggatcggtcttgccttgctcgtcggtgatgtacttcaccagctccgc
gaagtcgctcttcttgatggagcgcatggggacgtgcttggcaatcacgcgcaccccccggccgttttagc
ggctaaaaaagtcatggctctgccctcgggcggaccacgccatcatgacccttgccaagtcgtcctgct
tctcttcgatcttcgccagcagggcgaggatcgtggcatcaccgaaccgcgccgtgcgcgggtcgtcggt
gagccagagtttcagcaggccgcccaggcggcccaggtcgccattgatgcgggccagctcgcggacg
tgctcatagtccacgacgcccgtgattttgtagccctggccgacggccagcaggtaggccgacaggctc
atgccggccgccgccgccttttcctcaatcgctcttcgttcgtctggaaggcagtacaccttgataggtggg
ctgcccttcctggttggcttggtttcatcagccatccgcttgccctcatctgttacgccggcggtagccggcca
gcctcgcagagcaggattcccgttgagcaccgccaggtgcagtaagggacagtgaagaaggaaca
cccgctcgcgggtgggcctacttcacctatcctgcccggctgacgccgttggatacaccaaggaaagtct
acacgaacccctttggcaaaatcctgtatatcgtgcgaaaaaggatggatataccgaaaaaatcgtata
atgaccccgaagcagggttatgcagcggaaaagatccgtcgacctgcaggcatgcaagctctagcgat
tccagacgtcccgaaggcgtggcgcggcttcccgtgccggagcaatcgccctggtgggttacacga
cgcccctctatggcccgtactgacggacacaccgaagccccggcggcaacccctcagcggatgcccg |

| SEQ ID No. | Type | Name | Sequence |
|---|---|---|---|
| | | | gggcttcacgttttcccaggtcagaagcggttttcgggagtagtgccccaactggggtaacctttgagttctc
tcagttgggggcgtagggtcgccgacatgacacaaggggttgtgaccggggtggacacgtacgcggt
gcttacgaccgtcagtcgcgcgagcgcgagaattcgagcgcagcaagcccagcgacacagcgtagc
gccaacgaagacaaggcggccgaccttcagcgcgaagtcgagcgcgacggggccggttcaggttc
gtcgggcatttcagcgaagcgccgggcacgtcggcgttcgggacggcggagcgcccggagttcgaac
gcatcctgaacgaatgccgcgccgggcggctcaacatgatcattgtctatgacgtgtcgcgcttctcgcgc
ctgaaggtcatggacgcgattccgattgtctcggaattgctcgccctgggcgtgacgattgtttccactcag
gaaggcgtcttccggcagggaaacgtcatggacctgattcacctgattatgcggctcgacgcgtcgcac
aaagaatcttcgctgaagtcggcgaagattctcgacacgaagaaccttcagcgcgaattgggcgggta
cgtcggcgggaaggcgccttacggcttcgagcttgtttcggagacgaaggagatcacgcgcaacggcc
gaatggtcaatgtcgtcatcaacaagcttgcgcactcgaccactcccctaccggaccccttcgagttcgag
cccgacgtaatccggtggtggtggcgtgagatcaagacgcacaaacaccttcccttcaagccgggcag
tcaagccgccattcacccgggcagcatcacgggcctttgtaagcgcatggacgctgacgccgtgccga
cccggggcgagacgattgggaagaagaccgcttcaagcgcctgggacccggcaaccgttatgcgaat
ccttcgggaccccgcgtattgcgggcttcgccgctgaggtgatctacaagaagaagccggacggcacgc
cgaccacgaagattgagggttaccgcattcagcgcgacccgatcacgctccggccggtcgagcttgatt
gcggaccgatcatcgagcccgctgagtggtatgagcttcaggcgtggttggacggcaggggggcgggc
aagggctttcccgggggcaagccattctgtccgccatggacaagctgtactgcgagtgtggcgccgtc
atgacttcg |

DETAILED DESCRIPTION

Definitions

Unless otherwise defined, all scientific and technical terms used in the description, Figures and claims have their ordinary meaning as commonly understood by one of ordinary skill in the art. All publications, patent applications, patents, and other references mentioned herein are incorporated by reference in their entirety. In case of conflict, the present specification, including definitions, will prevail. If two or more documents incorporated by reference include conflicting and/or inconsistent disclosure with respect to each other, then the document having the later effective date shall control. The materials, methods, and examples are illustrative only and not intended to be limiting. Unless stated otherwise, the following terms used in this document, including the description and claims, have the definitions given below.

The terms "comprising", "including", "containing", "having" etc. shall be read expansively or open-ended and without limitation. Singular forms such as "a", "an" or "the" include plural references unless the context clearly indicates otherwise. Unless otherwise indicated, the term "at least" preceding a series of elements is to be understood to refer to every element in the series. The terms "at least one" and "at least one of" include for example, one, two, three, four, five, six, seven, eight, nine, ten or more elements.

It is furthermore understood that slight variations above and below a stated range can be used to achieve substantially the same results as a value within the range. Also, unless indicated otherwise, the disclosure of ranges is intended as a continuous range including every value between the minimum and maximum values.

Where protein or amino acid sequences are provided throughout the application it is also understood by the skilled person that single or multiple amino acids may be exchanged by amino acids with similar properties to achieve substantially the same effect, i.e. an equivalent result. The skilled person furthermore knows that a defined protein or amino acid sequence may be encoded by various nucleic acid sequences. For a given amino acid sequence as defined herein, each of the countable nucleic acid sequences encoding the specific amino acid sequence shall be deemed to be disclosed herein. Where nucleic acid sequences are provided throughout the application it is furthermore understood that silent mutations may be introduced.

Figure 5:
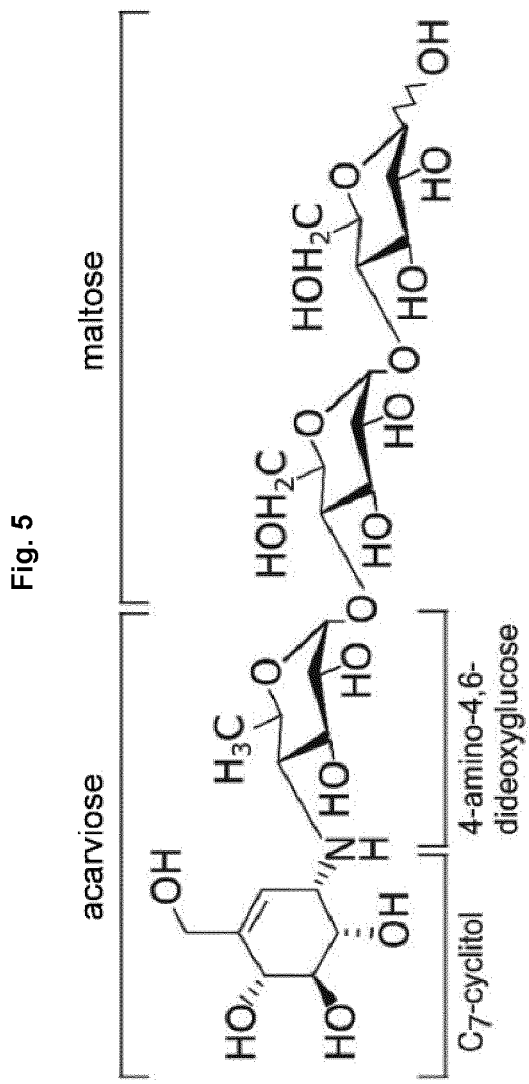
FIG. 5. Chemical structure of acarbose. Acarbose is a cyclitol-containing aminoglycosid composed of a pseudo-disaccharide (valienaminyl-4-amino-4,6-dideoxyglucose), called acarviose, and maltose. Both are connected by an α-1,4-glycosidic bond. Figure published in Wolf 2017.

O-{4,6-dideoxy-4 [1S-(1,4,6/5)-4,5,6-trihydroxy-3-hydroxymethyl-2-cyclohexen-1-yl]-amino-α-D-glucopyranosyl}-(1->4)-O-α-D-glucopyranosyl-(1->4)-D-glucopyranose or "acarbose" is a cyclitol-containing aminoglycoside, composed of a pseudodisaccharide and an α-1,4-glycosidic bound maltose (Wehmeier and Piepersberg 2009). The pseudodisaccharide, named acarviose, is built by an unsaturated C7-aminocyclitol, also referred as valienol or valienamine, which is connected to C4 of a 4,6-didesoxy-D-glucose by a nitrogen bond (cf. FIG. 5) (Wehmeier and Piepersberg 2009). This N-glycosidic bond cannot be hydrolyzed by foreign alpha-1,4-glucoside hydrolases, leading to an almost irreversible inhibitory effect (Wehmeier and Piepersberg 2009; Brayer et al. 2000).

"Overexpression" of a gene product or protein as described herein refers to an increase in expression compared to the wild type or a specified reference strain. Preferably, the reference strain or control is the strain which has not been engineered for the specific overexpression of the respective gene(s) or protein(s). For example, the control does not comprise a vector comprising an expression cassette for the respective gene product or protein. For example, the overexpression of the gene product may be an increase during the early growth phase, during the linear growth phase, during the stationary phase or an increase during any other time. Preferably, overexpression is an increase of the gene product or protein by a factor of at least 1.5 or at least a factor of 2 compared to the control. With regard to transcript amounts and if not defined otherwise herein, strong overexpression refers to a log 2 (fold change)>6. With regard to transcript amounts and if not defined otherwise herein, weak overexpression refers to a log 2 (fold change) <2. With regard to transcript amounts and if not defined otherwise herein, medium strong overexpression refers to a log 2 (fold change)≥2 and ≤6.

The expression of a gene product or protein as described herein is "absent or reduced" if the respective gene has been deleted or mutated in such a way that its gene product is not expressed at all or in a significantly decreased amount (e.g. less than 0.75 fold or less than 0.5 fold). The expression of a gene product or protein as described herein is also considered absent or reduced if the gene product or protein has lost functionality, e.g. in a transient or permanent way, e.g. by mutation or knockdown. Methods to monitor the amount and or activity of a gene product or protein are known in the art and are also described herein in an exemplary way. In general, suitable methods to obtain an absent or reduced expression of a gene product are methods that alter the genetic sequence or elements of gene expression (e.g. by deletion or point mutations) and/or methods that negatively affect the transcription and translation of a gene or the activity or half-life of the gene product (protein).

If not specified otherwise the symbol "Δ" refers to a "deletion mutant", i.e. a mutant wherein a specific gene sequence has been at least partially deleted.

The "early growth phase" is the time, in which the Actinoplanes strain adapts to the medium and in which the cell dry weight is below 3 g·L 1. After adaption to the environment, the culture metabolizes the nutrients supplied by the medium and starts to grow. Since Actinoplanes is growing in a spherical mycelium, which can only expand to the outside of the sphere, the cells in the middle are shielded from nutrients and have only limited space for cell division. Therefore, only the cell in the outer layer of the spherical mycelium are dividing. By this, growth of Actinoplanes are linear and not exponential—in contrast to other bacteria, which are growing unicellular. The growth phase is called "linear growth phase" for Actinoplanes ssp. and starts at a cell dry weight of 3 g·L$^{-1}$. The "stationary phase" is defined as growth phase, in which the cells reach the capacity limits (of space and nutrients) respectively in which growth decreases due to the formation of inhibitory by-products or other chemical and physical factors such as changes in the osmolarity or pH. The stationary phase is the growth phase, in which the number of dying cells equals the number of dividing cells. This phase usually starts at a cell dry weight of 16-18 g·L$^{-1}$ in maltose minimal medium.

The term "vector", as used herein, refers to a nucleic acid molecule capable of propagating a nucleic acid molecule to which it is linked.

The term "expression cassette", as used herein, refers to a nucleic acid molecule comprising at least a gene for expression and a regulatory sequence, such as a promoter.

A "promoter" is a nucleic acid sequence which leads to initiation of transcription of a particular gene.

A "strong promoter" as defined herein is a promoter, which leads to a normalized glucuronidase activity of at least 5.10$^4$ [L·g$^{-1}$·min$^{-1}$] in the glucuronidase assay, and/or which leads to a 350-fold relative transcription (in log 2 (fold change)) of the gusA gene compared to the promoterless pGUS control vector. A detailed description of a method for characterizing the strength of a promoter is provided within the examples and in (Schaffert, et al. 2019). Examples include the promoters of apm: 9.2.10$^{-4}$ [L·g$^{-1}$·min$^{-1}$] and log 2 (fold change)= 360.78 ermE*: 9.7-10$^{-4}$ [L·g$^{-1}$·min$^{-1}$] and log 2 (fold change)= 291.03 katE: 5.1.10$^{-4}$ [L·g$^{-1}$·min$^{-1}$] and log 2 (fold change)= 342.51 moeE5: 9.7.10$^{-4}$ [L·g$^{-1}$·min$^{-1}$] and log 2 (fold change)= 329.32 gapDH: 11.5.10$^{-4}$ [L·g$^{-1}$·min$^{-1}$] and log 2 (fold change)= 931.45, and actP: 22.9.10$^{-4}$ [L·g$^{-1}$·min$^{-1}$].

A "medium strong promoter" is defined as promoter, which leads to a normalized glucuronidase activity of at least 1.10$^4$ [L·g$^{-1}$·min$^{-1}$] was achieved in the glucuronidase assay, and/or which leads to a 10-fold relative transcription (in log 2 (fold change)) of the gusA gene compared to the promoterless pGUS control vector. Examples include the promoters of efp: 3.1.10-4 [L·g$^{-1}$·min$^{-1}$] and log 2 (fold change)=53.08 cdaR: 3.1.10-4 [L·g$^{-1}$·min$^{-1}$] and log 2 (fold change)= 86.82 rpsL: 3.5-10-4 [L·g$^{-1}$·min$^{-1}$] and log 2 (fold change)= 98.53 rpsJ: 3.7.10-4 [L·g$^{-1}$·min$^{-1}$] and log 2 (fold change)= 123.97 cgt: 2.5.10-4 [L·g$^{-1}$·min$^{-1}$] and log 2 (fold change)= 347.29, and tipA: 4.2.10-4 [L·g$^{-1}$·min$^{-1}$] and log 2 (fold change)=191.

In some cases, the medium strong promoter leads to a normalized glucuronidase activity of at least 1.10-4 [L·g$^{-1}$·min$^{-1}$] and maximal 5.10-4 [L·g$^{-1}$·min$^{-1}$] in the glucuronidase assay.

A "weak promotor" is defined as promoter, which leads to a normalized glucuronidase activity of below 1.104 [L·g$^{-1}$·min$^{-1}$], and/or which leads to a relative transcription of below 10-fold compared to the promoterless pGUS control vector.

The term "Cgt" (ACSP50_5024, previously: ACPL_5091) refers to extracellular small carbohydrate binding protein, previously described as cyclomaltodextrin glucanotransferase due the high similarity to the C-terminal domain of cyclodextrin glycosyltransferases, obtained from Actinoplanes sp., e.g. strain ATCC 31044/CBS 674.73/SE50/110. Cgt protein is encoded by the gene cgt. Sequence(s) are described herein (SEQ ID No. 20) or are accessible via UniProt Identifier G8S155 (G8S155_ACTS5). Different isoforms and variants may exist for the different strains and are all comprised by the term. Where a specific mutation can be exchanged without changing the described catalytic properties of the initial sequence, it is clear that the sequence having such a functionally silent mutation is equivalent with regard to the initial sequence. In addition, the protein may furthermore be subject to various modifications, e.g, synthetic or naturally occurring modifications.

The term "AcbB" (ACSP50_3608, previously ACPL_3681) refers to dTDP-D-glucose-4,6-dehydratase obtained from Actinoplanes sp., e.g. strain ATCC 31044/CBS 674.73/SE50/110, which is probably involved in the biosynthesis of the acarviosyl moiety of acarbose. AcbB protein is encoded by the gene acbB. Sequence(s) are described herein (SEQ ID No. 13) or are accessible via UniProt Identifier Q9ZAE8 (RMLB_ACTS5). Different isoforms and variants may exist for the different strains and are all comprised by the term. Where a specific mutation can be exchanged without changing the described catalytic properties of the initial sequence, it is clear, that the sequence having such a functionally silent mutation is equivalent with regard to the initial sequence. In addition, the protein may furthermore be subject to various modifications, e.g, synthetic or naturally occurring modifications.

The term "GtaB" also "GalU" (ACSP50_7820, previously ACPL_7811) refers to UTP-glucose-1-phosphate uridylyltransferase obtained from Actinoplanes sp., e.g. strain ATCC 31044/CBS 674.73/SE50/110. GtaB seems to catalyze the conversion of glucose-1P and UDP-glucose into each other and might be involved in the precursor supply for acarbose. GtaB protein is encoded by the gene gtaB. Sequence(s) are described herein (SEQ ID No. 19) or are accessible via UniProt Identifier G8S608 (ACPL_7811). Different isoforms and variants may exist for the different strains and are all comprised by the term. Where a specific mutation can be exchanged without changing the described catalytic properties of the initial sequence, it is clear that the sequence having such a functionally silent mutation is equivalent with regard to the initial sequence. In addition, the protein may furthermore be subject to various modifications, e.g, synthetic or naturally occurring modifications.

As defined herein, a "gene which is essential for carotenoid synthesis" is defined as a gene which is positively required for the synthesis of a carotenoid. Actinoplanes are known to produce a variety of soluble pigments including yellow, orange and pink pigments of the class carotenoids. In Actinoplanes, the set of genes which are essential for carotenoid synthesis include genes from the MEP/DOXP pathway, genes of terpene cluster 1, genes of terpene cluster 2a, genes of terpene cluster 2b and genes of camphene-like monoterpene biosynthesis terpene cluster 3. Genes of the MEP/DOXP pathway comprise
  i. 1-deoxy-D-xylulose-5-phosphate synthase gene dxs (ACSP50_7096, SEQ ID No. 23),
  ii. 4-hydroxy-3-methylbut-2-en-1-yl diphosphate synthase gene ispG (ACSP50_7248, SEQ ID No. 24),
  iii. 1-deoxy-D-xylulose-5-phosphate reductoisomerase gene dxr (ACSP50_7250, SEQ ID No. 25),
  iv. 4-hydroxy-3-methylbut-2-enyl diphosphate reductase gene ispH (ACSP50_7707, SEQ ID No. 26),
  v. 4-(cytidine 5'-diphospho)-2-C-methyl-D-erythritol kinase gene ispE (ACSP50_7802, SEQ ID No. 27),
  vi. 2-C-methyl-D-erythritol 2;4-cyclodiphosphate synthase gene ispF, ACSP50_8046, SEQ ID No. 28), and/or
  vii. 2-C-methyl-D-erythritol 4-phosphate cytidylyltransferase gene ispD (ACSP50_8047, SEQ ID No. 29).
Genes of Terpene Cluster 1 Comprise
  i. isopentenyl-diphosphate delta-isomerase gene idi (ACSP50_0146, SEQ ID No. 30),
  ii. zeta-phytoene desaturase gene crtI (ACSP50_0147, SEQ ID No. 10),
  iii. polyprenyl synthetase gene crtE/IdsA (ACSP50_0148, SEQ ID No. 31),
  iv. phytoene synthase gene crtB (ACSP50_0149, SEQ ID No. 32),
  v. deoxyribodipyrimidine photo-lyase gene (ACSP50_0150, SEQ ID No. 33), or
  vi. pyridine nucleotide-disulfide oxidoreductase gene (ACSP50_0151, SEQ ID No. 34).
Genes of Terpene Cluster 2a Comprise
  i. transcriptional regulator gene (ACSP50_1631, SEQ ID No. 35),
  ii. lycopene cyclase gene (ACSP50_1632, SEQ ID No. 36),
  iii. lycopene cyclase gene (ACSP50_1633, SEQ ID No. 37),
  iv. polyprenyl synthetase (farnesyl pyrophosphate synthetase 2 gene fps2/crtE (ACSP50_1634, SEQ ID No. 38), and
  v. methylenetetrahydrofolate reductase (NADPH) gene (ACSP50_1635, SEQ ID No. 39).
Genes of Terpene Cluster 2b Comprise
  i. LysR-family transcriptional regulator gene (ACSP50_1650, SEQ ID No. 40),
  ii. methyltransferase type 11 gene (ACSP50_1651, SEQ ID No. 41),
  iii. CDP-alcoholphosphatidyltransferase pgsA (ACSP50_1652, SEQ ID No. 42),
  iv. zeta-phytoene desaturase (crtI-family) gene crtD (ACSP50_1653, SEQ ID No. 43),
  v. glycosyl transferase gene cruC (ACSP50_1654, SEQ ID No. 44),
  vi. hypothetical protein (put. membrane prot,) gene cruF, (ACSP50_1655, SEQ ID No. 45),
  vii. GCN5 family acetyltransferase gene (ACSP50_1656, SEQ ID No. 46),
  viii. monooxygenase gene (ACSP50_1657, SEQ ID No. 47), and
  ix. short-chain dehydrogenase gene (ACSP50_1658, SEQ ID No. 48).
Another gene which is essential for carotenoid synthesis is polyprenyl synthetase gene crtE (ACSP50_3873, SEQ ID No. 49).
Genes of Camphene-Like Monoterpene Biosynthesis Terpene Cluster 3 Comprise
  i. transcriptional regulator (Crp/Fnr family) gene eshA (ACSP50_1949, SEQ ID No. 104),
  ii. camphene synthase gene (ACSP50_1950, SEQ ID No. 50),
  ili. methyltransferase (SAM-dependent) type 11 gene (ACSP50_1951, SEQ ID No. 105),
  iv. glycosyl-hydrolase gene (ACSP50_1952, SEQ ID No. 106), and
  v. oxidoreductase/aldo/ketoreductase (ACSP50_1953, SEQ ID No. 107).

EMBODIMENTS

While Actinomycetales strain Actinoplanes sp. SE50/110 was used as a model strain for the current invention, it is clear for the skilled person, that the general mechanisms and findings can be applied for other acarbose producing strains such as those strains which are currently used for the commercial production of acarbose. According to some embodiments, the Actinomycetales strain is a Micromonosporaceae strain. According to some embodiments, the Actinomycetales strain is an Actinoplanes strain. According to some embodiments, the Actinomycetales strain is Actinoplanes SE50 (ATCC 31042, CBS 961.70) (Frommer et al. 1973), Actinoplanes sp. SE50/110 (ATCC 31044, CBS 674.73) or an Actinoplanes strain derived thereof. In some embodiments, the Actinomycetales strain is an Actinoplanes strain which is commercially used for acarbose production. In some embodiments, the Actinomycetales strain is an Actinoplanes strain which is commercially used for Acarbose production, such as SN223-29-47, C445-P47, SN12755-38, SC3687-18-43, SC7177-40-17 or SN19910-37-21 as disclosed e.g. in EP 2601209 B1 and CN103298828 B, or a strain derived thereof.

Improvement of acarbose production refers to an increase in yield of acarbose over a specific time (either in total or relative to cell growth) and/or improvement of the purity of the acarbose, e.g. the decrease of side-products and/or acarbose analogs such as component C. Cultivation of the Actinoplanes strain can occur as known in the art or as described herein. In some embodiments, cultivation of the Actinoplanes strain occurs in maltose minimal medium.

According to a first aspect of the current invention, there is provided a method to engineer an Actinomycetales strain, such as an Actinoplanes strain, for the improved production of acarbose.

According to some first embodiments according to the first aspect, the method according to the first aspect comprises engineering the Actinomycetales strain for absent or reduced expression of extracellular small carbohydrate binding protein Cgt (SEQ ID No. 20).

Surprisingly, deletion of carbohydrate binding protein Cgt (SEQ ID No. 20) resulted in an improved production of acarbose. An increase of the final acarbose yield between 8.3 and 16.6% was achieved in three independent shake flask cultivations (cf. example "Δcgt displays improved acarbose formation on maltose minimal medium", FIG. 18, FIG. 19, Table E10, Table E11).

Figure 12:
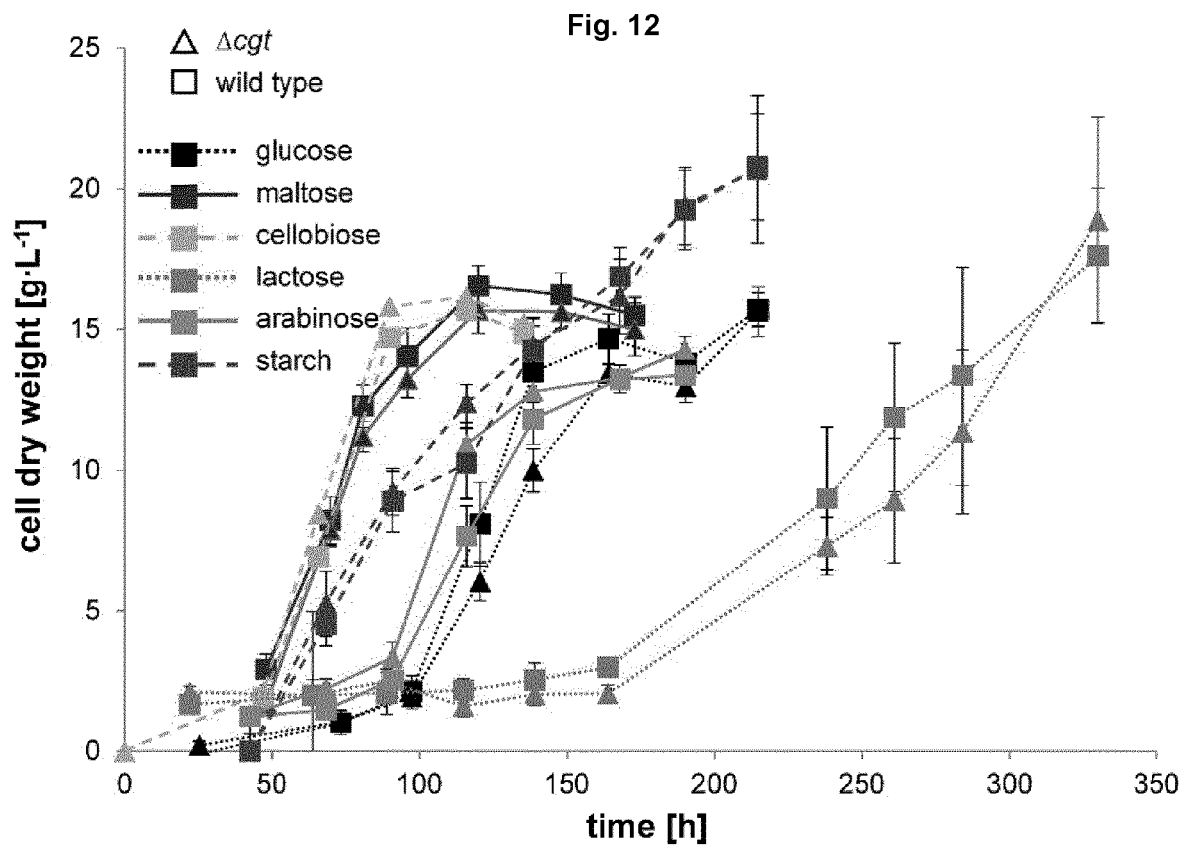
FIG. 12. Growth of the wild type and the deletion mutant Δcgt of Actinoplanes sp. SE50/110 in minimal medium complemented with different carbon sources. Shown are the cell dry weights and the standard deviation over time (wild type: $n_{glc}=3$, $n_{mal}=5$, $n_{cel}=4$, $n_{lac}=3$, $n_{ara}=5$, $n_{starch}=5$, Δcgt: $n_{glc}=2$, $n_{mal}=5$, $n_{cel}=4$, $n_{lac}=4$, $n_{ara}=5$, $n_{starch}=5$).
Figure 13:
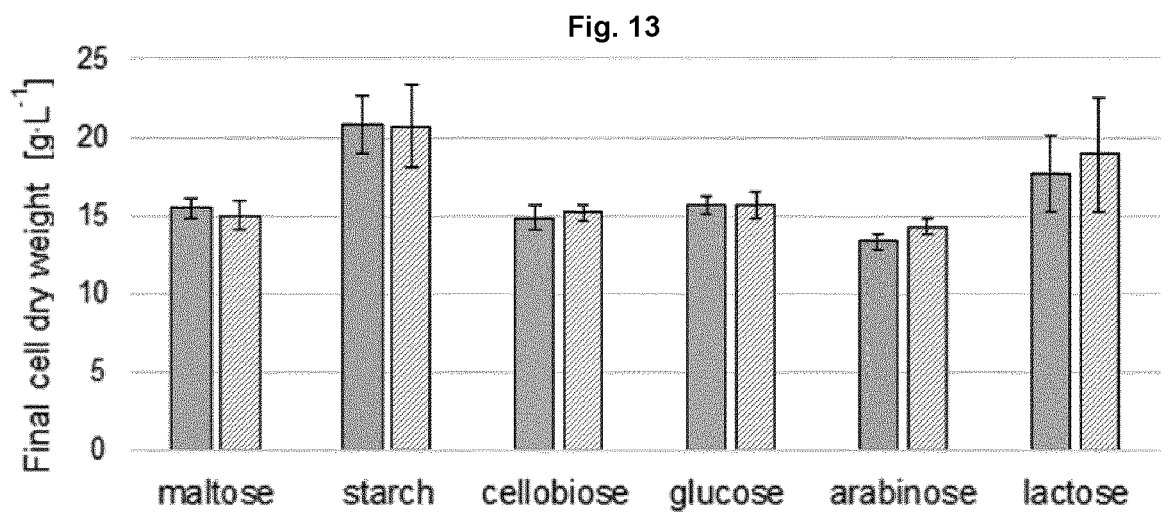
FIG. 13. Final cell dry weights obtained in cultivations of the wild type and the Δcgt mutant in minimal media supplemented with six different carbon sources. The error bars denote standard deviations.
Figure 14:
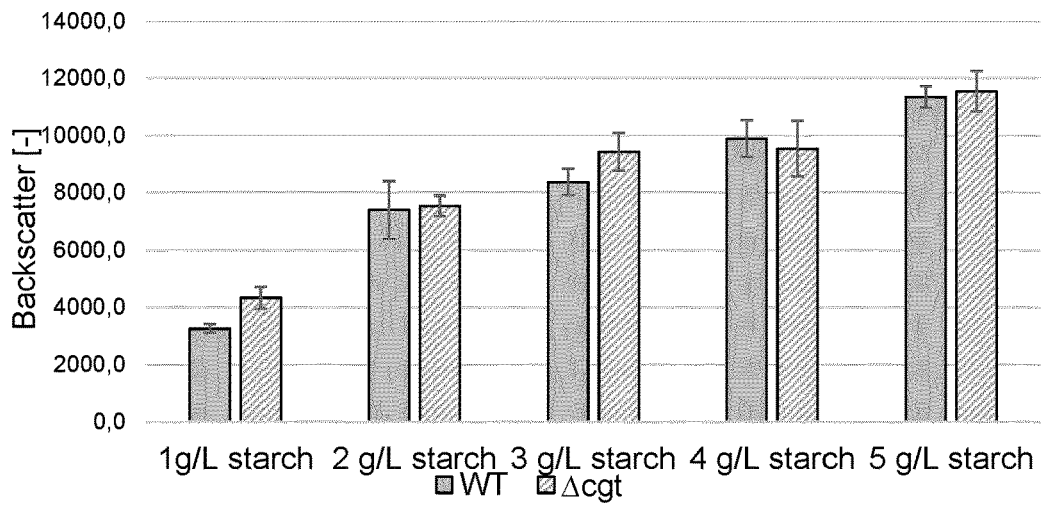
FIG. 14. Growth of Δcgt and the wild type under limited amounts of starch as carbon source. Medium was supplemented with 1 g·L$^{-1}$, 2 g·L$^{-1}$, 3 g·L$^{-1}$, 4 g·L$^{-1}$ and 5 g·L$^{-1}$ starch and cultivation was performed in the RoboLector® system of m2p labs. Shown are the backscatter signals in a bar diagram and standard deviation of at least three biological replicates. No restraint on growth was observed for Δcgt. For 1 g·L$^{-1}$ growth was even found to be significant enhanced (p-value of a two-sided t-test: 0.006141, $n_{wt}=3$, $n_{acgt}=4$).
Figure 15:
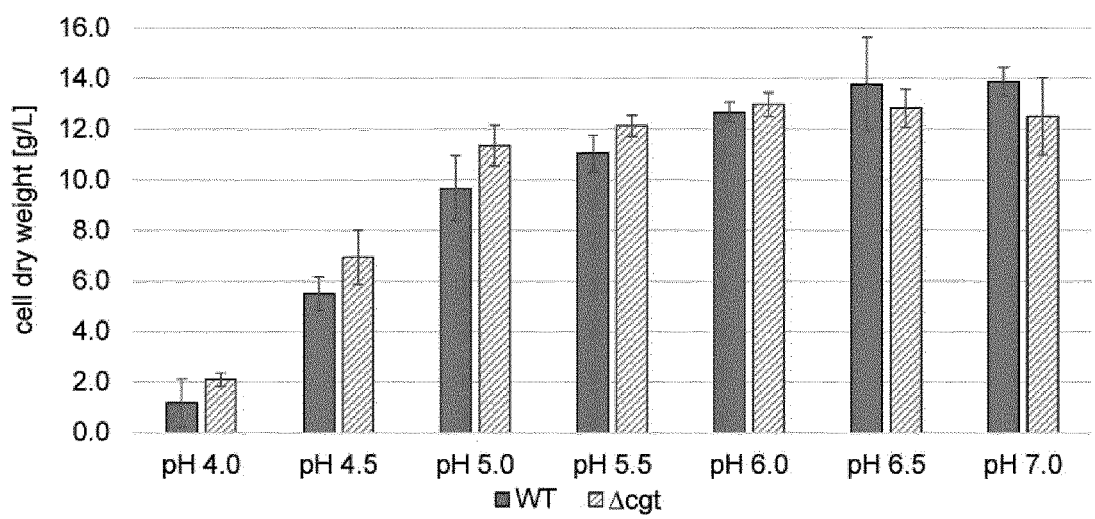
FIG. 15. Final cell dry weights of a pH screening experiment in maltose minimal medium. Wild type and Δcgt mutant of Actinoplanes sp. SE50/110 were grown in 1 mL reaction volume in a 48-well FlowerPlates in the RoboLector® system of m2p-labs. In pH ranging from 4 to 7, no significant differences in final cell dry weights were observed (tested by a two-sided t-test, $n_{wt}=3$, $n_{acgt}=4$).
Figure 16:
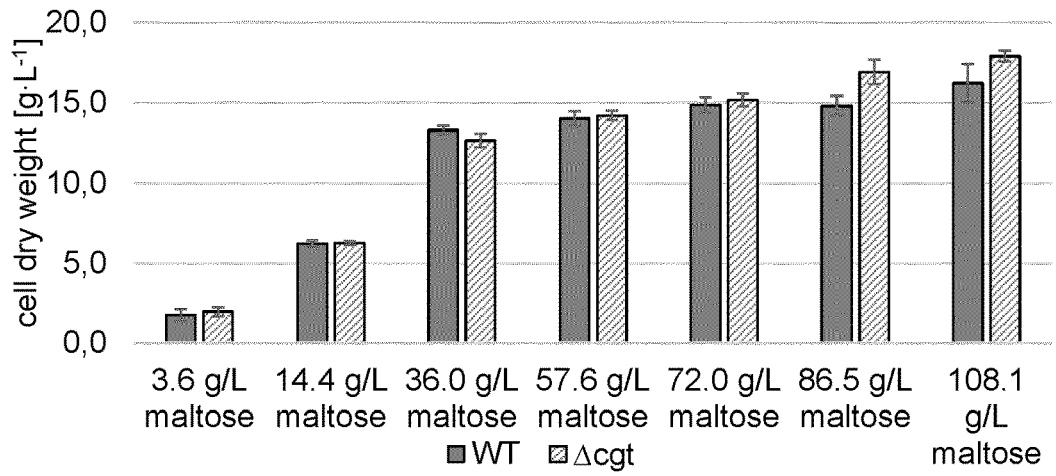
FIG. 16. Osmolarity tolerance screening in the RoboLector® system of m2p-labs: Final cell dry weights in maltose minimal medium with maltose monohydrate concentrations ranging between 3.6 and 108.1 g·L$^{-1}$. No significant growth differences were observed (tested by a two-sided t-test, $n_{wt}=3$, $n_{acgt}=4$).
Figure 17:
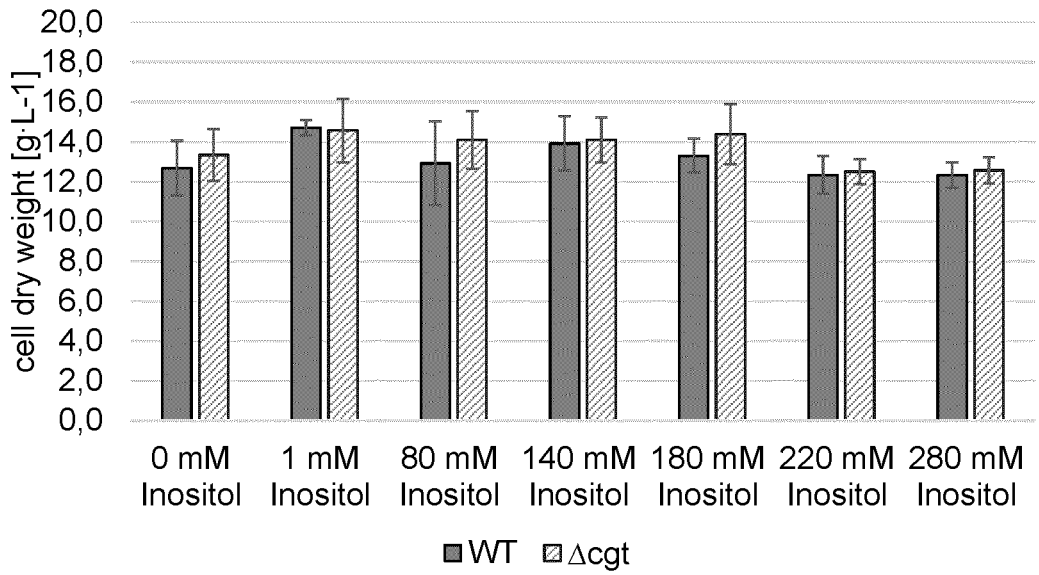
FIG. 17. Osmolarity tolerance screening in the RoboLector® system of m2p-labs: Final cell dry weights of an osmolarity-screening experiment in maltose minimal medium. The different osmolarities were achieved by addition of inositol in concentrations ranging from 0 mM to 280 mM. No significant growth differences between the wild type and Δcgt were observed (tested by a two-sided t-test, $n_{wt}=3$, $n_{acgt}=4$).

Furthermore, in comparison with the wildtype, the gene deletion mutant Δcgt displayed no apparent growth phenotype in screening experiments testing for different carbon sources, or under carbon-limited conditions (cf. examples "Analysis of cgt expression during growth on different carbon sources", "Δcgt on different carbon sources or under carbon-limited conditions", FIG. 12, FIG. 13, FIG. 14), or pH and osmolyte stress (cf. example "Δcgt has no impact on osmolarity- or pH-tolerance", FIG. 15, FIG. 16, FIG. 17). The inventors could furthermore show, that deletion of cgt had no negative impact on the expression of acarbose biosynthesis genes (cf. example "Δcgt has no impact on the expression of acarbose biosynthesis genes", FIG. 20).

Without being bound by theory, Cgt was found to be highly expressed in Actinoplanes sp. SE50/110 according to comprehensive studies of the extracellular proteome (Wendler et al. 2013; Ortseifen 2016) and transcriptome (Schwientek et al. 2013). Its gene product is exported into the extracellular space making up for about 8% of the whole secreted proteome. The inventors have analyzed the distribution of CBM-20 single-domain proteins in the prokaryotic world by BlastP analysis. Interestingly, singular CBM-20 domain-proteins were found in only 17 other species (cf. example "Distribution of single-domain CBM-20 proteins in the eubacterial world"). Most of these are found in species of the order Actinomycetales, for example in all strains of the genus Actinoplanes. Without being bound by theory, by deletion or reduced expression of cgt, energy and resources, such as ATP and amino acids, are relieved. These resources may then be redirected to the acarbose biosynthesis, which is a growth-associated product.

According to some embodiments according to the first aspect, the method comprises deletion or mutation of the gene encoding extracellular small carbohydrate binding protein Cgt (SEQ ID No. 20). The establishment of an intergeneric conjugation system (Gren et al. 2016) and the CRISPR/Cas9 technique (Wolf et al. 2016), allows genome editing in Actinoplanes sp. SE50/110. In some embodiments according to the first aspect engineering the Actinomycetales strain for absent or reduced expression may occur using CRISPR/Cas9 technique. In some embodiments, engineering the Actinomycetales strain for absent or reduced expression may occur as described by (Wolf et al. 2016). In some embodiments engineering the Actinomycetales strain for absent or reduced expression may occur as described herein, e.g. as described in the example "Deletion of the gene cgt by CRISPR/Cas9 technique" or "Deletion system based on homologous recombination and counterselection with the cytosine deaminase CodA". For example, the inventors have successfully established a novel deletion system by homologous recombination, which uses an integrase-free vector backbone and CodA for counter selection, like described by Zhao et al. (2017).

According to some second embodiments according to the first aspect, the method according to the first aspect comprises engineering the Actinomycetales strain for absent or reduced expression of at least one gene which is essential for carotenoid synthesis. In some embodiments, the carotenoid is the orange pigment of Actinoplanes or a derivative thereof. In some different or the same embodiments, the carotenoid is a C40-carotenoid.

Engineering the Actinomycetales strain for absent or reduced expression may occur as described previously for the current aspect. According to some embodiments according to the first aspect, the method comprises deletion or mutation of the gene which is essential for carotenoid synthesis.

Figure 22:
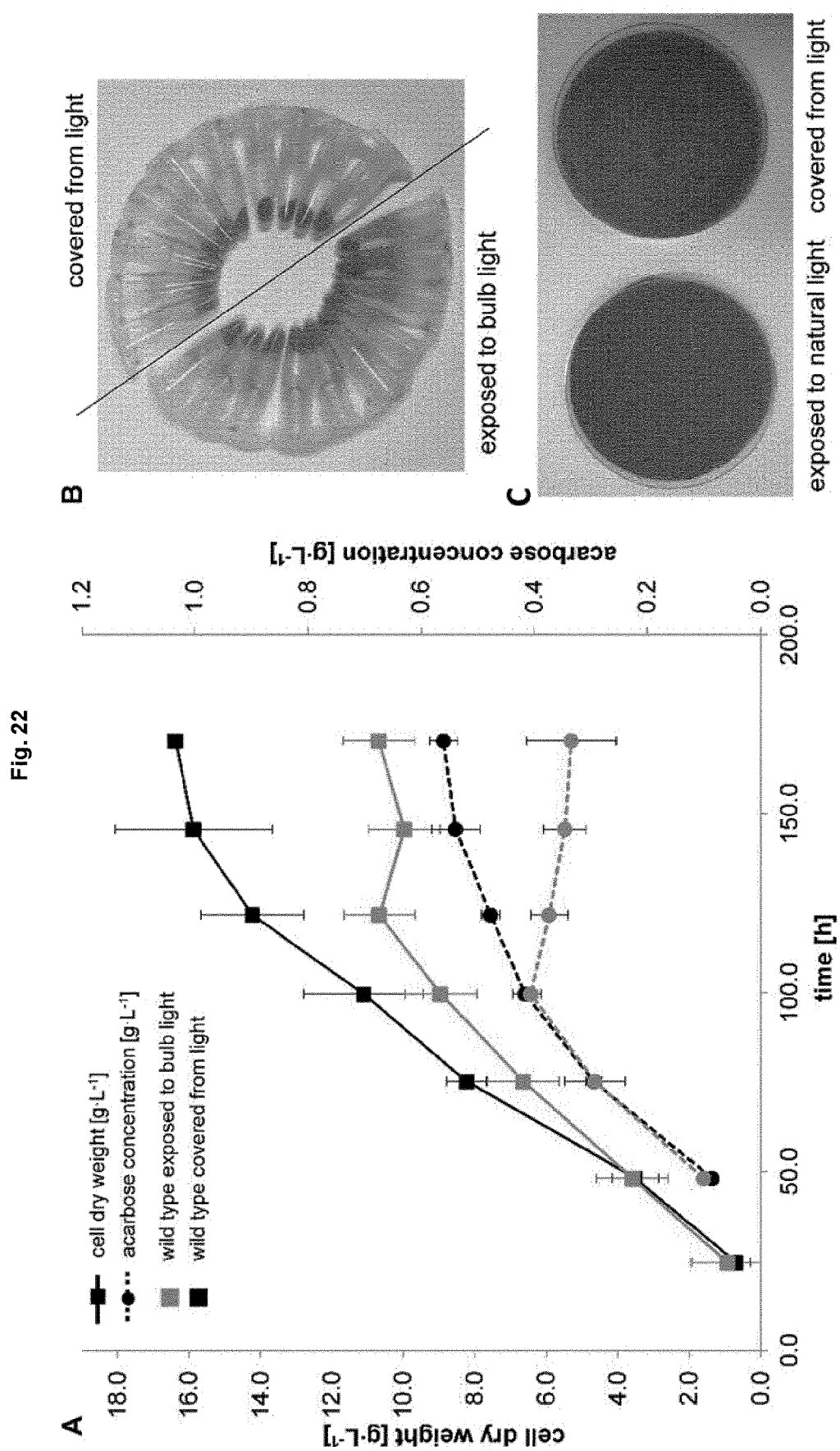
FIG. 22. Growth, acarbose and pigment formation of Actinoplanes sp. SE50/110 exposed to and covered from light. A. Cultivation of the wild type Actinoplanes sp. SE50/110 in maltose minimal medium exposed to or covered from bulb light (22-44 µE, 1 µE=µmol$_{photons}$ m$^2$ s$^{-1}$). Shown are the cell dry weights of five biological replicates and the acarbose concentration in the supernatant of three biological replicates. B. Pellets and supernatants at final cultivation time. C. Growth and pigment formation in solid culture on SFM agar plates exposed to or hidden from natural light.

Actinoplanes are known to produce a variety of soluble pigments including yellow, orange and pink pigments of the class carotenoids (Parenti and Coronelli 1979). The inventors observed, that strong pigmentation was associated with acarbose production losses. This was confirmed by comparing growth and acarbose yields of cultures exposed to and covered from light (cf. example "Light-dependent carotenoid-formation and oxidative stress reduce acarbose production in Actinoplanes sp. SE50/110", FIG. 22). While carotenoid formation was induced, acarbose production and growth of Actinoplanes sp. SE50/110 was strongly reduced, when exposed to bulb light (FIG. 22). In total, a loss of 39% of the final acarbose concentration was monitored.

From these findings it is not only plausible that the produced pigments are not essential (e.g. in a technical setup for commercial acarbose production) but also that reducing or depleting the carotenoid synthesis in Actinoplanes can be used to improve the acarbose formation. To this end, the method according to the first aspect comprises reducing or depleting the expression of at least one gene which is essential for carotenoid synthesis.

The inventors could furthermore reconstruct the carotenogenesis in Actinoplanes sp. SE50/110 (cf. example "Analysis of the functional relevance of carotenoid formation", FIG. 21). The set of genes which are essential for carotenoid synthesis in Actinoplanes include genes from the MEP/DOXP pathway, genes of terpene cluster 1, genes of terpene cluster 2a, genes of terpene cluster 2b, genes of camphene-like monoterpene biosynthesis terpene cluster 3.

According to some embodiments according to the current aspect and embodiments, the at least one gene essential for carotenoid synthesis is a gene of the MEP/DOXP pathway, such as i. 1-deoxy-D-xylulose-5-phosphate synthase gene dxs (ACSP50_7096, SEQ ID No. 23),
ii. 4-hydroxy-3-methylbut-2-en-1-yl diphosphate synthase gene ispG (ACSP50_7248, SEQ ID No. 24),
iii. 1-deoxy-D-xylulose-5-phosphate reductoisomerase gene dxr (ACSP50_7250, SEQ ID No. 25),
iv. 4-hydroxy-3-methylbut-2-enyl diphosphate reductase gene ispH (ACSP50_7707, SEQ ID No. 26),
v. 4-(cytidine 5'-diphospho)-2-C-methyl-D-erythritol kinase gene ispE (ACSP50_7802, SEQ ID No. 27),
vi. 2-C-methyl-D-erythritol 2;4-cyclodiphosphate synthase gene ispF, ACSP50_8046, SEQ ID No. 28), and/or
vii. 2-C-methyl-D-erythritol 4-phosphate cytidylyltransferase gene ispD (ACSP50_8047, SEQ ID No. 29).

According to some embodiments according to the current aspect and embodiments, the at least one gene essential for carotenoid synthesis is a gene of terpene cluster 1, such as i. isopentenyl-diphosphate delta-isomerase gene idi (ACSP50_0146, SEQ ID No. 30),
ii. zeta-phytoene desaturase gene crtI (ACSP50_0147, SEQ ID No. 10),
iii. polyprenyl synthetase gene crtE/IdsA (ACSP50_0148, SEQ ID No. 31),
iv. phytoene synthase gene crtB (ACSP50_0149, SEQ ID No. 32), v. deoxyribodipyrimidine photo-lyase gene (ACSP50_0150, SEQ ID No. 33), or vi. pyridine nucleotide-disulfide oxidoreductase gene (ACSP50_0151, SEQ ID No. 34).

According to some embodiments according to the current aspect and embodiments, the at least one gene essential for carotenoid synthesis is zeta-phytoene desaturase gene crtl (ACSP50_0147, SEQ ID No. 10). As discussed before, carotenoid formation is dispensable under laboratory conditions. In order to improve acarbose production, switching off the concurring carotenoid biosynthesis pathway, in particular by deletion of the central gene crtl, can be used for strain development.

According to some embodiments according to the current aspect and embodiments, the at least one gene essential for carotenoid synthesis is a gene of terpene cluster 2a, such as i. transcriptional regulator gene (ACSP50_1631, SEQ ID No. 35), ii. lycopene cyclase gene (ACSP50_1632, SEQ ID No. 36), iii. lycopene cyclase gene (ACSP50_1633, SEQ ID No. 37), iv. polyprenyl synthetase (farnesyl pyrophosphate synthetase 2 gene fps2/crtE (ACSP50_1634, SEQ ID No. 38), or v. methylenetetrahydrofolate reductase (NADPH) gene (ACSP50_1635, SEQ ID No. 39), According to some embodiments according to the current aspect and embodiments, the at least one gene essential for carotenoid synthesis is a gene of terpene cluster 2b, such as i. LysR-family transcriptional regulator gene (ACSP50_1650, SEQ ID No. 40), ii. methyltransferase type 11 gene (ACSP50_1651, SEQ ID No. 41), iii. CDP-alcoholphosphatidyltransferase pgsA (ACSP50_1652, SEQ ID No. 42), iv. zeta-phytoene desaturase (crtl-family) gene crtD (ACSP50_1653, SEQ ID No. 43), v. glycosyl transferase gene cruC (ACSP50_1654, SEQ ID No. 44), vi. hypothetical protein (put. membrane prot,) gene cruF, (ACSP50_1655, SEQ ID No. 45), vii. GCN5 family acetyltransferase gene (ACSP50_1656, SEQ ID No. 46), viii. monooxygenase gene (ACSP50_1657, SEQ ID No. 47), or ix. short-chain dehydrogenase gene (ACSP50_1658, SEQ ID No. 48), According to some embodiments according to the current aspect and embodiments, the at least one gene essential for carotenoid synthesis is polyprenyl synthetase gene crtE (ACSP50_3873, SEQ ID No. 49).

According to some embodiments according to the current aspect and embodiments, the at least one gene essential for carotenoid synthesis is a gene of camphene-like monoterpene biosynthesis terpene cluster 3, such as i. transcriptional regulator (Crp/Fnr family) gene eshA (ACSP50_1949, SEQ ID No. 104), ii. camphene synthase gene (ACSP50_1950, SEQ ID No. 50), iii. methyltransferase (SAM-dependent) type 11 gene (ACSP50_1951, SEQ ID No. 105), iv. glycosyl-hydrolase gene (ACSP50_1952, SEQ ID No. 106), or v. oxidoreductase/aldo/ketoreductase (ACSP50_1953, SEQ ID No. 107).

Since carotenoids influence the fluidity of membranes, lack of carotenoids and in particular of the C40-carotenoid can also affect the surface and mycelial structure of Actinoplanes sp. SE50/110. With regard to production break-up of mycelial lumps is advantageous to increase the mycelial surface and the number of biochemically available cells.

According to some further embodiments, the method according to the first aspect comprises engineering the Actinomycetales strain for overexpression of MerR-/HTH-transcriptional regulator gene merR (ACSP50_0145, SEQ ID No. 11). Engineering the Actinomycetales strain for overexpression may occur as described elsewhere herein.

Beside the mentioned genes which are essential for carotenoid synthesis, the inventors surprisingly identified a transcriptional repressor for the carotenoid synthesis among the genes of terpene cluster 1: ACSP50_0145 (SEQ ID No. 11, MerR-/HTH-transcriptional regulator gene merR) cf. example "Deletion of merR in SE50/110 induces carotenoid formation without exposure to light", FIG. 24. By CRISPR/Cas9 deletion of the corresponding gene in SE50/110, the carotenoid formation was strongly induced without exposure to light (FIGS. 24B and C). Consistent with this, the acarbose production was found to be decreased. When illuminated, both wild type and ΔmerR are strongly pigmented and the final acarbose concentrations were similar for both strains, reaching approx. 0.52 g·L$^{-1}$ (FIGS. 24B and D). This corresponds to a reduction of acarbose formation of approx. 38% compared to the wild type under dark conditions (reaching 0.83 g·L$^{-1}$). This is in accordance to the previous growth experiments of the wild type. Under dark conditions, ΔmerR produces approx. 15% less acarbose than the wild type (0.70 g·L$^{-1}$) (FIG. 24D). Without being bound by theory, these production losses are assumed to be caused by the waste of resources by carotenoid formation in the deletion mutant (FIG. 24C). In conclusion, the production losses under light conditions (38-39%) might be assigned to further light-induced stress in both the deletion mutant and the wild type.

According to some third embodiments according to the first aspect the method comprises engineering the Actinomycetales strain for overexpression of dTDP-D-glucose-4, 6-dehydratase AcbB (SEQ ID No. 13).

According to the current invention it was surprisingly found that overexpression of the acb gene encoding the dTDP-D-glucose-4,6-dehydratase AcbB increased the final acarbose concentration significantly by approx. 50%. This was particularly surprising, because other genes of the Acb cluster such as AcbC did not lead to an improved formation of acarbose. Furthermore, the observed increase was superior compared to the observed increase for overexpression of the complete Acb cluster as described by Zhao et al. (Zhao, Xie, et al. 2017). According to some embodiments, the strain does not comprise engineering the Actinomycetales strain for overexpression of other genes of the Acb cluster, except for AcbA.

The dTDP-D-glucose-4,6-dehydratase AcbB seems to be involved in the generation of an activated amino sugar from D-glucose-1P which is a feeding pathway of the acarbose biosynthesis (FIG. 1): Without being bound by theory, increased AcbB activity was surprisingly found to also improve the supply of the modified precursor.

Overexpression of AcbB as described herein refers to an increase in expression for AcbB compared to the wild type or a specified reference strain/control. For example, the overexpression of the gene product may be an increase during the early growth phase, during the linear growth phase, during the stationary phase or an increase during any other time. Preferably, as described herein, overexpression of AcbB refers to an increase of AcbB transcript and/or protein by a factor of at least 1.5 or at least a factor of 2 compared to the control. With regard to AcbB transcript amounts, and if not defined otherwise herein, strong overexpression refers to a log 2 (fold change)>6. With regard to AcbB transcript amounts and if not defined otherwise herein, medium strong overexpression refers to a log 2 (fold change)≥2 and ≤6.

According to some embodiments the overexpression of dTDP-D-glucose-4,6-dehydratase AcbB (SEQ ID No. 13) is the increase of the expression of AcbB transcript and/or protein by a factor of a log 2 (fold change) of at least 1.5 or at least 2, during the early growth phase, during the linear growth phase, during the stationary phase or an increase during any other time.

According to some embodiments the overexpression of dTDP-D-glucose-4,6-dehydratase AcbB (SEQ ID No. 13) is the increase of the expression of AcbB transcript and/or protein by a log 2 (fold change)>2 and ≤6 during the early growth phase, during the linear growth phase, during the stationary phase or an increase during any other time, such as during the early growth phase and/or during the linear growth phase.

According to some embodiments the overexpression of dTDP-D-glucose-4,6-dehydratase AcbB (SEQ ID No. 13) is the increase of the expression of AcbB transcript and/or protein by a log 2 (fold change)>3 and <5 during the early growth phase, during the linear growth phase, during the stationary phase or an increase during any other time.

According to some embodiments the overexpression of dTDP-D-glucose-4,6-dehydratase AcbB (SEQ ID No. 13) is the increase of the expression of AcbB transcript and/or protein by a log 2 (fold change)>6 during the early growth phase, during the linear growth phase, during the stationary phase or an increase during any other time.

In overexpression mutants with expression vectors comprising heterologous promoters the relative transcription of acbB decelerated from 4.06- to 3.33-fold (log 2 (fold change)) between the two sampling times in pSETT4tip::acbB (medium strong promoter) and from 6.54- to 2.05-fold in in pSETT4gap::acbB (strong promoter) (cf. example "Medium overexpression of acbB leads to improved acarbose formation").

According to some embodiments, engineering the Actinomycetales strain for overexpression of a gene according to the first aspect may occur by any method known in the art or described herein.

Figure 27:
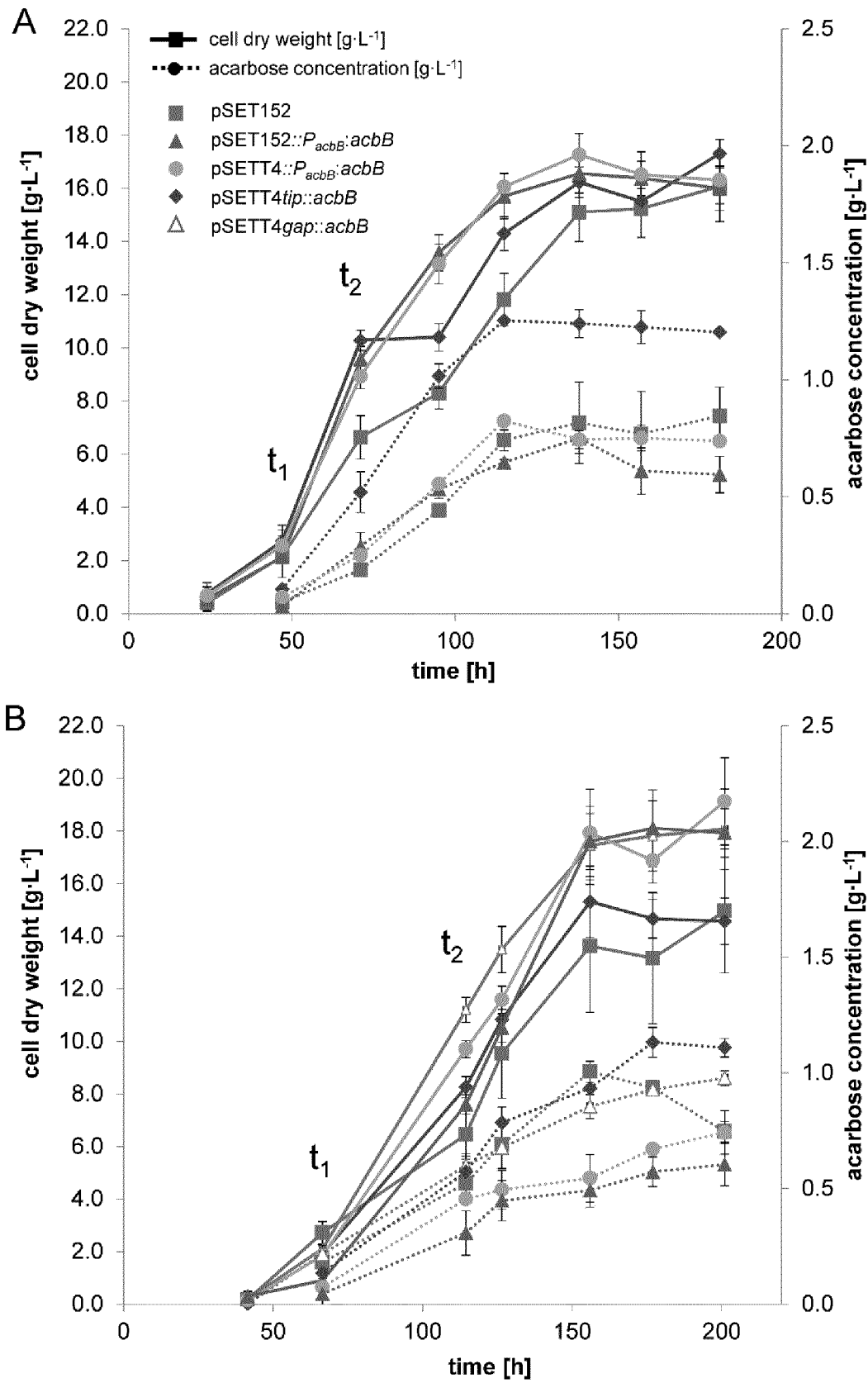
FIG. 27. Growth and acarbose production of acbB overexpression strains in maltose minimal medium. Shown are two independent cultivations (A and B). The sampling times for RNA-isolation are indicated by $t_1$ ("early growth phase") and $t_2$ ("linear growth phase").
Figure 28:
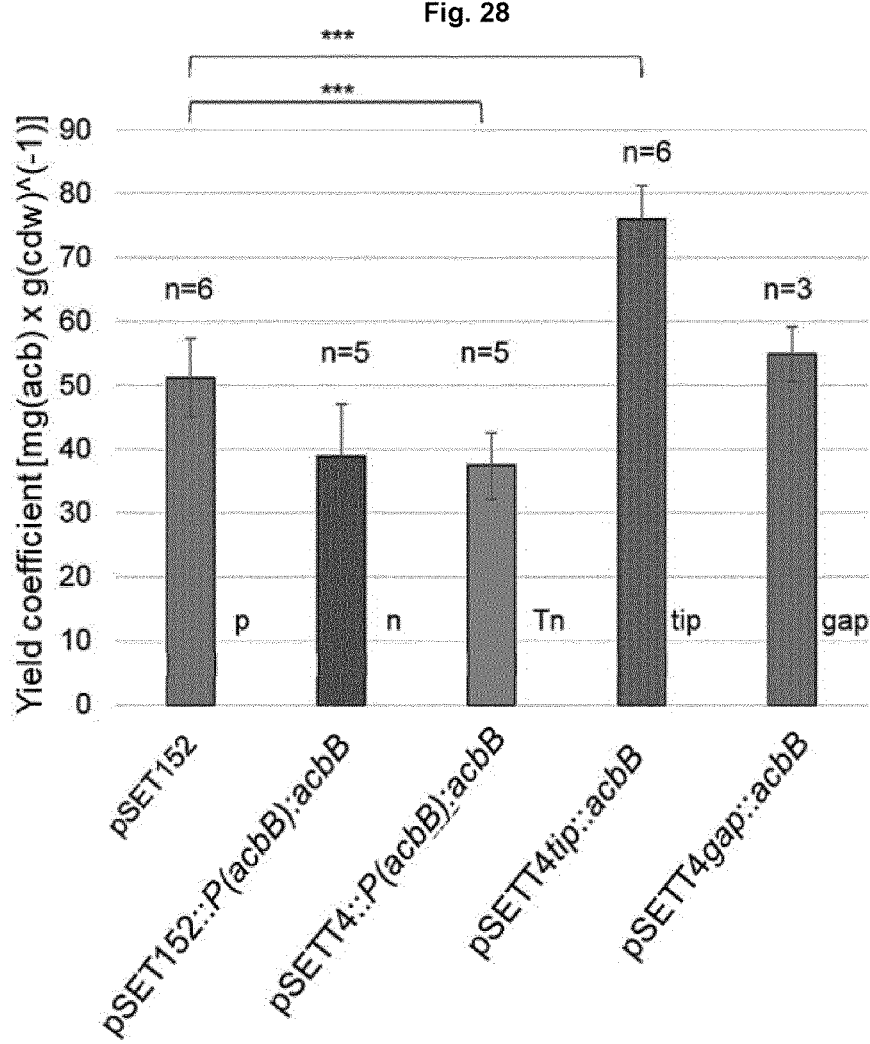
FIG. 28. Yield coefficient of acbB overexpression mutants in maltose minimal medium. The mutant with acbB transcribed under control of the heterologous tipA-promoter displayed an enhanced yield coefficient (approx. 50%), whereas only minor differences were observed for the construct with gapDH-promoter. Errors were calculated by Gaussian error propagation. All differences were tested for significance by a two-sided t-test (abbreviations assigned in the picture). Asterisks indicate the significance level: * p-value<a=5%, p-value<a=1%, *p-value<a=0.1%.

As described within the example "Medium overexpression of acbB leads to improved acarbose formation", two pSETT4-based overexpression mutants were created, in which acbB is transcribed under control of the medium strong tipA-promoter or the strong gapDH-promoter. The native promoter was used in both the pSET152- and the pSETT4-vector background as control. In particular the mutant with acbB transcribed under control of the heterologous tipA-promoter displayed enhanced acarbose production compared to the control strains (FIG. 27, FIG. 28). The yield coefficient was increased to 48.6 and 51.9% compared to the empty vector control. By usage of the strong gapDH-promoter, the acarbose yield coefficient was found to be slightly increased (FIG. 28).

According to some embodiments, engineering the Actinomycetales strain for overexpression of a gene according to the first aspect may occur by introducing a vector comprising an expression cassette for AcbB (SEQ ID No. 13) into the Actinomycetales strain. In some embodiments, the expression vector is derived from pSET152. In some embodiments, the expression vector is derived from pSETT4. A vector is derived from another vector, if it comprises at least one, two, three, four elements of the second vector.

According to some embodiments, engineering the Actinomycetales strain for overexpression of a gene according to the first aspect may occur by introducing a vector comprising an expression cassette for AcbB (SEQ ID No. 13) into the Actinomycetales strain. In some of these or other embodiments the expression cassette is under the control of a medium strong promoter, as characterized by a normalized glucuronidase activity of at least $1 \times 10^{-4}$, preferably between $1 \times 10^{-4}$ and $5 \times 10^{-4}$ $[L \cdot g^{-1} \cdot min^{-1}]$ in a glucuronidase assay, e.g. as described elsewhere herein. In some embodiments said promoter is selected from efp promoter (SEQ ID No. 92), cdaR promoter (SEQ ID No. 97), rpsL promoter (SEQ ID No. 99), rpsJ promoter (SEQ ID No. 93), cgt promoter (SEQ ID No. 91), or tipA promoter (SEQ ID No. 81). In some embodiments the promoter is the tipA promoter (SEQ ID No. 81). Excellent results for acarbose production were obtained with pSETT4tip::acbB, cf. FIG. 27, FIG. 28.

In some embodiments the expression cassette is under the control of a strong promoter, as characterized by a normalized glucuronidase activity of at least $5 \times 10^{-5}$ $[L \cdot g^{-1} \cdot min^{-1}]$ in a glucuronidase assay, e.g. as described elsewhere herein. In some embodiments said promoter is selected from apm promoter (SEQ ID No. 96), ermE*promoter (SEQ ID No. 98), katE promoter (SEQ ID No. 94), moeE5 promoter (SEQ ID No. 95) or gapDH promoter (SEQ ID No. 82).

According to some embodiments, the method according to the first aspect comprises engineering the Actinomycetales strain for medium overexpression of dTDP-D-glucose-4,6-dehydratase AcbB (SEQ ID No. 13) and optionally AcbA (SEQ ID No. 12). In some embodiments, which are also compatible with all other embodiments described herein if not explicitly stated otherwise, genetic engineering does not result in an increase of transcript and/or protein by a log 2 (fold change)≥2 for Acb genes other than AcbB and AcbA. In some of embodiments which are also compatible with all other embodiments described herein, genetic engineering does not result in an increase of transcript and/or protein by a log 2 (fold change)≥ 2 for AcbC.

Figure 30:
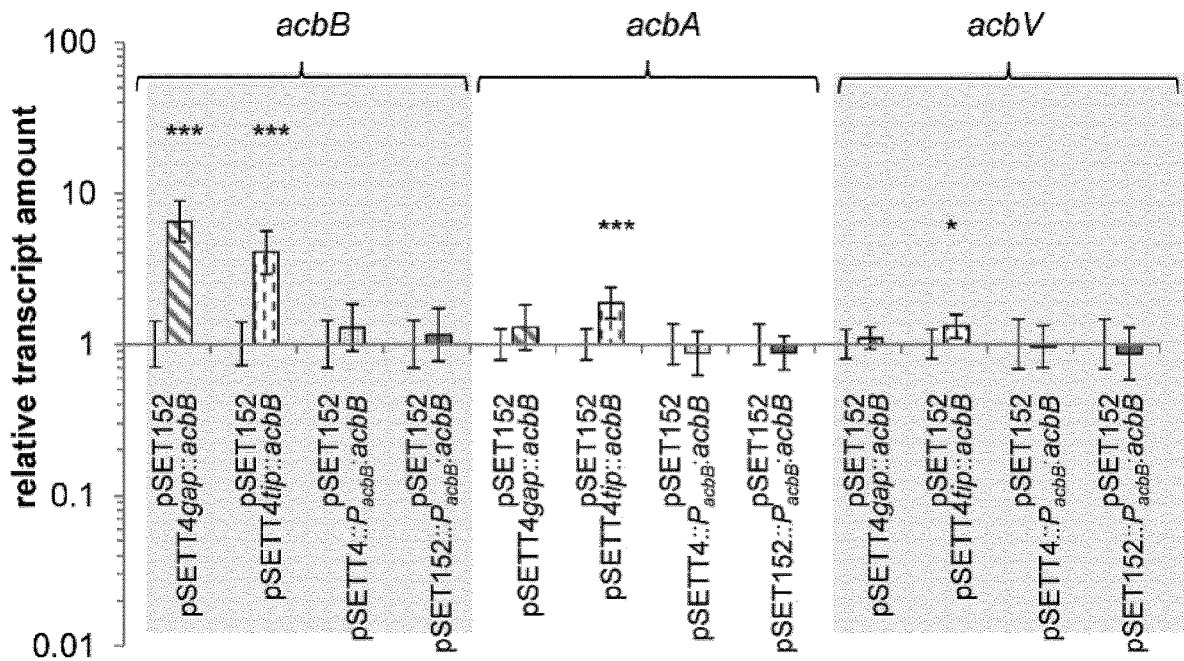
FIG. 30. Relative transcript amounts of the genes acbB, acbA and acbV in acbB-overexpression mutants in the initial growth phase. Shown are the means and standard deviations of at least three biological replicates. The differences to the empty vector control (set to a value of 1) were tested by a two-sided t-test (p-values from left to right corresponding to pSETT4gap: acbB, pSETT4tip: acbB, pSETT4: $P_{acbB}$: acbB, pSET152: $P_{acbB}$: acbB): acbB: 4.332e-05, 4.561e-06, 0.3511, 0.7082; acbA: 0.3384, 0.0001164, 0.5967, 0.4246; acbV: 0.3033, 0.0423, 0.73, 0.4687). Asterisks indicate the significance level: * p-value<a=5%, p-value<a=1%, *p-value<a=0.1%.

Upon overexpression of AcbB, further genes of the acb gene cluster were not significantly affected, e.g. in the early growth phase, like shown for acbA and acbV (FIG. 30). Only exception is a slightly higher transcription abundance of acbA in pSETT4tip: acbB (log 2 (fold change)=1.87).

According to some embodiments, the method according to the first aspect comprises engineering the Actinomycetales strain for overexpression of AcbB (SEQ ID No. 13) and AcbS (ACSP50_3596) and/or Acbl (ACSP50_3599).

By (additional) overexpression of AcbS and/or Acbl, the transfer reaction of the amino sugar to the cyclitol precursor can be strengthened. According to the current model (see FIG. 1), this reaction is catalyzed by AcbS (ACSP50_3596) or Acbl (ACSP50_3599).

According to some embodiments, the method according to the first aspect comprises engineering the Actinomycetales strain for overexpression of AcbB (SEQ ID No. 13) and AcbCUJ (AcbC (ACSP50_3607) and/or AcbU (ACSP50_3595) and/or AcbJ (ACSP50_3600)) and/or AcbSI (AcbS (ACSP50_3596) and/or Acbl (ACSP50_3599)). Without being bound by theory, this combination can plausibly reinforce both acarbose synthesis strands.

According to some fourth embodiments according to the first aspect, the method comprises engineering the Actinomycetales strain for overexpression of UDP-glucose-1P uridyltransferase GtaB (SEQ ID No. 19).

Figure 32:
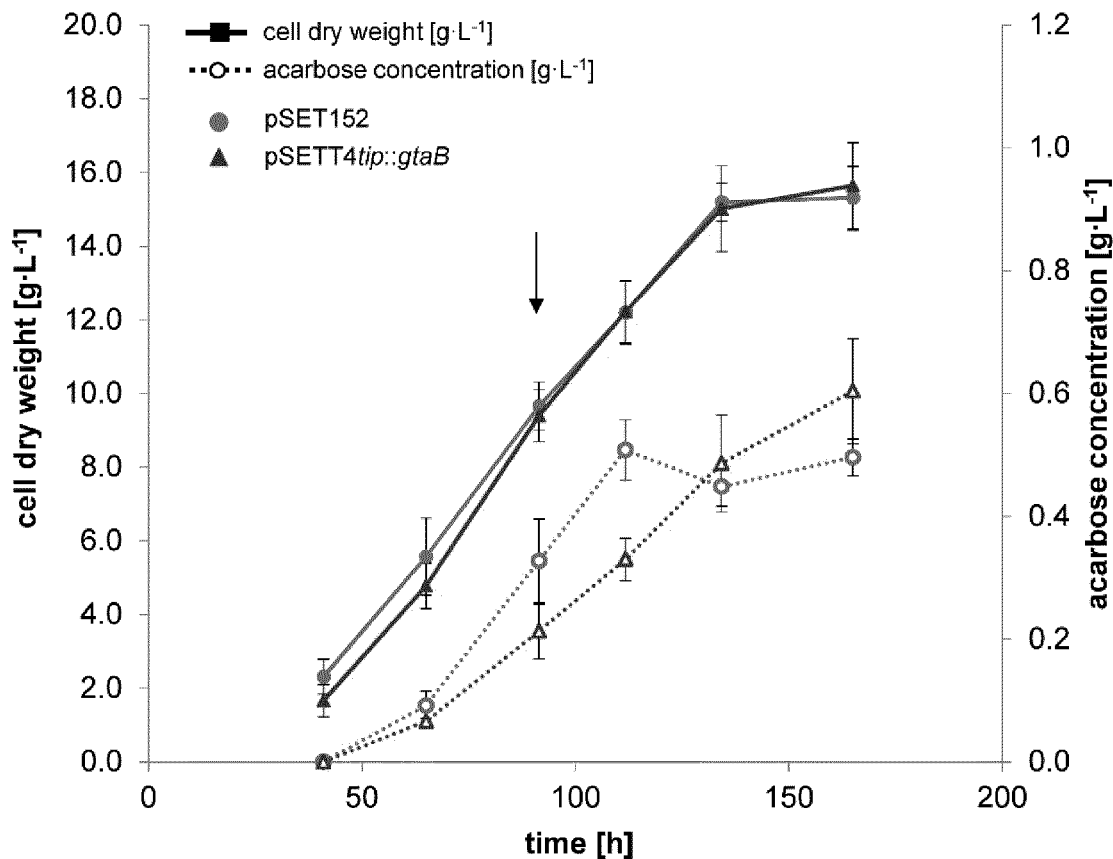
FIG. 32. Growth and acarbose production of a gtaB overexpression mutant in maltose minimal medium. The sampling time for RNA-isolation is indicated by an arrow.
Figure 33:
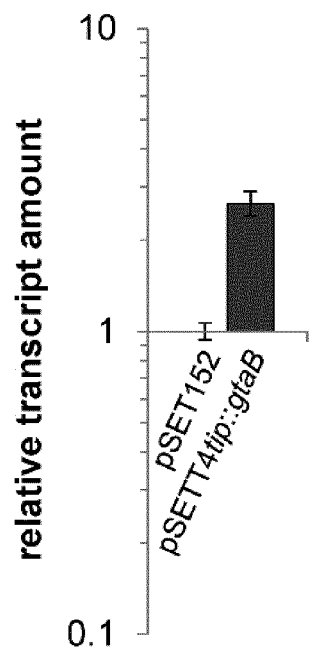
FIG. 33. Relative transcript amount of gtaB in an overexpression mutant. The RT-qPCR indicates significant increase of gtaB expression compared to the empty vector control (set to a value of 1) (p-value of a two-sided t-test: 0.01295). Asterisk indicates the significance level: * p-value<a=5%, **p-value<a=1.

By medium overexpression of gtaB, an increase of 8.5% of the final acarbose concentration was observed, cf. example "Medium overexpression of gtaB leads to improved acarbose formation", FIG. 32, FIG. 33. Interestingly, the acarbose formation is particularly increased in the late linear to stationary growth phase (FIG. 32). Without being bound by theory, this may result from the improved deployment of the precursor glucose-1P (cf. FIG. 34).

Overexpression of GtaB (SEQ ID No. 19) as described herein refers to an increase in expression for GtaB transcript and/or protein compared to the wild type or a specified reference strain/control. For example, the overexpression of the gene product may be an increase during the early growth phase and/or during the linear growth phase and/or during the stationary phase, and/or an increase during any other time.

Preferably, overexpression is an increase of GtaB transcript and/or protein by a factor of at least 1.5 or at least a factor of 2 compared to the control. With regard to GtaB transcript amounts and if not defined otherwise herein, strong overexpression refers to a log 2 (fold change)>6. With regard to GtaB transcript amounts and if not defined otherwise herein, medium strong overexpression refers to a log 2 (fold change)≥2 and ≤6.

According to some embodiments the overexpression of UDP-glucose-1P uridyltransferase GtaB is the increase of the expression of GtaB by a factor of a log 2 (fold change) of at least 1.5 or at least 2 during the early growth phase and/or during the linear growth phase and/or during the stationary phase, and/or an increase during any other time.

In one of the overexpression mutants described herein, the relative transcript amount of the gene gtaB is 2.64-fold increased (log 2 (fold change)) (FIG. 33).

According to some embodiments the overexpression of UDP-glucose-1P uridyltransferase GtaB is the increase of the expression of GtaB transcript and/or protein by a log 2 (fold change)≥2 and ≤6 during the early growth phase and/or during the linear growth phase and/or during the stationary phase, and/or an increase during any other time. According to some embodiments the overexpression of UDP-glucose-1P uridyltransferase GtaB is the increase of the expression of GtaB by a log 2 (fold change)>3 and ≤5 during the early growth phase and/or during the linear growth phase and/or during the stationary phase, and/or an increase during any other time. According to some embodiments the overexpression of UDP-glucose-1P uridyltransferase GtaB is the increase of the expression of GtaB by a log 2 (fold change) ≥6 during the early growth phase and/or during the linear growth phase and/or during the stationary phase.

According to some embodiments, engineering the Actinomycetales strain for overexpression of a gene according to the first aspect may occur by introducing a vector comprising an expression cassette for GtaB (SEQ ID No. 19) into the Actinomycetales strain. In some embodiments, the expression vector is derived from pSET152. In some embodiments, the expression vector is derived from pSETT4. A vector is derived from another vector, if it comprises at least one, two, three, four elements of the second vector.

According to some embodiments, engineering the Actinomycetales strain for overexpression of a gene according to the first aspect may occur by introducing a vector comprising an expression cassette for GtaB (SEQ ID No. 19) into the Actinomycetales strain.

In some of these or other embodiments the expression cassette is under the control of a medium strong promoter, as characterized by a normalized glucuronidase activity of between $1 \times 10^{-4}$ and $5 \times 10^{-5}$ [L·g$^{-1}$·min$^{-1}$] in a glucuronidase assay, e.g. as described elsewhere herein. In some embodiments said promoter is selected from efp promoter (SEQ ID No. 92), cdaR promoter (SEQ ID No. 97), rpsL promoter (SEQ ID No. 99), rpsJ promoter (SEQ ID No. 93), cgt promoter (SEQ ID No. 91), or tipA promoter (SEQ ID No. 81). In some embodiments the promoter is the tipA promoter (SEQ ID No. 81). Good results for acarbose production were obtained for example with pSETT4tip::gtaB, cf. FIG. 32, FIG. 33.

In some embodiments the expression cassette is under the control of a strong promoter, as characterized by a normalized glucuronidase activity of at least $5 \times 10^{-5}$ [L·g$^{-1}$·min$^{-1}$] in a glucuronidase assay, e.g. as described elsewhere herein. In some embodiments said promoter is selected from apm promoter (SEQ ID No. 96), ermE*promoter (SEQ ID No. 98), katE promoter (SEQ ID No. 94), moeE5 promoter (SEQ ID No. 95) or gapDH promoter (SEQ ID No. 82).

According to some further or the same embodiments of the first aspect, the method comprises engineering the Actinomycetales strain for medium overexpression of dTDP-D-glucose-4,6-dehydratase AcbB (SEQ ID No. 13) and GtaB (SEQ ID No. 19).

It was surprisingly found that overexpression of GtaB triggers improved acarbose formation. By medium overexpression of acbB (e.g. by use of the tipA-promoter), a positive effect on acarbose production was observed yielding approx. 50% more acarbose in two independent cultivations.

Therefore, the improvement of the acarbose biosynthesis by overexpression of singular acb gene AcbB was achieved. Furthermore, by medium overexpression of gtaB, an increase of 8.5% of the final acarbose concentration was observed. It is plausible, that by a combined overexpression of acbB and gtaB, the flux through the amino sugar biosynthesis is improved leading to a further enhancement of acarbose production.

Without being bound by theory, strong overexpression of AcbB induced only smaller increases of acarbose production compared to medium strong overexpression of AcbB. This may be due to an imbalance in glucose-phosphate-metabolism, occurring upon massive overexpression of AcbB. Overexpression of gtaB might cure this imbalance, and combined overexpression of both, acbB and gtaB therefore plausibly leads to a further increase in acarbose production.

Figure 34:
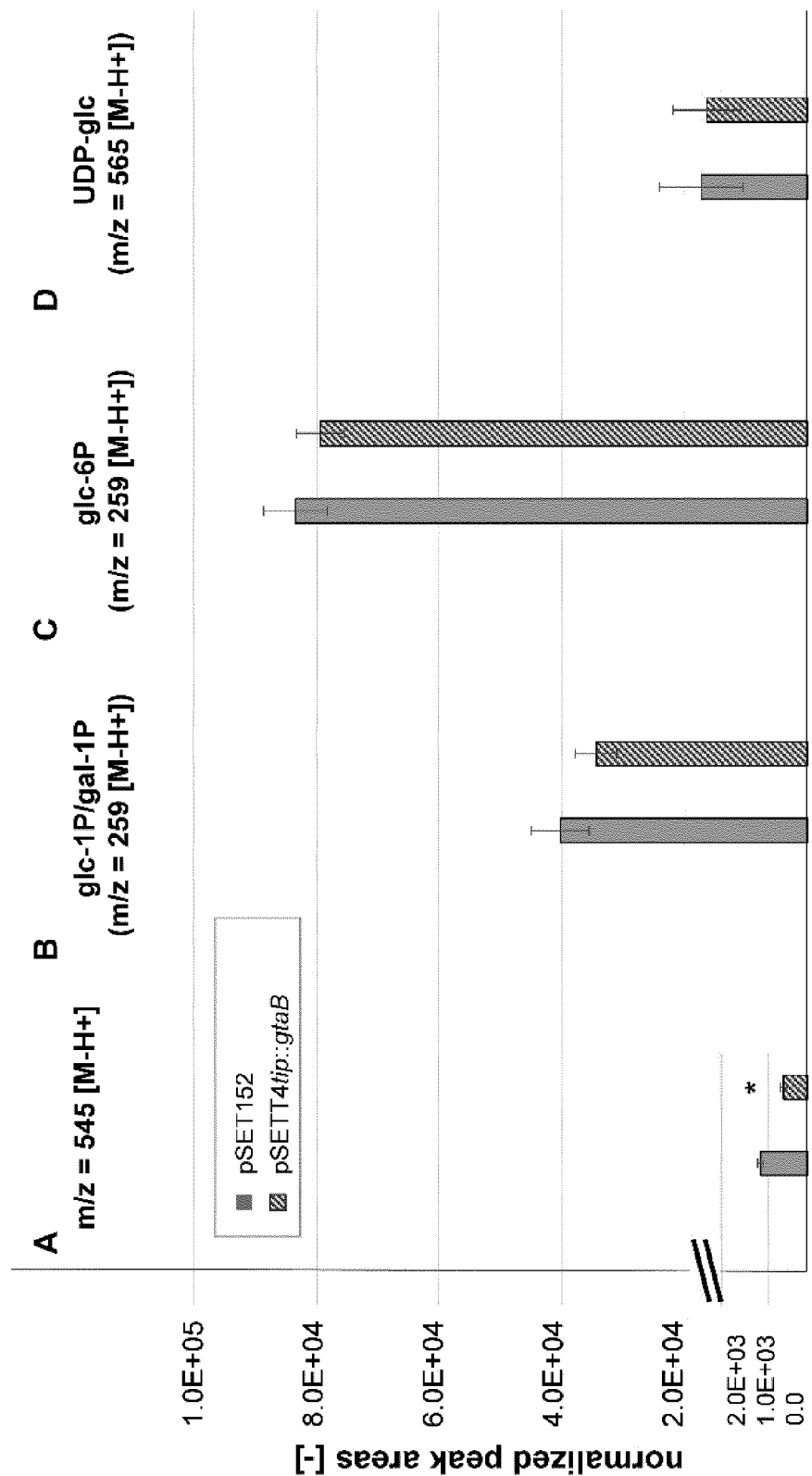
FIG. 34. Analysis of the intracellular metabolites of a gtaB-overexpression mutant by LC-MS. Shown are the peak areas of the masses m/z=545 [M–H$^+$](A), glucose-1P and galactose-1P (m/z=259 [M–H$^+$], B), glucose-6P (m/z=259 [M–H$^+$], C) and UDP-glucose (m/z=565 [M–H$^+$], D) in an overexpression strain of the gene gtaB. Significant differences compared to the empty vector control were observed for the normalized peak areas of the mass m/z=545 [M–H$^+$] (p-value of a two-sided t-test: 0.01531). All other peak areas are not significantly different according to a two-sided t-test.

Interestingly, a significant decreased amount of the mass m/z=545 [M-H$^+$] was found in pSETT4tip::gtaB (approx. decrease of 48%), which might correspond to dTDP-4-keto-6-deoxy-D-glucose, the proposed product of AcbB. This may indicate, that the flow through the synthesis strand is more balanced, since the accumulation of this metabolite is reduced in comparison to the empty vector control and AcbB-overexpression mutants (FIG. 34).

According to some embodiments, the method according to the first aspect comprises engineering the Actinomycetales strain
  (i) for absent or reduced expression of extracellular small carbohydrate binding protein Cgt (SEQ ID No. 20) and/or,
  (ii) for absent or reduced expression of at least one gene involved in carotenoid synthesis, and/or,
  (iii) for overexpression of dTDP-D-glucose-4,6-dehydratase AcbB (SEQ ID No. 13), and/or (iv) for overexpression of UDP-glucose-1P uridyltransferase GtaB (SEQ ID No. 19).

According to some embodiments; the method according to the first aspect further comprises engineering the Actinomycetales strain for absent or reduced expression of treY.

According to some embodiments, the method according to the first aspect further comprises
- (i) deletion or mutation of the gene encoding extracellular small carbohydrate binding protein Cgt (SEQ ID No. 20) and/or,
- (ii) deletion or mutation of at least one gene involved in carotenoid synthesis and/or,
- (iii) introducing a vector comprising an expression cassette for AcbB (SEQ ID No. 13) into the Actinomycetales strain and/or
- (iv) introducing a vector comprising an expression cassette for GtaB (SEQ ID No. 19) into the Actinomycetales strain.

According to some embodiments, the expression cassette according to (iii) and/or (iv) is under the control of a medium strong promoter, as characterized by a normalized glucuronidase activity of between $1 \times 10^{-4}$ and $5 \times 10^{-5}$ [L·g$^{-1}$·min$^{-1}$] in a glucuronidase assay.

According to a second aspect there is provided an Actinomycetales strain, such as an Actinoplanes strain, for the production of acarbose. According to some embodiments the Actinomycetales strain is a strain generated by a method according to the first aspect. According to some other embodiments the Actinomycetales strain is genetically engineered for absent or reduced expression of extracellular small carbohydrate binding protein Cgt (SEQ ID No. 20). According to some embodiments the Actinomycetales strain is a Δcgt mutant. A Δcgt mutant is a variant of an Actinomycetales strain wherein the gene Cgt (SEQ ID No. 20) has been at least partially deleted or inverted.

According to some of these or other embodiments the Actinomycetales strain is genetically engineered for absent or reduced expression of at least one gene which is essential for carotenoid synthesis. According to some embodiments the at least one gene which is essential for carotenoid synthesis has been at least partially deleted or inverted. According to some of these embodiments the at least one gene which is essential for carotenoid synthesis comprises at least one gene selected from any of
- a. the genes of the MEP/DOXP pathway, such as
  - i. 1-deoxy-D-xylulose-5-phosphate synthase gene dxs (ACSP50_7096, SEQ ID No. 23),
  - ii. 4-hydroxy-3-methylbut-2-en-1-yl diphosphate synthase gene ispG (ACSP50_7248, SEQ ID No. 24),
  - iii. 1-deoxy-D-xylulose-5-phosphate reductoisomerase gene dxr (ACSP50_7250, SEQ ID No. 25),
  - iv. 4-hydroxy-3-methylbut-2-enyl diphosphate reductase gene ispH (ACSP50_7707, SEQ ID No. 26),
  - v. 4-(cytidine 5'-diphospho)-2-C-methyl-D-erythritol kinase gene ispE (ACSP50_7802, SEQ ID No. 27),
  - vi. 2-C-methyl-D-erythritol 2;4-cyclodiphosphate synthase gene ispF, ACSP50_8046, SEQ ID No. 28), and/or
  - vii. 2-C-methyl-D-erythritol 4-phosphate cytidylyltransferase gene ispD (ACSP50_8047, SEQ ID No. 29),
- b. the genes of terpene cluster 1, such as
  - i. isopentenyl-diphosphate delta-isomerase gene idi (ACSP50_0146, SEQ ID No. 30),
  - ii. zeta-phytoene desaturase gene crtI (ACSP50_0147, SEQ ID No. 10),
  - iii. polyprenyl synthetase gene crtE/IdsA (ACSP50_0148, SEQ ID No. 31),
  - iv. phytoene synthase gene crtB (ACSP50_0149, SEQ ID No. 32),
  - v. deoxyribodipyrimidine photo-lyase gene (ACSP50_0150, SEQ ID No. 33), or
  - vi. pyridine nucleotide-disulfide oxidoreductase gene (ACSP50_0151, SEQ ID No. 34)
- c. the genes of terpene cluster 2a, such as
  - i. transcriptional regulator gene (ACSP50_1631, SEQ ID No. 35),
  - ii. lycopene cyclase gene (ACSP50_1632, SEQ ID No. 36),
  - iii. lycopene cyclase gene (ACSP50_1633, SEQ ID No. 37),
  - iv. polyprenyl synthetase (farnesyl pyrophosphate synthetase 2 gene fps2/crtE (ACSP50_1634, SEQ ID No. 38), or
  - v. methylenetetrahydrofolate reductase (NADPH) gene (ACSP50_1635, SEQ ID No. 39),
- d. the genes of terpene cluster 2b, such as
  - i. LysR-family transcriptional regulator gene (ACSP50_1650, SEQ ID No. 40),
  - ii. methyltransferase type 11 gene (ACSP50_1651, SEQ ID No. 41),
  - iii. CDP-alcoholphosphatidyltransferase pgsA (ACSP50_1652, SEQ ID No. 42),
  - iv. zeta-phytoene desaturase (crtI-family) gene crtD (ACSP50_1653, SEQ ID No. 43),
  - v. glycosyl transferase gene cruC (ACSP50_1654, SEQ ID No. 44),
  - vi. hypothetical protein (put. membrane prot,) gene cruF, (ACSP50_1655, SEQ ID No. 45),
  - vii. GCN5 family acetyltransferase gene (ACSP50_1656, SEQ ID No. 46),
  - viii. monooxygenase gene (ACSP50_1657, SEQ ID No. 47),
  - ix. short-chain dehydrogenase gene (ACSP50_1658, SEQ ID No. 48),
- e. polyprenyl synthetase gene crtE (ACSP50_3873, SEQ ID No. 49), or
- f. the genes for camphene-like monoterpene biosynthesis terpene cluster 3, such as
  - i. transcriptional regulator (Crp/Fnr family) gene eshA (ACSP50_1949, SEQ ID No. 104),
  - ii. camphene synthase gene (ACSP50_1950, SEQ ID No. 50),
  - iii. methyltransferase (SAM-dependent) type 11 gene (ACSP50_1951, SEQ ID No. 105),
  - iv. glycosyl-hydrolase gene (ACSP50_1952, SEQ ID No. 106),
  - v. oxidoreductase/aldo/ketoreductase (ACSP50_1953, SEQ ID No. 107).

According to some of these or other embodiments the Actinomycetales strain is genetically engineered for overexpression of MerR-/HTH-transcriptional regulator gene merR (ACSP50_0145, SEQ ID No. 11).

According to some of these or other embodiments the Actinomycetales strain is genetically engineered for overexpression of dTDP-D-glucose-4,6-dehydratase AcbB (SEQ ID No. 13).

As described elsewhere herein, overexpression of AcbB refers to an increase of AcbB by a factor of at least 1.5 or at least a factor of 2 compared to the control. Preferably, the control is the strain which has not been engineered for the specific overexpression of dTDP-D-glucose-4,6-dehydratase AcbB (SEQ ID No. 13). For example, the control does not comprise a vector comprising an expression cassette for AcbB.

For example, the overexpression of the gene product may be an increase during the early growth phase, during the linear growth phase, during the stationary phase or an increase during any other time.

According to some embodiments the overexpression of dTDP-D-glucose-4,6-dehydratase AcbB (SEQ ID No. 13) is the increase of the expression of AcbB transcript and/or protein by a factor of a log 2 (fold change) of at least 1.5 or at least 2, during the early growth phase, during the linear growth phase, during the stationary phase or an increase during any other time.

According to some embodiments the overexpression of dTDP-D-glucose-4,6-dehydratase AcbB (SEQ ID No. 13) is the increase of the expression of AcbB transcript and/or protein by a log 2 (fold change)≥2 and ≤6 during the early growth phase, during the linear growth phase, during the stationary phase or an increase during any other time, such as during the early growth phase and/or during the linear growth phase.

According to some embodiments the overexpression of dTDP-D-glucose-4,6-dehydratase AcbB (SEQ ID No. 13) is the increase of the expression of AcbB transcript and/or protein by a log 2 (fold change)>3 and <5 during the early growth phase, during the linear growth phase, during the stationary phase or an increase during any other time.

According to some embodiments the overexpression of dTDP-D-glucose-4,6-dehydratase AcbB (SEQ ID No. 13) is the increase of the expression of AcbB transcript and/or protein by a log 2 (fold change)>6 during the early growth phase, during the linear growth phase, during the stationary phase or an increase during any other time.

According to some embodiments the Actinomycetales strain genetically engineered for overexpression of dTDP-D-glucose-4,6-dehydratase AcbB (SEQ ID No. 13) comprises a vector for overexpression of AcbB. According to some of these embodiments, the vector is a vector as described herein, preferably according to an aspect described herein.

According to some embodiments the Actinomycetales strain genetically engineered for overexpression of dTDP-D-glucose-4,6-dehydratase AcbB (SEQ ID No. 13) comprises an expression cassette for AcbB (SEQ ID No. 13) under the control of a medium strong promoter.

According to some embodiments the Actinomycetales strain genetically engineered for overexpression of dTDP-D-glucose-4,6-dehydratase AcbB (SEQ ID No. 13) comprises an expression cassette for AcbB (SEQ ID No. 13) under the control of strong promoter. Preferably, the promoter is not the native promoter of AcbB.

According to some of these or other embodiments the Actinomycetales strain is genetically engineered for overexpression of UDP-glucose-1P uridyltransferase GtaB (SEQ ID No. 19).

Overexpression of GtaB (SEQ ID No. 19) as described elsewhere herein refers to an increase in expression for GtaB compared to the wild type or a specified reference strain/control. Preferably, the control is the strain which has not been engineered for the specific overexpression of GtaB (SEQ ID No. 19). For example, the control does not comprise a vector comprising an expression cassette for GtaB (SEQ ID No. 19). For example, the overexpression of the gene product may be an increase during the early growth phase and/or during the linear growth phase and/or during the stationary phase, and/or an increase during any other time.

According to some embodiments the overexpression of GtaB is the increase of the expression of GtaB transcript and/or protein by a factor of a log 2 (fold change) of at least 1.5, or at least 2, during the early growth phase, during the linear growth phase, during the stationary phase or an increase during any other time.

According to some embodiments the overexpression of GtaB is the increase of the expression of GtaB transcript and/or protein by a log 2 (fold change)≥2 and ≤6 during the early growth phase, during the linear growth phase, during the stationary phase or an increase during any other time, such as during the early growth phase and/or during the linear growth phase.

According to some embodiments the overexpression of GtaB is the increase of the expression of GtaB transcript and/or protein by a log 2 (fold change)>3 and <5 during the early growth phase, during the linear growth phase, during the stationary phase or an increase during any other time.

According to some embodiments the overexpression of GtaB is the increase of the expression of GtaB transcript and/or protein by a log 2 (fold change)>6 during the early growth phase, during the linear growth phase, during the stationary phase or an increase during any other time.

According to some embodiments the Actinomycetales strain genetically engineered for overexpression of GtaB comprises a vector for overexpression of GtaB. According to some of these embodiments, the vector is a vector as described herein, preferably according to an aspect described herein.

According to some embodiments the Actinomycetales strain genetically engineered for overexpression of GtaB (SEQ ID No. 19) comprises an expression cassette for GtaB (SEQ ID No. 19) under the control of a medium strong promoter.

According to some embodiments the Actinomycetales strain genetically engineered for overexpression of GtaB (SEQ ID No. 19) comprises an expression cassette for GtaB (SEQ ID No. 19) under the control of strong promoter. Preferably, the promoter is not the native promoter of GtaB.

According to a third aspect there is provided an Actinomycetales strain, such as an Actinoplanes strain, for the production of acarbose for use in the production of acarbose.

According to some embodiments there is provided a method for the production of acarbose, wherein the method comprises the use of an Actinomycetales strain according to the second aspect.

For genetic engineering of Actinoplanes, an expression system is required for the overexpression of singular or multiple genes. According to a fourth aspect there is provided an expression vector for Actinoplanes.

According to some embodiments, the vector according to the fourth aspect comprises a medium strong promoter characterized by a normalized glucuronidase activity of at least $1 \times 10^{-4}$ $[L \cdot g^{-1} \cdot min^{-1}]$ in a glucuronidase assay. In some embodiments, the medium strong promoter is selected from efp according to SEQ ID No. 92, cdaR according to SEQ ID No. 97, rpsL according to SEQ ID No. 99, rpsJ according to SEQ ID No. 93, cgt according to SEQ ID No. 91, or tipA according to SEQ ID No. 81.

According to some embodiments, the vector according to the fourth aspect comprises a strong promoter characterized by a normalized glucuronidase activity of at least $5 \times 10^{-4}$ $[L \cdot g^{-1} \cdot min^{-1}]$ in a glucuronidase assay. In some embodiments, the strong promoter is selected from apm according to SEQ ID No. 96, ermE* according to SEQ ID No. 98, katE according to SEQ ID No. 94, moeE5 according to SEQ ID No. 95 or gapDH according to SEQ ID No. 82.

Figure 3:
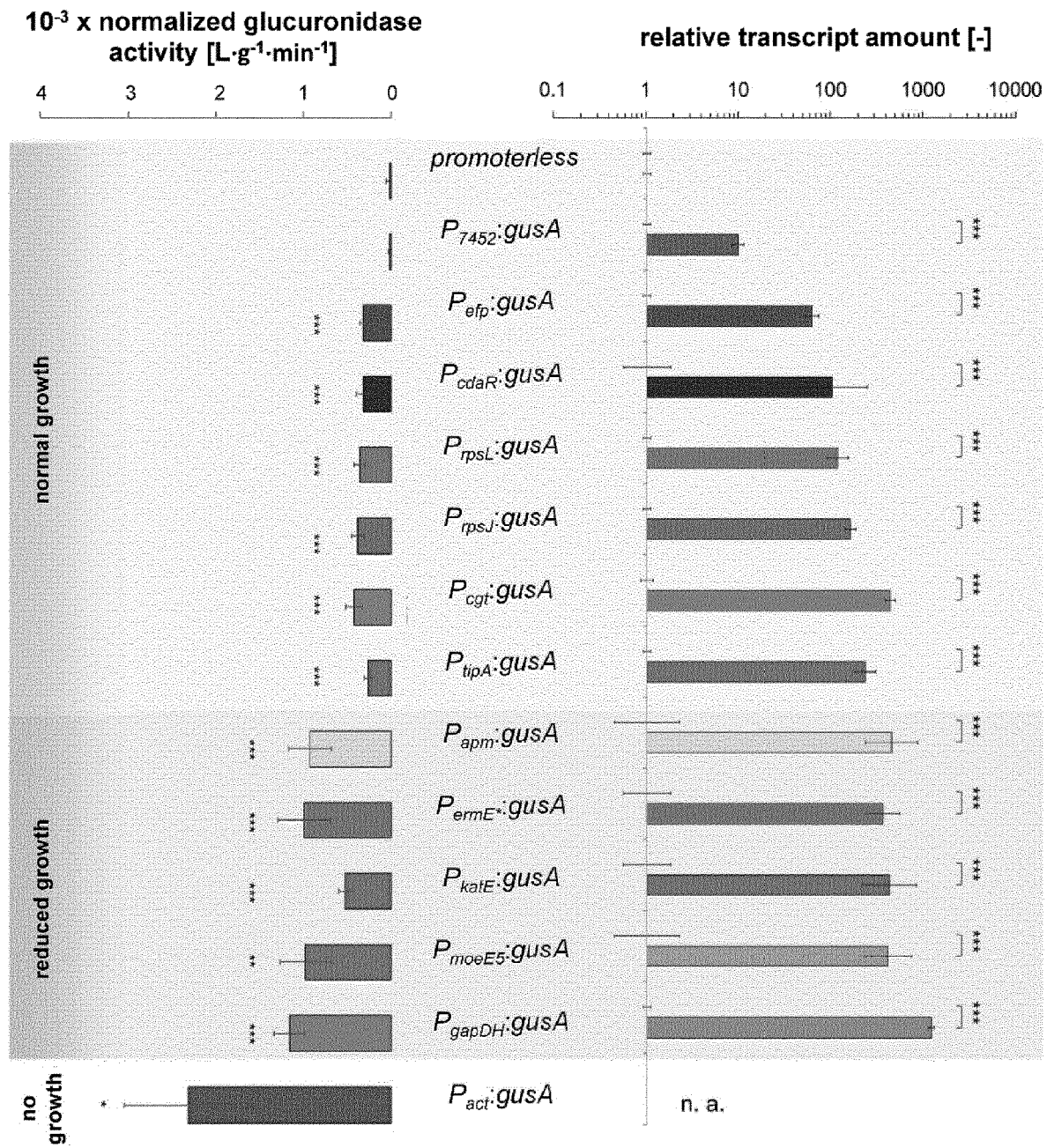
FIG. 3. Promoter screening on protein and transcript level in Actinoplanes sp. SE50/110 strains, cf. Table 1. Shown are the normalized glucuronidase activities on the left side (absolute values) and the relative transcript amount of gusA gene calculated by RT-qPCR on the right side. For the glucuronidase assay, the slope of absorption curves of indigo was calculated by linear regression and normalized by the cell dry weights. The normalized activities were tested for significant differences compared to pGUS in a two-sided t-test (p-values: $P_{2475}$: 0.8889, $P_{efp}$: 3.048e-07, $P_{cdaR}$: 8.967e-07, $P_{rpsI}$: 1.296e-08, $P_{rpsJ}$: 0.0003677, $P_{cgt}$: 2.183e-06, $P_{tipA}$: 0.0001651, $P_{apm}$: 0.0001078, $P_{ermE}$*: 0.007406, $P_{katE}$: 0.002577, $P_{moeEs}$: 0.001809, $P_{gapDH}$: 0.0005821, Pact: 0.02042). The relative transcription amounts of gusA gene were analyzed in relation to the pGUS-vector (set to 1). For the act-promoter, no RNA could be isolated due to severe growth deficiencies. For the residual promoters, a significant increase in the relative transcript amount was measured (p-values of a two-sided t-test: $P_{2475}$: 0.0001133, $P_{efp}$: 4.871e-05, $P_{cdaR}$: 0.002509, $P_{rps}$: 9.928e-06, $P_{rpsj}$: 1.167e-08, $P_{cgt}$: 5.9Ile-08, $P_{tipA}$: 7.158e-06, $P_{apm}$: 4.596e-05, $P_{ermE}$: 0.0009364, $P_{katE}$: 0.0001373, $P_{moeEs}$: 0.0002518, $P_{gapDH}$: 4.207e-06). Significance levels of the calculated p-values are shown by asterisks: *<a=5%, <a=1%, *<a=0.1%. Figure published in (Schaffert, et al. 2019).
Figure 4:
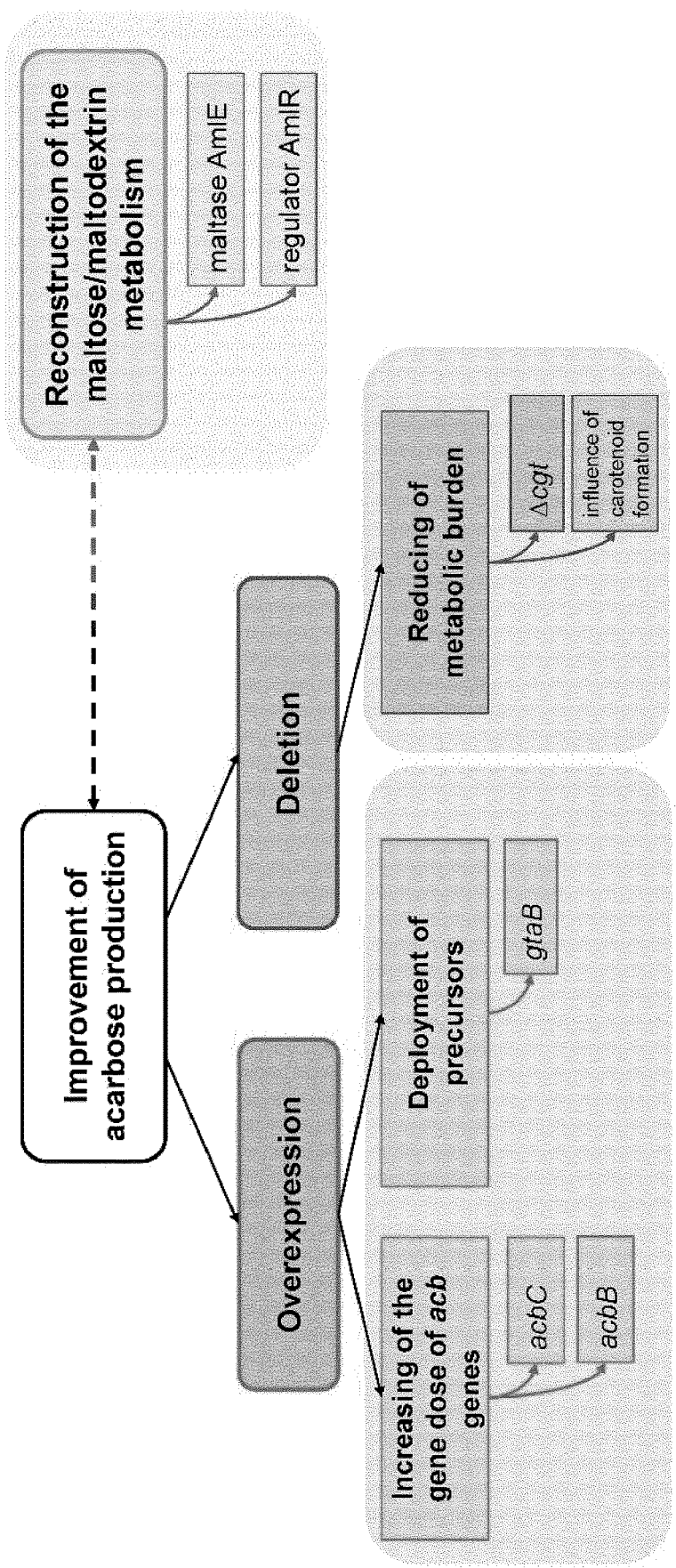
FIG. 4. Strategies for improved acarbose production. Three different strategies are provided to improve the acarbose production: 1. Increasing the gene dose of acarbose biosynthesis genes, 2. Deployment of precursors of acarbose biosynthesis and 3. Reducing the metabolic burden by gene deletion. Shown are the target genes evaluated in this work. Furthermore, an overexpression system had to be implemented for the overexpression of single genes.

To find further suitable promoters, that allow medium to strong gene expression, a promoter screening can be carried out by use of the screening system of Horbal et al. (2013) and Myronovskyi et al. (2011), which is based on the reporter GusA cloned in a pSET152-vector system, cf. FIG. 3, Table 1.

In some embodiments the vector according to the first aspect comprises an expression cassette. Preferably the vector comprises an expression cassette for AcbB (SEQ ID No. 13) and/or an expression cassette for GtaB (SEQ ID No. 19) and/or an expression cassette for MerR. In some embodiments, the expression cassette may furthermore comprise a lacZα-gene under control of the lac-promoter. The lacZα-gene encodes a catalytic domain of a β-galactosidase, that enables quick selection of the integration of a target sequence by blue/white-selection in the cloning strain Escherichia coli DH5aMCR (NC_017638.1) (Grant et al. 1990).

Without being bound by theory, the vector according to the current aspect comprises elements for vector replication, transfer, maintenance and selection. In some embodiments, at least one of these elements is derived from pSET152.

In some embodiments, the vector according to the current aspect comprises parts of the sequence of the pSET152 vector of Bierman et al. (1992).

Figure 26:
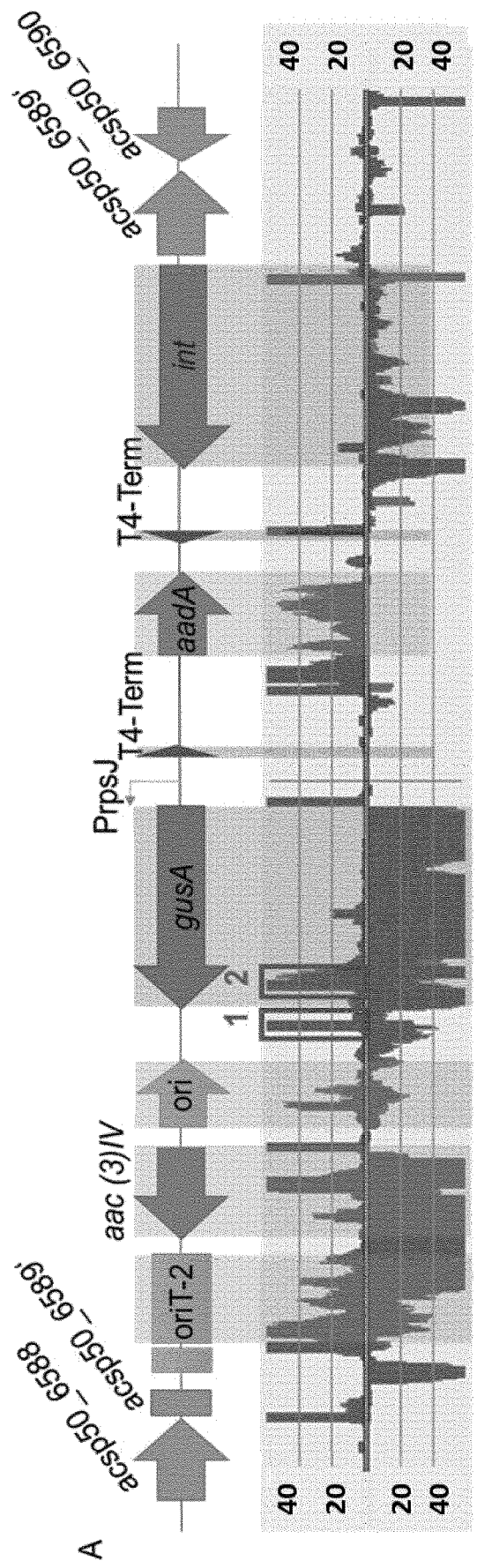
FIG. 26. ReadXplorer (Hilker et al. 2016; Hilker et al. 2014) view showing the TSS of putative antisense promoters behind the gene of interest in the pSET152-vector system. TSS were determined by sequencing of a pooled primary transcript library. Shown are the stacked reads exemplary mapped to the integrated vector-mutant of pGUS::Papm:gusA. Two TSS (surrounded by boxes), are localized behind the gene of interest in antisense orientation (A). These TSS can be assigned to sequence motifs (B) on the vector backbone, which are putatively recognized as promoter sequences by the oA/RNA-polymerase complex. Conserved nucleotides of the −10- and −35-hexamer are highlighted. TG-dimers are shown in bold black letters, if present. The distance between the hexamers is shown by s1; the distance between the −10-motif to the TSS is shown by s2.

Preferably, the vector does not comprise putative antisense promoters according to SEQ ID NO 108 and/or SEQ ID No. 109. These antisense promoters were identified by the inventors by sequencing of a 5'-primary transcript library and impair suitability of the vector pSET152. In brief, identification occurred by sequencing of an enriched primary transcript library. The two putative promoters were identified behind the gene of interest in antisense orientation (FIG. 26). These two pseudo-promoters were removed in order to prevent antisense transcription.

Figure 6:
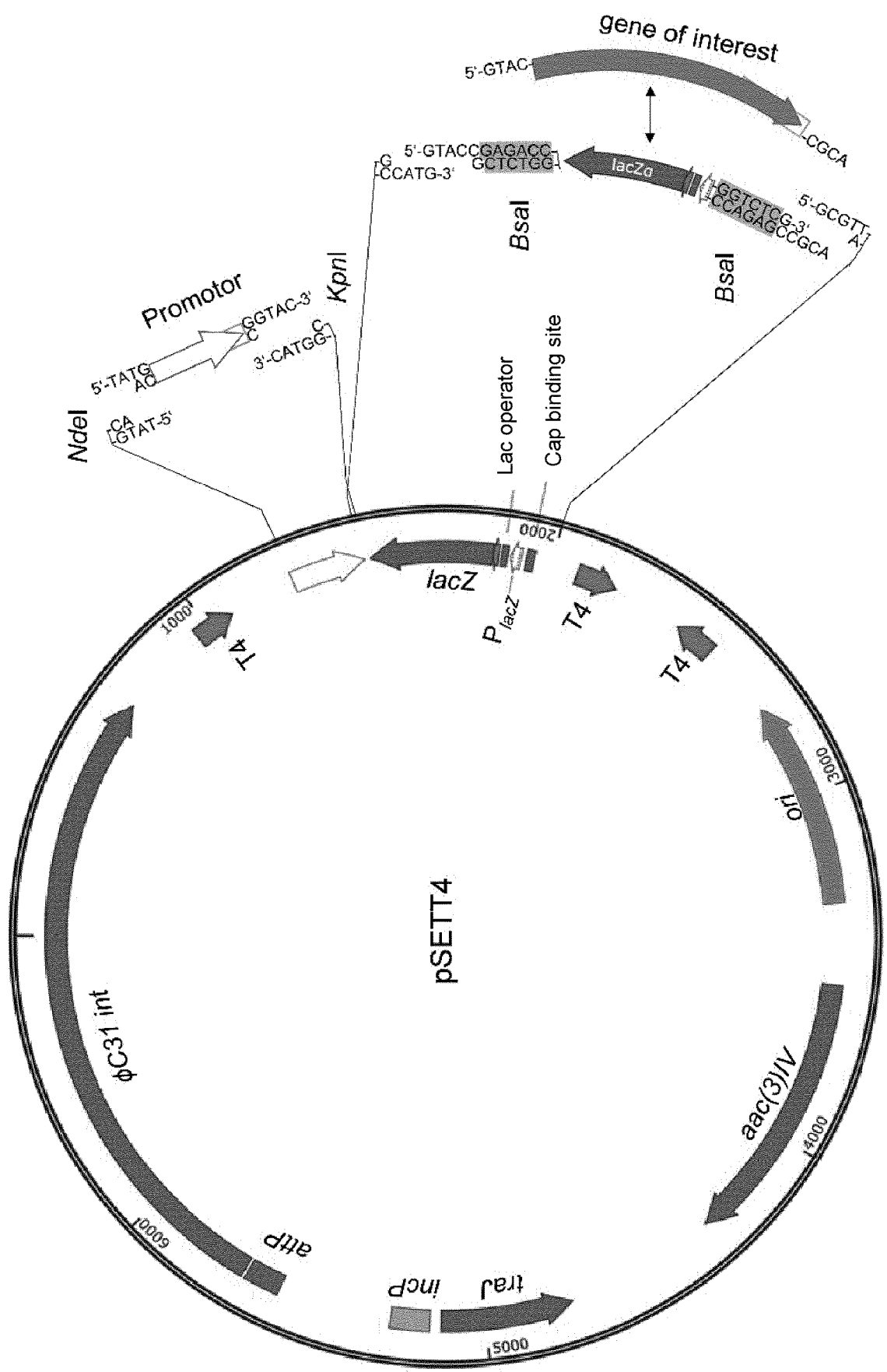
FIG. 6. Vector card of novel cloning system pSETT4 (cf. SEQ ID No. 110, SEQ ID No. 111). A promoter, such as the strong promoter of the gene gapDH from Eggerthella lenta or the tipA promoter is cloned in front of an expression cassette, e.g. the IacZ-cassette. The IacZ-cassette is flanked by a recognition side of a restriction enzyme e.g. Bsal. The restricition site enables exchange of IacZ by the gene of interest by Gibson Assembly, restriction/ligation cloning or Golden Gate cloning. For termination, T4-terminators are introduced before and after the cloning side. Behind the cloning side, two antiparallel oriented T4-terminators shall prevent read-through from both directions. For exchange of the promoter sequence, further restriction sites, e.g. NdeI and KpnI restriction sites were introduced. Furthermore, the vector comprises the integrase gene int and the attachement site attP of the phage qC31, the origin of transfer (ncP) and relaxosome gene traJ, the high-copy-number ColE1/pMB1/pBR322/pUC origin of replication and an resistance gene (here: apramycin resistance gene aac (3) IV (apmR)).

Furthermore, a T4-terminator was introduced behind the expression cassette in opposite orientation to prevent further putative antisense reads (cf. e.g. FIG. 6). In some embodiments, the vector comprises at least one T4-terminator (derived from the bacteriophage T4). T4-terminators can block transcription efficiently and prevent read-through from the integrase gene into the gene of interest. In some embodiments, the vector comprises a T4-terminator behind the expression cassette in opposite orientation to prevent further putative antisense reads. For example, the vector may comprise at least one T4-terminator before and/or at least one T4-terminator after the expression cassette. In some embodiments, the vector may comprise three terminators, one before and two after the expression cassette.

In some embodiments the vector comprises the φC31 integrase gene int. In some of these embodiments the φC31 integrase gene int is derived from pSET152. In some embodiments, the vector according to the first aspect furthermore comprises the attachment site attP. The integrase of the φC31 integrase gene int mediates the integration of the vector into the host chromosome at a distinct genomic location by catalyzing the targeted and unidirectional recombination of two attachment sites: attP, localized on the vector, and attB, localized in the host chromosome in the gene ACSP50_6589 (former: ACPL_6602) (the Poele et al. 2008; Gren et al. 2016). Without being bound by theory, after integration, the vector is flanked by the attachment site left (attL) and right (attR), which are derived from attP-attB-recombination (the Poele, Bolhuis und Dijkhuizen 2008).

In some embodiments the vector comprises an origin of transfer such as the origin of transfer (incP) and/or a relaxosome gene such as the relaxosome gene traJ. In some of these embodiments the origin of transfer such as the origin of transfer (incP) and/or the relaxosome gene, such as traJ are derived from pSET152. The origin of transfer and the relaxosome gene enable the transfer of the plasmid from the donor strain (e.g. Escherichia coli ET12567/pUZ8002 (Kieser et al. 2000)).

In some embodiments the vector according to the first aspect comprises an origin of replication such as the high-copy-number ColE1/pMB1/pBR322/pUC origin of replication (ori). In some of these embodiments the origin of replication such as the high-copy-number ColE1/pMB1/pBR322/pUC origin of replication (ori) is derived from pSET152. The origin of replication such as the high-copy-number ColE1/pMB1/pBR322/pUC origin of replication (ori) enables replication of the plasmid in the cloning strain (Escherichia coli DH5aMCR) and donor strain (Escherichia coli ET12567/pUZ8002).

In some embodiments the vector according to the first aspect comprises at least one resistance marker such as a resistance marker mediating apramycin resistance (aac (3) IV, apmR). Resistance markers mediating apramycin resistance (aac (3) IV, apmR) can be used for selection.

According to some embodiments according to the fourth aspect the expression vector comprises at least one element of pSET152, such as (a) the φC31 integrase gene int according to SEQ ID No. 85, (b) the origin of transfer (incP) according to SEQ ID No. 87, (c) the relaxosome gene traJ according to SEQ ID No. 88, or (d) the high-copy-number ColE1/pMB1/pBR322/pUC according to SEQ ID No. 89, and furthermore does not comprise putative antisense promoters according to SEQ ID NO 108 and SEQ ID No. 109.

According to some embodiments according to the fourth aspect the expression vector comprises (a) the C31 integrase gene int according to SEQ ID No. 85, and (b) the origin of transfer (incP) according to SEQ ID No. 87, and (c) the relaxosome gene traJ according to SEQ ID No. 88, and (d) an origin of replication, such as the high-copy-number ColE1/pMB1/pBR322/pUC, origin of replication (ori) according to SEQ ID No. 89 and (e) optionally at least one resistance marker, such as a resistance marker mediating apramycin resistance, such as aac (3) IV according to SEQ ID No. 90, apmR, and (f) optionally at least one T4-terminator, and (g) optionally, wherein the vector does not comprise putative antisense promoters according to SEQ ID NO 108 and/or SEQ ID No. 109.

According to some embodiments, the vector comprises the sequence according to SEQ ID No. 110 or SEQ ID No. 111. According to some embodiments, the vector comprises the sequence according to SEQ ID No. 110 or SEQ ID No. 111, or a fragment thereof.

In some embodiments, the vector is excelled by an easy cloning mechanism allowing integration of different promoters. By this, the system can be quickly adapted to further species, e.g. production strains of Acarbose.

EXAMPLES

General Tools and Methods

Strains and Plasmids

All strains used in this work are listed in Table E1. Recombinant strains used or created in this work are listed in Table E2, Table E3 and Table E4 (plasmid-based expression systems in Table E2, deletion and integration constructs cloned and stored in E. coli DH5aMCR in Table E3, deletion and integration mutants of Actinoplanes sp. SE50/110 in Table E4).

TABLE E1

Culture collection of microorganisms.

| strain | strain collection | NCBI reference sequence | reference |
|---|---|---|---|
| Actinoplanes sp. SE50/110 | ATCC ®31044, CBS 674.73 | NZ_LT827010.1 | (Wolf etal. 2017b; Frommer et al. 1979; Parenti and Coronelli 1979) |
| Escherichia coli DH5αMCR | Mcr-deficient derivative of E. coli DH1 | NC_017638.1 | (Grant et al. 1990) |
| Escherichia coli ET12567/pUZ8002 | — | — | (Kieser et al. 2000) |
| Streptomyces lividans TK23 | plasmid-free derivative of S. lividans 66 | NZ_CP009124.1 (TK24 as representative genome) | (Kieser et al. 2000) |
| Streptomyces coelicolor A3(2) M145 | ATCC ®BAA-471D-5, plasmid-free derivative of S. coelicolor A3(2) ATCC ®BAA-471 | NC_003888.3 | (Bentley et al. 2002; Dyson and Schrempf 1987) |
| Streptomyces glaucescens GLA.O | DSM ®40922 | NZ_CP009438.1 | (Ortseifen et al 2015) |

TABLE E2

Replicative and integrative vector systems.

| vector name | promoter and insert | | E. coli DH5αMCR | Actinoplanes sp. SE50/110 | source |
|---|---|---|---|---|---|
| pSETT4 constructs (backbone created in this work) | | | | | |
| pSETT4gap | $P_{gapDH}$ | — | Ec112 | — | this work |
| pSETT4tip | $P_{tipA}$ | — | Ec117 | — | this work |
| pSETT4::$P_{acbB}$:acbB | $P_{acbB}$ | acbB (ACSP50_3608) | Ec120 | Ac152 | this work |
| pSETT4tip::acbB | $P_{tipA}$ | acbB (ACSP50_3608) | Ec119 | Ac153 | this work |
| pSETT4gap::acbB | $P_{gapDH}$ | acbB (ACSP50_3608) | Ec118 | Ac154 | this work |
| pSETT4tip::gtaB | $P_{tipA}$ | gtaB (ACSP50_7820) | Ec115 | Ac150 | this work |

TABLE E3

Vector systems for targeted deletion and integration based on pCRISPomyces-2 of Cobb et al. (2015).

| vector name | insert | E. coli DH5αMCR | source |
|---|---|---|---|
| pCRISPomyces-2::sp:cgt_flanks | flanks for deletion of the gene cgt (ACSP50_5024) | Ec018 | this work |
| pCRISPomyces-2::sp1:merR_flanks | flanks for deletion of the gene merR (ACSP50_0145) | Ec109 | this work |

TABLE E4

Deletion and integration mutants obtained in Actinoplanes ssp. by CRISPR/Cas9- technique.

| strain | description | Actinoplanes sp. SE50/110 | source |
|---|---|---|---|
| Actinoplanes sp. SE50/110 Δcgt | deletion mutant of the gene cgt (ACSP50_5024) | Ac064 | this work |
| Actinoplanes sp. SE50/110 ΔmerR | deletion mutant of the gene merR (ACSP50_0145) | Ac146 | this work |

Media and Cultivation Conditions

Unless otherwise specified, all chemicals and media components were obtained from Carl Roth GmbH & Co. KG (Karlsruhe, Germany), Sigma-Aldrich (St. Louis, USA), SERVA Electrophoresis GmbH (Heidelberg, Germany) or VWR International (Pennsylvania, USA).

Preparation of Glycerol Stocks of Actinoplanes Sp. SE50/110

For preparation of glycerol stocks, Actinoplanes sp. SE50/110 (ATCC 31044) was grown in the complex medium NBS (11 g·L$^{-1}$ glucose-1H$_2$O, 4 g·L$^{-1}$ peptone, 4 g·L$^{-1}$ yeast extract, 1 g·L$^{-1}$ MgSO$_4$·7H$_2$O, 2 g·L$^{-1}$ KH$_2$PO$_4$, 4 g·L$^{-1}$ K$_2$HPO$_4$) and mixed 2:3 with sterile 86% (v/v) glycerol. Glycerol stocks are stored at −80° C.

Growth on Solid Media and Preparation of Spore Solutions

For spore formation, 200-300 µL of a glycerol stock were grown on agar plates of soy flour medium (SFM-agar) (20 g·L$^{-1}$ soy flour (SOBOR Naturkost (Cologne, Germany)), 20 g·L$^{-1}$ D-mannitol, 20 g·L$^{-1}$ Bacto™ agar (Becton-Dickinson, Heidelberg, Germany), 167 µL 10 N NaOH in tap water). Spores could be harvested after 5-7 days of incubation at 28° C. by washing them off in 3 mL ddH$_2$O with a cotton swab, like described by Wolf et al. (2016).

Preparation of Minimal Medium

Maltose minimal medium (72.06 g·L$^{-1}$ maltose· 1H$_2$O, 5 g·L$^{-1}$ (NH$_4$)$_2$SO$_4$, 0.184 g·L$^{-1}$ FeCl$_2$·4H$_2$O, 5.7 g·L$^{-1}$ Na$_3$C$_6$H$_5$O$_7$·2H$_2$O, 1 g·L$^{-1}$ MgCl$_2$·6H$_2$O, 2 g·L$^{-1}$ CaCl$_2$·2H$_2$O, trace elements (final concentration: 1 M CuCl$_2$, 50 UM ZnCl$_2$, 7.5 UM MnCl$_2$ dissolved in 1 M HCl) and phosphate buffer consisting of 5 g·L$^{-1}$ each K$_2$HPO$_4$ and KH$_2$PO$_4$ in ddH$_2$O) was prepared and filter sterilized following the protocol of Wendler et al. (2013).

For substitution of the carbon source maltose, 79.2 g·L$^{-1}$ glucose·1H$_2$O, 72.0 g·L$^{-1}$ C-pur (Cerestar 01908, Cerestar GmbH, Krefeld, Germany), 71.9 g·L$^{-1}$ galactose, 68.4 g·L$^{-1}$ cellobiose, 71.9 g·L$^{-1}$ D-arabinose or 72.0 g·L$^{-1}$ D-lactose were used respectively, instead of maltose-monohydrate. Mixtures of maltose and glucose were prepared in the ratio of 90:10, 80:20 and 50:50 (v/v).

For the starch medium, a 4% (w/v) opalescent solution of "starch soluble" from Acros Organics (part of Thermo Fisher Scientific, Geel, Belgium) was generated. For this, sterile water was preheated to 90° C. in a water bath and the weighed portion of starch added with stirring. Afterwards, the residual media components were added. To allow comparison to the starch-cultivation, a maltose minimal medium was created with comparable C-molarity (here net weight of 44.4 g·L$^{-1}$ maltose·1H$_2$O). Media of different pH and osmolarity were created by addition of correcting agents (HCl or NaOH), by varying of the concentration of the carbon-sources maltose respectively by addition of inositol, which is not metabolized according to our study (data not shown).

Furthermore, minimal media with 1 g·L$^{-1}$, 2 g·L$^{-1}$, 3 g·L$^{-1}$, 4 g·L$^{-1}$ and 5 g·L$^{-1}$ "starch soluble" from Acros Organics were created for cultivation under limited carbon-source.

The pH and osmolarity of all media were determined by the pH-meter Calimatic of Knick GmbH (Berlin, Germany) and the Osmomat 3000 of Gonotec GmbH (Berlin, Germany) according to the manufacturer's instructions.

Shake Flask Cultivation

Cultivations were performed in 250 ml Corning® Erlenmeyer baffled cell culture flasks at 28° C. and 140 rpm for seven days in the GFL shake-imcubators 3032 or 3033 (Burgwedel, Germany). For inoculation of 50 mL medium, 1 mL spore solution of an OD=3-5 was used. Cell dry weights were determined like described by Wolf et al. (2017a). The supernatant was stored at −20° C. for later analysis.

Miniaturized Cultivation in the BioLector System of m2p-Labs GmbH (Baesweiler, Germany)

Comparative growth experiments were performed in a 1 mL reaction volume in a 48-well FlowerPlate covered by a gas-permeable sealing foil (m2p-labs GmbH, Baesweiler, Germany) and incubated for 1 week at 28° C. and 800 rpm in the RoboLector® of m2p-labs. Growth was recorded by the backscatter signal. For determination of final cell dry weights, 800 µL of each well was sampled in a weighed reaction tube (14,000 g, 2 min), washed with deionized water and dried for 1 day at 60-70° C. The supernatant was stored at −20° C. for later analyses.

Recombinant DNA Work

Unless otherwise specified, plasmid construction and assembly was performed by Gibson Assembly (Gibson et al. 2009). Fragments were amplified by PCR (Phusion® High-Fidelity PCR Master Mix with GC Buffer, NEB, Ipswich, MA, USA) in the Eppendorf thermocycler vapo.protect (Hamburg, Germany) and treated with Dpnl (Thermo Fisher Scientific, Waltham, MA, USA), when necessary. Purification of PCR products and gel extracts was performed by use of the NucleoSpin® Gel and PCR Clean-up kit (Macherey-Nagel, Düren, Germany). Equimolar amounts of the DNA fragments were added to the Gibson Assembly Master Mix in a ratio of 1:4. The master mix consists of 0.64 µL T5 Exonuclease (10 U·µL$^{-1}$, NEB, Ipswich, MA, USA), 20 µL Phusion High-Fidelity DNA Polymerase (2 U·µL$^{-1}$, Thermo Fisher Scientific, US), 160 µL Taq DNA Ligase (NEB, Ipswich, MA, USA), 699.36 µL aqua distilled and 320 µL isothermal reaction buffer (25% PEG-8000, 1 mL 1 M Tris-HCl, 100 µL 1 M MgCl$_2$, 100 µL 1 M DTT, 20 µL each 1 mM dNTP, 200 µL NAD). The sample was incubated at 50° C. for at least 1 h and subsequently transferred to Escherichia coli DH5aMCR by chemical transformation according to a protocol of Beyer et al (2015). Selection of E. coli was performed on Luria/Miller broth medium with 15 g·L$^{-1}$ agar-agar (Carl Roth, GmbH&Co.KG, Karlsruhe, Germany)) and 50 mg·L$^{-1}$ apramycin-sulfate. Positive colonies were tested by PCR and gel-electrophoresis as well as by Sanger sequencing by our in-house sequencing core facility.

Construction of Plasmids for the gusA Reporter System

For the construction of plasmids for the gusA reporter system see Schaffert et al. (2019).

Construction of the Novel pSETT4 Expression System

For cloning of the novel pSETT4 expression system, the pSET152 vector of Bierman et al. (1992) was used as template. The vector backbone was linearized by PCR (Table E5).

The cloning cassette, consisting of the gapDH-promoter, a IacZ-gene under control of the lac-promoter and several restriction sites flanked by three T4-terminators, was ordered as string DNA at Integrated DNA Technologies (Iowa, USA). Due to the complex structure, the cassette was ordered in three parts and assembled by GeneSOEing (Horton 1995) by use of the primers in Table E5. Finally, backbone and insert were assembled by Gibson Assembly (Gibson et al. 2009). The novel vector system was named pSETT4gap.

For exchange of the gapDH-promoter by the tipA-promoter, pSETT4gap was digested with Ndel and Kpnl and treated with shrimp alkaline phosphatase following the instructions of the supplier. All enzymes were purchased from Thermo Fisher Scientific (Waltham, MA, USA). The tipA-promoter was amplified from pSETGUS (Myronovskyi et al. 2011) by use of the primers tipA_GAF and tipA_GAR and assembled with the linearized backbone by Gibson assembly (Gibson et al. 2009). The vector was named pSETT4tip (cf. FIG. 6).

TABLE E5

Gibson Assembly primer for assembly of the novel expression system pSETT4gap and pSETT4tip.

| fragment | template | size (bp) | primer sequence (5'-3') |
|---|---|---|---|
| pSET152_lin | pSET152 | 5114 | CTACGGTGCCGCTTACCGGgctcactcaaaggcggtaatacgg |
|  |  |  | CAGACGTCAGCGACGACAGAGaaccatcggcgcagctattac |
| genesoeing_for | IDT-order 1 and 2 | 1473 | CTCTGTCGTCGCTGACGTCTG |
| genesoeing_1r |  |  | CAGATCTGGAGTCGGTCTAATTT |
| genesoeing_2f | IDT-order 2 and 3 | 878 | AGGGTTTTCCCAGTCACGACG |
| genesoeing_rev |  |  | CCGGTAAGCGGCACCGTAG |
| tipA_GAF | pSETGUS | 146 | GTGGCCCATGCGAGAGTACAATCCCTAGAACGTCCGGG |
| tipA_GAR |  |  | TCAACATAAGGTCTCGGTACCATCGGAATACCTCCGTTGCT |

Overexpression of Single Genes in the Novel pSETT4 Expression System

For the overexpression of single genes, the insert was amplified by PCR (Table E6). The vector (pSETT4gap or pSETT4tip), was digested with BsaI (NEB, Ipswich, MA, USA) and assembled with the insert by Gibson Assembly (Gibson et al. 2009). For expression of the acbB gene under control of the native promoter, the vector backbone pSETT4gap was digested with BsaI and NdeI, leading to the linearization of the vector under removal of the promoter. The gene of interest and the native promoter were amplified by use of the primers in Table E6 and assembled with the vector backbone by Gibson Assembly (Gibson et al. 2009).

Construction of pCRISPomyces-2 Deletion and Integration Vectors

For the construction of deletion and integration mutants by CRISPR/Cas9 technique, the plasmid pCRISPomyces-2 (Cobb et al. 2015) was used according to a protocol of Wolf et al. (2016). The spacer and its reverse complement were ordered at metabion GmbH (Steinkirchen, Germany) or Sigma-Aldrich (Taufkirchen, Germany) as oligonucleotides with overlap (Table E7).

The oligonucleotides were annealed to a double-strand and assembled with the plasmid by Golden Gate Assembly (Engler et al. 2008) according to the protocol of Cobb et al. (2015). For repair of the Cas9-induced double-strand break, a DNA template was cloned into the vector backbone by

TABLE E6

Primer for amplification of inserts for Golden Gate cloning and restriction cloning into the pSETT4gap and pSETT4tip vector system.

| fragment | template | size (bp) | primer sequence (5'-3') |
|---|---|---|---|
| acbB for pSETT4gap | gDNA | 1008 | GAGTATCTGAAAGGGGATACGCATGAAAATCTTGGTCACCCGGCGGAGC |
|  |  |  | GGCGGAAAATCACGCGGCACGAATCAGGTCCACCAGGAACGGTTGGC |
| acbB for pSETT4tip | gDNA | 1006 | CGAGCAACGGAGGTATTCCGATGAAAATCTTGGTCACCGGCGGAGC |
|  |  |  | GGCGGAAAATCACGCGGCACGAATCAGGTCCACCAGGAACGGTTGGC |
| $P_{acbB}$:acbB for pSETT4 | gDNA | 1136 | GGCCCATGCGAGAGTACATAGCCAGCCTTTCATGATATATCTC |
|  |  |  | AATCACGCGGCACGAAACGCACCGGATCCATGTTGTGTGG |
| gtaB for pSETT4tip | gDNA | 950 | GCAACGGAGGTATTCCGATGACGACGAACGCGCAAGGG |
|  |  |  | GGAAAATCACGCGGCACGAAGTCATCCCTTCTGACCACCGACG |

Gibson Assembly (Gibson et al. 2009). As DNA template, flanking sequences up- and downstream of the target gene (each round about 1 kB) were amplified by PCR (Table E8) from genomic DNA.

TABLE E7

Spacer and the reverse complement used in a Golden Gate Assembly with pCRISPomyes-2.

| gene | oligo 1 (5'-3') | oligo 2 (5'-3') |
|---|---|---|
| cgt (ACSP50_5024) | acgcAGCGTCGCCCGCTGGGAGAA | aaacTTCTCCCAGCGGGCGACGCT |
| merR (ACSP50_0145) | acgcGACCGGGGGCTGTCCGGGAG | aaacCTCCCGGACAGCCCCCGGTC |

TABLE E8

Gibson Assembly primer for pCRISPomyes-2 deletion and integration vectors.

| gene | primers for flank 1 (5'-3') | size (bp) | primers for flank 2 (5'-3') | size (bp) |
|---|---|---|---|---|
| cgt (ACSP50_5024) | tcggttgccgccgggcgtttttatCCGGTACCCTGCTCCTCGTC | 1101 | gtatctgagccatatccctcGACCTGCGTCAATGCGTCAC | 982 |
|  | gtgacgcat tgacgcaggtcGAG |  | gcggccttttacggttcctggcctACCTGACCCTGCTGAAATGG |  |
|  | GG ATATGGCTCAGATAC |  |  |  |
| merR (ACSP50_0145) | tcggttgccgccgggcgtttttatCTCCGGGCGCCGACCGGCAC | 1115 | gcaggtggacggcctcggtATCTCGGCGCTCAACGCCTC | 1129 |
|  | gaggcgttgagcgccgagatCACCGAGGCCGTCCACCTGC |  | gcggccttttacggttcctggcctCGGCAAACAGACCTACTACG |  |

1:4 to the Gibson Assembly Master Mix consisting of 0.64 µL T5 Exonuclease (10 U/µL, NEB, Ipswich, MA, USA), 20 µL Phusion High-Fidelity DNA Polymerase (2 U/µL, Thermo Fisher Scientific, US) and 160 µL Taq DNA Ligase Deletion of the Gene Cgt by CRISPR/Cas9 Technique For the construction of a Δcgt (AACSP50_5024) deletion mutant by CRISPR/Cas9 technique (clustered regular interspaced short palindromic repeats/CRISPR-associated endonuclease 9), the plasmid pCRISPomyces-2 was used (Cobb et al. 2015). The spacer sequence was selected according to Wolf et al. (2016) and ordered as oligonucleotides together with its reverse complement at metabion GmbH (Steinkirchen, Germany) (spacer_1: 5'-acgcAGCGTCGCCCGCTGGGAGAA-3', spacer_2: 5'-aaacTTCTCCCAGCGGGCGACGCT-3'). The oligonucleotides were annealed to a double-strand and assembled with the plasmid by Golden Gate Assembly (Engler et al. 2008) by use of BsaI (NEB, Ipswich, MA, USA) according to the protocol of Cobb et al. (2015) (Cobb et al. 2015). For repair of the Cas9-induced double-strand break, a deoxyribonucleic acid (DNA) template was cloned into the XbaI-linearized vector by Gibson Assembly (Gibson et al. 2009). As DNA template, flanking sequences up- and downstream of the target gene (each round about 1 kB) were amplified by polymerase chain reaction (PCR) with the Phusion® High-Fidelity PCR Master Mix with GC Buffer (NEB, Ipswich, MA, USA) (Primer sequences: cgt_flank1_fw: 5'-tcggttgccgccgggcgttttt-tatCCGGTACCCTGCTCCTCGTC-3', cgt_flank1_rv: 5'-gtgacgcattgacgcaggtcGAGGGATATGGCTCAGATAC-3', cgt_flank2_fw: 5'-gtatctgagccatatccctcGACCTGCGTCAATGCGTCAC-3', cgt_flank2_rv: 5'-gcggccttttt-tacggttcctggcctACCTGACCCTGCTGAAATGG-3'). For Gibson Assembly, the DNA fragments (flank_1: 1101 bp and flank_2: 982 bp) were mixed equimolar added in a ratio of (40 U/µL NEB, Ipswich, MA, USA), 699.36 µL aqua distilled and 320 µL isothermal reaction buffer (25% PEG-8000, 1 mL 1 M Tris-HCl, 100 µL 1 M MgCl$_2$, 100 µL 1 M DTT, 20 µL each 1 mM dNTP, 200 µL NAD). After incubation at 50° C. for at least 1 h, the reaction mix was transferred to *Escherichia coli* DH5aMCR by chemical transformation according to a protocol of (Beyer et al. 2015). Growth and selection of *E. coli* was performed by plating them on Luria/Miller broth (LB-media) with 15 g·L$^{-1}$ agar-agar Kobel (both: Carl Roth, GmbH&Co.KG, Karlsruhe, Germany)) supplemented with 50 mg·L$^{-1}$ apramycin-sulfate. Plates were incubated for 10-14 h at 37° C. Apramycin-resistant colonies were tested by PCR and gel-electrophoresis first, and second by Sanger sequencing by our in-house sequencing core facility (primer sequences for PCR: for: 5'-GGCGTTCCTGCAATTCTTAG-3', rev: 5'-TCGCCACCTCTGACTTGAGC-3', walking primer for sequencing: w1: 5'-CGCTGATCTTCAGCTTCC-3', w2: 5'-GCCTTCACCTTCCATCTG-3', w3: 5'-TCGG-GAAAGCCGCCGGAG-3')).

Conjugal Transfer to Actinoplanes Sp. SE50/110

Competent Actinoplanes sp. SE50/110 cells were prepared from a freshly grown NBS-culture (see above). Cells were washed twice in 10% (w/v) ice-cold sucrose and twice in ice-cold 15% (v/v) glycerol. Finally, the cells were taken up in 15% (v/v) ice-cold glycerol (by addition of round about the four-fold volume of the cell pellet), aliquoted to 100 µL in reaction tubes and snap-frozen in liquid nitrogen. The competent Actinoplanes cells are stored at −80° C.

For conjugation, *Escherichia coli* ET12567/pUZ8002 (Kieser et al. 2000) was used. After transfer of the desired construct into *E. coli* ET12567/pUZ8002 according to Beyer et al. (2015) and selection on LB agar plates supplemented with 50 mg·L$^{-1}$ apramycin-sulfate, 50 mg·L$^{-1}$ kanamycin-sulfate and 15 mg L$^{-1}$ chloramphenicol, cells were grown in liquid culture (LB-medium with the same supplements) and harvested at an optical density of 0.4-0.6. The cells were washed twice in ice-cold LB medium and mixed with competent cells of Actinoplanes sp. SE50/110. The cell suspension was plated on SFM agar plates. After 20-24 h of incubation at 28° C., 1 mL 500 mg·L$^{-1}$ apramycin-sulfate dissolved in ddH$_2$O was distributed on the plate with a sterile swab. First exconjugants of Actinoplanes sp. SE50/110 can be observed after 1 week. Exconjugants were transferred to an SFM agar plate supplemented with 50 mg·L$^{-1}$ apramycin-sulfate. Repeated streaking is performed for several times to purify Actinoplanes exconjugants from *E. coli*. To expedite this process, 50 mg·L$^{-1}$ fosfomycin or trimethoprim can be supplemented to the medium to get rid of the donor strain.

Plasmid Curing to Obtain Marker-Free CRISPR/Cas9 Deletion/Integration Mutants of Actinoplanes Sp. SE50/110

Plasmid curing was performed according to the protocol of Wolf et al. (2016) by cultivation in the complex medium NBS at elevated temperatures. Colonies were tested for the presence of the plasmid by parallel streaking on apramycin-containing and apramycin-free SFM plates. Apramycin-sensitive exconjugants were tested for the deletion by PCR (primer sequence data not shown). The PCR fragment was excised from the gel and sequenced by our in-house Sanger sequencing core facility.

Additionally, also genomic DNA of the deletion or integration mutant was sequenced by the Oxford Nanopore technique (Oxford, UK) to exclude off-target effects. For this, genomic DNA of an NBS-grown culture was isolated with the NucleoSpin® Microbial DNA kit (Macherey-Nagel, Düren, Germany). A library was prepared with help of the 1D Genomic DNA by ligation-kit (Oxford Nanopore, Oxford, UK).

Deletion System Based on Homologous Recombination and Counterselection with the Cytosine Deaminase CodA.

Vector integration into genes of the acb gene cluster has occurred by use of the replicative vector pKC1139. Based on this observation, a novel deletion system using homologous recombination was developed and tested by example of the gene cgt (ACSP50_5024).

Figure 7:
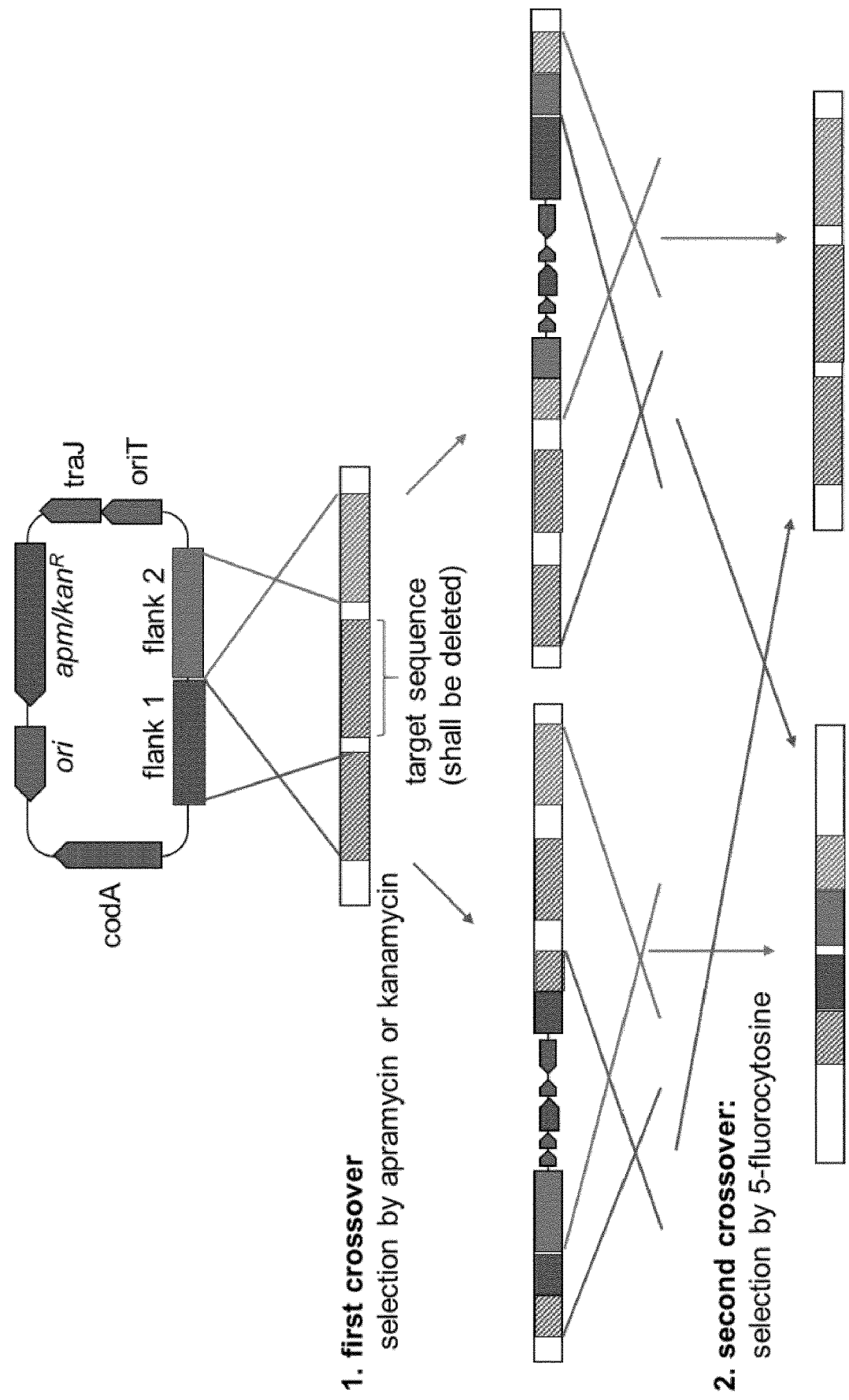
FIG. 7. Scheme of the novel deletion system and the processes during the homologous recombination (first and second crossover). Selection of vector integration is performed by use of either apramycin or kanamycin (first crossover, resistance mediated by apmR or kanR). Counter-selection is performed by use of 5-flourouracil (second crossover, sensitivity mediated by codA).

A vector backbone with origin of transfer (ncP) and relaxosome gene traJ was used to allow conjugation into Actinoplanes sp. SE50/110. In this work, two different antibiotic resistance markers mediating apramycin and kanamycin resistance were tested for selection: aph (3') II (kanR, kanamycin) and aac (3) IV (apmR, apramycin). Furthermore, the high-copy-number ColE1/pMB1/pBR322/pUC origin of replication was integrated to allow replication in the donor strain *E. coli*. The ori, the oriTncP, tra gene and resistance cassettes were taken from pRT802 respectively pRT801 (Gregory et al. 2003). Since no replicon for replication in Actinoplanes sp. SE50/110 neither an integrase gene with attachment site are contained in the novel deletion system, the vector can only be maintained in Actinoplanes sp. SE50/110 when being integrated into the genome by homologous recombination (FIG. 7). For this, homologous sequences of 2 KB were integrated, which are flanking the gene cgt. After conjugal transfer in Actinoplanes sp. SE50/110, mutants, in which the first crossover has taken place, can be selected by apramycin or kanamycin resistance. To force desintegration of the vector backbone (second crossover), 5-fluorocytosine (5-FC) is added, which is converted into the toxic product 5-fluorouracil (5-FU) by the cytosine deaminase CodA. In this work, codA(s) is used, which is codon-optimized for *Streptomyces* ssp. (Dubeau et al. 2009). After second crossover either the genotype of the wild type or the genotype of the deletion mutant is present.

Figure 8:
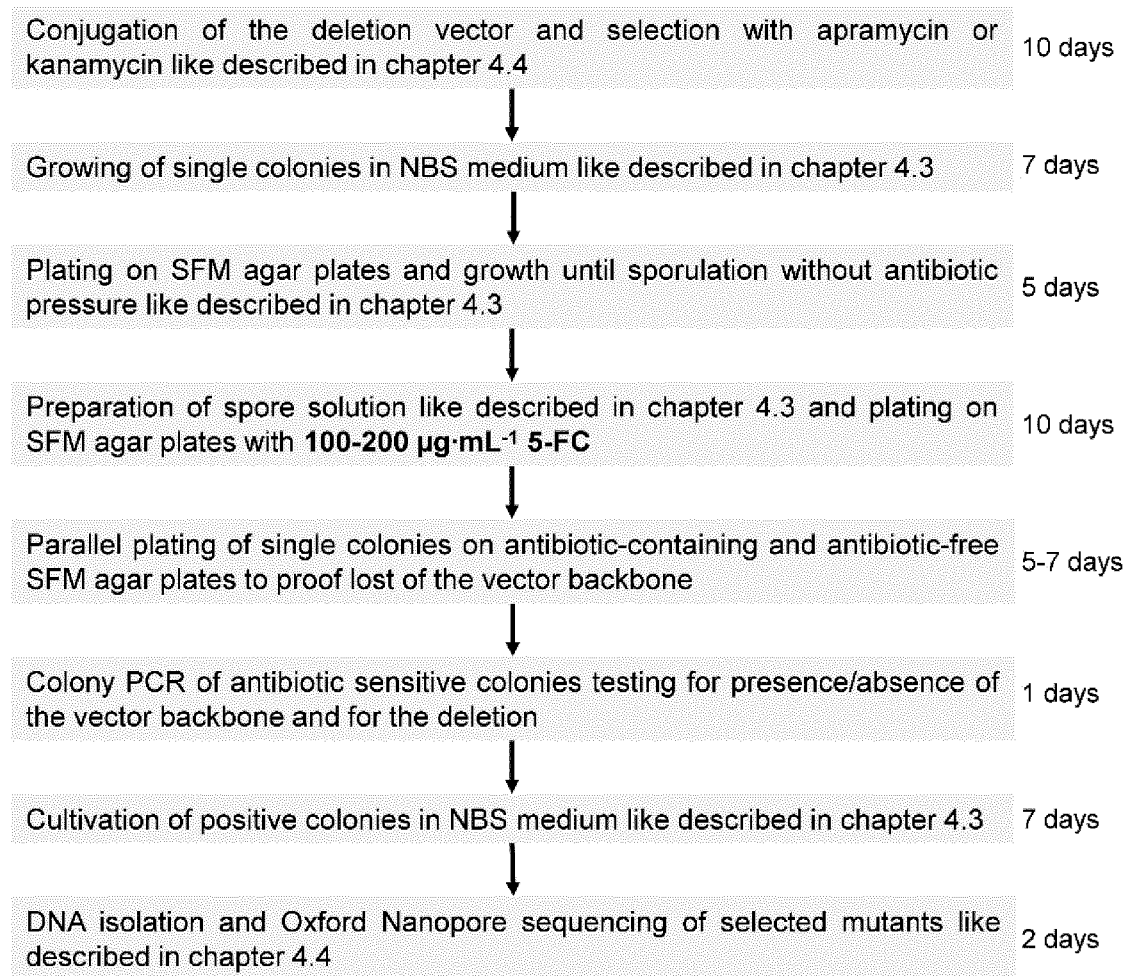
FIG. 8. Workflow of novel deletion system using homologous recombination.

The novel deletion system was successfully tested for the gene cgt, which was shown by colony PCR and ONT-sequencing. The proportion of deletion mutants after successful second crossover was between 25% and 32%. The workflow is illustrated in FIG. 8.

Analytical Methods

Acarbose Quantification from the Supernatant by High Performance Liquid Chromatography (HPLC)

Supernatants of maltose-grown cultures of Actinoplanes ssp. were centrifuged (20,000 g, 2 min), mixed 1:5 with methanol by vortexing and centrifuged again to remove the precipitate (20,000 g, 2 min). The samples were transferred to HPLC vials and analyzed in the HPLC system 1100 series of Agilent (G1312A Binary Pump Serial #DE43616357, G1329A ALS autosampler Serial #DE43613/10, G1315A diode-array detector (DAD) Serial #DE72002469). As stationary phase the Hypersil APS-2 column (125×4 mm, 3 μm particle size) of Thermo Fisher Scientific Inc. (Waltham, MA, USA) was used, heated to 40° C. As mobile phase an isocratic flow of 1 mL·min$^{-1}$ 68% acetonitrile (solvent B) and 32% phosphate buffer (0.62 g·L$^{-1}$ KH$_2$PO$_4$ and 0.38 g·L$^{-1}$ Na$_2$HPO$_4$·2H$_2$O) (solvent A) was applied. 40 μL of each sample was injected and separated in a 10 min run. Detection of acarbose was carried out with a DAD detector at 210 nm (Reference 360 nm) and quantified from the peak areas of a calibration curve.

Liquid Chromatography-Mass Spectrometry (LC-MS)

Sample Preparation for Analysis of Intracellular Metabolites

Triplicates of Actinoplanes sp. SE50/110 strains were grown in maltose minimal medium for at least 4 days. 10 mL of the culture were quickly filtrated through filtering paper by a Büchner funnel and washed with 2.63 g·L$^{-1}$ NaCl solution. Cells were transferred into pre-weighted round bottom screw-cap tubes, snap-frozen in liquid nitrogen and stored at −80° C. Cells were dried overnight in the Centrifugal Evaporator (SpeedVac) of Thermo Fisher Scientific (Waltham, MA, USA). 4 mg dried cells were transferred into a fresh 2 mL screw-cap tube containing round about 500 μL of a mixture of zirconia/silica micro beads of the sizes 0.1 mm, 0.05 mm and 0.01 mm (Bio Spec Products Inc., Bartlesville, USA). 700 μL 80% MeOH was added to the cells and beads. Cell disruption was carried out in a homogenizer (FastPrep FP120, Thermo Fisher Scientific, Waltham, MA, USA) for three times 30 s at speed setting 6.5. Samples were cooled for 5 min on ice in between. The cell suspension was centrifuged for 5 min at 13,000 g and 4° C. 500 μL of the supernatant was transferred into HPLC vials, dried under nitrogen flow and taken up in 50 μL distilled water.

Sample Preparation for Analysis of Extracellular Acarviosyl-Metabolites

The sample preparation was conducted according to a protocol described by Ortseifen (2016). Sugars and pseudo-sugars were enriched from 10 mL of the supernatant by solid phase extraction using the Chromabond® Easy columns (Macherey-Nagel, Düren, Germany, REF 730753). The columns were equilibrated with 3 mL methanol, afterwards washed with 3 ml distilled water before loading of the sample. Unspecific bound metabolites were rinsed by 3 mL 95% (v/v) methanol. Elution was conducted in 3 mL methanol.

LC-ESI-MS of Intracellular and Extracellular Metabolites

For LC-MS, the LaChromUltra (Hitachi Europe Ltd., UK) HPLC system coupled to a microTOF-Q hybrid quadrupole/time-of-flight mass spectrometer (Bruker Daltonics, Bremen, Germany) was used, which was equipped with an electrospray ionization (ESI) source.

For the analysis of intracellular metabolites, 2 µL of the sample was separated with the SeQuant® ZIC®-PHILIC 5 µm Polymeric column (150×2.1 mm) (Merck, Darmstadt, Germany). Eluent A (20 mM $NH_4HCO_3$, pH 9.3, adjusted with aqueous ammonia solution) and eluent B (acetonitrile) were applied at a flow rate of 0.2 mL·min$^{-1}$ by use of the following gradient: 0 min B: 90%, 30 min B: 25%, 37.5 min B: 25%, 40.0 min B: 80%.

As standards for the peak identification, 2 µL of 10 µM of UDP-glucose, glucose-1-phosphate, galactose-1-phosphate, glucose-6-phosphate and dTDP-glucose were injected.

For the analysis of extracellular acarviosyl-metabolites, 10 µL of the sample was separated with the Cogent Diamond Hydride™ HPLC column (MicroSolv Technology Corporation; 150 mm×2.1 mm; 3 µL particle size). Eluent A (50% (v/v) acetonitrile, 50% (v/v) $H_2O$ und 0.1% (v/v) formic acid) and eluent B (90% (v/v) acetonitrile, 10% (v/v) $H_2O$ und 0.1% (v/v) formic acid) were applied at a flow rate of 0.4 mL·min$^{-1}$ by use of the following gradient: 0 min B: 100%, 8 min B: 0%, 13 min B: 0%, 15.5 min B: 100%, 18 min B: 100%.

The ESI source was operated in the negative ionization mode for analysis of intracellular metabolites and in the positive ionization mode for analysis of extracellular acarviosyl-metabolites. The temperature of the dry gas and the capillary was set to 180° C. The scan range of the MS was set to 200-1,000 m/z (intracellular metabolites) respectively 50-3,000 m/z (extracellular acarviosyl-metabolites)

The peak areas of specific masses were integrated by use of the software Compass™ (Bruker Daltonics, Bremen, Germany). Peaks were normalized on the weighed amount of dried cells (intracellular metabolites) respectively the cell dry weight at sampling time (extracellular acarviosyl-metabolites).

Extraction and Analysis of Carotenoids

Extraction

Cell pellets from Actinoplanes sp. SE50/110 were transferred into a 2 mL screw-cap tube with round about 500 µL of a mixture of zirconia/silica micro beads of the sizes 0.1 mm, 0.05 mm and 0.01 mm (Bio Spec Products Inc., Bartlesville, USA). 1 mL acetone or methanol was added as extracting solvent. Cell disruption was carried out in a homogenizer (FastPrep FP120, Thermo Fisher Scientific, Waltham, MA, USA) for three times 45 s at speed setting 6.5. Samples were cooled for 5 min on ice in between. The homogenized cell suspension was centrifuged for 20 min at 13,000 g and 4° C. The supernatants were transferred into glass vials. For HPLC-analysis, mixtures of the acetone- and methanol-extracts were created in the ratio of 7:3 and transferred into a novel glass vial.

Thin Layer Chromatography (TLC) and Spectral Analysis

50 µL of the extracted carotenoids were applied in 5 µL-steps onto a silica gel matrix (HPTLC-HL, Cat. 58077, Analtech Inc., Newark, USA) and incubated in a TLC-chamber filled with 100 mL petroleum, 11 mL isopropanol and 50 µL water. The run was carried out in darkness. After drying of the TLC-plate, bands were stripped off with a scalpel and transferred into a novel tube. After addition of 1 mL ethanol, the absorption spectrum was analyzed by use of the Genesys 10S UV-Vis spectrophotometer of Thermo Fisher Scientific (Waltham, MA, USA).

HPLC Analysis of Carotenoids with Absorbance Scan

Carotenoids were separated by reversed-phase HPLC according to Henke et al. (2017) and Heider et al. (2014) using the Agilent 1200 series HPLC system (Agilent Technologies GmbH&Co. KG, Boblingen, Germany) including diode array detector (DAD) for the UV-Vis spectrum. 20 µL sample volume was applied to a flow of 0.5 mL·min$^{-1}$. As stationary phase a pre-column (10×4 mm MultoHigh 100 RP18-5) and a main column (ProntoSIL 200-5 C30, 250×4 mm) from CS ChromatographieService GmbH (Langerwehe, Germany) were used, like described before (Heider et al. 2014; Henke et al. 2017).

Following gradient was applied: 0 min A: 100%, 32 min A: 75%, 47 min A: 0%, 70 min A: 0%, 75 min A: 100%, with eluent A consisting of 0.1 M ammonium acetate in deionized water and methanol in the ratio of 15:85 (v/v). Eluent B consists of a mixture of methanol, acetonitrile and acetone in the ratio of 44:43:13 (v/v). Detection of carotenoids was conducted at 470 nm. Additionally, wavelength scans between 360 nm and 700 nm were performed each second during the run.

Assays

Promoter Screening Experiment by Spectrophotometric Measurement of the Glucuronidase Activity Two different types of glucuronidase assay were carried out: one with protein raw extract and one with entire cells. The protocols described by Horbal et al. (2013) and Siegl et al. (2013) were adapted to Actinoplanes sp. SE50/110. The substrate 5-bromo-4-chloro-3-indolyl-β-D-glucuronide (X-Gluc, AppliChem GmbH, Darmstadt, Germany) was chosen, as the substrate p-nitrophenyl-D-glucuronide turned out to dissociate under our assay conditions.

Growth Conditions and Sample Preparation

Actinoplanes mutants carrying promoter constructs with gusA gene, were cultivated for one week in maltose minimal medium, like described above. The assays were conducted during growth phase. 500 µL of each culture was sampled for an assay with entire cells. 1 mL was sampled for an assay with protein raw extract and transferred to a screw cap tube containing zirconia/silica micro beads (Bio Spec Products Inc., Bartlesville, USA) of the sizes 0.1 mm and 0.05 mm. Cells were disrupted in a homogenizer (FastPrep FP120, Thermo Fisher Scientific, Waltham, MA, USA) for two times 30 s at speed setting 6.5 and 5 min on ice in between. After centrifugation, the lysate was transferred to a new reaction tube and centrifuged. The supernatant was used for a cell-free assay. Total protein quantification was carried out by a Bradford assay (see above).

Glucuronidase (Gus) Assay

The gus assay was performed in a black microtiter plate (96 well PS F-bottom uCLEAR, black, med. binding, Greiner Bio-One, Kremsmünster, Österreich, REF 655096). 100 µL of each sample (either cell suspension or lysate) was pipetted in three wells, of which one serves as negative control and two as technical replicates. The gus buffer (50 mM phosphate buffer pH 7.0 (5.136 g·L$^{-1}$ $Na_2HPO_4$·$2H_2O$, 3.299 g·L$^{-1}$ $NaH_2PO_4$: $2H_2O$) with 5 mM DTT and 0.1% Triton-X-100) was complemented with 2 mM substrate X-Gluc (stock solution: 0.2 M in DMF). 100 µL was added to 100 µL of the sample. For the negative control, 100 µL gus buffer without substrate was added. Beside of the individual negative control of each sample, also medium and substrate controls were prepared.

The microtiter plate was measured in a pre-warmed Tecan reader Infinite M200 (Ref 30016056, Tecan Group AG, Mannedorf, Switzerland) (37° C.) for 3 hours (assay with entire cells), respectively for 2 hours (assay with lysate). The absorption maxima of indigo were measured at 610 and 660 nm. After discounting the absorption value of all controls, the slope of each absorption curve was calculated by linear regression and normalized either on cell dry weight (assay with entire cells) or on whole protein amount (assay with lysate). The normalized slope was used to compare the β-glucuronidase activities in the different mutants.

Screening Experiments in the Biolog® OmniLog Phenotypic Microarray System

Pre-screening experiments were performed in the Biolog® OmniLog Identification System (Hayward, CA, USA) to evaluate respiration on different carbon sources (panel PM1 and PM2). Actinoplanes sp. SE50/110 wild type and the deletion mutant Δcgt were grown on SFM agar plates, as described elsewhere herein. Cells were harvested by use of a sterile swab and diluted in the inoculating fluid IF-Oa for PM1 and PM2. The turbidity of the cell suspension was checked to achieve 80% transmittance in the turbidimeter of Biolog®, according to manufacturer's protocol. 2.32 mL of the cell suspension was added to 20 mL IF-0a, 0.24 mL 0.5 M $MgCl_2$, 0.24 mL 0.5 M $Na_2SO_4$, 0.24 mL 1.5 M $NH_4Cl$, 0.24 mL 1.0 M $NasPO_4$, 0.24 mL aqua distilled, 0.24 mL Biolog redox dye mix G, and 0.24 mL metal ion cocktail (5.0 mM each: $ZnCl_2 \cdot 7H_2O$, $FeCl_2 \cdot 6H_2O$, $MnCl_2 \cdot 4H_2O$, $CaCl_2 \cdot 2H_2O$), according to the manufacturer's protocol. The PM panels were inoculated with 100 μL per well of the prepared solution and incubated for 1 week in the OmniLog system (Mode 71000 Serial #406) at 28-30° C. Data evaluation was carried out with the manufacturer's software (Kinetic Analysis, Biolog and Omnilog 2.3, Biolog).

RNA Work

Sampling and RNA Isolation

For transcriptome analysis, 2×1 mL culture were taken during growth phase, separated from the supernatant by centrifugation (10 s) and snap-frozen in liquid nitrogen. Pellets were stored at −80° C. until further processing.

For isolation of ribonucleic acid (RNA), frozen cell pellets were resuspended in 500 μL LB-buffer (NucleoSpin® RNA Plus, Macherey-Nagel, Düren, Germany) and transferred to 2 mL lysing matrix tubes (0.1 mm spherical silica beads, MP Biomedicals, Santa Ana, California, USA). Cell disruption was carried out in a homogenizer (FastPrep FP120, Thermo Fisher Scientific, Waltham, MA, USA) for three times 20 s at speed setting 6.5 and 5 min on ice in between. Subsequently, the cell suspension was centrifuged for 5 min at 13,000 g and 4° C. The supernatant was used for RNA extraction using the NucleoSpin® RNA Plus kit in combination with rDNase Set (Macherey-Nagel, Düren, Germany) for an on-column DNA digestion. After clean-up and elution according to the manufacturer's protocol, the DNA-digestion was repeated (in solution) and the sample cleaned up again by use of the same kit. With two primer pairs binding to the genomic DNA of Actinoplanes sp. SE50/110 and amplifying small fragments at round about 200-300 nt, the sample was tested for residual DNA. DNA digestion and RNA clean-up was repeated, if necessary. The quantity of RNA was analyzed with the NanoDrop 1000 spectrometer (Peqlab, Erlangen, Germany).

Reverse Transcription Quantitative PCR

Reverse transcription quantitative PCR was carried out according to the protocol of Wolf et al. (2017a) by use of SensiFast SYBR No-Rox One-Step kit (Bioline, London, UK) and 96 well lightcycler plates (Sarstedt, Numbrecht, Germany) in a LightCycler 96 System of Roche (Mannheim, Germany). The relative RNA amount was normalized on total RNA (100 ng) and calculated as $2^{-\Delta cq}$. ΔCq is the difference of the mean Cq in the mutant strain compared to the control strain. The primers in Table E9 were used for determination of the relative transcription of a gene.

TABLE E9

Primers used in RT-qPCR experiments.

| genetic locus | forward primer (5'-3') | reverse primer (5'-3') | fragment size (bp) |
|---|---|---|---|
| merR (ACSP50_0145) | GAGCGATACGCCCCTGACC | GGTGATGTCCGGGCTCGTG | 309 |
| idi (ACSP50_0146) | GCCTTCTCGGTCTTCCTCAC | CGCCAATTCCTCGGTGAGAC | 168 |
| crtI (ACSP50_0147) | CTCTCGGTCGGCGGATAC | GAGCCGTCCGGGTAGTACGC | 158 |
| crtE (ACSP50_0148) | TTCCTCGCCTCCCAGATCG | CGCGAAGGTGTGCATCAG | 210 |
| crtB (ACSP50_0149) | CATGTGCACGCTCTGTATGG | AAGACCGCGATGGTGTCAG | 185 |
| acbZ (ACSP50_3590) | CGGCAATTCGCTGTTCAGTG | TGTGCTTGACGGTGTCCATC | 167 |
| acbY (ACSP50_3591) | TCCGAACGGTTCCTCTATCC | AACTCGCTGAGCTGGTTGAC | 239 |
| acbX (ACSP50_3592) | TCGGGATGCTGCACACCAAC | CGACGCGAACATCGCGAAAC | 191 |
| acbW (ACSP50_3593) | GGTGTACGACCGGAACATGC | GTTCGGCGTGGATGTGGTTG | 224 |
| acbV (ACSP50_3594) | GCTTCCACGGCAAGACGATG | GCGCTCACGTTGGGTTTCT C | 196 |

TABLE E9-continued

Primers used in RT-qPCR experiments.

| genetic locus | forward primer (5'-3') | reverse primer (5'-3') | fragment size (bp) |
|---|---|---|---|
| acbS (ACSP50_3596) | GTTGCCGGACCGGTTCTATC | CCCGGTACACCGACTTGTTG | 248 |
| acbQ (ACSP50_3601) | TGCTGGCGCAGATCTACTCC | AGCCGCAGATACATCGGGTC | 211 |
| acbK (ACSP50_3602) | CGAGGTCTACGCCTTCAACG | AGAGGAAGCCGGACACGAAC | 248 |
| acbC (ACSP50_3607) | GATCGCGCTGATCAAGGATG | CTGAACGTGTGCCCGTAGTC | 213 |
| acbB (ACSP50_3608) | GTCGACAAACTGGGTTACGG | GTCCAGTAGCACCTGAGTG | 231 |
| acbA (ACSP50_3609) | TCATGCTCGGCGACAACCTG | GACCGGTTTCTCCTCGATGG | 173 |
| acbE (ACSP50_3610) | GCGCGGCATGAAGATCTACC | CGGACGGCTTCTCGAAGAAC | 218 |
| acbD (ACSP50_3611) | ACGCCAACTACTGGATGGAC | TCGAGCGGTTGGTGTAGAAG | 231 |
| cgt (ACSP50_5024) | CACCACGTACTGGAACTC | GCGACCTTCAACGTGAC | 192 |
| gtaB/galU (ACSP50_7820) | CTCGCCTTCATCGAGGTCAC | GGCGATCGTCTCGAAGATCC | 192 |
| gusA | ACGCGGACATCCGCAACTAC | CCCTGGTGCTCCATCACTTC | 157 |

Whole Genome Oligonucleotide Microarray

Whole genome oligonucleotide microarrays were performed according to a protocol of Wolf et al. (2017a), who adapted the hybridization procedure to the high G+C content of Actinoplanes sp. SE50/110.

RNA of triplicates was isolated and equimolar pooled (total amount of 5 µg pooled RNA in 12 µL). For cDNA synthesis, labeling and microarray hybridization the Two-Color Microarray-Based Prokaryote Analysis FairPlay III Labeling kit (Version 1.4, Agilent Technologies, Santa Clara, CA, USA) was used according to the manufacturer's instructions with practical adjustments described by Wolf et al. (2017a). The Amersham CyDy® mono-reactive dye packs (GE Healthcare, Little Chalfont, UK) were utilized for labeling. A custom whole genome oligonucleotide microarray representing the coding sequence of Actinoplanes sp. SE50/110 was used, which was designed by Wolf et al. (2017a) (4×44K format, 43,803 features representing 8,238 genes and 1,417 control spots, supplier: Agilent Technologies, Santa Clara, CA, USA). All microarray specific reagents and device including hybridization oven and scanner were used from Agilent Technologies (Santa Clara, CA, USA). The Agilent Feature Extraction Software Version 10.7.3.1 (Agilent Technologies, Santa Clara, CA, USA) was used for feature extraction (protocol GE2_107_Sep09). Subsequent data analysis, including LOWESS normalization and statistical analysis were performed by use of the microarray and gene expression (MAGE)-compliant system EMMA 2 (Dondrup et al. 2009). A p-value of 0.05 was used as a cut-off for significance. The M-value cut-offs for a false discovery rate of 0.01 were determined as 1.1 and −1.1 according to previous "yellow experiments" performed by Wolf et al. (2017a).

Analysis of the Functional Relevance of Cgt
Distribution of Single-Domain CBM-20 Proteins in the Eubacterial World The inventors have analyzed the distribution of CBM-20 single-domain proteins in the prokaryotic world by BlastP analysis.

In brief, the distribution of singular CBM-20-domain proteins was analyzed by BlastP analyses using the NCBI non-redundant protein database (Altschul et al. 2005; Altschul et al. 1990). As CBM-20 domains occur in a variety of different proteins and enzymes, data filtering had to be performed: Of the initial 3,316 BlastP hits, all of eukaryotic origin and all enzymes with function-specific annotation or sizes above 350 amino acids were excluded. The domain structures of the remaining 80 BlastP hits were analyzed (Marchler-Bauer et al. 2017; Marchler-Bauer and Bryant 2004; Marchler-Bauer et al. 2015; Marchler-Bauer et al. 2010). Most of these, 53 proteins in total, contain two CBM-20 domains traversed by a higher domain described as glyco-hydro-77-superfamiliy 4-alpha-glucanotransferase. Ten contain different additional domains: Five of them alpha-amylase inhibitor domains, two CBM-25, respectively, CBM-26 binding domains at the N-terminus, two N-terminal domains of IPT-superfamily with probable regulatory function and one a DUF1393-domain, which was described to occur in several alpha-amylases (information taken from the NCBI database). These candidates were also excluded. Only 18 candidates (including Cgt from Actinoplanes sp. SE50/110) displayed a singular CBM-20 domain. A protein tree was created by Blast tree view 1.17.5 of the NCBI database (NCBI database) on basis of a multiple sequence alignment performed by BlastP (Altschul et al. 1990; Altschul et al. 2005).

Figure 9:
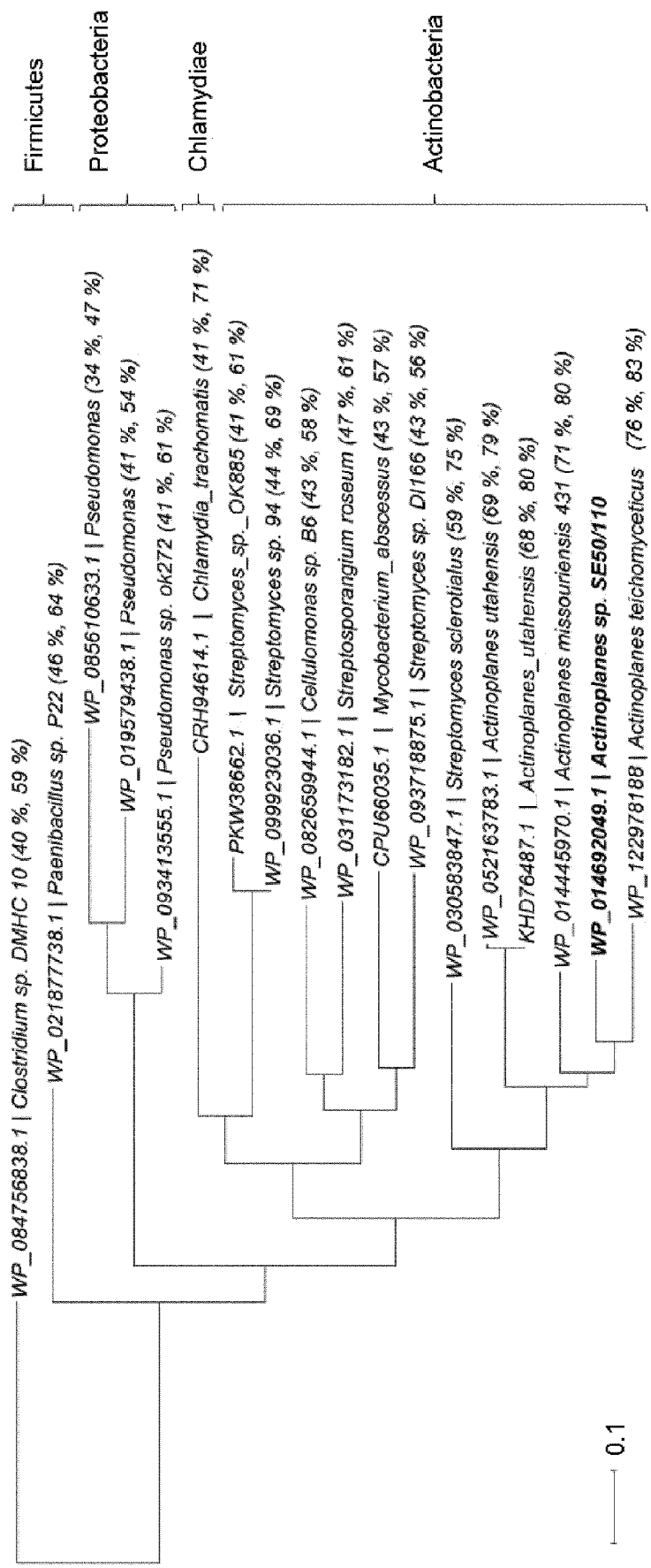
FIG. 9. BlastP analysis of the amino acid sequence of Cgt leads to the identification of 17 other proteins consisting of a singular CBM-20 domain. The protein tree was created and visualized on the basis of multiple sequence alignment performed by BlastP (Altschul et al. 1990). The protein tree shows the distance of the 18 singular CBM-20 domain proteins, identified by the NCBI accession number and their hosts. In brackets the sequence identity and positives of BlastP analysis are shown in percentages.

Interestingly, singular CBM-20 domain-proteins were found in only 17 other species (FIG. 9). Most of these are found in species of the order Actinomycetales, for example in all strains of the genus Actinoplanes. The majority of the 17 species were originally isolated from soil and environmental samples, namely *A. missouriensis* (Parenti and Coronelli 1979), *A. utahensis* (described by Parenti and Coronelli (1979) and first isolated by Couch (1963)), A. teichomyceticus (Wink et al. 2006), *Streptomyces* sp. 94 (Chu et al. 1996), *Streptomyces* sp. OK885 (isolated from roots, Tennessee, USA, information taken from GenBank (Benson et al. 2013) of the NCBI (NCBI database)), Streptosporangium *roseum* (Nolan et al. 2010), Streptosporangium *sclerotialus* (syn. Chainia *antibiotica*) (Thirumalachar 1955), Cellulomonas sp. B6 (Piccinni et al. 2016), *Paenibacillus* sp. P22 (Hanak et al. 2014), and *Clostridium* sp. DMHC 10, which was isolated from the sludge of a distillery waste treatment plant (Kamalaskar et al. 2010). CBM-20 proteins also occur in *Streptomyces* sp. DI166, for which the sampling sites has not been reported, and in multi-species of the family Pseudomonadaceae. They belong to genera, which are known to include soil-inhabiting members.

Strains carrying singular CBM-20 proteins without direct connection to the habitats soil or environment occur only occasionally, like in singular isolates of the human pathogens *Chlamydia trachomatis* (Thomson et al. 2008) and *Mycobacterium abscessus* (Ryan and Byrd 2018; Moore and Frerichs 1953).

Confirmation of the Starch Binding Function by an In Vitro Assay

CBM-20 domains are described to have a starch binding function, which the inventors wanted to test by an in vitro assay. As the small carbohydrate binding protein Cgt is highly expressed and enriched in the extracellular space due to an N-terminal signal peptide (Wendler et al. 2015a), the protein could be directly concentrated from the supernatant by filtration. A starch binding assay was performed with starch from potato in different concentrations. Both—the starch fraction as well as the supernatant-were analyzed by SDS-PAGE. In all starch fractions (ranging from 1 to 10% (w/v) of starch), a protein band at about 15 kDA was detected, which was clearly identified as Cgt by MALDI-TOF-MS. In contrast, the supernatant fractions were almost completely depleted by Cgt. Residual Cgt in the supernatant was found, indicating, that the added starch was completely saturated by Cgt. In the negative control without starch, most of Cgt remains in the supernatant fraction. Beside Cgt, another small extracellular protein of unknown function, ACSP50_6253, was identified by the starch binding assay (data not shown).

Analysis of Cgt Expression During Growth on Different Carbon Sources

Figure 10:
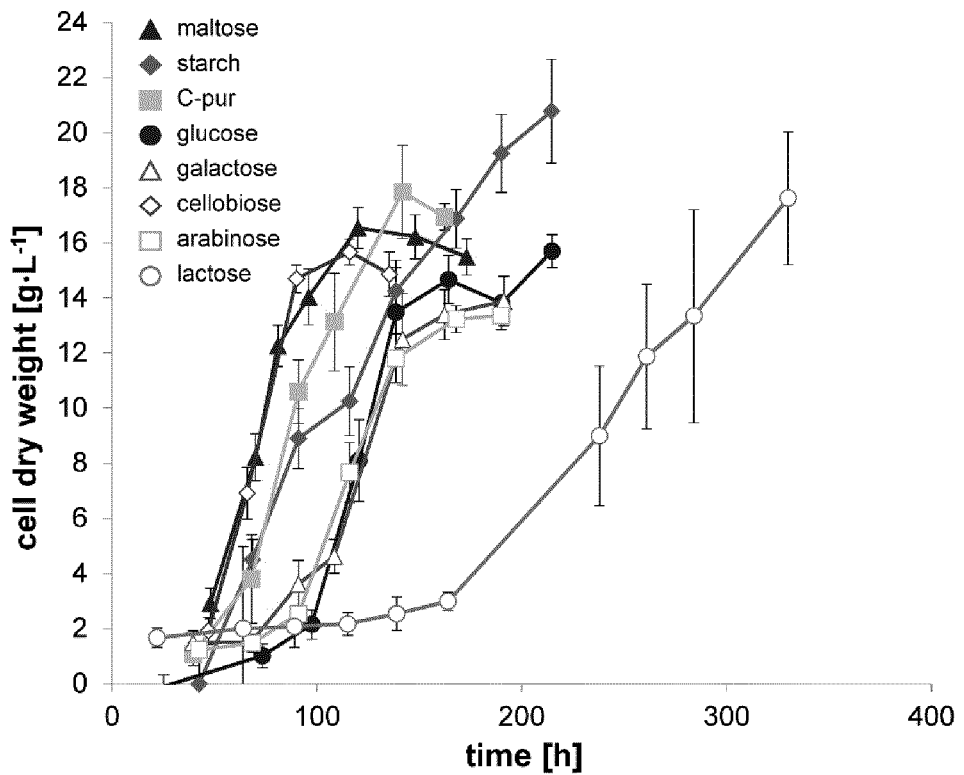
FIG. 10. Growth of the wild type of Actinoplanes sp. SE50/110 in minimal medium supplemented with different carbon sources (in equal C-molar amounts). Shown are the cell dry weights of at least three biological replicates and the standard deviation ($n_{glc}=3$, $n_{mal}=5$, $n_{cel}=4$, $n_{lac}=3$, $n_{ara}=5$, $n_{starch}=5$).

The gene cgt has been reported of being differentially expressed in the presence of different carbon sources, as determined by transcriptome and proteome analysis on glucose and maltose (Schwientek et al. 2013; Wendler et al. 2015a; Ortseifen 2016). The inventors have tested the effects of several carbon sources on the expression of cgt gene by measuring the transcript amounts by reverse transcription quantitative PCR (RT-qPCR). For this purpose, the wild type strain of Actinoplanes sp. SE50/110 was grown on minimal medium supplemented with maltose, glucose, starch, galactose, cellobiose, lactose and C-Pur (Cerestar 01908) (FIG. 10). The latter is a sugar-containing product from the degradation of starch mainly consisting of maltose and maltotriose. All carbon sources were supplemented in equivalent C-molar amounts. The only exception was starch: Due to the low solubility, here, a 4% (w/v) opalescent solution of "starch soluble" from Acros Organics was generated. For comparison, a maltose minimal medium with reduced amount of maltose was prepared (here: 44.40 g·L$^{-1}$ maltose monohydrate), in which the C-molarity should approximate the one in the starch medium.

Figure 11:
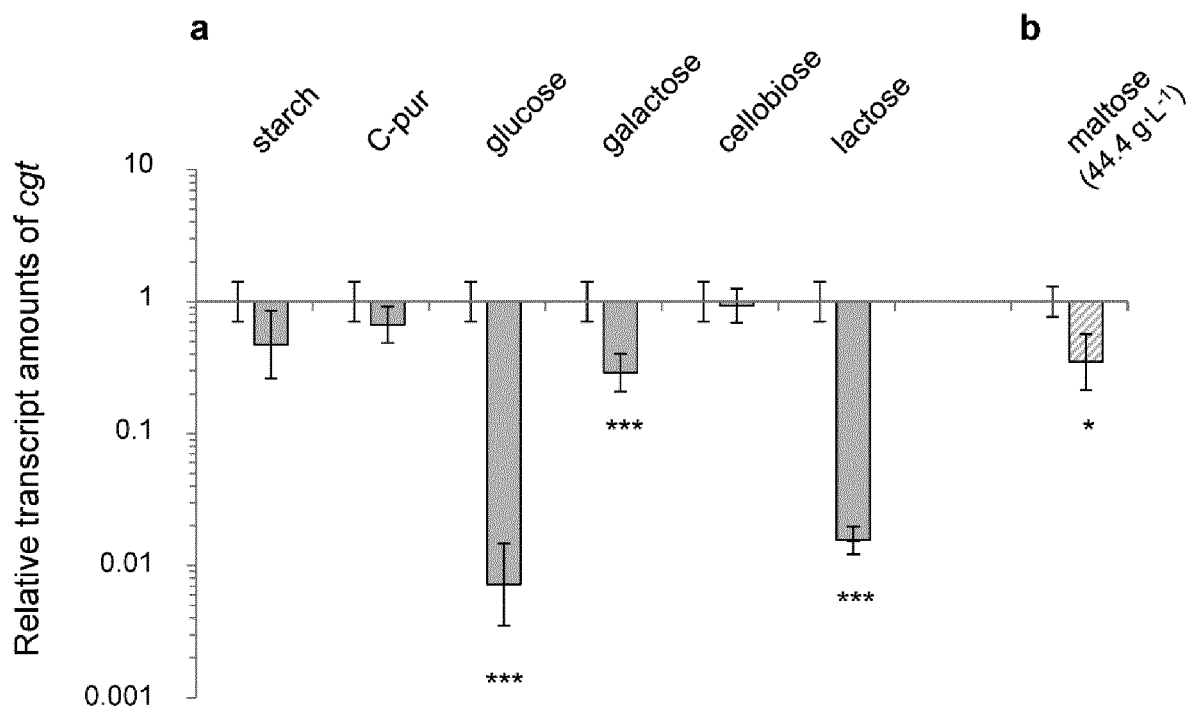
FIG. 11. A. Relative transcript amounts of cgt in Actinoplanes sp. SE50/110 grown on minimal medium supplemented with starch, C-Pur, glucose, galactose, cellobiose, or lactose as carbon source, compared to a culture grown on maltose minimal medium. Testing for differences in a two-sided t-test displayed significant differential gene expression of the cgt gene on the carbon sources glucose (p-value=0.002848), galactose (p-value=0.002945) and lactose (p-value=0.00114) compared to maltose. B. Relative transcript amount of cgt in Actinoplanes sp. SE50/110 grown on maltose minimal medium complemented with 44.40 g·L$^{-1}$ maltose compared to a culture grown on 72.06 g·L$^{-1}$ maltose. Testing for differences in a two-sided t-test displayed significant reduced gene expression of cgt in the medium containing reduced amounts of maltose (p-value=0.04141).

For most tested carbon sources, the transcription of the cgt gene was similar or just slightly and insignificantly reduced compared to a maltose grown culture (FIG. 11A). Differential transcription was observed for galactose to a minor extent (3.4-less transcribed, log 2 (fold-change)=0.291). A significant reduction of cgt transcript was measured for the carbon sources glucose (142-fold less transcribed, log 2 (fold-change)=0.007) and lactose (62-fold less transcribed, log 2 (fold-change)=0.016). When cells were grown on maltose minimal medium with reduced amount of maltose (here: 44.4 g·L$^{-1}$ instead of 72.06 g·L$^{-1}$), a 2.9-fold decreased transcription of cgt gene was observed (log 2 (fold-change)=0.345) (FIG. 11B).

Analysis of Gene Deletion Mutant ΔCgt

ΔCgt on Different Carbon Sources or Under Carbon-Limited Conditions

The differential transcription profile of cgt in dependence of the carbon source indicated a function within sugar metabolism, like it has been presumed before (Ortseifen 2016). Ortseifen (2016) (Ortseifen 2016) suggested Cgt of being responsible for the retention of carbon as energy source in the context of the carbophore model. Growth of the wild type and the CRISPR/Cas9 deletion mutant Δcgt was tested on different carbon sources in liquid culture.

Before, a pre-screening experiment was performed in the OmniLog Phenotypic Microarray System (Biolog Inc., Hayward, United States of America), which allows fast phenotypic screening by measurement of cellular respiration activity on a total of 190 different carbon sources in multi-well plates. Of these, Actinoplanes displayed respiration on 103 carbon sources. Except for arabinose and lactose, no differential respiration profile was observed for Δcgt on the remaining 101 carbon sources. In order to validate these results on the level of growth, the carbonsources arabinose and lactose were furthermore tested in a shake flask cultivation. Also, the standard laboratory sugars maltose and glucose, and the complex carbon source starch as well as the disaccharide cellobiose were tested, to imitate natural carbon sources of the habitat soil. No restraint on growth was observed for Δcgt (FIG. 12 and FIG. 13).

Furthermore, growth under carbon-limited conditions (here: 1 g·L$^{-1}$, 2 g·L$^{-1}$, 3 g·L$^{-1}$, 4 g·L$^{-1}$ and 5 g·L$^{-1}$ starch) was tested in the RoboLector®-system of m$^2$p-labs. No growth disadvantages for the Δcgt mutant were observed in case of carbon source constraints compared to the wild type (FIG. 14).

ΔCgt has No Impact on Osmolarity- or pH-Tolerance

Cgt multimers have been proposed to form surface layers through multimerization (Wendler et al. 2015a). This might suggest a potential role in protection against environmental changes, like drought, pH and osmolarity.

A pH screening was performed on solid media as well as in liquid culture in the RoboLector®-system. For screening on solid media, SFM-agar plates of pH ranging from pH 4 to 11 (in steps of 1) were prepared and droplets of a dilution series of spores of the wild type and the deletion mutant Δcgt were applied. Both mutant and wild type were able to grow from pH 5 to 11. No differences in growth or spore formation on agar-plates were observed.

Since an effect of drought tolerance is difficult to assess, the inventors analyzed the colony and spore formation on the surface of the bacterial lawn and found no differences between the wild type and Δcgt.

For pH screening in liquid culture, maltose minimal medium of pH ranging from 4 to 7 was prepared. Higher pH values could not be tested in liquid culture, as medium components tend to precipitate. Both strains grew from pH 4.5 to 7 (FIG. 15). Regarding the final cell dry weights, no differences were observed.

For osmolarity screening, maltose minimal medium was prepared with different concentrations of maltose ranging from 3.6 to 108.1 g·L$^{-1}$ maltose monohydrate and osmolarity ranging from 323.5 to 681.0 mOsmol·kg$^{-1}$ (Table E11). No significant growth differences were observed between the wild type and the deletion mutant Δcgt (FIG. 16).

Also, inositol was tested as osmolyte, since it is not consumed by Actinoplanes. Here, osmolarity ranged from 388.5 to 695.0 mOsmol·kg$^{-1}$, but no growth differences were observed (FIG. 17).

Figure 19:
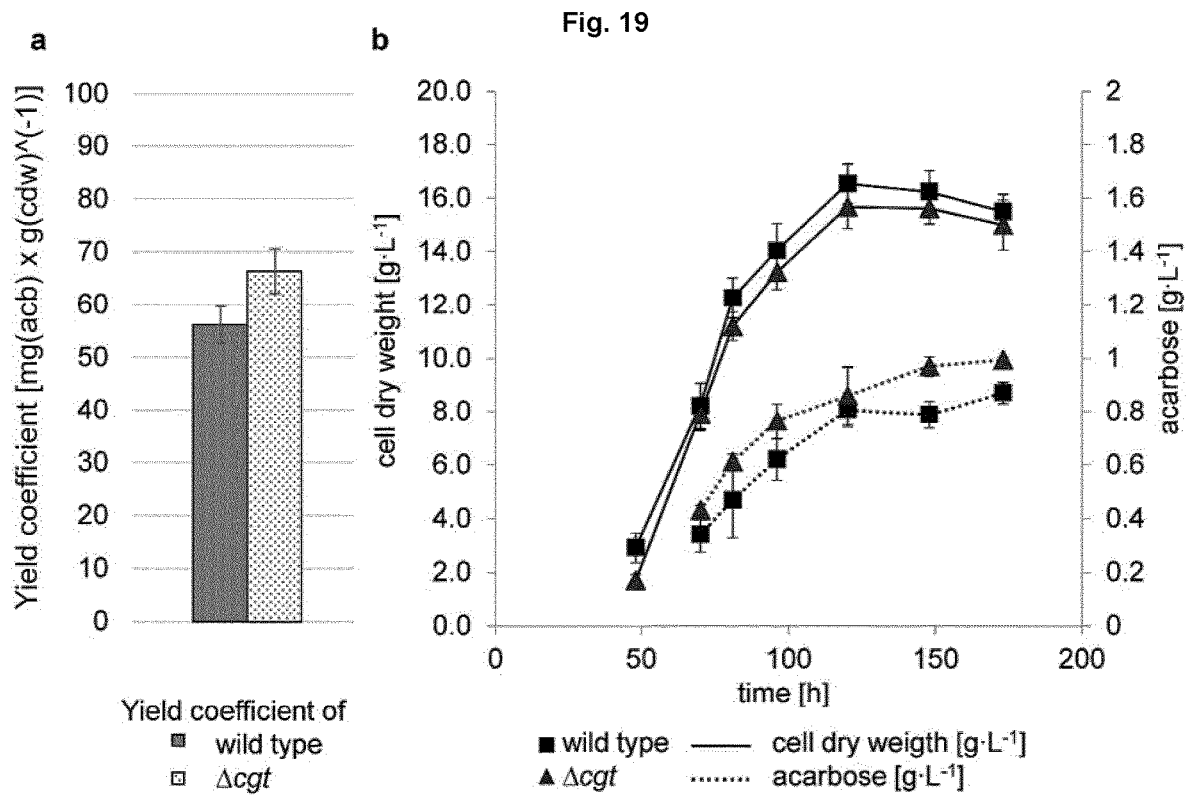
FIG. 19. A. Final yield coefficient of acarbose with reference to the cell dry weight in a bar chart. Error bars was calculated by Gaussian error propagation. B. Cell dry weights and acarbose concentration in the supernatant during cultivation in maltose minimal medium ($n_{cdw}$=5, $n_{ach}$=4).

Lower osmolarities between 159-190 mOsmol·kg$^{-1}$ were tested by use of the complex medium NBS (FIG. 19, Table E10). Again, no significant differences in growth were observed between the wild type strain and the deletion mutant Δcgt.

Δcgt Displays Improved Acarbose Formation on Maltose Minimal Medium

Figure 18:
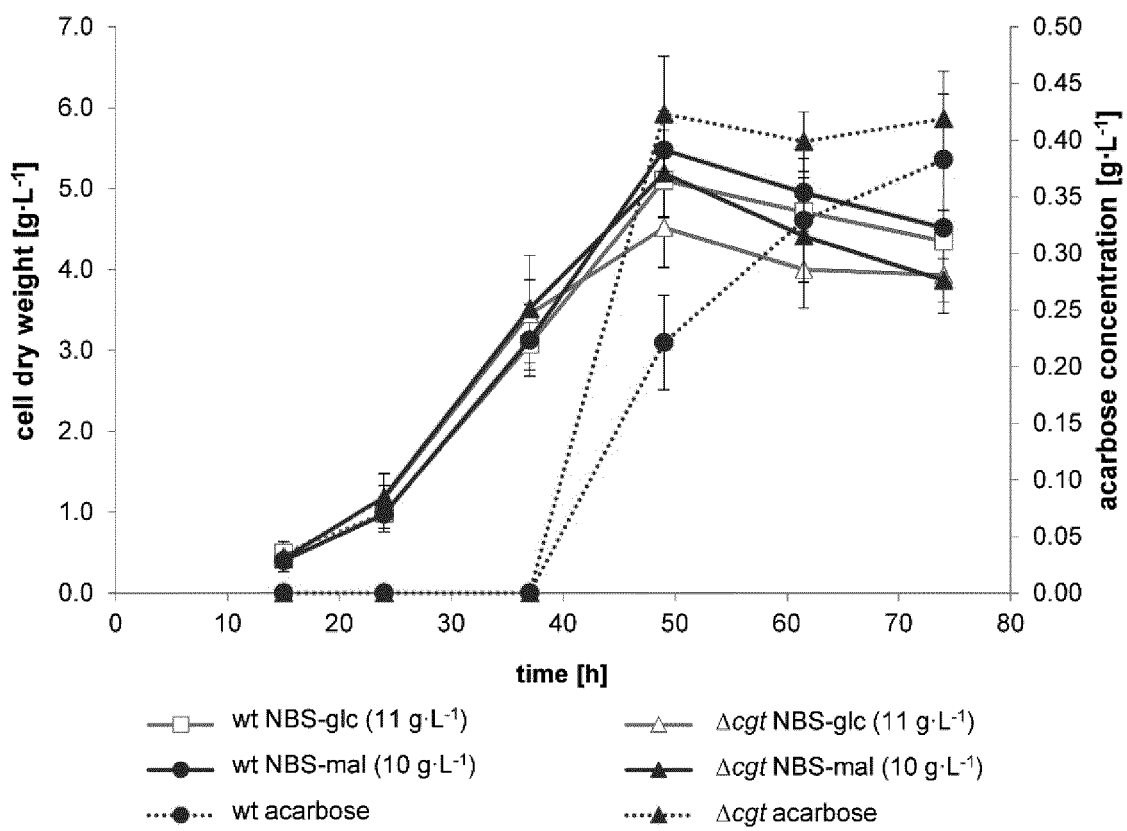
FIG. 18. Growth and acarbose production of Actinoplanes sp. SE50/110 wild type and Δcgt mutant in the complex medium NBS supplemented with 11.0 g·L$^{-1}$ maltose-respectively 10.0 g·L$^{-1}$ glucose-monohydrate. No differential growth was detected. During growth phase, a significant increased acarbose concentration was measured in Δcgt (significance of t-test after 49 h of cultivation: p-value=0.006778, $n_{wt-acb}$=3, $n_{acgt-acb}$=3, $n_{wt-cdwGlc}$=4, $N_{Acgt-cdwGlc}$=3, $n_{wt-cdwMal}$=4, $n_{acgt-cdwMal}$=4).

Although no distinct growth phenotype could be observed under the tested conditions, lack of the highly expressed Cgt protein seems to save metabolic resources of the cell, such as ATP and amino acids. These might be used for cellular growth or other anabolic processes. In the experiments, Δcgt has not displayed significant growth advantages. However, remarkably higher final acarbose concentrations were detected for the deletion mutant Δcgt compared to the wild type (Table E10). For the cultivation in complex medium, this was most striking during the growth phase (FIG. 18).

The improved acarbose-producing phenotype was validated by three independent shake flask cultivations in maltose minimal medium (FIG. 19 and Table E11). Quantification of acarbose from the supernatant displayed an enhanced acarbose yield coefficient of the deletion mutant compared to the wild type. The differences in the final acarbose yields were significant (tested by a two-sided t-test, p-value=0.04608). Thereby, in Δcgt an increase of 8.3 to 16.6% of final acarbose concentration was reached (cf. Table E11).

TABLE E10

Tabular summary of screening experiments. Final cell dry weights, final acarbose concentrations, pH and osmolarity of different minimal media used in this work for screening of osmolarity and pH. Different osmolarities in the media used for pH screening are caused by addition of correcting agents.

| maltose x1H$_2$O (g·L$^{-1}$) | glucose x1H$_2$O (g·L$^{-1}$) | inositol (mM) | osmolarity (mOsmol·kg$^{-1}$) | pH | final cell dry weights (g·L$^{-1}$) | | final acarbose concentration (g·L$^{-1}$) | | significance (p-value) |
|---|---|---|---|---|---|---|---|---|---|
| | | | | | wild type | Δcgt | wild type | Δcgt | |
| pH Screening | | | | | | | | | |
| 72.06 | — | — | 629.0 | 4.0 | 1.17 ± 0.95 | 2.09 ± 0.26 | not detectable | | — |
| 72.06 | — | — | 630.0 | 4.5 | 5.50 ± 0.66 | 6.94 ± 1.07 | 0.27 ± 0.18 | 0.38 ± 0.05 | *0.02216 |
| 72.06 | — | — | 606.0 | 5.0 | 9.67 ± 1.28 | 11.34 ± 0.80 | 0.47 ± 0.003 | 0.65 ± 0.03 | *0.00136 |
| 72.06 | — | — | 587.0 | 5.5 | 11.04 ± 0.71 | 12.13 ± 0.42 | 0.66 ± 0.03 | 0.80 ± 0.02 | *0.00124 |
| 72.06 | — | — | 569.0 | 6.0 | 12.67 ± 0.38 | 12.97 ± 0.47 | 0.97 ± 0.17 | 0.89 ± 0.01 | — |
| 72.06 | — | — | 569.0 | 6.5 | 13.79 ± 1.84 | 12.83 ± 0.76 | 1.14 ± 0.13 | 1.06 ± 0.04 | — |
| 72.06 | — | — | 563.0 | 7.0 | 13.86 ± 0.57 | 12.50 ± 1.53 | 0.94 ± 0.10 | 0.85 ± 0.06 | — |
| Osmo-Screening 1 | | | | | | | | | |
| 3.6 | — | — | 323.5 | 6.5 | 1.75 ± 0.38 | 1.97 ± 0.28 | not detectable | | — |
| 14.41 | — | — | 361.5 | 6.4 | 6.21 ± 0.19 | 6.25 ± 0.10 | not detectable | | — |
| 36.03 | — | — | 420.5 | 6.4 | 13.29 ± 0.26 | 12.66 ± 0.41 | 0.33 ± 0.04 | 0.39 ± 0.08 | — |
| 57.65 | — | — | 485.0 | 6.4 | 14.00 ± 0.45 | 14.19 ± 0.30 | 0.49 ± 0.01 | 0.61 ± 0.08 | — |
| 72.06 | — | — | 531.0 | 6.4 | 14.83 ± 0.47 | 15.17 ± 0.38 | 0.58 ± 0.05 | 0.65 ± 0.06 | — |
| 86.47 | — | — | 605.0 | 6.4 | 14.79 ± 0.63 | 16.91 ± 0.77 | 0.67 ± 0.04 | 0.69 ± 0.01 | — |
| 108.09 | — | — | 681.0 | 6.3 | 16.21 ± 1.20 | 17.91 ± 0.33 | 0.56 ± 0.03 | 0.66 ± 0.02 | *0.01432 |
| Osmo- | | | | | | | | | |
| 20 | — | 0 | 388.5 | 6.4 | 11.88 ± 0.22 | 12.25 ± 0.25 | not detectable | | — |
| 20 | — | 1 | 406.5 | 6.4 | 12.83 ± 0.47 | 12.75 ± 0.98 | not detectable | | — |
| 20 | — | 80 | 469.5 | 6.4 | 12.75 ± 0.45 | 12.06 ± 0.95 | not detectable | | — |
| 20 | — | 140 | 550.0 | 6.4 | 15.13 ± 0.25 | 13.16 ± 0.75 | not detectable | | — |
| 20 | — | 180 | 580.0 | 6.4 | 14.63 ± 0.45 | 14.03 ± 1.15 | not detectable | | — |
| 20 | — | 220 | 610.3 | 6.4 | 14.79 ± 0.44 | 13.13 ± 1.76 | not detectable | | — |
| 20 | — | 280 | 695.0 | 6.3 | 15.33 ± 0.51 | 14.00 ± 1.45 | not detectable | | — |
| NBS- | | | | | | | | | |
| 0 | 10 | 0 | 190 | 6.9 | 4.35 ± 0.22 | 3.93 + 0.47 | acarbose is not main component | | |
| NBS- | | | | | | | | | |
| 11 | — | 0 | 159 | 6.9 | 4.51 + 0.22 | 3.87 ± 0.27 | 0.38 ± 0.06 | 0.42 ± 0.04 | *0.006778 |

TABLE E11

Tabular summary of growth experiments under acarbose producing conditions. Final acarbose concentrations, final cell dry weights and the number of replicates n of three independent cultivations of Δcgt and the wild type in maltose minimal medium.

|  |  | No.1 | No.2 | No.3 |
|---|---|---|---|---|
| acarbose ($g \cdot L^{-1}$) | WT | 0.76 (+/− 0.07) | 0.87 (+/− 0.04) | 0.69 (+/− 0.02) |
|  | n | 5 | 4 | 3 |
|  | Δcgt | 0.88 (+/− 0.05) | 0.99 (+/−0.01)) | 0.74 (+/− 0.03 |
|  | n | 6 | 4 | 3 |
| % |  | 116.6 | 114.2 | 108.3 |
| cell dry weight ($g \cdot L^{-1}$) | WT | 14.72 (+/− 1.71) | 15.49 (+/− 0.65) | 15.30 (+/− 1.25) |
|  | n | 7 | 5 | 5 |
|  | Δcgt | 16.12 (+/− 0.89) | 14.99 (+/− 0.94) | 13.85 (+/− 1.46) |
|  | n | 6 | 5 | 5 |
| % |  | 109.5 | 96.8 | 90.5 |

ΔCgt has No Impact on the Expression of Acarbose Biosynthesis Genes

Figure 20:
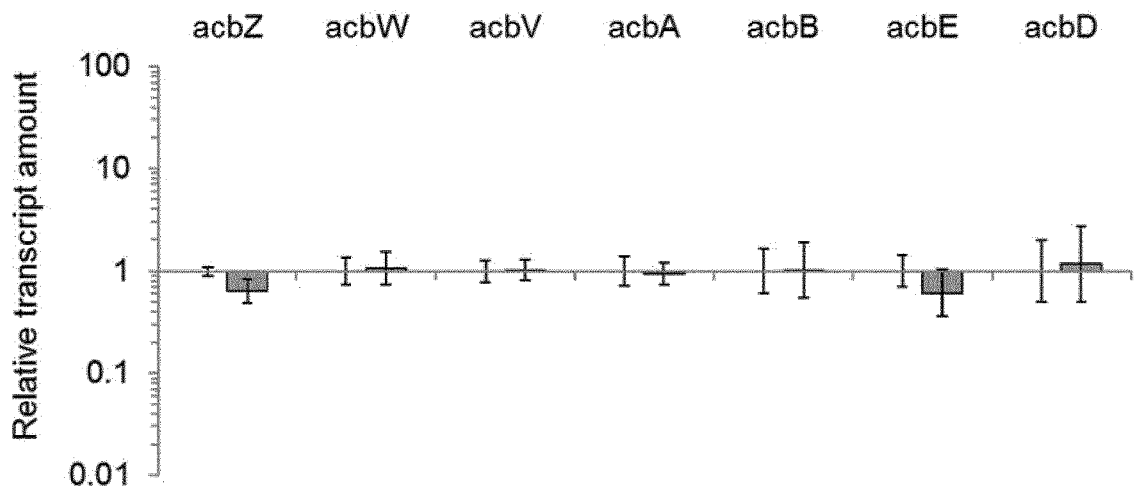
FIG. 20. Relative transcript amounts of the genes acbZ, acbW, acbV, acbA, acbB, acbE and acbD of the mutant Δcgt compared to the wild type of Actinoplanes sp. SE50/110 grown on maltose minimal medium (n=3-6).

Findings that the deletion of the highly expressed gene cgt has no negative impact on growth or viability of the organism under various conditions, but yields into an enhanced acarbose producing phenotype, was surprising. Due to this and to rule out a direct impact on the regulation of acarbose biosynthesis (acb) genes, RT-qPCR of representative acb genes were performed. For this, wild type and Δcgt were grown on maltose·minimal medium and RNA was isolated from samples of the early growth phase. The relative transcript amount of the acarbose biosynthesis cluster genes acbZ, acbW, acbV, acbA, acbB, acbD and acbE were calculated for Δcgt in comparison to the wild type (FIG. 20). The gene acbV is the first of several polycistronically transcribed genes within the main operon of the acarbose biosynthesis gene cluster (Wolf et al. 2017b). The monocistronically transcribed genes acbD and acbE, encoding for proteins of the extracellular acarbose metabolism, have shown to be strongly regulated by the acarbose regulator AcrC (Wolf et al. 2017a). The genes acbA, acbB and acbZ are monocistronically transcribed, too, and are annotated as enzymes of the acarbose biosynthesis (acbAB) and its extracellular metabolism (acbZ), respectively. AcbW is the first gene of the acbWXY-operon, putatively encoding for an ABC transporter. For all selected transcripts, no significant change in relative transcript levels was measured in the deletion mutant Δcgt compared to the wild type (FIG. 20).

Discussion

The connection of carbohydrate metabolism and acarbose biosynthesis is of high interest. Recent research has pointed out the importance of carbon utilization in the context of the biosynthesis of acarbose and further acarviosyl metabolites in the wild type (Wendler et al. 2014).

In this context, the starch binding protein Cgt is striking. It is one of the strongest expressed genes in Actinoplanes sp. SE50/110 (Schwientek et al. 2013) making up for about 8% of the whole secreted proteome (unpublished data of the inventors). Its gene product is exported into the extracellular space (Wendler et al. 2013). Excess production and export means high costs for the cell: Only for the translational process, 4 ATP are required per peptide bond (Campbell and Reece 2011; Purves 2006), i.e. not including additional costs for RNA synthesis, amino acid production, protein folding and export. The inventors therefore concluded that Cgt has a significant role in Actinoplanes sp. SE50/110 physiology. Two different functions of Cgt are proposed and analyzed herein: A role within the sugar metabolism and a role as surface protein. Due to the starch binding domain Ortseifen (2016) (Ortseifen 2016) suggested, that Cgt might be involved in binding and retention of energy sources in the context of the carbophore model (Wehmeier 2003). Evidence was also given here by RT-qPCR, which displayed differential expression of the gene cgt in glucose-, galactose- and lactose-grown cultures compared to cultures grown on maltose, higher maltodextrins and cellobiose. This is in accordance with differential proteome analyses on the carbon sources maltose and glucose (Wendler et al. 2015a; Wendler et al. 2015b). These results indicate a carbon-dependent expression of cgt. It would be exciting to elucidate the regulatory mechanism. However, it remains to be considered that over 900 genes are putatively involved in transcriptional regulation in Actinoplanes sp. SE50/110, of which 697 are annotated as transcriptional regulators according to the annotation of Wolf et al. (2017b) (GenBank: LT827010.1).

A sugar-dependent expression of cgt might indicate a function within the utilization of maltose, higher maltodextrins and—potentially—also cellobiose. However, our studies of the deletion mutant Δcgt have not unveiled phenotypical differences regarding the carbon utilization. This was tested for a total of 105 different carbon sources, of which 103 were analyzed in the OmniLog screening system and six in liquid culture.

As the function of Cgt might be negligible under excess of carbon source but indispensable when growing under conditions with limited carbon source, the inventors have tested growth of the deletion mutant Δcgt and the wild type on minimal medium with low concentrations of starch. Starch was chosen as carbon source, due to the starch binding activity of Cgt, which was confirmed in a starch binding assay here. Nevertheless, no growth phenotype of the mutant could be observed under limited carbon source conditions.

Another function within the sugar metabolism could consist in binding of insoluble crystalline substrates, which might lead to structural changes, that increases substrate accessibility and enhances the activity of other hydrolyzing enzymes like amylases. Such mechanisms have already been described in the soil bacteria *Serratia marcescens* for chitinolysis (Vaaje-Kolstad et al. 2005) and *Thermobifida fusca* for cellulysis (Moser et al. 2008). In the genome of Actinoplanes sp. SE50/110 several genes are encoded with putative α-glyosidic function, of which three, the α-amylases/pullulanases AcbE, AcbZ and PulA, were shown to accumulate in the extracellular space (Wendler et al. 2015a). Additionally, another small extracellular protein of unknown function and starch binding capability (ACSP50_6253) was identified in a starch binding assay. By heterologous expression of extracellular amylases and enzyme assays in presence and absence of both-Cgt and ACSP50_6253-, a supporting function during starch degradation might be detected in future experiments.

Apart from the sugar metabolism, also a function as surface layer protein is conceivable, which is supported by the fact, that Cgt forms multimers (Ortseifen 2016; Wendler et al. 2013). Wendler et al. (2015) (Wendler et al. 2015a) identified two transmembrane domains in the Cgt protein, of which one is involved in translocation by the Sec pathway as part of the leader peptide and the second is assumed to be required for multimerization. Although Cgt is not likely to be physically anchored in the membrane (Wendler et al. 2015a), Cgt proteins may remain as multimers in the mesh of the mycelium, due to the reduced fluid flow. In this context, the starch binding domain might serve also as anchor.

In the role as putative surface protein, the inventors initially assumed a protective function in the context of pH and osmolyte stress or drought. However, the screening experiments showed that the deletion of cgt gene did not lead to significant growth inhibition at different pH in liquid culture. From the screening experiments on solid media, there was no indication, that Cgt might have a protective function in case of pH or drought.

Hints for a putative function in the context of osmoregulation were given by reverse transcription quantitative PCR of the wild type, grown on different amounts of maltose. Here, the inventors observed a 2.9-fold reduced transcription of the gene cgt, when growing on 44.4 g·L$^{-1}$ maltose compared to a 72 g·L$^{-1}$, which might be an effect of osmolarity. The inventors analyzed growth of the deletion mutant Δcgt in several screening experiments in liquid culture with media ranging from 159 to 681 mOsmol·kg$^{-1}$. Under all tested conditions, no differences in growth and viability were observed for the deletion mutant Δcgt compared to the wild type.

As surprisingly no apparent physiological impact was observed by the deletion of cgt gene neither in utilization of different carbon sources in excess nor in limitation, neither under different pH nor osmolyte conditions, it might be possible that the function of Cgt only becomes apparent in its natural environment and in possible competition with other soil organisms. Interestingly, the inventors found similar independent singular CBM-20 domain proteins in 17 other prokaryotic species, most of which belong to the order Actinomycetales. Although rare, this at least displays a certain distribution and shows, that Cgt is not a strain-specific protein. Most of the species harboring single domain CBM-20 proteins were associated with soil habitats. Together with the fact, that cgt is highly expressed in Actinoplanes sp. SE50/110, this supports the hypothesis that proteins like Cgt fulfill a crucial function in bacteria living within this habitat. A function of Cgt could be tested in future by co-cultivations in direct contact with other microbial competitors.

While it was surprising, that Cgt turned out to be dispensable under the tested laboratory conditions, the inventors observed a positive phenotype regarding the acarbose production. An increase of the acarbose yield between 8.3 and 16.6% was achieved by deletion of cgt. Although the final product yields differ slightly between batch cultivation, the Δcgt mutant always performed significantly better. This was shown over a time period of several month (data not shown) in three independent shake flask and several microscale cultivations performed in maltose minimal medium. Thus, the improved production was robust over long time periods and in different cultivation settings.

We assume that this is due to metabolic burden by expression of cgt gene in the wild type, which brings relief of energy and of free resources in Δcgt. These resources are probably redirected to the acarbose biosynthesis, which is a growth-associated product. A direct regulatory effect by deletion of cgt on the expression of the acb genes was not observed.

Analysis of the Functional Relevance of Carotenoid Formation

Light-Dependent Carotenoid-Formation and Oxidative Stress Reduce Acarbose Production in Actinoplanes Sp. SE50/110

Figure 21:
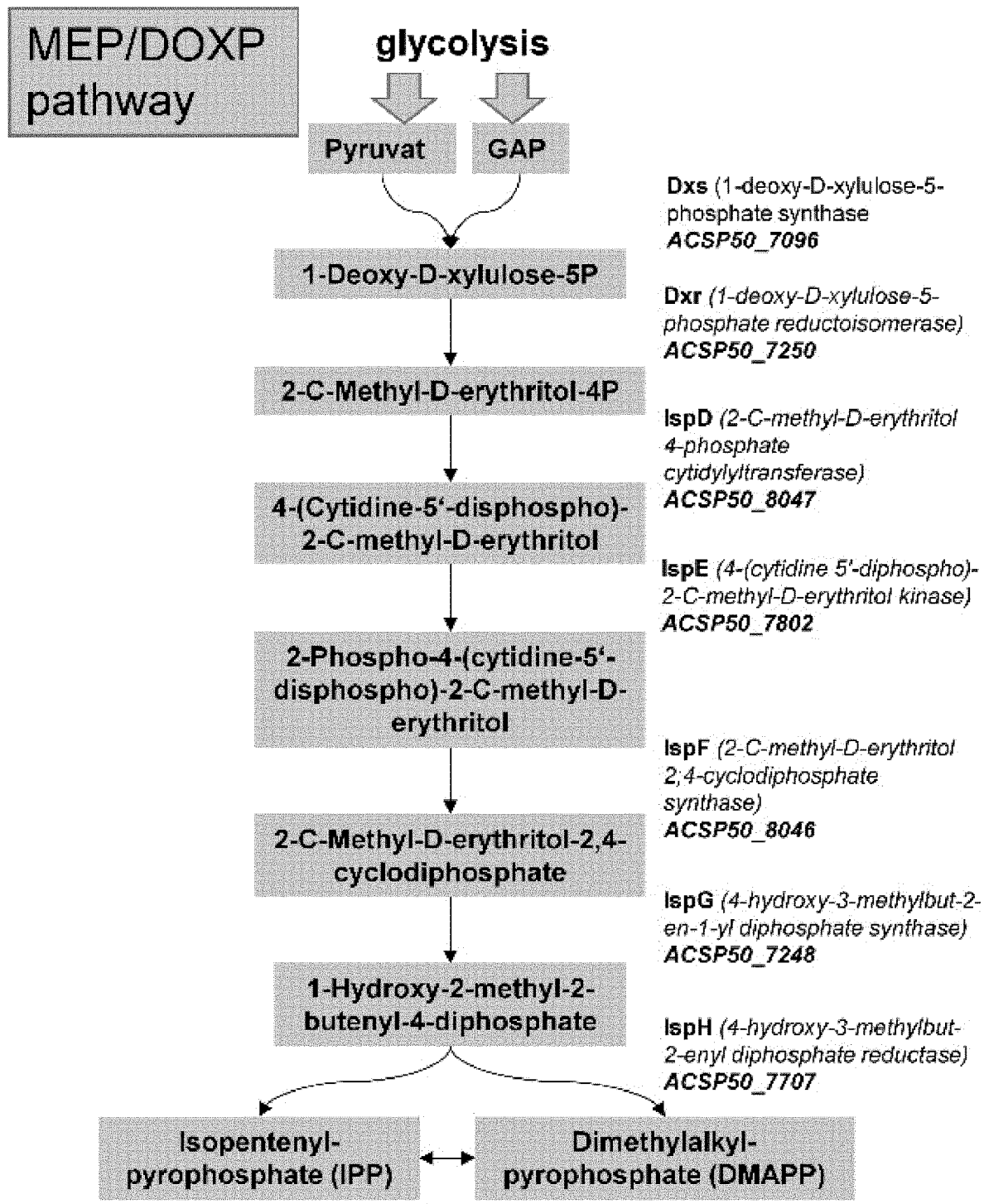
FIG. 21. Reconstruction of the carotenogenesis in Actinoplanes sp. SE50/110. Shown are putative homologous genes in Actinoplanes sp. SE50/110 identified by BLASTX analysis against the NCBI database. Reconstruction was performed by help of the Kyoto Encyclopedia of Genes and Genomes (Kanehisa et al. (2014))
- A. Methylerythritolphosphate (MEP) pathway for the biosynthesis of the isoprenoid precursors isopentenyl pyrophosphate (IPP) and dimethylallyl pyrophosphate (DMAPP), which is also known as alternative metabolic pathway of the mevalonate pathway.
- B-C: Carotenogenesis. B. Formation of Lycopene from isoprenoid precursors. C. Synthesis of the glycosylated carotenoid Sioxanthin in Salinospora *tropica* CNB-440 (FIG. 1 of Richter et al. (2015)).
- D. Genomic organization of the identified genes in Actinoplanes sp. SE50/110. Gene cluster 2b displays homologies to the sioxanthin gene cluster from Salinospora *tropica* CNB-440 according to analysis by antiSMASH, a rapid genome-wide identification tool for the annotation and analysis of secondary metabolite biosynthesis gene clusters in bacterial and fungal genomes (Weber et al., 2015).
Figure 21:
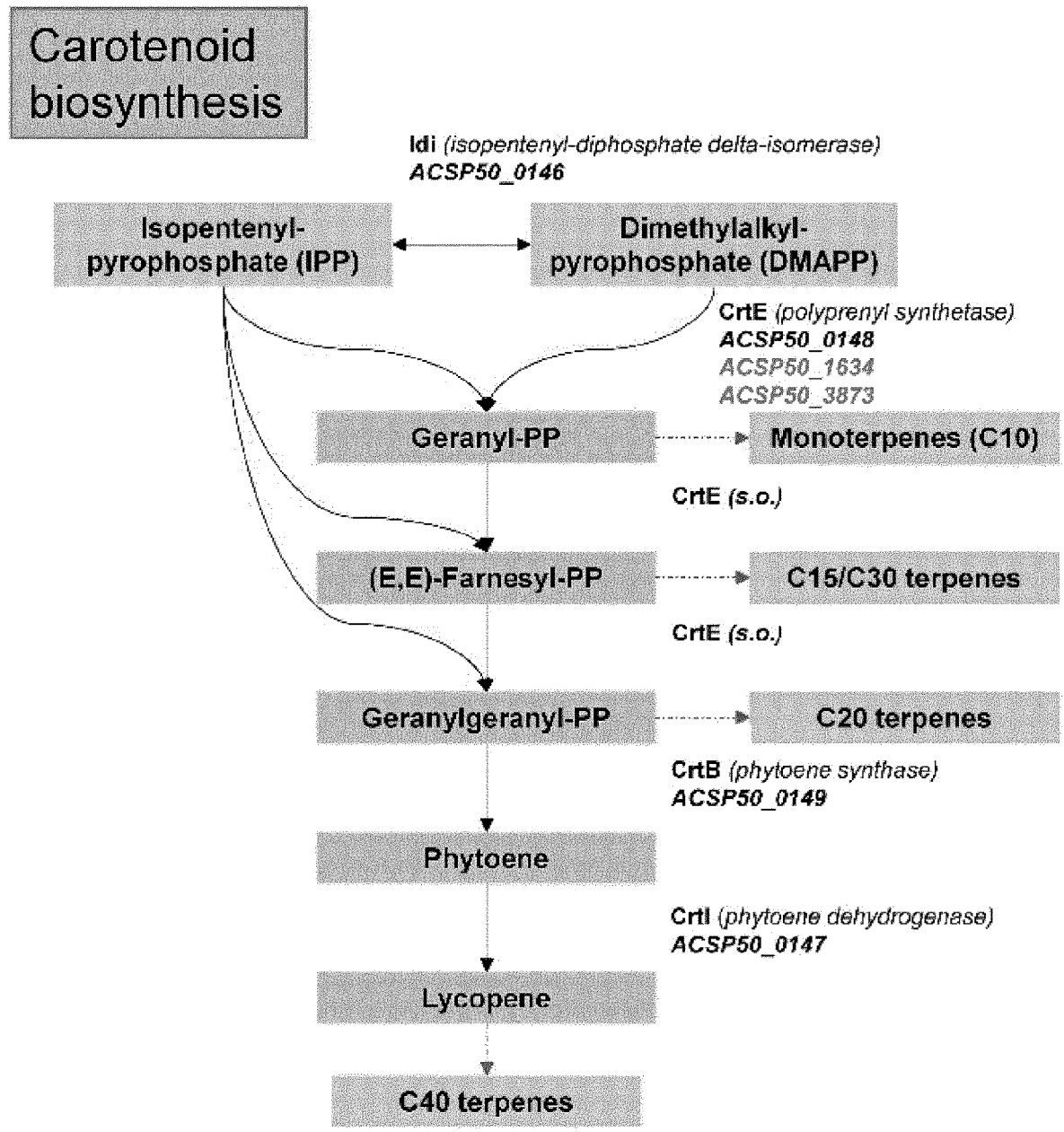
Figure 21:
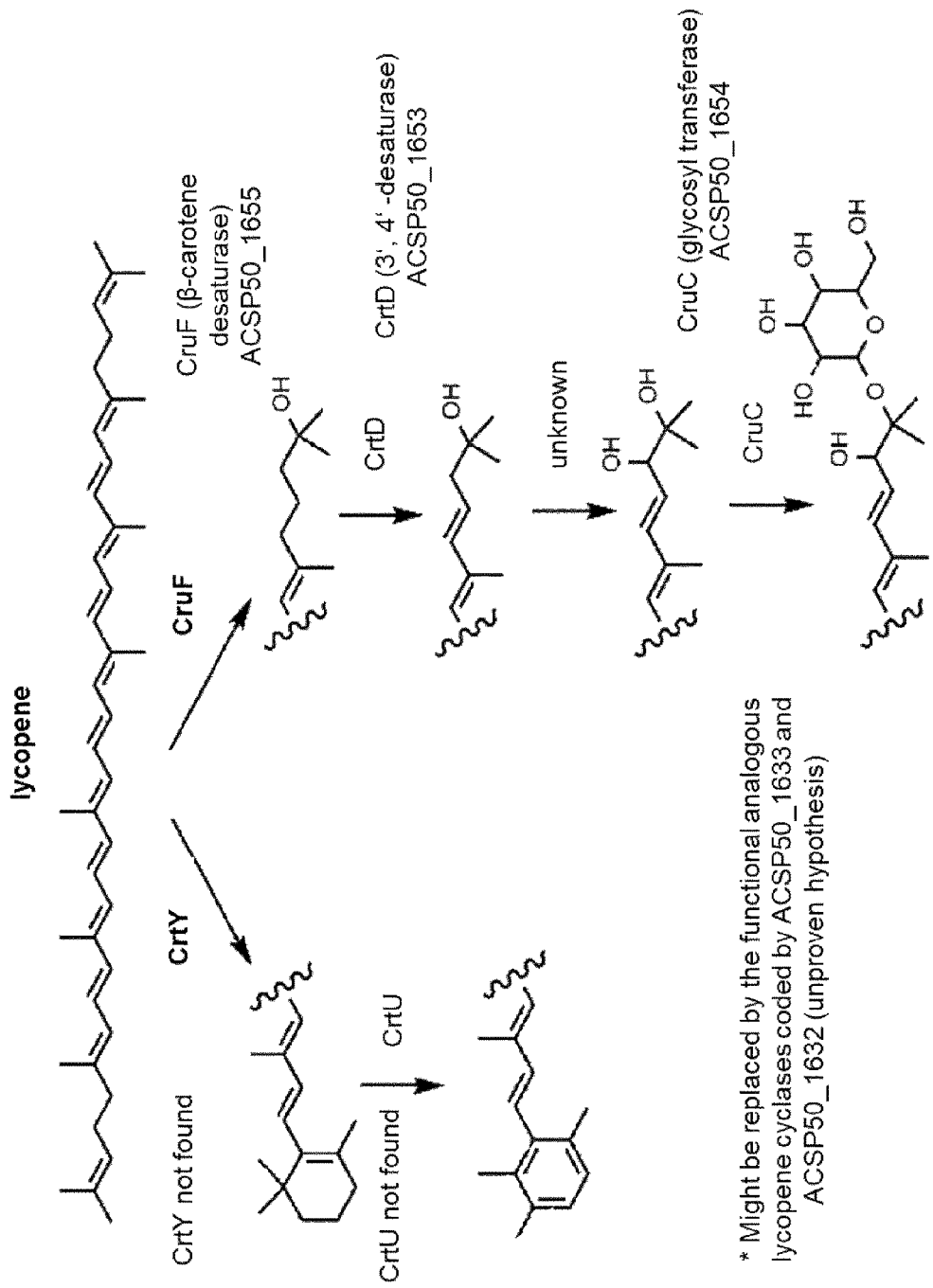
Figure 21:
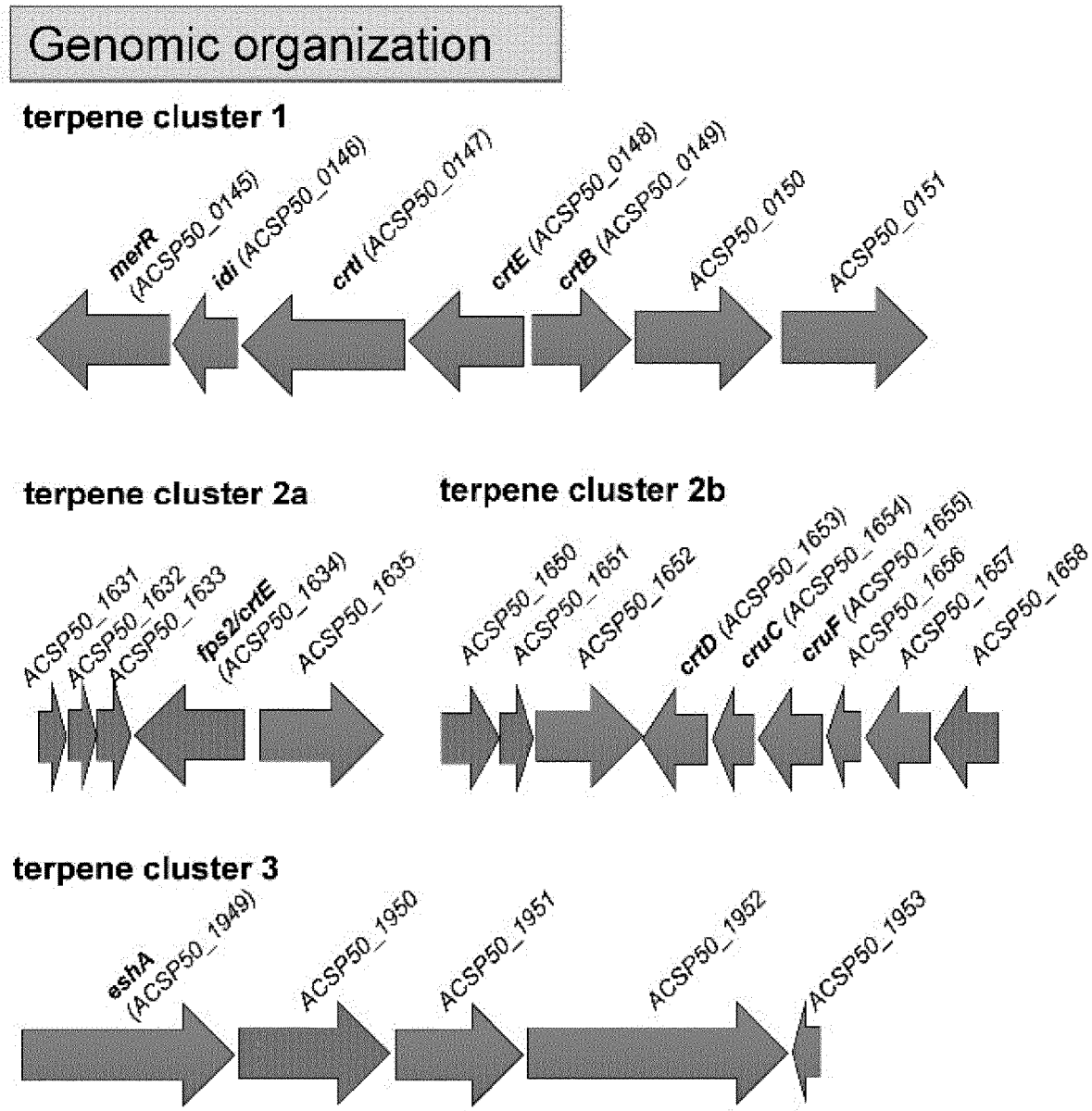

Actinoplanes are known to produce a variety of soluble pigments including yellow, orange and pink pigments of the class carotenoids (Parenti and Coronelli 1979). The pigment of Actinoplanes sp. SE50/110 is orange. Its formation is intensified when cultivated exposed to light. Since the pigment was found likewise in the supernatant, it seems to be soluble in watery solutions. After cell extraction and separation by thin layer chromatography, spectral analysis display absorption maxima at 450, 475 und 505-510, which was confirmed by an absorbance scan performed during HPLC-separation. Consistent with these findings in silico reconstruction shows, that Actinoplanes sp. SE50/110 has the full genetic equipment to produce a C40-carotenoid with similarity to sioxanthin from *Salinospora tropica* CNB-440 (Richter et al. 2015; Wolf et al. 2017b) (FIG. 21 and Table E12).

TABLE E12

Reconstruction of the carotinoid synthesis in Actinoplanes sp. SE50/110. Two terpene synthesis gene cluster were identified by antiSMASH analysis (Blin et al. 2017; Weber et al. 2015), which could be assigned to the formation of a C40-carotenoid with similarity to the sioxanthin gene cluster from *Salinospora tropica* CNB-440 (Richter et al. 2015) (terpene cluster 1-2). Furthermore, a camphene-like monoterpene gene cluster (terpene cluster 3), all genes of the MEP/DOXP-pathway and a gene coding for the degradation of lycopene were identified by BLASTP analysis (Altschul et al. 2005) and KEGG (Kanehisa et al. 2014).

| locus tag | name | annotation |
|---|---|---|
| genes of MEP/DOXP pathway | | |
| ACSP50_7096 | dxs | 1-deoxy-D-xylulose-5-phosphate synthase |
| ACSP50_7248 | ispG | 4-hydroxy-3-methylbut-2-en-1-yl diphosphate synthase |

TABLE E12-continued

Reconstruction of the carotinoid synthesis in Actinoplanes sp. SE50/110. Two terpene synthesis gene cluster were identified by antiSMASH analysis (Blin et al. 2017; Weber et al. 2015), which could be assigned to the formation of a C40-carotenoid with similarity to the sioxanthin gene cluster from *Salinospora tropica* CNB-440 (Richter et al. 2015) (terpene cluster 1-2). Furthermore, a camphene-like monoterpene gene cluster (terpene cluster 3), all genes of the MEP/DOXP-pathway and a gene coding for the degradation of lycopene were identified by BLASTP analysis (Altschul et al. 2005) and KEGG (Kanehisa et al. 2014).

| locus tag | name | annotation | | |
|---|---|---|---|---|
| ACSP50_7250 | dxr | 1-deoxy-D-xylulose-5-phosphate reductoisomerase | | |
| ACSP50_7707 | ispH | 4-hydroxy-3-methylbut-2-enyl diphosphate reductase | | |
| ACSP50_7802 | ispE | 4-(cytidine 5'-diphospho)-2-C-methyl-D-erythritol kinase | | |
| ACSP50_8046 | ispF | 2-C-methyl-D-erythritol 2;4-cyclodiphosphate synthase | | |
| ACSP50_8047 | ispD | 2-C-methyl-D-erythritol 4-phosphate cytidylyltransferase | | | genes proposed for the biosynthesis of a glycosylated C40-carotenoid with similarity to sioxanthin terpene cluster 1

| locus tag | name | annotation | homol. genes in *S. tropica* CNB-440 | identity / positives |
|---|---|---|---|---|
| ACSP50_0145 | merR | MerR-/HTH-transcriptional regulator | merR (STROP_4437) | 55% / 65% |
| ACSP50_0146 | idi | isopentenyl-diphosphate delta-isomerase | idi (STROP_4438) | 62% / 66% |
| ACSP50_0147 | crtI | zeta-phytoene desaturase | crtI (STROP_4439) | 76% / 84% |
| ACSP50_0148 | crtE/IdsA | polyprenyl synthetase | crtE (STROP_4440) | 60% / 67% |
| ACSP50_0149 | crtB | phytoene synthase | crtB (STROP_4441) | 73% / 80% |
| ACSP50_0150 | | deoxyribodipyrimidine photo-lyase | not found | — |
| ACSP50_0151 | | pyridine nucleotide-disulfide oxidoreductase | STROP_4442 | 58% / 70% | terpene cluster 2a

| ACSP50_1631 | | transcriptional regulator | STROP_3252 | 70% / 83% |
| ACSP50_1632 | | lycopene cyclase | not found | — |
| ACSP50_1633 | | lycopene cyclase | not found | — |
| ACSP50_1634 | fps2/crtE | polyprenyl synthetase (farnesyl pyrophosphate synthetase 2) | crtE (STROP_3251) | 69% / 78% |
| ACSP50_1635 | | methylenetetrahydrofolate reductase (NADPH) | STROP_3250 | 77% / 87% | terpene cluster 2b

| ACSP50_1650 | | LysR-family transcriptional regulator | STROP_1711 | 58% / 70% |
| ACSP50_1651 | | methyltransferase type 11 | not found | — |
| ACSP50_1652 | | CDP-alcoholphosphatidyltransferase pgsA | STROP_3594 | 27% / 39% |
| ACSP50_1653 | crtD | zeta-phytoene desaturase (crtI-family) | crtD (STROP_3248) | 66% / 73% |
| ACSP50_1654 | cruC | glycosyl transferase | cruC (STROP_3247) | 63% / 71% |
| ACSP50_1655 | cruF | hypothetical protein (put. membrane prot.) | cruF (STROP_3246) | 64% / 73% |
| ACSP50_1656 | | GCN5 family acetyltransferase | STROP_3245 | 75% / 82% |
| ACSP50_1657 | | monooxygenase | crtA (STROP_3244) | 65% / 61% |
| ACSP50_1658 | | short-chain dehydrogenase | STROP_0722 | 53% / 64% |
| ACSP50_3873 | crtE-hom. | polyprenyl synthetase | crtE (STROP_3251) | 54% / 65% | put. genes for camphene-like monoterpene biosynthesis terpene cluster 3

| ACSP50_1949 | eshA | transcriptional regulator (Crp/Fnr family) | | |
| ACSP50_1950 | | camphene synthase | | |
| ACSP50_1951 | | methyltransferase (SAM-dependent) type 11 | | |

TABLE E12-continued

Reconstruction of the carotinoid synthesis in Actinoplanes sp. SE50/110. Two terpene synthesis gene cluster were identified by antiSMASH analysis (Blin et al. 2017; Weber et al. 2015), which could be assigned to the formation of a C40-carotenoid with similarity to the sioxanthin gene cluster from Salinospora tropica CNB-440 (Richter et al. 2015) (terpene cluster 1-2). Furthermore, a camphene-like monoterpene gene cluster (terpene cluster 3), all genes of the MEP/DOXP-pathway and a gene coding for the degradation of lycopene were identified by BLASTP analysis (Altschul et al. 2005) and KEGG (Kanehisa et al. 2014).

| locus tag | name | annotation |
| --- | --- | --- |
| ACSP50_1952 | | glycosyl-hydrolase |
| ACSP50_1953 | | oxidoreductase/aldo/ketoreductase degradation of lycopene |
| ACSP50_5522 | ccd | carotenoid oxygenase/carotenoid cleavage dioxygenase (RPE65 superfamily) |

The genes of the C40-carotenoid biosynthesis are organized in three gene cluster: terpene cluster 1,2a and 2b (cf. FIG. 21D).

In contrast to S. tropica, homologues of crtY and crtU, encoding a cyclase and a desaturase, could not be identified in Actinoplanes sp. SE50/110 (Wolf et al. 2017b). Instead, two cyclases of the CarR-domain superfamily were found in this work. They are localized in the terpene cluster 2b (FIG. 21). CarR-domain cyclases are common in fungal, archaeal and bacterial genomes (information taken from CDD-search of the NCBI (Marchler-Bauer et al. 2017)). Since the pigment of SE50/110 is orange-colored, a terminal cycling of the red-colored precursor lycopene is highly likely and might be catalyzed by one or both CarR-domain cyclases. Similar to S. tropica, the carotenoid gene cluster of SE50/110 contains a glycosyltransferase CruC (FIG. 21, Table E12). This strongly indicates for a glycosylated carotenoid, which is in accordance with the observation, that the pigment seems to have polar characteristic, since it was found in the supernatant (FIG. 22B).

Comparative genome analysis by the software platform EDGAR 2.0 (Blom et al. 2016), display similar terpene cluster arrangements in related species of the genus Actinoplanes, whereas a different organization was found in Streptomyces (data not shown). By this, the gene arrangements found in SE50/110 and CNB-440 (Richter et al. 2015; Wolf et al. 2017b) seem to be characteristic for the family Micromonosporaceae.

Besides, genes for the synthesis of the building blocks IPP and DMAPP via the MEP/DOXP-pathway (Table E12), a gene coding for a camphene-like monoterpene synthase (terpene cluster 3, Table E12) as well as a carotenoid cleavage dioxygenase (ACSP50_5522, Table E12) were found in the genome of SE50/110. The latter two might be involved in the formation of odorous substances (Yamada et al. 2015). The inventors observed, that strong pigmentation was associated with production losses. This was confirmed by comparing growth and acarbose yields of cultures exposed to and covered from light (FIG. 22). While carotenoid formation was induced, acarbose production and growth of Actinoplanes sp. SE50/110 was strongly reduced, when exposed to bulb light (36 W, Osram 830U) with an intensity of 22-44 µE (1 µE=µmol$_{photons}$ m$^{-2}$ s$^{-1}$). In total, a loss of 39% of the final acarbose concentration was monitored.

Figure 23:
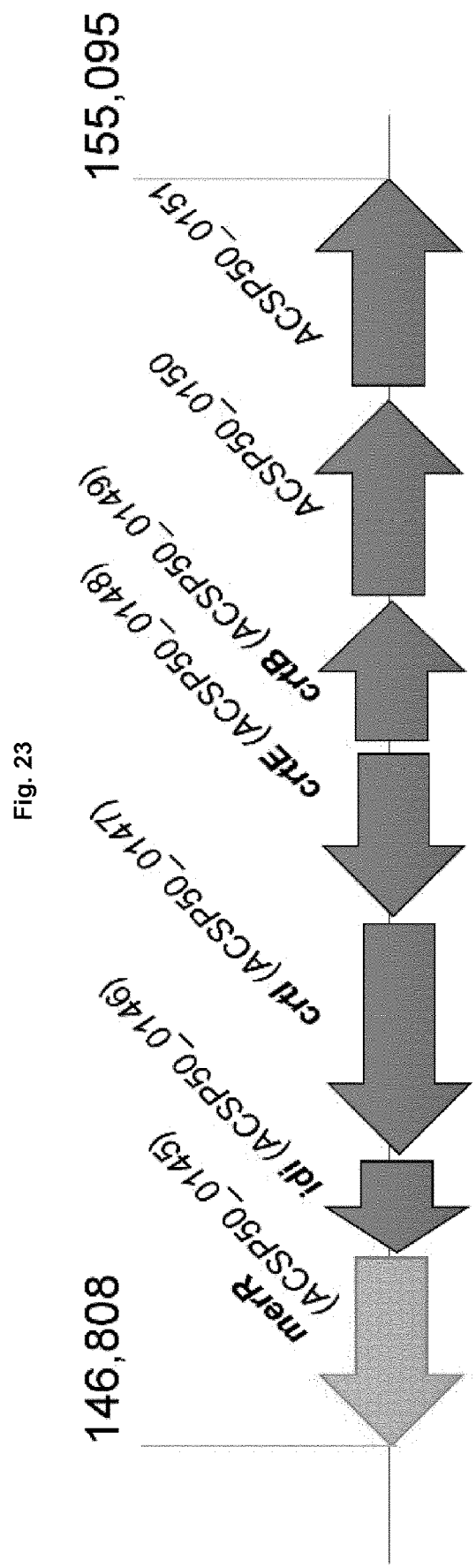
FIG. 23. Position of a gene encoding a MerR-regulator in terpene cluster 1 and its disposition in the genome of Actinoplanes sp. SE50/110 (cf.

Deletion of merR in SE50/110 Induces Carotenoid Formation without Exposure to Light Since natural or bulb light was able to induce carotenoid formation (FIG. 22B, C), this study searched for possible regulatory genes in SE50/110. A MerR-regulator was found within terpene cluster 1 (ACSP50_0145, FIG. 23).

The MerR-family mainly consists of activators, which are able to respond to environmental stimuli, like oxidative stress, heavy metals or antibiotics (Brown et al. 2003). Indeed, several members of the MerR-family have been described as both light-dependent activators or repressors of the carotenoid biosynthesis in non-photosynthetic bacteria, f. e. LitR in the related actinomycete S. coelicolor (Takano et al. 2005; Takano et al. 2006), in the Gram-negative Thermus thermophiles HB27. (Takano et al. 2011) and in the Gram-positive Bacillus megaterium QM B1551 (Takano et al. 2015). Here, cobalamin (vitamin B12) acts as cofactor, which mediates light sensitivity, since it is able to absorb ultraviolet and blue light: By either binding covalently to the regulator or falling off after light excitation, it is able to modulate the conformation and activity of the regulator (van der Horst et al. 2007). The mechanisms of regulation and the binding sites are quite different: Whereas in T. thermophiles and B. megaterium the promoter regions of litR/crtB (Takano et al. 2011) or litR and crtI (Takano et al. 2015) are repressed in the dark and relieved after illumination, LitR in S. coelicolor seems to be an essential light-induced transcriptional activator of the adjacent localized litS, which encodes an ECF sigma factor and directs the transcription of the carotenoid biosynthesis genes (Takano et al. 2005). A gene encoding an ECF sigma factor does not occur within the gene cluster of SE50/110. In the Gram-negative bacterium Myxococcus xanthus a B12-dependent MerR regulator is part of a complex regulatory cascade including eight further regulatory genes (Fontes et al. 2003; Galbis-Martínez et al. 2012). Indeed, no homologues of the regulatory network from M. xanthus were identified in the genome of SE50/110 by BLASTP-analysis (data not shown).

The MerR-family regulator ACSP50_0145 of Actinoplanes sp. SE50/110 contains an N-terminal HTH-motif and a C-terminal B12-binding domain (according to BLASTP-analysis and CDD-search (Marchler-Bauer et al. 2015; Marchler-Bauer et al. 2010; Altschul et al. 2005)). The position of the HTH-domain accounts for a transcriptional repressor (Pérez-Rueda and Collado-Vides 2000).

By CRISPR/Cas9 deletion of the corresponding gene in SE50/110, the carotenoid formation was strongly induced without exposure to light (FIG. 24B, C). This confirms a function as transcriptional repressor.

Indeed, it has to be noted, that the repressor/operator system is leaky, since the typical orange color is also produced in the wild type without exposure to light. According to this, the transcription of the genes crtEBI and idi (ACSP50_0146-0149) was only doubled in ΔmerR compared to the wild type under dark conditions (FIG. 24E). These differences were significant for crtE, crtB and idi. No effects on the transcription of acb genes were observed.

However, in the context of this work, the question was examined, whether pigment formation in ΔmerR influences the formation of the fine-chemical acarbose. Again, higher carotenoid formation was associated with lower acarbose formation (FIG. 24A, D). When illuminated, both wild type and ΔmerR are strongly pigmented and the final acarbose concentrations were similar for both strains, reaching approx. 0.52 g·L$^{-1}$ (FIG. 24B, D). This corresponds to a reduction of acarbose formation of approx. 38% compared to the wild type under dark conditions (reaching 0.83 g·L$^{-1}$). This is in accordance to the previous growth experiments of the wild type as described herein.

Under dark conditions, ΔmerR produces approximately 15% less acarbose than the wild type (0.70 g·L$^{-1}$) (FIG. 24D). It is suggested, that these production losses are assigned to the waste of resources by carotenoid formation in the deletion mutant (FIG. 24C). In conclusion, the production losses under light conditions (38-39%) might result from further light-induced stress in both the deletion mutant and the wild type.

Figure 25:
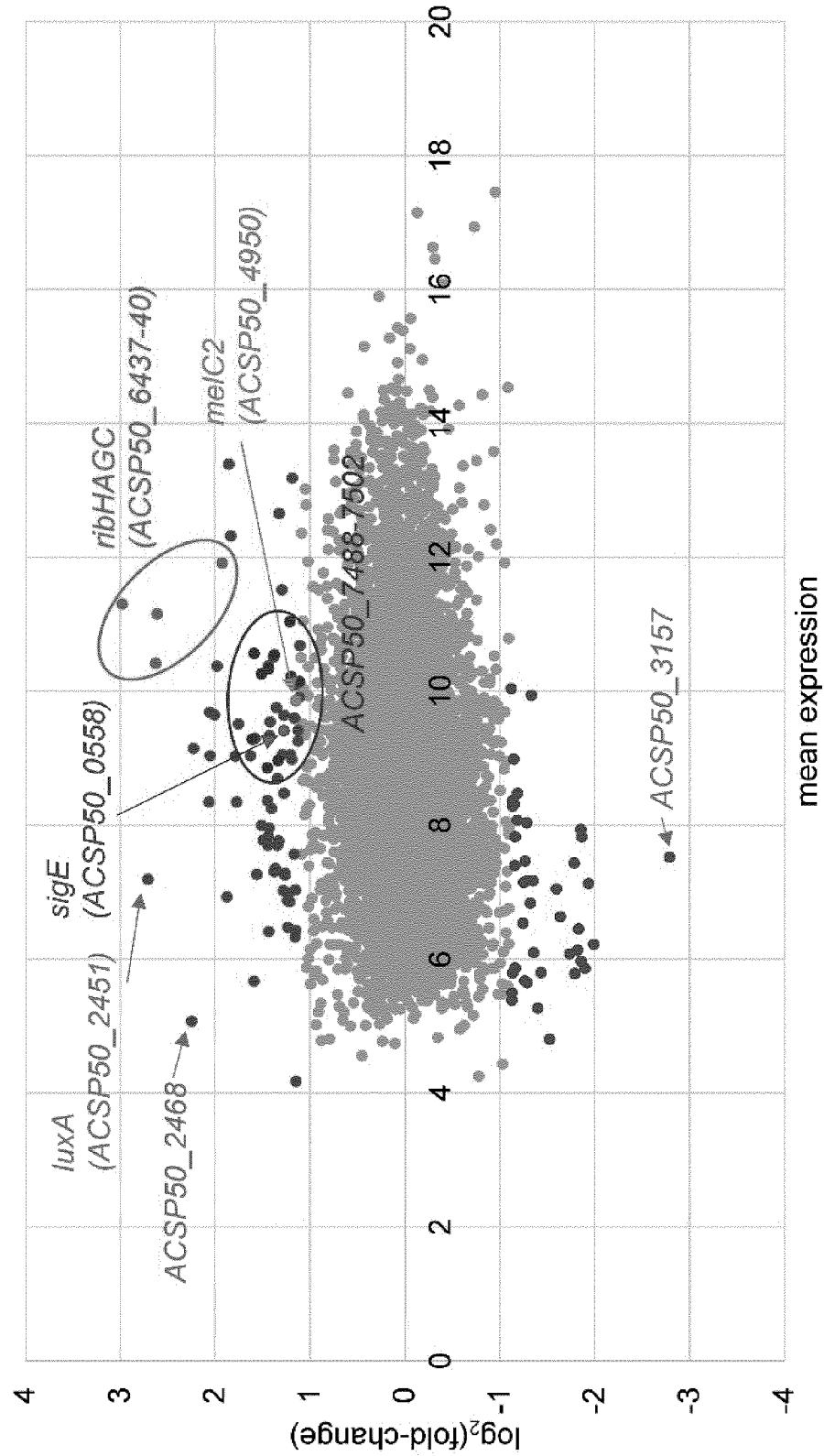
FIG. 25. A ratio/intensity plot of differentially transcribed genes in Actinoplanes sp. SE50/110 exposed to light compared to a cultivation grown in the dark. The ratio (log 2 (fold-change)) is plotted against the mean average intensity of a microarray experiment. Darker dots represent genes with significant differential transcription levels in the culture exposed to light compared to a culture hidden from light.

Comparative transcriptome analyses of the wild type cultivated under dark and light conditions using the microarray technique, display a complex response on transcript level affecting various genes (cf. FIG. 25). Several of the differentially expressed genes indicate a cellular response to combat oxidative stress. Oxidative stress is caused by reactive oxygen species (ROS), which are formed by energy transfer (leading to singlet oxygen) or electron transfer (leading to superoxide, hydrogen peroxides and hydroxyl radicals) (Ziegelhoffer and Donohue 2009). At high concentrations, ROS are toxic and cause protein and membrane oxidation and DNA damage (Ziegelhoffer and Donohue 2009; Gout 2019).

In SE50/110, the tyrosinase MelC (ACSP50_4950, previously: ACPL_5017), a photo-protector, which is involved in the formation of the brown pigment eumelanin (Wolf et al. 2016), and genes of the riboflavin biosynthesis (ACSP50_6437-40) are stronger transcribed when exposed to light (FIG. 25). Riboflavin is a water-soluble photooxidative sensitizer absorbing at 374 and 445 nm (Silva et al. 1999; Kim et al. 1993). It is the precursor of flavin mononucleotide (FMN) and flavin adenine dinucleotide (FAD). These are cofactors of proteins, that are involved in cellular redox metabolism, light-sensing, DNA-repair and further functions (reviewed in García-Angulo (2017)). By this, riboflavin and its derivates are important micro-nutrients, that enable the cells to overcome oxidative stress (Chen et al. 2013).

According to this, also several flavin-dependent oxygenases are stronger transcribed, when exposed to light. One of them is annotated as taurine dioxygenase, which substrate is a degradation product of cysteine. Sulfur-containing amino acids like cysteine belong to the group of low molecular weight thiols (LMW thiols), that are able to catch ROS and function as redox buffers (Gout 2019). Corresponding to this, further genes probably involved in cysteine and methionine metabolism and transport are stronger transcribed in cells exposed to light. Remarkably, several transcriptional regulator genes and a gene encoding the sigma factor SigE (ACSP50_0558) are stronger transcribed, too (FIG. 25). SigE was associated with oxidative stress-response in the photosynthetic bacterium *Rhodococcus sphaeroides* (reviewed in Ziegelhoffer and Donohue (2009)) and with envelope stress response in the related species *S. coelicolor* (Hutchings et al. 2006) and *C. glutamicum* (Park et al. 2008). It might be possible, that SigE is involved in oxidative stress response in SE50/110.

Interestingly, genes of the carotenoid biosynthesis and of the regulator MerR are not significantly stronger transcribed in the wild type exposed to light compared to the wild type hidden from light. This is noteworthy, since a clear effect of light on carotenoid formation can be observed in the wild type. Since the carotenoid synthesis takes place both in the dark and in the light and the enhancement of relative transcript amounts is quite moderate in the regulator mutant (see above), the effects on transcript level might be inconspicuous. It is assumed, that further regulation of carotenoid synthesis on protein level or metabolome level might exists, f. e. by degradation of carotenoids or terpenoid-precursors by the carotenoid cleavage dioxygenase (ACSP50_5522). However, according to the results obtained from the microarray of the wild type, the crt gene expression does not seem to be a primary target of the global oxidative stress response, similar to findings from *Rhodococcus sphaeroides* (reviewed in Ziegelhoffer and Donohue (2009)).

Taken all together, illumination triggers oxidative stress response and seems to have an important impact on the distribution of metabolic resources towards growth, carotenoid and acarbose formation. The regulation of carotenoid biosynthesis seems to be decoupled from the global response to oxidative stress, which needs further investigation. With view to direct the metabolic fluxes towards the production of acarbose, it is desirable to gain a better understanding of these processes in future. The sigma factor SigE might be responsible for the oxidative stress response, since it is higher transcribed when exposed to light.

Apart from light stress, this work demonstrates, that a large portion of production losses can be directly assigned to the carotenoid formation. Carotenoids of non-photosynthetic bacteria are assumed to have a function as photoprotectors (Lee and Schmidt-Dannert 2002), since they have shown to protect from photodynamic killing (Mathews and Sistrom 1959). As the influence of light can be excluded by simple structural measures, carotenoid formation is assumed to be dispensable under laboratory conditions. In order to improve acarbose production, switching off the concurring carotenoid biosynthesis pathway, f. e. by deletion of the central gene crtI, can be used for strain development. Since carotenoids influence the fluidity of membranes (Gruszecki and Strzałka 2005), lack of the C40-carotenoid can also affect the surface and mycelial structure of Actinoplanes sp. SE50/110. With regard to production, a break-up of mycelial lumps is advantageous to increase the mycelial surface and the number of biochemically available cells.

Overexpression of acbB and gtaB

Expression vector pSETT4 was tested for the genes acbB and gtaB. Both genes, acbB and gtaB, are probably involved in the amino sugar synthesis, a feeding branch of acarbose biosynthesis: AcbB catalyzes the dehydration of dTDP-D-glucose to dTDP-4-keto-6-deoxy-D-glucose and GtaB is assumed to be involved in the supply of the precursor glucose-1P. Interestingly, both proteins display increased protein amounts in the cytosol of acarbose producer.

pSETT4gap and pSETT4tip Vectors for Overexpression of Single Genes

A novel cloning system was implemented, that allows easy cloning and overexpression of singular genes in Actinoplanes strains such as Actinoplanes sp. SE50/110. For this, the strong promoter of the gene gapDH from Eggerthella *lenta* was cloned in front of a lacZ-cassette in a pSET152-backbone. The gene lacZ is transcribed under control of the lac-promoter and flanked by the recognition side of the restriction enzyme BsaI, which enables exchange of lacZ by the gene of interest by Gibson Assembly (Gibson et al. 2009), restriction/ligation cloning or Golden Gate cloning (Engler et al. 2008). As strong expression requires strong termination, T4-terminators were introduced before and after the cloning side of the novel expression system. T4-terminators have already been successfully used in the pGUS-cloning system developed by Myronovskyi et al. (2011). Whole track RNAseq analysis of a pGUS-integration mutant performed herein showed, that the T4-terminators block transcription efficiently and prevent read-through from the integrase gene into the gene of interest. Like shown by a pre-experiment, T4-terminators do not have any side effects on the transcription of acb genes, when introduced into Actinoplanes sp. SE50/110 via pSET152-integration.

Besides, by sequencing of an enriched primary transcript library derived from the promoter-screening experiment, two putative promoters were identified behind the gene of interest in antisense orientation (FIG. 26). These two pseudo-promoters were removed in the novel expression system in order to prevent antisense transcription. Furthermore, an additional (third) T4-terminator was introduced behind the cloning side in opposite orientation to prevent further putative antisense reads.

To allow exchange of the promoter sequence, NdeI and KpnI restriction sites were introduced. In this work, the strong gapDH-promoter was exchanged by the medium-strong tipA-promoter from *S. lividans*. By this, it was shown, that the system can be easily modified, f. e. to adjust it for other species of the order Actinomycetales. The vectors (named pSETT4gap and pSETT4tip) were tested for strong and medium strong overexpression of the genes acbB and gtaB.

Medium Overexpression of acbB Leads to Improved Acarbose Formation

The dTDP-D-glucose-4,6-dehydratase AcbB seems to be involved in the generation of an activated amino sugar from D-glucose-1P—a feeding pathway of the acarbose biosynthesis (FIG. 1): Increased AcbB-activity was found to improve the supply of the modified precursor: In brief, two overexpression mutants were created based on expression vector pSETT4 described elsewhere herein. In these mutants acbB is transcribed under control of the medium strong tipA-promoter or the strong gapDH-promoter. As previously published in (Schaffert, et al. 2019), expression vectors using the native promoter did not lead to a significant overexpression of the genes of the Acb gene cluster. The native promoter was therefore used in both the pSET152- and the pSETT4-vector background as control. Growth and acarbose formation were monitored in two shake flask cultivations in maltose minimal medium (FIG. 27).

The mutant with acbB transcribed under control of the heterologous tipA-promoter displayed enhanced acarbose production compared to the control strains: The yield coefficient was increased to 48.6 and 51.9% compared to the empty vector control in two independent cultivations (FIG. 28). By usage of the strong gapDH-promoter, the acarbose yield coefficient was slightly increased (FIG. 28).

Figure 29:
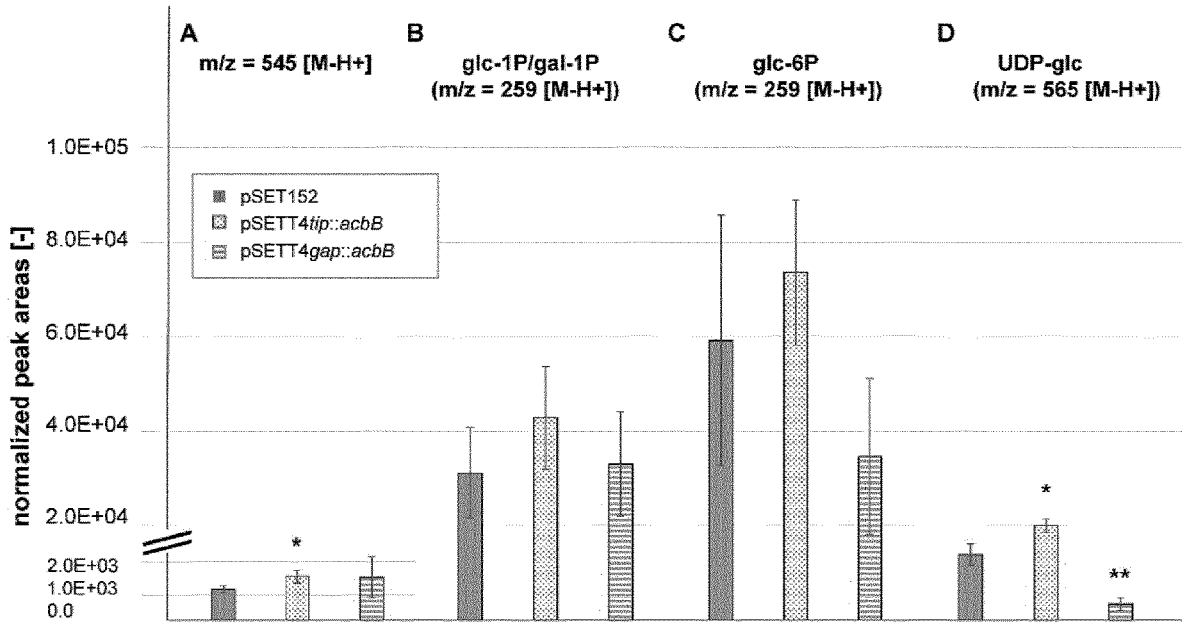
FIG. 29. Analysis of intracellular metabolites of acbB-overexpression mutants by LC-MS. Shown are the normalized peak areas of the masses m/z=545 [M−H$^+$]. A glucose-1P and galactose-1P (m/z=259 [M−H$^+$]. B. glucose-6P (m/z=259 [M−H$^+$] and C. UDP-glucose (m/z=565 [M−H$^+$]. D. Significant differences compared to the empty vector control were observed for the normalized peak areas of UDP-glucose (p-values of a two-sided t-test: Ptip: 0.01068, Pgap: 0.001356) and of the mass m/z=545 [M−H$^+$](p-value of a two-sided t-test: Ptip: 0.0412).

In pSETT4tip::acbB, the normalized peak areas of phosphorylated glucose/galactose and UDP-glucose were similar or even slightly increased compared to the empty vector control (FIG. 29). Therefore, the supply of activated glucose moieties seems to be guaranteed. In this mutant, increased amounts of the mass m/z=545 [M−H$^+$] were found (FIG. 29, approx. 41%). Without being bound by theory this intermediate accumulates by medium AcbB-overexpression, e.g. using pSETT4tip: acbB.

At beginning growth phase enhanced expression of acbB was observed in the expected range: Strongest overexpression was achieved by use of the gapDH-promoter (log 2 (fold-change)=6.54) followed by use of the tipA-promoter (log 2 (fold-change)=4.06) (FIG. 30). Usage of the native promoter does not lead to a significant increase of relative transcript amounts of acbB. This was tested in both the pSET152- and pSETT4-vector background (FIG. 30). Further genes of the acb gene cluster were not significantly affected, like shown for acbA and acbV (FIG. 30). Only exception is a slightly higher transcription abundance of acbA in pSETT4tip: acbB (log 2 (fold-change)=1.87).

Figure 31:
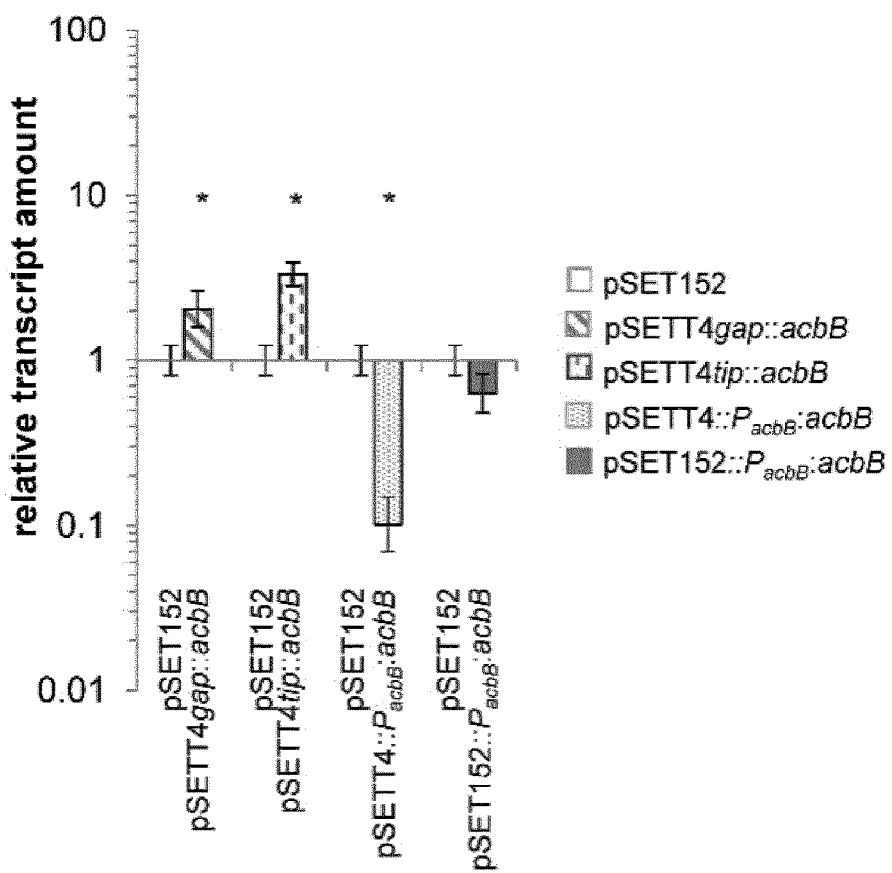
FIG. 31. Relative transcript amounts of the gene acbB in acbB-overexpression mutants in the linear growth phase. Shown are the means and standard deviations of at least three biological replicates. The RT-qPCR indicates significant differences in gene expression compared to the empty vector control (set to a value of 1), which was tested by a two-sided t-test (p-values from left to right corresponding to pSETT4gap: acbB, pSETT4tip: acbB, pSETT4: : $P_{acbB}$: acbB, pSET152: $P_{acbB}$: acbB): acbB: 0.02217, 0.02771, 0.03895, 0.1582). Asterisks indicate the significance level: * p-value<a=5%, p-value<a=1%, *p-value<a=0.1%.

Remarkably, the transcription profile in the linear growth phase differs from the early growth phase: Here, only a doubling of transcript amounts was reached by use of the gapDH-promoter (log 2 (fold-change)=2.05), whereas by use of the tipA-promoter the overexpression of acbB was maintained, but to a lesser extent (log 2 (fold-change)=3.33) (FIG. 30, FIG. 31). In overexpression mutants including heterologous promoters the relative transcription of acbB decreases from 4.06- to 3.33-fold (log 2 (fold-change)) between the two sampling times in pSETT4tip: acbB and from 6.54- to 2.05-fold in in pSETT4gap: acbB. It is assumed, that whereas the transcription of the chromosomal acbB-copy is down-regulated in these mutants, the transcription of the vector copy is maintained by the heterologous promoters. The differences in acbB-transcription at different sampling times furthermore suggest, that the down-regulation of acb gene transcription occurs stronger respectively earlier in pSETT4gap: acbB compared to pSETT4tip: acbB. Overexpression of acbB (pSETT4gap: acbB and pSETT4tip: acbB) seems to decelerate during linear growth phase.

In summary, in particular medium overexpression of acbB by usage of the tipA-promoter seems to be beneficial for acarbose production, whereas strong overexpression by use of the gapDH-promoter seems to have only a smaller effect on acarbose formation. Further improvement in acarbose formation may be achieved by varying of the expression level of acbB, e.g. by using alternative promoters from the promoter screening or by introducing multiple gene copies. In summary, this work demonstrates, that medium overexpression of AcbB increases the acarbose yields, possibly due to improved amino sugar supply. By medium overexpression of acbB (e.g. by use of the tipA-promoter), a positive effect on acarbose production was observed yielding into round about 50% more acarbose in two independent cultivations. Therefore, the improvement of the acarbose biosynthesis by overexpression of singular acb genes was achieved.

Medium Overexpression of gtaB Leads to Improved Acarbose Formation

GtaB is supposed to catalyze the conversion of UDP-glucose and glucose-1P into each other. It was surprisingly found that overexpression of GtaB triggers acarbose formation. Without being bound by theory this may occur by improved deployment of the precursor glucose-1P. As shown by a shake flask cultivation in maltose minimal medium (FIG. 32), the final yield coefficient for acarbose of overexpression mutants of gtaB introduced into pSETT4tip is increased to 8.56%. Interestingly, the acarbose formation is particularly increased in the late linear to stationary growth phase. In the overexpression mutant, the relative transcript amount of the gene gtaB is 2.64-fold increased (log 2 (fold-change)) (FIG. 33).

Since the metabolism of activated sugars is connected or redirected to other metabolic pathways, they are not supposed to accumulate. But—like shown in previous experiments—the supply can be seriously disturbed. Analysis of the intracellular metabolome displays similar amounts of phosphorylated hexoses and/or UDP-glucose (FIG. 34). Therefore, the pool of activated C6-sugars is not significantly affected by overexpression of gtaB.

Interestingly, a significant decreased amount of the mass m/z=545 [M−H⁺] was found in pSETT4tip::gtaB (approx. decrease of 48%), which might correspond to dTDP-4-keto-6-deoxy-D-glucose, the proposed product of AcbB. This may indicate, that the flow through the synthesis strand is more balanced, since the accumulation of this metabolite is reduced in comparison to the empty vector control and AcbB-overexpression mutants (FIG. 34). Taken together, the introduction of a second gene copy of gtaB has a positive effect on the acarbose production, although the impact of gtaB-overexpression on the distribution of cellular goods remains unclear. Transfer of this construct to producer strains of Actinoplanes can result in an increase of the beneficial effect, as here the demand for the precursor is higher compared to the wild type. Since strong overexpression of AcbB leads to an imbalance in glucose-phosphate-metabolism combined overexpression of acbB and gtaB would plausibly further improve acarbose production beyond the observed effect for the single overexpressions.

The invention claimed is:

1. A method to engineer an Actinoplanes strain for the improved production of acarbose, the method comprising engineering the Actinoplanes strain by deleting the gene encoding extracellular small carbohydrate binding protein Cgt according to SEQ ID No. 20.

2. An Actinoplanes strain for the improved production of acarbose, wherein the Actinoplanes strain is genetically engineered by deleting the gene encoding the extracellular small carbohydrate binding protein Cgt according to SEQ ID No. 20.

* * * * *

SEQUENCE LISTING

<160> NUMBER OF SEQ ID NOS: 111

<210> SEQ ID NO 1
<211> LENGTH: 912
<212> TYPE: DNA
<213> ORGANISM: Artificial Sequence
<220> FEATURE:
<223> OTHER INFORMATION: >acbA (ACSP50_3609)

<400> SEQUENCE: 1

```
gtgcgcggaa tattgctggc cgggggaacc ggctcacggc ttcgaccggt gacctgggcg      60
gtttccaaac aactgatgcc ggtctatgac aaaccgatga tctactatcc gctggccacg     120
ctcgtcagct gcgggatccg ggagatcctg gtcatcacga ccgagaccga ggccgcccag     180
ttccagcggt tgctgggtga cggctcgcag tggggcctgc gtctggagtt cgccgtgcag     240
cagcgccccg ggggcatcgc cgaggccttc ctcatcggcg aggagttcct ggccggtggg     300
ccggtggcgc tcatgctcgg cgacaacctg ctgcacgggg tggacttccg cccctgcgtg     360
cagcgggcac gcgagacggc cggtgggcac gtcttcgag tggcggtggc cgacccgtcg     420
gcctacgggg tggtcgagtt cgacgccgcc gggcgggtgc tgtccatcga ggagaaaccg     480
gtccgtcccc gctcgccgta cgcggttccc ggcttctacc tctacgacgc cgatgtggtc     540
gagacggccc ggtcgctgcg gcccagcgcc cgcggggagc tggagatcac cgaggtcaac     600
caggcctacc tgcggcgcgg cgcactctcg gtgacgctgc tgggtcgggg cgcggtctgg     660
ctcgacaccg gcaccctggc cgactgcatg cgcgcggtcg actacgtgcg cgccatcgac     720
gagggccagg gcatcaagat cggctgtgtg gaggaggcgg cctggcgggc cggtttcctc     780
gacaccgcgc agctgcgtgc cctcgccgag ccgttgatga gcagcggcta cggacagtac     840
ctgctggctc tgaccggcga cgggctcagc cgtacccgc agtggccggc cttgaccgcc     900
gccgccgggt ga                                                        912
```

<210> SEQ ID NO 2
<211> LENGTH: 963
<212> TYPE: DNA
<213> ORGANISM: Artificial Sequence
<220> FEATURE:
<223> OTHER INFORMATION: >acbB (ACSP50_3608)

<400> SEQUENCE: 2

```
atgaaaatct tggtcaccgg cggagccggc tttatcgggt cccattttgt aacttccctg      60
atcagtggcg acattgccac accacaaccc gtgacgcagg ttacggtcgt cgacaaactg     120
ggttacggag gcaatctcag aaatctcgcc gaagcgtcgg cggaccctcg tttcagcttc     180
```

-continued

| | |
|---|---:|
| gttcggggcg acatctgtga cgaaggtcta atcgagggc tgatggcgcg gcacgacacc | 240 |
| gtggcgcact tcgccgccga gacccacgtc gaccgctcgg tggtcgcctc cggcccttc | 300 |
| gtggccagca acctggtcgg cactcaggtg ctactggacg ccgcgctacg ccaccatatc | 360 |
| ggccgcttcc tgcatgtttc caccgacgag gtgtacgggt cgatcgacac cggctcgtgg | 420 |
| gccgagggcc atccgctggc gcccaactcg ccgtacgccg cgagcaaagc cgggtccgac | 480 |
| ctcctcgctc tggcctacca ccagacgcac gggatggacg tcgtggtgac ccgctgctcg | 540 |
| aacaactacg ggccccggca attcccggag aaaatgattc cgctgttcgt caccaggctg | 600 |
| ctcgacgggc tcgacgtacc ggtctacggc gacggccgca acatccgcga ctggctccac | 660 |
| gtcagcgacc attgccgcgg tctcgccctg gccctgggtg ccggccgggc aggcgaggtc | 720 |
| tatcacatcg gcggtgggtg ggaggcgacg aatctcgaat tgaccgagat cctcctcgag | 780 |
| gcgtgcggcg ccccggcttc gcgcatatct ttcgtgaccg atcgcaaagg tcacgaccgg | 840 |
| cgctattctc tcgactattc gaaaatcgcc ggggaactcg gttaccggcc gcgggtcgat | 900 |
| ttcaccgacg catcgcgga aacggtcgcg tggtatcgcg ccaaccgttc ctggtggacc | 960 |
| tga | 963 |

<210> SEQ ID NO 3
<211> LENGTH: 1197
<212> TYPE: DNA
<213> ORGANISM: Artificial Sequence
<220> FEATURE:
<223> OTHER INFORMATION: >acbC (ACSP50_3607)

<400> SEQUENCE: 3

| | |
|---|---:|
| gtgagtggtg tcgagacggt aggggtgcac gcggatgcgc accgcgactc gtggcaggtg | 60 |
| cgggcccaga agcagatcac ctacgaggtg cgcttccggg acgacgtgtt cgggctggac | 120 |
| tccaccgacc tgctggaggc cggggcggac ggggccggtt cacggcggcg gttcgtggtg | 180 |
| gtggacagcg ccgtcgacgc cttgtacggg tcccggatcc gggagtactt cacccatcac | 240 |
| ggcatcgatc attcgatcct ggtgatgcgg gtgggcgaga cggtcaagga cttcgacacg | 300 |
| gcgggccgca tcgtcgccgc gatggacgcc ttcggactgg cccgccgccg ggagccgatg | 360 |
| atcgtcgtcg gtggtggggt gctgatggac gtggccggtc tggtggccag cctctaccgg | 420 |
| cgcggcacgc cgttcctgcg ggtgccgacg acactggtcg gactgatcga cgcgggtgtc | 480 |
| ggcgcgaaga ccggggtcaa cttcaacggc cacaagaacc ggctgggtac gtacgccccg | 540 |
| gctgatctga ccctgctgga ccgccgcttc tggccacccc tggaccggcg ccacctcagc | 600 |
| aacgggctcg ccgagatgct caagatcgcg ctgatcaagg atgccgagct gttccagctg | 660 |
| ctggagcggc acgggcgggt cctgatcgag aacggttcc agggccgtac cggaaccggt | 720 |
| gaccgggccg ccgtccgggc cctgcgcgcg gccacccatg gcatgctgga ggaactcggc | 780 |
| cccaatctgt gggagagccg gctggaacgc agtgtcgact acgggcacac gttcagcccg | 840 |
| accatcgaga tgcgcgcgct gccggctctg ctgcacggcc aggccgtgtg tgtggacatg | 900 |
| gcgctgacca cggtgctggc gtaccggcgg ggtctgctcg acgtcgcgca gcgggaccgg | 960 |
| atcttcgcgt tgatgaccgc cctgggcctg ccgacctggc atccgctgct cacgccggag | 1020 |
| gtgctggagg cggcgttgca ggacaccgtc cggcaccggg acgggtggca gcggctgcca | 1080 |
| ctgccggtgg ggatcggggg tgtcacgttc gtcaacgacg tgacggccgc cgagctgcag | 1140 |
| gccgccgcgc tgatgcagca ccggctcgcc gaggacgccc tgctgctgcg cgcctag | 1197 |

```
<210> SEQ ID NO 4
<211> LENGTH: 2130
<212> TYPE: DNA
<213> ORGANISM: Artificial Sequence
<220> FEATURE:
<223> OTHER INFORMATION: >acbS (ACSP50_3596)

<400> SEQUENCE: 4
atgcacatca tcgagacgta cttcgaatgc ggcggcttcg accaccggtt catccagggc      60
ggcacctcgg tctatctctg gcagctgtcg cgtggcctgg ccgacctggg acaccgggtc     120
tccatcgtca caccggcgca cggccgcctg gacgatctgc gccggctgca cgaggtcgag     180
gacctgcccg gcaccgacga gtacgaactg ccgctggtgc tcgacccgcg cgtgtgggc      240
gaacggttcc cggcccagat ggacatcgcc ctgcggacca ccgcgcatcg gatccggctg     300
gcgggcgtgg acctgtactt cctctccaac gaactgctcg atcagttgcc ggaccggttc     360
tatccccgt acgagagcaa ggggttgat ctggtcttct tcaagccgct cgcctatcag       420
gtggcggcca tccggttcat caggtcgcac ttcggtgacc agcgcgcgat cgtgcacgca     480
cacgagccgt tctaccacta cctgatgccg ccgccttcg ccgcggaccc ggccaaacac      540
gtggtcagca cggtgcagag caacatgccg atcaacaagt cggtgtaccg ggccgaggtg     600
gcgcggctgc tcggcttcct cggcgccccg aacgcgctgc ccgccgacga tccggccggc     660
agccgttcgc cgcacaccgt ggcgatgagc cagtaccagc agctgaccca cctgcactac     720
gaatacccgc cggaccacgt gcgggtctac gacctggtgg ccgagcacgc cgaccggatc     780
gacttcctgt cgccggggca ccgcgactac tacacctgct cgccgacac cccgttcgcg      840
cagctgttcg ccaccctgcc ggtgtcgcgg acggtacggc gcaacgcgga caagacgttc     900
gtcggcggct cgccgtcgg tgacgagtgg gtgaccggcg agctgccccc ggtcgaccgg      960
gagaaggtgc tggccgggct cggcctggac ccggacctgc cggccttcta ccacaacgcc    1020
cggtacgcgg tcaaccacaa ggggcaggtc gagctgatcc gggccgtcga ccgggtgctg    1080
agcggcggcg tgcgggccag cttcatcgtg cgctgcctca gcgacgccgg gatcgccgac    1140
ccgctcttcc acgaggtggt ggcccgccac ccgggccggg tgaatctgga gtggcaccgg    1200
gtgccggagg accagctgcg ggagtacgcc cgagccgcgc acttctgtct cttcccgtcc    1260
aagttcgaga tggacacctt cctgatcgcc cagggtgagg cgatggctgc cggtgcggta    1320
ccgatcgcca ccgcccagct ggggatggcg cacttcggtc acgtcgccga cccgctgacc    1380
gggccggacg cggcgacggc caccggattc gccgtcaacc gctcgttcgc gaggacgat     1440
ccgctgctgg tccagggcct gaccgagcag atccgccggg ccgtcacgct ctggaacgag    1500
cagcccggcc agtaccgccg gttgtccgcc aacgccgtcg cccgggcccg cgagttcacc    1560
tggcggcggg cggcccaggc gcacgaggcc gcgttcgccg gggtgtgggc cggccgtacc    1620
ccccgcctgc cggtcggtga cctgctgcgg ttcggctggt cgacgagct gcccgcggac     1680
gcctggacgc tgcaccgcga cgagatcgcg gaggtggccc tggcccacgg cgacgccgac    1740
gcctacctgc gctgccggcc cgacgacctc gacgccctgg cggcactctt cgagcgggcc    1800
tgggcccggg ccgacttccc ggcctgcgcg cggaccgtag agctggccga ggagcaccgg    1860
caggagcggg tgccgcagtg gcgggcccgg ctcgccggcc gcggccgcat cgaccgcgac    1920
ggtcggctgc actaccgtcc gccgtccgcc gaacgggtcg aactggtctt gcccgacctg    1980
gccgaacccc tgcgcggaac ggtcaccgtg accgcgatgg ctccgaccgg cgacaccttc    2040
accggacagc tgccggccgg aacccggcgt gccgacctgc tgctcaccct cagtgacggg    2100
```

```
cgcaccgtct gggacgaggt gacggcatga                                    2130

<210> SEQ ID NO 5
<211> LENGTH: 1074
<212> TYPE: DNA
<213> ORGANISM: Artificial Sequence
<220> FEATURE:
<223> OTHER INFORMATION: >acbW (ACSP50_3593)

<400> SEQUENCE: 5
atgcccgggt acgccggca tgcccggccg gacggcacga ccggcatgat cgtcgccgag     60
cacctcagca agcacttcaa gcgctaccgg cgcgagccgg tctgcgggg cagcctgcga    120 accatgttct cggcccggta cgacgtggtc cgggccgtcg acgacatcag cttcgaggtc    180
ccgtccggtg tcaagatcgc ctacatcggg gcgaacggcg cgggcaagtc caccacgatc    240
aaactcctga ccggcatcat gcgcccgacc accggcgggg tccgggtcga cggcctcgac    300
ccgcaccggc agcgcacccg ggtcgccggc cggatcggcg tggtcttcgg ccagcgcagc    360
cagctctggt gggatctgcc ggtcctcgac tcgttccgca tcctgcggca cgtctacgag    420
gtgccgcagg cggtgtacga ccggaacatg cgcctgttcc gggaccggct ggacctcggc    480
gccctcggca cacccccggt ccgccagctg agcctgggcc agcgcatgcg ggccgagatc    540
gccgcctcgc tgctgcacga cccggccgtg gtcttcctcg acgaacccac catcggcctg    600
gacctggtcc tcaagcaggc ggtccgggac ctgatcaacc acatccacgc gaactgggc     660 accacggtca tgctgaccag ccacgacatc ggcgacatca ccagcatctg cgatcaggcg    720
ctggtcgtgg accgcgggac gatcgtccac cagggaacga tgcgggacct gctgcggtcg    780
gtggacaccc gggcggtcac cttcgagtac gccgccggca gcgtctccga ggccgccgcg    840
ctgcgcatca tcaccgaagg actgcccgag gtggacgcca ctccggccga gtccggccgg    900
atccgggtcg agttcccggt ggaccgctgg tcggcccggc aggtgatcgc cttcctgctg    960
gaccggttcg acctgagcga cgtgctggtg ccggacgcca atctggagac actgctgcgc   1020
cgcatctacg ccgggtcgcg cccggagccg gtcaccgccg gggacggcgc atga          1074

<210> SEQ ID NO 6
<211> LENGTH: 804
<212> TYPE: DNA
<213> ORGANISM: Artificial Sequence
<220> FEATURE:
<223> OTHER INFORMATION: >acbX (ACSP50_3592)

<400> SEQUENCE: 6
atgatccgcg ccgcgcgccg gtacgcgccg ttcgccctcg ccggactgca cgccgtcacc     60
cgttaccgct cgaccatcgt cctgagcgca ctcacggcgg ctgcggccac ctcgttgcag    120
gtgttcctgt ggcgagccgt ctacgccggc ggaccggcac cggccggcct cccgttcgca    180
cagctcacct cgtacatcgt gctcgcgcag gtgctcggga tgctgcacac caaccggatc    240
gacgagatga tcgccggcga ggtgtaccgc ggggacatcg cggtctccct ggtacgcccg    300
gcgaactacg cgctcagctg tctggcggtg aacctgccga ccgccgcgct cagtgcgctg    360
ctggccggcg ccccggtgct cgccggtttc gcgatgttcg cgtcgctgcc cgtcccccg     420 cccgccaacc tgctgctgtt cgccgtcgcg ctgctgctct cggtgatcct cgccttcgag    480
atcaacttcc tggtgggtct cgccgccttc gtcacgacca acacctgggg catccgtacg    540
atcaagaacg cgctcgtcgc cttcctggcc ggccaggtcg tcccgctcgc gctgttcccg    600
gacggcgtgg cccggctgct gcggctgctg ccgttccagg gcctgatcga cagcccgttg    660
```

| | |
|---|---:|
| cggctgctgc tcggcggcta ctccggcggt tccggcgccg ctgccatcct cggtgtccag | 720 |
| gcgctctggg cggtactgct gtacggcgtg ctggccctgg cctggaaccg gtcgctgcgc | 780 |
| agggtggagg tgctcggcgg atga | 804 |

<210> SEQ ID NO 7
<211> LENGTH: 804
<212> TYPE: DNA
<213> ORGANISM: Artificial Sequence
<220> FEATURE:
<223> OTHER INFORMATION: >acbY (ACSP50_3591)

<400> SEQUENCE: 7

| | |
|---|---:|
| atgaccgtct ccacggcgcg ccggtacctg cgcctcacgg cggtgctgtg cggggcgagc | 60 |
| ctgcaccggc tcaccgcgta ccggatggac ttcctcatcg gggcggccag cttcgtcatc | 120 |
| cggatcgcct gccagatcgc cctgatcggg gtgatcttcc agtacgttcc ggcgctcggc | 180 |
| ggctggaccc gccagcaggc gctgttcctg ctcgggttct ccctgctgcc ccgcgggctg | 240 |
| gaccggctct tcaccgacca gctgtggatc ctggcctggc agctggtgcg caccggcgac | 300 |
| ttcttccgct acctgatccg gccggtgaac ccgttctacg cgctgctgtc cgaacggttc | 360 |
| ctctatccgg acgggttcgg ggagctggcc accggcatcg ccatcgtggt caccgcggcc | 420 |
| gggacgatgg acctgcacct gaccgtgcga cagtggctgc tgttgctgcc cctggtcctc | 480 |
| ggcggcgccc tgatccacac cttcctcaag gcgttcctgg cctccctgtc gttctggatg | 540 |
| accagcagcc tcaacgtgat ggtggcggtc aaccagctca gcgagttcac cgcgtacccg | 600 |
| ctcaacctct accaccggt gctgcgcggg gtgctcacct gggtgctgcc gttcgcgttc | 660 |
| accgcctacc taccggtgcg ctacctgctc accggggacg ccgggccgct gctgtggatg | 720 |
| ctgccggtca ccacgctcac cgtcctgctg ggtacggca ccttccggct cgggctgcgg | 780 |
| cgctacgaga tgcccggcag ctga | 804 |

<210> SEQ ID NO 8
<211> LENGTH: 912
<212> TYPE: DNA
<213> ORGANISM: Artificial Sequence
<220> FEATURE:
<223> OTHER INFORMATION: >gtaB galU (ACSP50_7820)

<400> SEQUENCE: 8

| | |
|---|---:|
| atgacgacga acgcgcaagg gtcgggcaag cgcgcggtga agcagtgat tccggcggcc | 60 |
| ggcctagcca cgcgtttcct gcctgccacc aaagccgttc cgaaagagct gctgccggtc | 120 |
| gtcgaccggc cggtcctgca gtacatcgtc gaggaggccg ccgcggccgg catcaccgac | 180 |
| gtgctgctgg tgaccgggcg tggcaagacc tcgatggtcg accacttcga ccgtcgcccc | 240 |
| gacgtggagc agcggctgga ggagaagggc gacaccgagc ggctcgccgc cgtccggcgc | 300 |
| accagtgagc tggccgacat ctacacctgc gacaggggg agccgctcgg cctcggccat | 360 |
| gccgtcggga ccgccgcctc gcacgtcggg gacaacccgt cgcggtgct gctcggggac | 420 |
| gagttcgtcg aggagggcag cccgctgctg cccgacatgc tcgacctgca ggcccgcacc | 480 |
| ggcggcatcg tgctcgccctt catcgaggtc accccgagg agacgtcgcg ctacgggatc | 540 |
| gcctcggtgc gggagtccga cctgggcgag gcgtggtcg aggtgaccgg cctggtggag | 600 |
| aagccgtcgc cggaggaggc gccgagcaac cttgccgtgg tggggcggta cgtgctgcct | 660 |
| ggcaggatct tcgagacgat cgccggcacc aagccgggca gcggggcgga gatccagctg | 720 |

```
accgacgcga tggcgacgct gctggccgag ggcaccccgg tgcacggcat cgtctaccgc    780
ggtgtccggt acgacaccgg ccagccgctg ggctacctgc agaccgtcgt ccagctcgcg    840
gctcagcgtc ccgacctggg tgccgagttc cgggcctggc tcaccgactt cgtcggtggt    900
cagaagggat ga                                                        912

<210> SEQ ID NO 9
<211> LENGTH: 450
<212> TYPE: DNA
<213> ORGANISM: Artificial Sequence
<220> FEATURE:
<223> OTHER INFORMATION: >cgt (ACSP50_5024)

<400> SEQUENCE: 9
atgaatcgca ccaccgttcg ggccggcgtg ctggccaccg ccctgatcag cggcgtgctc     60
ggggtggccg gcccggcgct cgccgccccg gtcaccgacg cggcgccggt cgccgccgcc    120
ggcaccgccg tcgcgccgat cgccgcgacc ttcaacgtga ccgccgggtt caccagctgg    180
ggtcagaacg tctacgtcgt cggcagcatc ccggcgctcg gctcctggga cgtctccaag    240
gcggtgccgc tgaccaccac gagcagcgcc ttcccgacct ggaccgggag cgtggcgctg    300
ccggcgaaca cgtacaccga gttccagtac gtggtgaaga cgccgacgg cagcgtcgcc     360 cgctgggaga agggtttcca gcagaaccgc accacgatca ccccgccgac cggcacctac    420
gtcacgcacg acaccttcgg cgcgtactga                                    450

<210> SEQ ID NO 10
<211> LENGTH: 1515
<212> TYPE: DNA
<213> ORGANISM: Artificial Sequence
<220> FEATURE:
<223> OTHER INFORMATION: >crtI (ACSP50_0147)

<400> SEQUENCE: 10
atgatgaaac cccccacccc ctggagccgc ggcgtgcgca ctgttaccgg acccaccgat     60
cgtgtcgtga tagtgggggc cggcctggcc ggcctctcct gcgccttgca cctggccgca    120
gccgggcggc aggtcaccgt cgtcgagcgg gagccggtgc cggcggcc cgccgggcgc    180 ctctcggtcg gcggatacga cttcgacacc ggcccgaccg tgctgaccat gccggaactg    240
atcgccgagc cgctcgccgc ggtcggcgag aatctctccg actggctgga gctgaccccg    300
ctcgacccgg cctaccgggc gtactacccg gacggctcca cgctggacgt ccgcaccgac    360
accacccgga tggcggccga gatcccccag gtctgcggcg cccgcgaggc cgacggctac    420
ctgcggttcg tcgactacac ccggcggctc tggcagctgg aacgggacca cttcatcgac    480
cggaacctgg acagtccgct cgacctgctc aacctcaacc tgctgaagct gctcgggatg    540
ggcgctttcg gtcgcctgca gccgaagatc aacgagttct tccgcgatcc gcggacccag    600
cggatcttct cgttccaggc gatgtacgcc ggtctcgccc gcacgacgc gatggccatc    660 tacgcggtga tcgcctacct cgactcggtc gccggggtgt actacccaa gggcggcatg    720 cacgccgtcc ccaaggcgct ggccggcgcc gccgagaagc acggggtcac cttccgttac    780
gacacgacgg tcgagcgggt gctcacccag cacggccggg cgaccggggt ggtgaccgtc    840 ggcgggacg tgatcgaggc ggacaccgtc gtactcaatc ccgacctgcc catcgcgtac    900
cgcgacctgc tgcctgcccg gaacagccgc aacctgcgct tttcgccctc tgcgtggta    960 ctccacatcg gatcgtcaca gcggtattcg aagatcgcac accacaacat ccactttggt   1020
acgacgtggc gccgcacctt cgacgaagtg atcaaccgtg ggctgctgat gagcgacccg   1080
```

```
tcactgctgg tcaccaatcc cacgcacacc gaccctctg ccgcgcccga cggcaaacag    1140
acctactacg tgctggcgcc cgccccgaac ctcgtctccg gtccgatgaa ctggcgcggc    1200
ggcctcgccg aacggtatgc cgacgagctg ctgcgtaccc tggagcagcg cggctacatc    1260
ggcttccggg acggggtcga ggtcgaacgg atcatcacgc cggccgactg ggccgacgac    1320
gggatggcgg ccggcacgcc gttcgccgcc gcgcacacct cgcccagac cggcccgttc    1380 cggccggcga acctgcaccc cacgctgccg aacgtggtct tcaccggttc gggcacacaa    1440
cccggggtcg gcgtgccgat ggtgctcatc tccgggaagc tggccgcgag ccggatcaca    1500
cagggagcct catga                                                    1515
```

<210> SEQ ID NO 11
<211> LENGTH: 1260
<212> TYPE: DNA
<213> ORGANISM: Artificial Sequence
<220> FEATURE:
<223> OTHER INFORMATION: >merR (ACSP50_0145)

<400> SEQUENCE: 11

```
gtggccggtg aggcgttgag cgccgagatc cccacctcgc cgggcagctc ggtcgcctcc      60
tcgcacgaca tcccggccac agccggtccc ggcgccgtcc ggaccggccc ggtggctgcc     120
gcgcccggtg gcccgagcga tacgcccctg accgacgcga cagctgccgc gtcgggtgcc     180
gcggacgacg cctcccgggc ccgccccggcg accgccacgg acgacgcctc ccgcaccggc     240
ccggcgaccg ccgcgacgga ttctccggac gacgccgtcc ggaccggcgt ggcagatgcc     300
gcgccggccg ggcgggcggg cgatgtggcg ttgagtgccg gggcggccgc gcggcggctg     360
ggagtggcgg tcacgaccct gcgcacctgg caccagcggt acgggctcgg gccgagccgg     420
cacgagcccg gacatcaccg gcggtacacc gccgaggaca tggaccggct gcaggtgatg     480
cagcggctca ccactcaggg cgtggcgccc gccgaggccg ccgcctgggc gcggtccagg     540
cccctcaccc caccggagcc cggcgcggcg ctgtacgacc ccaccgccgt ggcgtcgcca     600
cccaccccgg ccgctcccgg acagccccg gtcggcccg ccggccgggg cacccgcccg     660
acccgcggac cggccccggc cgctcgcggg ctgacccggg ccgcgatgcg gctcgacgtg     720
cgcggcatgc gcgacatcct ctgcagcacg ctgcacgacc gcggcgtgat acccgcctgg     780
accgaggtga tggtccccggc tctggccgcg atcggcgacc ggtacgaggc cactcggcgt     840
ttcgtcgagg tcgaacacct gctgtcgcgc gccgtcaccg aaatcctcgc ctcggtccca     900
caccccgccg gctctccccg ggtgctgctc gccgccgccg acgaggaaca gcacacactg     960
cccctggagg ccctggccgc cgccctggcc gagggaggcg tgccgagccg tctgttcggc    1020
gcccgggtgc cgtcacaggc cctgctggac gccatcgccc gcaccggccc ggctgccgtc    1080
gtgctctggt cgcagcgccc ggccaccggc atcgtcaccc agctgacccg gtccgcgac    1140 atcccgcacc cgccgctggt catcgccgcc gccggccccg gctggccgca tgacctgcct    1200
tccgggatca cccgcctgac cggcctcacc gaggccgtcc acctgctcgc cacggtctag    1260
```

<210> SEQ ID NO 12
<211> LENGTH: 303
<212> TYPE: PRT
<213> ORGANISM: Artificial Sequence
<220> FEATURE:
<223> OTHER INFORMATION: >AcbA (ACSP50_3609)

<400> SEQUENCE: 12

Met Arg Gly Ile Leu Leu Ala Gly Gly Thr Gly Ser Arg Leu Arg Pro
1               5                   10                  15

Val Thr Trp Ala Val Ser Lys Gln Leu Met Pro Val Tyr Asp Lys Pro
            20                  25                  30

Met Ile Tyr Tyr Pro Leu Ala Thr Leu Val Ser Cys Gly Ile Arg Glu
        35                  40                  45

Ile Leu Val Ile Thr Thr Glu Thr Ala Ala Gln Phe Gln Arg Leu
50                  55                  60

Leu Gly Asp Gly Ser Gln Trp Gly Leu Arg Leu Glu Phe Ala Val Gln
65                  70                  75                  80

Gln Arg Pro Gly Gly Ile Ala Glu Ala Phe Leu Ile Gly Glu Glu Phe
                85                  90                  95

Leu Ala Gly Gly Pro Val Ala Leu Met Leu Gly Asp Asn Leu Leu His
            100                 105                 110

Gly Val Asp Phe Arg Pro Cys Val Gln Arg Ala Arg Glu Thr Ala Gly
        115                 120                 125

Gly His Val Phe Gly Val Ala Val Ala Asp Pro Ser Ala Tyr Gly Val
    130                 135                 140

Val Glu Phe Asp Ala Ala Gly Arg Val Leu Ser Ile Glu Glu Lys Pro
145                 150                 155                 160

Val Arg Pro Arg Ser Pro Tyr Ala Val Pro Gly Phe Tyr Leu Tyr Asp
                165                 170                 175

Ala Asp Val Val Glu Thr Ala Arg Ser Leu Arg Pro Ser Ala Arg Gly
            180                 185                 190

Glu Leu Glu Ile Thr Glu Val Asn Gln Ala Tyr Leu Arg Arg Gly Ala
        195                 200                 205

Leu Ser Val Thr Leu Leu Gly Arg Gly Ala Val Trp Leu Asp Thr Gly
    210                 215                 220

Thr Leu Ala Asp Cys Met Arg Ala Val Asp Tyr Val Arg Ala Ile Asp
225                 230                 235                 240

Glu Gly Gln Gly Ile Lys Ile Gly Cys Val Glu Glu Ala Ala Trp Arg
                245                 250                 255

Ala Gly Phe Leu Asp Thr Ala Gln Leu Arg Ala Leu Ala Glu Pro Leu
            260                 265                 270

Met Ser Ser Gly Tyr Gly Gln Tyr Leu Leu Ala Leu Thr Gly Asp Gly
        275                 280                 285

Leu Ser Arg Thr Pro Gln Trp Pro Ala Leu Thr Ala Ala Gly
    290                 295                 300

<210> SEQ ID NO 13
<211> LENGTH: 320
<212> TYPE: PRT
<213> ORGANISM: Artificial Sequence
<220> FEATURE:
<223> OTHER INFORMATION: >AcbB (ACSP50_3608)

<400> SEQUENCE: 13

Met Lys Ile Leu Val Thr Gly Gly Ala Gly Phe Ile Gly Ser His Phe
1               5                   10                  15

Val Thr Ser Leu Ile Ser Gly Asp Ile Ala Thr Pro Gln Pro Val Thr
            20                  25                  30

Gln Val Thr Val Val Asp Lys Leu Gly Tyr Gly Gly Asn Leu Arg Asn
        35                  40                  45

Leu Ala Glu Ala Ser Ala Asp Pro Arg Phe Ser Phe Val Arg Gly Asp
    50                  55                  60

```
Ile Cys Asp Glu Gly Leu Ile Glu Gly Leu Met Ala Arg His Asp Thr
 65                  70                  75                  80

Val Ala His Phe Ala Ala Glu Thr His Val Asp Arg Ser Val Val Ala
                 85                  90                  95

Ser Gly Pro Phe Val Ala Ser Asn Leu Val Gly Thr Gln Val Leu Leu
            100                 105                 110

Asp Ala Ala Leu Arg His His Ile Gly Arg Phe Leu His Val Ser Thr
        115                 120                 125

Asp Glu Val Tyr Gly Ser Ile Asp Thr Gly Ser Trp Ala Glu Gly His
    130                 135                 140

Pro Leu Ala Pro Asn Ser Pro Tyr Ala Ala Ser Lys Ala Gly Ser Asp
145                 150                 155                 160

Leu Leu Ala Leu Ala Tyr His Gln Thr His Gly Met Asp Val Val Val
                165                 170                 175

Thr Arg Cys Ser Asn Asn Tyr Gly Pro Arg Gln Phe Pro Glu Lys Met
            180                 185                 190

Ile Pro Leu Phe Val Thr Arg Leu Leu Asp Gly Leu Asp Val Pro Val
        195                 200                 205

Tyr Gly Asp Gly Arg Asn Ile Arg Asp Trp Leu His Val Ser Asp His
    210                 215                 220

Cys Arg Gly Leu Ala Leu Ala Leu Gly Ala Gly Arg Ala Gly Glu Val
225                 230                 235                 240

Tyr His Ile Gly Gly Gly Trp Glu Ala Thr Asn Leu Glu Leu Thr Glu
                245                 250                 255

Ile Leu Leu Glu Ala Cys Gly Ala Pro Ala Ser Arg Ile Ser Phe Val
            260                 265                 270

Thr Asp Arg Lys Gly His Asp Arg Arg Tyr Ser Leu Asp Tyr Ser Lys
        275                 280                 285

Ile Ala Gly Glu Leu Gly Tyr Arg Pro Arg Val Asp Phe Thr Asp Gly
    290                 295                 300

Ile Ala Glu Thr Val Ala Trp Tyr Arg Ala Asn Arg Ser Trp Trp Thr
305                 310                 315                 320

<210> SEQ ID NO 14
<211> LENGTH: 398
<212> TYPE: PRT
<213> ORGANISM: Artificial Sequence
<220> FEATURE:
<223> OTHER INFORMATION: >AcbC (ACSP50_3607)

<400> SEQUENCE: 14

Met Ser Gly Val Glu Thr Val Gly Val His Ala Asp Ala His Arg Asp
 1               5                  10                  15

Ser Trp Gln Val Arg Ala Gln Lys Gln Ile Thr Tyr Glu Val Arg Phe
                 20                  25                  30

Arg Asp Asp Val Phe Gly Leu Asp Ser Thr Asp Leu Leu Glu Ala Gly
             35                  40                  45

Ala Asp Gly Ala Gly Ser Arg Arg Phe Val Val Asp Ser Ala
        50                  55                  60

Val Asp Ala Leu Tyr Gly Ser Arg Ile Arg Glu Tyr Phe Thr His His
 65                  70                  75                  80

Gly Ile Asp His Ser Ile Leu Val Met Arg Val Gly Glu Thr Val Lys
                 85                  90                  95

Asp Phe Asp Thr Ala Gly Arg Ile Val Ala Ala Met Asp Ala Phe Gly
            100                 105                 110
```

Leu Ala Arg Arg Arg Glu Pro Met Ile Val Gly Gly Val Leu
            115                 120                 125

Met Asp Val Ala Gly Leu Val Ala Ser Leu Tyr Arg Arg Gly Thr Pro
130                 135                 140

Phe Leu Arg Val Pro Thr Thr Leu Val Gly Leu Ile Asp Ala Gly Val
145                 150                 155                 160

Gly Ala Lys Thr Gly Val Asn Phe Asn Gly His Lys Asn Arg Leu Gly
                165                 170                 175

Thr Tyr Ala Pro Ala Asp Leu Thr Leu Leu Asp Arg Arg Phe Leu Ala
            180                 185                 190

Thr Leu Asp Arg Arg His Leu Ser Asn Gly Leu Ala Glu Met Leu Lys
        195                 200                 205

Ile Ala Leu Ile Lys Asp Ala Glu Leu Phe Gln Leu Leu Glu Arg His
    210                 215                 220

Gly Arg Val Leu Ile Glu Glu Arg Phe Gln Gly Arg Thr Gly Thr Gly
225                 230                 235                 240

Asp Arg Ala Ala Val Arg Ala Leu Arg Ala Ala Thr His Gly Met Leu
                245                 250                 255

Glu Glu Leu Gly Pro Asn Leu Trp Glu Ser Arg Leu Glu Arg Ser Val
            260                 265                 270

Asp Tyr Gly His Thr Phe Ser Pro Thr Ile Glu Met Arg Ala Leu Pro
        275                 280                 285

Ala Leu Leu His Gly Glu Ala Val Cys Val Asp Met Ala Leu Thr Thr
    290                 295                 300

Val Leu Ala Tyr Arg Arg Gly Leu Leu Asp Val Ala Gln Arg Asp Arg
305                 310                 315                 320

Ile Phe Ala Val Met Thr Ala Leu Gly Leu Pro Thr Trp His Pro Leu
                325                 330                 335

Leu Thr Pro Glu Val Leu Glu Ala Ala Leu Gln Asp Thr Val Arg His
            340                 345                 350

Arg Asp Gly Trp Gln Arg Leu Pro Leu Pro Val Gly Ile Gly Gly Val
        355                 360                 365

Thr Phe Val Asn Asp Val Thr Ala Ala Glu Leu Gln Ala Ala Ala Leu
    370                 375                 380

Met Gln His Arg Leu Ala Glu Asp Ala Leu Leu Leu Arg Ala
385                 390                 395

<210> SEQ ID NO 15
<211> LENGTH: 709
<212> TYPE: PRT
<213> ORGANISM: Artificial Sequence
<220> FEATURE:
<223> OTHER INFORMATION: >AcbS (ACSP50_3596)

<400> SEQUENCE: 15

Met His Ile Ile Glu Thr Tyr Phe Glu Cys Gly Gly Phe Asp His Arg
1               5                   10                  15

Phe Ile Gln Gly Gly Thr Ser Val Tyr Leu Trp Gln Leu Ser Arg Gly
            20                  25                  30

Leu Ala Asp Leu Gly His Arg Val Ser Ile Val Thr Pro Ala His Gly
        35                  40                  45

Arg Leu Asp Asp Leu Arg Arg Leu His Glu Val Glu Asp Leu Pro Gly
    50                  55                  60

Thr Asp Glu Tyr Glu Leu Pro Leu Val Leu Asp Pro Arg Val Trp Gly
65                  70                  75                  80

```
Glu Arg Phe Pro Ala Gln Met Asp Ile Ala Leu Arg Thr Thr Ala His
                85                  90                  95

Arg Ile Arg Leu Ala Gly Val Asp Leu Tyr Phe Leu Ser Asn Glu Leu
            100                 105                 110

Leu Asp Gln Leu Pro Asp Arg Phe Tyr Pro Pro Tyr Glu Ser Lys Gly
        115                 120                 125

Val Asp Leu Val Phe Phe Lys Pro Leu Ala Tyr Gln Val Ala Ala Ile
    130                 135                 140

Arg Phe Ile Arg Ser His Phe Gly Asp Gln Ala Ile Val His Ala
145                 150                 155                 160

His Glu Pro Phe Tyr His Tyr Leu Met Pro Ala Ala Phe Ala Ala Asp
                165                 170                 175

Pro Ala Lys His Val Val Ser Thr Val Gln Ser Asn Met Pro Ile Asn
            180                 185                 190

Lys Ser Val Tyr Arg Ala Glu Val Ala Arg Leu Leu Gly Phe Leu Gly
        195                 200                 205

Ala Pro Asn Ala Leu Pro Ala Asp Pro Ala Gly Ser Arg Ser Pro
    210                 215                 220

His Thr Val Ala Met Ser Gln Tyr Gln Gln Leu Thr His Leu His Tyr
225                 230                 235                 240

Glu Tyr Pro Pro Asp His Val Arg Val Tyr Asp Leu Val Ala Glu His
                245                 250                 255

Ala Asp Arg Ile Asp Phe Leu Ser Pro Gly His Arg Asp Tyr Tyr Thr
            260                 265                 270

Cys Phe Ala Asp Thr Pro Phe Ala Gln Leu Phe Ala Thr Leu Pro Val
        275                 280                 285

Ser Arg Thr Val Arg Arg Asn Ala Asp Lys Thr Phe Val Gly Gly Cys
    290                 295                 300

Ala Val Gly Asp Glu Trp Val Thr Gly Glu Leu Pro Pro Val Asp Arg
305                 310                 315                 320

Glu Lys Val Leu Ala Gly Leu Gly Leu Asp Pro Asp Leu Pro Ala Phe
                325                 330                 335

Tyr His Asn Ala Arg Tyr Ala Val Asn His Lys Gly Gln Val Glu Leu
            340                 345                 350

Ile Arg Ala Val Asp Arg Val Leu Ser Gly Gly Val Arg Ala Ser Phe
        355                 360                 365

Ile Val Arg Cys Leu Ser Asp Ala Gly Ile Ala Asp Pro Leu Phe His
    370                 375                 380

Glu Val Val Ala Arg His Pro Gly Arg Val Asn Leu Glu Trp His Arg
385                 390                 395                 400

Val Pro Glu Asp Gln Leu Arg Glu Tyr Ala Arg Ala Ala Asp Phe Cys
                405                 410                 415

Leu Phe Pro Ser Lys Phe Glu Met Asp Thr Phe Leu Ile Ala Gln Gly
            420                 425                 430

Glu Ala Met Ala Ala Gly Ala Val Pro Ile Ala Thr Ala Gln Leu Gly
        435                 440                 445

Met Ala His Phe Gly His Val Ala Asp Pro Leu Thr Gly Pro Asp Ala
    450                 455                 460

Ala Thr Ala Thr Gly Phe Ala Val Asn Arg Ser Phe Ala Glu Asp Asp
465                 470                 475                 480

Pro Leu Leu Val Gln Gly Leu Thr Glu Gln Ile Arg Arg Ala Val Thr
                485                 490                 495

Leu Trp Asn Glu Gln Pro Gly Gln Tyr Arg Arg Leu Ser Ala Asn Ala
```

```
            500                 505                 510
Val Ala Arg Ala Arg Glu Phe Thr Trp Arg Ala Ala Gln Ala His
        515                 520                 525
Glu Ala Ala Phe Ala Gly Val Trp Ala Gly Arg Thr Pro Arg Leu Pro
        530                 535                 540
Val Gly Asp Leu Leu Arg Phe Gly Trp Phe Asp Glu Leu Pro Ala Asp
545                 550                 555                 560
Ala Trp Thr Leu His Arg Asp Glu Ile Ala Glu Val Ala Leu Ala His
                565                 570                 575
Gly Asp Ala Asp Ala Tyr Leu Arg Cys Arg Pro Asp Asp Leu Asp Ala
            580                 585                 590
Leu Ala Ala Leu Phe Glu Arg Ala Trp Ala Arg Ala Asp Phe Pro Ala
        595                 600                 605
Cys Ala Arg Thr Val Glu Leu Ala Glu Glu His Arg Gln Glu Arg Val
        610                 615                 620
Pro Gln Trp Arg Ala Arg Leu Ala Gly Arg Gly Arg Ile Asp Arg Asp
625                 630                 635                 640
Gly Arg Leu His Tyr Arg Pro Pro Ser Ala Glu Arg Val Glu Leu Val
                645                 650                 655
Leu Pro Asp Leu Ala Glu Pro Leu Arg Gly Thr Val Thr Val Thr Ala
            660                 665                 670
Met Ala Pro Thr Gly Asp Thr Phe Thr Gly Gln Leu Pro Ala Gly Thr
        675                 680                 685
Arg Arg Ala Asp Leu Leu Leu Thr Leu Ser Asp Gly Arg Thr Val Trp
    690                 695                 700
Asp Glu Val Thr Ala
705

<210> SEQ ID NO 16
<211> LENGTH: 357
<212> TYPE: PRT
<213> ORGANISM: Artificial Sequence
<220> FEATURE:
<223> OTHER INFORMATION: >AcbW (ACSP50_3593)

<400> SEQUENCE: 16

Met Pro Gly Tyr Ala Arg His Ala Arg Pro Asp Gly Thr Thr Gly Met
1               5                   10                  15
Ile Val Ala Glu His Leu Ser Lys His Phe Lys Arg Tyr Arg Arg Glu
            20                  25                  30
Pro Gly Leu Arg Gly Ser Leu Arg Thr Met Phe Ser Ala Arg Tyr Asp
        35                  40                  45
Val Val Arg Ala Val Asp Asp Ile Ser Phe Glu Val Pro Ser Gly Val
    50                  55                  60
Lys Ile Ala Tyr Ile Gly Ala Asn Gly Ala Gly Lys Ser Thr Thr Ile
65              70                  75                  80
Lys Leu Leu Thr Gly Ile Met Arg Pro Thr Thr Gly Arg Val Arg Val
                85                  90                  95
Asp Gly Leu Asp Pro His Arg Gln Arg Thr Arg Val Ala Gly Arg Ile
            100                 105                 110
Gly Val Val Phe Gly Gln Arg Ser Gln Leu Trp Trp Asp Leu Pro Val
        115                 120                 125
Leu Asp Ser Phe Arg Ile Leu Arg His Val Tyr Glu Val Pro Gln Ala
    130                 135                 140
Val Tyr Asp Arg Asn Met Arg Leu Phe Arg Asp Arg Leu Asp Leu Gly
```

```
                       145                 150                 155                 160
Ala Leu Gly Asn Thr Pro Val Arg Gln Leu Ser Leu Gly Gln Arg Met
                    165                 170                 175

Arg Ala Glu Ile Ala Ala Ser Leu Leu His Asp Pro Ala Val Val Phe
                180                 185                 190

Leu Asp Glu Pro Thr Ile Gly Leu Asp Leu Val Leu Lys Gln Ala Val
            195                 200                 205

Arg Asp Leu Ile Asn His Ile His Ala Glu Leu Gly Thr Thr Val Met
        210                 215                 220

Leu Thr Ser His Asp Ile Gly Asp Ile Thr Ser Ile Cys Asp Gln Ala
225                 230                 235                 240

Leu Val Val Asp Arg Gly Thr Ile Val His Gln Gly Thr Met Arg Asp
                245                 250                 255

Leu Leu Arg Ser Val Asp Thr Arg Ala Val Thr Phe Glu Tyr Ala Ala
            260                 265                 270

Gly Ser Val Ser Glu Ala Ala Leu Arg Ile Ile Thr Glu Gly Leu
        275                 280                 285

Pro Glu Val Asp Ala Thr Pro Ala Glu Ser Gly Arg Ile Arg Val Glu
    290                 295                 300

Phe Pro Val Asp Arg Trp Ser Ala Arg Gln Val Ile Ala Phe Leu Leu
305                 310                 315                 320

Asp Arg Phe Asp Leu Ser Asp Val Leu Val Pro Asp Ala Asp Leu Glu
                325                 330                 335

Thr Leu Leu Arg Arg Ile Tyr Ala Gly Ser Arg Pro Glu Pro Val Thr
            340                 345                 350

Ala Gly Asp Gly Ala
        355

<210> SEQ ID NO 17
<211> LENGTH: 267
<212> TYPE: PRT
<213> ORGANISM: Artificial Sequence
<220> FEATURE:
<223> OTHER INFORMATION: >AcbX (ACSP50_3592)

<400> SEQUENCE: 17

Met Ile Arg Ala Ala Arg Arg Tyr Ala Pro Phe Ala Leu Ala Gly Leu
1               5                   10                  15

His Ala Val Thr Arg Tyr Arg Ser Thr Ile Val Leu Ser Ala Leu Thr
                20                  25                  30

Ala Ala Ala Ala Thr Ser Leu Gln Val Phe Leu Trp Arg Ala Val Tyr
            35                  40                  45

Ala Gly Gly Pro Ala Pro Ala Gly Leu Pro Phe Ala Gln Leu Thr Ser
        50                  55                  60

Tyr Ile Val Leu Ala Gln Val Leu Gly Met Leu His Thr Asn Arg Ile
65                  70                  75                  80

Asp Glu Met Ile Ala Gly Glu Val Tyr Arg Gly Asp Ile Ala Val Ser
                85                  90                  95

Leu Val Arg Pro Ala Asn Tyr Ala Leu Ser Cys Leu Ala Val Asn Leu
            100                 105                 110

Pro Thr Ala Ala Leu Ser Ala Leu Ala Gly Ala Pro Val Leu Ala
        115                 120                 125

Gly Phe Ala Met Phe Ala Ser Leu Pro Ala Pro Pro Ala Asn Leu
    130                 135                 140

Leu Leu Phe Ala Val Ala Leu Leu Leu Ser Val Ile Leu Ala Phe Glu
```

```
                145                 150                 155                 160
Ile Asn Phe Leu Val Gly Leu Ala Ala Phe Val Thr Thr Asn Thr Trp
                165                 170                 175

Gly Ile Arg Thr Ile Lys Asn Ala Leu Val Ala Phe Leu Ala Gly Gln
                180                 185                 190

Val Val Pro Leu Ala Leu Phe Pro Asp Gly Val Ala Arg Leu Leu Arg
                195                 200                 205

Leu Leu Pro Phe Gln Gly Leu Ile Asp Ser Pro Leu Arg Leu Leu Leu
    210                 215                 220

Gly Gly Tyr Ser Gly Ser Gly Ala Ala Ile Leu Gly Val Gln
225                 230                 235                 240

Ala Leu Trp Ala Val Leu Leu Tyr Gly Val Leu Ala Leu Ala Trp Asn
                245                 250                 255

Arg Ser Leu Arg Arg Val Glu Val Leu Gly Gly
            260                 265

<210> SEQ ID NO 18
<211> LENGTH: 267
<212> TYPE: PRT
<213> ORGANISM: Artificial Sequence
<220> FEATURE:
<223> OTHER INFORMATION: >AcbY (ACSP50_3591)

<400> SEQUENCE: 18

Met Thr Val Ser Thr Ala Arg Arg Tyr Leu Arg Leu Thr Ala Val Leu
1               5                   10                  15

Cys Gly Ala Ser Leu His Arg Leu Thr Ala Tyr Arg Met Asp Phe Leu
            20                  25                  30

Ile Gly Ala Ala Ser Phe Val Ile Arg Ile Ala Cys Gln Ile Ala Leu
        35                  40                  45

Ile Gly Val Ile Phe Gln Tyr Val Pro Ala Leu Gly Gly Trp Thr Arg
    50                  55                  60

Gln Gln Ala Leu Phe Leu Leu Gly Phe Ser Leu Leu Pro Arg Gly Leu
65                  70                  75                  80

Asp Arg Leu Phe Thr Asp Gln Leu Trp Ile Leu Ala Trp Gln Leu Val
                85                  90                  95

Arg Thr Gly Asp Phe Phe Arg Tyr Leu Ile Arg Pro Val Asn Pro Phe
            100                 105                 110

Tyr Ala Leu Leu Ser Glu Arg Phe Leu Tyr Pro Asp Gly Phe Gly Glu
        115                 120                 125

Leu Ala Thr Gly Ile Ala Ile Val Val Thr Ala Ala Gly Thr Met Asp
    130                 135                 140

Leu His Leu Thr Val Ala Gln Trp Leu Leu Leu Pro Leu Val Leu
145                 150                 155                 160

Gly Gly Ala Leu Ile His Thr Phe Leu Lys Ala Phe Leu Ala Ser Leu
                165                 170                 175

Ser Phe Trp Met Thr Ser Ser Leu Asn Val Met Val Ala Val Asn Gln
            180                 185                 190

Leu Ser Glu Phe Thr Ala Tyr Pro Leu Asn Leu Tyr His Pro Val Leu
        195                 200                 205

Arg Gly Val Leu Thr Trp Val Leu Pro Phe Ala Phe Thr Ala Tyr Leu
    210                 215                 220

Pro Val Arg Tyr Leu Leu Thr Gly Asp Ala Gly Pro Leu Leu Trp Met
225                 230                 235                 240

Leu Pro Val Thr Thr Leu Thr Val Leu Leu Gly Tyr Gly Thr Phe Arg
```

```
                    245                 250                 255

Leu Gly Leu Arg Arg Tyr Glu Met Pro Gly Ser
            260                 265

<210> SEQ ID NO 19
<211> LENGTH: 303
<212> TYPE: PRT
<213> ORGANISM: Artificial Sequence
<220> FEATURE:
<223> OTHER INFORMATION: >GtaB GalU (ACSP50_7820)

<400> SEQUENCE: 19

Met Thr Thr Asn Ala Gln Gly Ser Gly Lys Arg Ala Val Lys Ala Val
1               5                   10                  15

Ile Pro Ala Ala Gly Leu Ala Thr Arg Phe Leu Pro Ala Thr Lys Ala
            20                  25                  30

Val Pro Lys Glu Leu Leu Pro Val Asp Arg Pro Val Leu Gln Tyr
        35                  40                  45

Ile Val Glu Glu Ala Ala Ala Gly Ile Thr Asp Val Leu Leu Val
50                  55                  60

Thr Gly Arg Gly Lys Thr Ser Met Val Asp His Phe Asp Arg Arg Pro
65                  70                  75                  80

Asp Val Glu Gln Arg Leu Glu Lys Gly Asp Thr Glu Arg Leu Ala
            85                  90                  95

Ala Val Arg Arg Thr Ser Glu Leu Ala Asp Ile Tyr Thr Cys Arg Gln
            100                 105                 110

Gly Glu Pro Leu Gly Leu Gly His Ala Val Gly Thr Ala Ala Ser His
        115                 120                 125

Val Gly Asp Asn Pro Phe Ala Val Leu Leu Gly Asp Glu Phe Val Glu
130                 135                 140

Glu Gly Ser Pro Leu Leu Pro Asp Met Leu Asp Leu Gln Ala Arg Thr
145                 150                 155                 160

Gly Gly Ile Val Leu Ala Phe Ile Glu Val Thr Pro Glu Glu Thr Ser
                165                 170                 175

Arg Tyr Gly Ile Ala Ser Val Arg Glu Ser Asp Leu Gly Glu Gly Val
            180                 185                 190

Val Glu Val Thr Gly Leu Val Glu Lys Pro Ser Pro Glu Glu Ala Pro
        195                 200                 205

Ser Asn Leu Ala Val Val Gly Arg Tyr Val Leu Pro Gly Arg Ile Phe
    210                 215                 220

Glu Thr Ile Ala Gly Thr Lys Pro Gly Ser Gly Gly Glu Ile Gln Leu
225                 230                 235                 240

Thr Asp Ala Met Ala Thr Leu Leu Ala Glu Gly Thr Pro Val His Gly
                245                 250                 255

Ile Val Tyr Arg Gly Val Arg Tyr Asp Thr Gly Gln Pro Leu Gly Tyr
            260                 265                 270

Leu Gln Thr Val Val Gln Leu Ala Ala Gln Arg Pro Asp Leu Gly Ala
        275                 280                 285

Glu Phe Arg Ala Trp Leu Thr Asp Phe Val Gly Gly Gln Lys Gly
    290                 295                 300

<210> SEQ ID NO 20
<211> LENGTH: 149
<212> TYPE: PRT
<213> ORGANISM: Artificial Sequence
<220> FEATURE:
<223> OTHER INFORMATION: >Cgt (ACSP50:5024)
```

```
<400> SEQUENCE: 20

Met Asn Arg Thr Thr Val Arg Ala Gly Val Leu Ala Thr Ala Leu Ile
1               5                   10                  15

Ser Gly Val Leu Gly Val Ala Gly Pro Ala Leu Ala Ala Pro Val Thr
            20                  25                  30

Asp Ala Ala Pro Val Ala Ala Gly Thr Ala Val Ala Pro Ile Ala
        35                  40                  45

Ala Thr Phe Asn Val Thr Ala Gly Phe Thr Ser Trp Gly Gln Asn Val
    50                  55                  60

Tyr Val Val Gly Ser Ile Pro Ala Leu Gly Ser Trp Asp Val Ser Lys
65                  70                  75                  80

Ala Val Pro Leu Thr Thr Thr Ser Ser Ala Phe Pro Thr Trp Thr Gly
                85                  90                  95

Ser Val Ala Leu Pro Ala Asn Thr Tyr Thr Glu Phe Gln Tyr Val Val
            100                 105                 110

Lys Asn Ala Asp Gly Ser Val Ala Arg Trp Glu Lys Gly Phe Gln Gln
        115                 120                 125

Asn Arg Thr Thr Ile Thr Pro Pro Thr Gly Thr Tyr Val Thr His Asp
    130                 135                 140

Thr Phe Gly Ala Tyr
145

<210> SEQ ID NO 21
<211> LENGTH: 504
<212> TYPE: PRT
<213> ORGANISM: Artificial Sequence
<220> FEATURE:
<223> OTHER INFORMATION: >CrtI (ACSP50_0147)

<400> SEQUENCE: 21

Met Met Lys Pro Pro Thr Pro Trp Ser Arg Gly Val Arg Thr Val Thr
1               5                   10                  15

Gly Pro Thr Asp Arg Val Val Ile Val Gly Ala Gly Leu Ala Gly Leu
            20                  25                  30

Ser Cys Ala Leu His Leu Ala Ala Ala Gly Arg Gln Val Thr Val Val
        35                  40                  45

Glu Arg Glu Pro Val Pro Gly Gly Arg Ala Gly Arg Leu Ser Val Gly
    50                  55                  60

Gly Tyr Asp Phe Asp Thr Gly Pro Thr Val Leu Thr Met Pro Glu Leu
65                  70                  75                  80

Ile Ala Glu Pro Leu Ala Ala Val Gly Glu Asn Leu Ser Asp Trp Leu
                85                  90                  95

Glu Leu Thr Pro Leu Asp Pro Ala Tyr Arg Ala Tyr Tyr Pro Asp Gly
            100                 105                 110

Ser Thr Leu Asp Val Arg Thr Asp Thr Thr Arg Met Ala Ala Glu Ile
        115                 120                 125

Ala Gln Val Cys Gly Ala Arg Glu Ala Asp Gly Tyr Leu Arg Phe Val
    130                 135                 140

Asp Tyr Thr Arg Arg Leu Trp Gln Leu Glu Arg Asp His Phe Ile Asp
145                 150                 155                 160

Arg Asn Leu Asp Ser Pro Leu Asp Leu Leu Asn Leu Asn Leu Leu Lys
                165                 170                 175

Leu Leu Gly Met Gly Ala Phe Gly Arg Leu Gln Pro Lys Ile Asn Glu
            180                 185                 190
```

```
Phe Phe Arg Asp Pro Arg Thr Gln Arg Ile Phe Ser Phe Gln Ala Met
            195                 200                 205

Tyr Ala Gly Leu Ala Pro His Asp Ala Met Ala Ile Tyr Ala Val Ile
210                 215                 220

Ala Tyr Leu Asp Ser Val Ala Gly Val Tyr Tyr Pro Lys Gly Gly Met
225                 230                 235                 240

His Ala Val Pro Lys Ala Leu Ala Gly Ala Ala Glu Lys His Gly Val
                245                 250                 255

Thr Phe Arg Tyr Asp Thr Thr Val Glu Arg Val Leu Thr Gln His Gly
            260                 265                 270

Arg Ala Thr Gly Val Val Thr Val Gly Gly Asp Val Ile Glu Ala Asp
        275                 280                 285

Thr Val Val Leu Asn Pro Asp Leu Pro Ile Ala Tyr Arg Asp Leu Leu
290                 295                 300

Pro Ala Arg Asn Ser Arg Asn Leu Arg Phe Ser Pro Ser Cys Val Val
305                 310                 315                 320

Leu His Ile Gly Ser Ser Gln Arg Tyr Ser Lys Ile Ala His His Asn
                325                 330                 335

Ile His Phe Gly Thr Thr Trp Arg Arg Thr Phe Asp Glu Val Ile Asn
            340                 345                 350

Arg Gly Leu Leu Met Ser Asp Pro Ser Leu Leu Val Thr Asn Pro Thr
        355                 360                 365

His Thr Asp Pro Ser Ala Ala Pro Asp Gly Lys Gln Thr Tyr Tyr Val
370                 375                 380

Leu Ala Pro Ala Pro Asn Leu Val Ser Gly Pro Met Asn Trp Arg Gly
385                 390                 395                 400

Gly Leu Ala Glu Arg Tyr Ala Asp Glu Leu Leu Arg Thr Leu Glu Gln
                405                 410                 415

Arg Gly Tyr Ile Gly Phe Arg Asp Gly Val Glu Val Glu Arg Ile Ile
            420                 425                 430

Thr Pro Ala Asp Trp Ala Asp Asp Gly Met Ala Ala Gly Thr Pro Phe
        435                 440                 445

Ala Ala Ala His Thr Phe Ala Gln Thr Gly Pro Phe Arg Pro Ala Asn
450                 455                 460

Leu His Pro Thr Leu Pro Asn Val Val Phe Thr Gly Ser Gly Thr Gln
465                 470                 475                 480

Pro Gly Val Gly Val Pro Met Val Leu Ile Ser Gly Lys Leu Ala Ala
                485                 490                 495

Ser Arg Ile Thr Gln Gly Ala Ser
            500

<210> SEQ ID NO 22
<211> LENGTH: 419
<212> TYPE: PRT
<213> ORGANISM: Artificial Sequence
<220> FEATURE:
<223> OTHER INFORMATION: >MerR (ACSP50_0145)

<400> SEQUENCE: 22

Met Ala Gly Glu Ala Leu Ser Ala Glu Ile Pro Thr Ser Pro Gly Ser
1               5                   10                  15

Ser Val Ala Ser Ser His Asp Ile Pro Ala Thr Ala Gly Pro Gly Ala
                20                  25                  30

Val Arg Thr Gly Pro Val Ala Ala Pro Gly Gly Pro Ser Asp Thr
            35                  40                  45
```

```
Pro Leu Thr Asp Ala Thr Ala Ala Ser Gly Ala Ala Asp Asp Ala
    50                  55                  60

Ser Arg Ala Arg Pro Ala Thr Ala Thr Asp Asp Ala Ser Arg Thr Gly
 65                  70                  75                  80

Pro Ala Thr Ala Ala Thr Asp Ser Pro Asp Asp Ala Val Arg Thr Gly
                 85                  90                  95

Val Ala Asp Ala Ala Pro Ala Gly Arg Ala Gly Asp Val Ala Leu Ser
            100                 105                 110

Ala Gly Ala Ala Ala Arg Arg Leu Gly Val Ala Val Thr Thr Leu Arg
        115                 120                 125

Thr Trp His Gln Arg Tyr Gly Leu Gly Pro Ser Arg His Glu Pro Gly
    130                 135                 140

His His Arg Arg Tyr Thr Ala Glu Asp Met Asp Arg Leu Gln Val Met
145                 150                 155                 160

Gln Arg Leu Thr Thr Gln Gly Val Ala Pro Ala Glu Ala Ala Ala Trp
                165                 170                 175

Ala Arg Ser Arg Pro Leu Thr Pro Pro Glu Pro Gly Ala Ala Leu Tyr
            180                 185                 190

Asp Pro Thr Ala Val Ala Ser Pro Pro Thr Pro Ala Ala Pro Gly Gln
        195                 200                 205

Pro Pro Val Gly Pro Ala Gly Arg Gly Thr Arg Pro Thr Arg Gly Pro
    210                 215                 220

Ala Pro Ala Ala Arg Gly Leu Thr Arg Ala Ala Met Arg Leu Asp Val
225                 230                 235                 240

Arg Gly Met Arg Asp Ile Leu Cys Ser Thr Leu His Asp Arg Gly Val
                245                 250                 255

Ile Pro Ala Trp Thr Glu Val Met Val Pro Ala Leu Ala Ala Ile Gly
            260                 265                 270

Asp Arg Tyr Glu Ala Thr Arg Arg Phe Val Glu Val Glu His Leu Leu
        275                 280                 285

Ser Arg Ala Val Thr Glu Ile Leu Ala Ser Val Pro His Pro Ala Gly
    290                 295                 300

Ser Pro Arg Val Leu Leu Ala Ala Ala Asp Glu Glu Gln His Thr Leu
305                 310                 315                 320

Pro Leu Glu Ala Leu Ala Ala Leu Ala Glu Gly Gly Val Pro Ser
                325                 330                 335

Arg Leu Phe Gly Ala Arg Val Pro Ser Gln Ala Leu Leu Asp Ala Ile
            340                 345                 350

Ala Arg Thr Gly Pro Ala Ala Val Val Leu Trp Ser Gln Arg Pro Ala
        355                 360                 365

Thr Gly Ile Val Thr Gln Leu Thr Arg Val Arg Asp Ile Pro His Pro
    370                 375                 380

Pro Leu Val Ile Ala Ala Ala Gly Pro Gly Trp Pro His Asp Leu Pro
385                 390                 395                 400

Ser Gly Ile Thr Arg Leu Thr Gly Leu Thr Glu Ala Val His Leu Leu
                405                 410                 415

Ala Thr Val

<210> SEQ ID NO 23
<211> LENGTH: 1923
<212> TYPE: DNA
<213> ORGANISM: Artificial Sequence
<220> FEATURE:
<223> OTHER INFORMATION: >dxs (ACSP50_7096)
```

<400> SEQUENCE: 23

```
atgagcgact cccccttcgac cccggccggc ctgctggcga gcgtcaccgg tcccggtgct    60
ctcaagcgac tgtccgcgga gcagctgacc ctgctcgcgg ccgagatccg tgacttcctc   120
gtggccaagg tgtcgaagac cgggggggcac ctcggaccga acctgggcgt ggtcgagatg   180
accctcgcca tgcaccgggt cttcgactcg ccgcgcgaca agatcctctt cgacaccggc   240
caccaggcgt acgtgcacaa gatcgtcacc ggccggcagg acggtttcga cctgctccgc   300
cagcggggtg gcctgaccgg ctacccgagc caggcggaga gcgagcacga cctcatcgag   360
aactcgcacg cctccaccgc gttgtcctac gccgacggcc tggccaaggc gttcgcgctg   420
cgcggcgagg accggcacgt ggtggccgtg gtcgcgacg gcgcgctcac cggcggcatg   480
tgctgggagg cgctcaacaa catcgccgcc acgaagaaca ggctggtcat cgtcgtcaac   540
gacaacggtc ggtcgtacgc gccgacgatc ggcggcctgg ccgaccacct ctccacgctg   600
cggctcaacc ccggctacga gaaggtgctc gacctggtca aggacgcgct cggctcgacc   660
ccgctggtcg gaaagccggt cttcgaggtg ctgcacgcgt caagcgcgg gatcaaggac   720
gcggtcagcc cgcagccgat gttcgaggac ctcggcctga agtacatcgg gccggtcgac   780
ggtcacgacc agcaggcgat ggagtccgcg ctgcgccggg ccaaggggtt caacgcgccg   840
gtgatcgtgc acgcgtgac ccgcaagggc tacggctacc gtcccgccga gcaggacgag   900
gcggactgcc tgcacggccc gggcgccttc gacccgcaga ccggcgcgct caccgccaag   960
ccgtcgctca gtggaccaa ggtcttcgcc gaggagctgg tgaagatcgc cgacgaacgc  1020
cccgacgtgt gggcatcac ggccgccatg gccgagccga ccggcatcgc cgctctcgcc  1080
aagaagtacc ccgaccgggc gtacgacgtg ggcatcgccg agcagcacgc cgcgaccagc  1140
gccgcgggcc tggcgatggg cggcctgcac ccggtggtgg cggtctacgc caccttcctg  1200
aaccgcgctt tcgaccaggt gctgctggac gtcgcgatgc atcggctgcc ggtgaccttc  1260
gtgctggacc gggccggcat caccgggccg gacggcccca gccactacgg catctgggac  1320
atgagtgtct tcggcgccgt ccccggcctg cgcatcgccg ccccgcggga cgccgccacc  1380
ctgcgcgagg aactgcgcga ggcggtcgcg gtcgacgacg gcccgaccat cgtgcggttc  1440
ccgaccggtg cggtcgccgc ggacaccccg gcggtgcgcc gggtcggtca ggtcgacgtg  1500
ctgcgcgagg cggagaagaa ggacatcctg ctggtcgcgg tcggctcgtt cgtcggcctc  1560
gggctggacg ccgccgagcg gctcgccgag caggggtacg gcgtgaccgt ggtcgacccg  1620
cgctgggtgc gccggtgcc gatcgagctg accggcctgg ccgccagca ccgcctggtg  1680
gtgaccctgg aggacgggat ccgcgccggt ggtgtcggtg acgcggtggc cgccgcgctg  1740
cgcgacgccg gggtgcacgt gccgctgcgc gatttcggcg tgccggccgg tttccacccg  1800
cacggcaccc gggccgagat cctcgcctcg ctgggtctga ccgcgcagga cgtcgcgcgg  1860
gacgtgaccg gctgggtgtc cggcctggac gccggcacgt cggtggcggc cccggcgatc  1920
tga                                                                1923
```

<210> SEQ ID NO 24
<211> LENGTH: 1173
<212> TYPE: DNA
<213> ORGANISM: Artificial Sequence
<220> FEATURE:
<223> OTHER INFORMATION: >ispG (ACSP50_7248)

<400> SEQUENCE: 24

```
gtgaccgcga tcagtctcgg aatgccggcc gtccccccgc cgccgctggc cccgcgccgc    60
```

| | |
|---|---|
| cagagccggc agatcaacgt cggaggagtc ctggtcggcg ggggcgcccc ggtcagcgtc | 120 |
| cagtcgatga ccaccaccct cacctccgac gtcaacgcga ccctgcagca gatcgccgag | 180 |
| ctgaccgcgg ccggctgcca gatcgtccgg gtcgccgtgc cgtcccagga cgacgtcgag | 240 |
| gcgctgccga cgatcgccaa gaagtcgcag atcccggtga tcgccgacat ccacttccag | 300 |
| cccaagtacg tgttcgccgc gatcgacgcg ggctgcgcgg cggtccgggt caatccgggc | 360 |
| aacatccgcc agttcgacga caaggtcaag gagatcgccc gggccgcgtc cgacgccggc | 420 |
| gtgccgatcc ggatcggggt caacgccggc tcgctcgaca gcggcttct cgagaaatac | 480 |
| ggcaaggcca ccgccgaggc gctggtggag tcggcgctct gggagtgctc gctgttcgag | 540 |
| gagcacggtt ccgggacat caagatctcg gtcaaacaca acgatccggt cgtgatgatc | 600 |
| cgcgcctacc gtcagctcgc cgagcagtgc gactacccgc tgcacctggg cgtgaccgag | 660 |
| gccgggccgg ccttccaggg cacgatcaag tcggcggtgg cgttcggcgc gctgctcgcc | 720 |
| gagggatcg gcgacaccat ccgggtctcg ctgtccgcgc cgccggtcga ggagatcaag | 780 |
| gtcgggcagc agatcctgga gtcgctcggc ctgcgcgaac gcggcctgga gatcgtctcc | 840 |
| tgcccgtcct gcgggcggc ccaggtcgac gtctacacgc tggccgagca ggtgaccgcg | 900 |
| gcgctcgacg ggttcccggt gccgctgcga gtggccgtga tgggctgcgt cgtgaacggg | 960 |
| cccggggagg ctcgcgaggc cgacctcggg gtcgcctccg gcaacggcaa ggggcagatc | 1020 |
| ttcgtcaagg gcaaggtgat caagacggtg ccggaggcgg tgatcgtcga gacgctggtc | 1080 |
| gaggaggcgc tgcggctcgc cgacgagatg ggcgcggagc tgcccgacga gctgcgcgag | 1140 |
| ctgctgcccg gtcccacggt caccgtgcac tag | 1173 |

<210> SEQ ID NO 25
<211> LENGTH: 1200
<212> TYPE: DNA
<213> ORGANISM: Artificial Sequence
<220> FEATURE:
<223> OTHER INFORMATION: >dxr (ACSP50_7250)

<400> SEQUENCE: 25

| | |
|---|---|
| atgcgtgagc ttgtgctgct ggggtcgacc gggtccatcg gcacccaggc catcgatatc | 60 |
| gtccggcgca acccggagct gttccggggtg gtcgcgatcg gggccggggg tggcaacgtc | 120 |
| gcgttgctcg cggcgcaggc gctggagctg ggcgtcgagg tggtcggggt ggcccggggcc | 180 |
| tcggtcgtgc aggatctgca gctggccttc tacgccgagg cgcagaagcg tggctggtcg | 240 |
| tccggcgact tcaaactgcc gaagatcgtg gccgggccgg acgcgatgac cgagctggcc | 300 |
| cgctggccgt gtgacgtcgt tctcaacggg gtggtcggca gcctcggcct ggcgccgacc | 360 |
| ctggccgctc tggagtccgg gcggatcctt gcgctgccca acaaggagtc gctggtcgcc | 420 |
| ggcggcccgc tggtccggcg gatcgccaag gacgggcaga tcgtcccggt cgactcggag | 480 |
| cattcggcgc tggcccagtg cctgcgcggc gggcggggcc cggaggtgcg ccggctggtg | 540 |
| ctgaccgcca gcggggagc cttccgcggg cggcggcgcg cggagctgac gaacgtcacc | 600 |
| cccgaggagg cgctcaagca cccgacctgg gacatggggc cggtcgtcac gatcaactcg | 660 |
| gcgaccatgg tgaacaaggc gctggaagtg atcgaggcgc acgagctgtt cggcgtgccg | 720 |
| tacgacgaca tcgcggtgat ggtgcacccg cagtcggtgc tgcattcgct ggtcgagttc | 780 |
| accgacgtct cgacgctggc ccaggccagc ccgccggaca tgcggctgcc gatcgcgctg | 840 |
| gcgctggcct ggccggaccg ggtgccgggg cggccgcccg cggtggactg gacgctggcg | 900 |

| | |
|---|---:|
| cacaactggg agctgcgacc gctggacgac gaggcgttcc cggcggtcga gctggccaag | 960 |
| gcggccggcc ggtacggtcg ctgccgtccg gcgatcttca acgccgccaa cgaggagtgt | 1020 |
| gtggccgctt tcgccgccgg tcggctacct ttcttgggca tcgtcgacac cctggaacgg | 1080 |
| gtgctcgcgg cggccccgga tttcgcggag ccgagtaccg tcgatgacgt gctggccgca | 1140 |
| gaatcctggg cgcgtgccca ggcacagcgg acgatcgcga ctgtggctga aggagcctga | 1200 |

<210> SEQ ID NO 26
<211> LENGTH: 963
<212> TYPE: DNA
<213> ORGANISM: Artificial Sequence
<220> FEATURE:
<223> OTHER INFORMATION: >ispH (ACSP50_7707)

<400> SEQUENCE: 26

| | |
|---|---:|
| gtgttgctcg ccaagccgcg tggttactgc gccggtgtcg accgcgccgt gcagaccgtc | 60 |
| gaggaggcgc tgaaactcta cggcgccccg gtctacgtgc gtaagcagat cgtgcacaac | 120 |
| aagcacgtgg tcagcacgct ggaggcccgc ggcgcgatct tcgtcgagga gaactacgag | 180 |
| gtgcccgagg gcgccaccgt ggtgttctcc gcgcacggcg tcgccccga ggtgcacgac | 240 |
| caggcccgcg agcgccggct caaggcgatc gacgcgacct gcccgctggt caccaaggtg | 300 |
| caccacgagg cgaaacggtt cgccgccgag gactacgaca tcctgctgat cggtcacgag | 360 |
| gggcacgagg aggtcatcgg cacctccggc gaggcccccgg cgcacatcca gctcgtcgac | 420 |
| ggccccgacg acgtggcgaa cgtcgtcgtc cgcgacccgg ccaaggtcgt ctggctgtcg | 480 |
| cagaccacgc tgtcggtgga cgagacgatg gagacggtgg cccggctcaa gacccggctg | 540 |
| ccgctgctgc agtcgccgcc cagcgacgac atctgctacg ccacctcgaa ccggcagcac | 600 |
| gtgatcaagg agatcgcgcc ggagtgcgac gtggtgatcg tggtcggctc gaccaactcg | 660 |
| tcgaactcgg tccgcctggt cgaggtcgcc ctcggtgccg gcgcccgggc cggtcacctc | 720 |
| gtcgactacg ccgccgagat ccaggacgag tggctggccg gcgccaccac ggtcggtgtc | 780 |
| tcctccggcg ccagcgtgcc ggacgagctg gtgatggagg tgctggcgca cctcgcggag | 840 |
| cgtggcttcg gcgaggtcac cgagttcacc acggccgagg agcggctcac cttctccctc | 900 |
| ccgcaggagc tccgcaagga catgaaggcc gccgaggcgg cccgggccgc tgccgccggc | 960 |
| tga | 963 |

<210> SEQ ID NO 27
<211> LENGTH: 948
<212> TYPE: DNA
<213> ORGANISM: Artificial Sequence
<220> FEATURE:
<223> OTHER INFORMATION: >ispE (ACSP50_7802)

<400> SEQUENCE: 27

| | |
|---|---:|
| atgaccgagg cgtggggtcc ggacgacgac gagccgcgcc cgtacagcgg cccggtcaag | 60 |
| gtccgcgtgc cggccaaaat caacctgcac ctcgcggtcg gcccgctgcg acccgacggc | 120 |
| taccacgagc tgaacaccgt ctaccacgcc atctcgctgt tcgacgagat caccgcccgg | 180 |
| cacggcgaca ccctcaccct caccatggag ggcgagggca ccggcgacct cgccctcgac | 240 |
| gagaccaacc tgatcatccg cgccgccgc gccctggccg ccgcgcccg cgtccccgcc | 300 |
| tacgcccggc tgcacctgcg caagagcatc ccgctcgccg gcggcctggc cggcggcagc | 360 |
| gccgacgccg ccgccaccct gatcgcctgc gacctgctct ggggcctcgg catgagccgc | 420 |
| gacgagctcg ccgaggtcgg cgcccaactc ggctccgaca tccccttcct gctgcacggc | 480 |

```
ggcaccgccc tcggcaccgg ccacggcgag gcggtcagcc ccatcctggc ccgccccacc      540
acctggcact ggaccgtcgc catcgccgac ggcggcctgg ccaccccgcc cgtctaccgc      600
gagctcgaca ccctgcgcgc cggcacctgg ccacccactc cgctcggcag cgccgacacc      660
ctgatggccg ccctgcgcca gcgcaacccg gaaatcctcg cgccgccct cggcaacgac       720 ctgcaaccgg ccgccctcgc cctgcgcccc cagctcgccg acgtgctcaa agccggcacc      780
gaggccggcg ccctcgccgg cctcgtctcc ggctccggcc ccacctgcgt cttcctcgcc      840
gccgacgcca cacacgccca ggagatcgcc gacagcctca ccgaagccgg cgtctgccgg      900
gccgcggtca ccgcccgcgg accccagccc ggcgcgcggg taatctag                  948
```

<210> SEQ ID NO 28
<211> LENGTH: 489
<212> TYPE: DNA
<213> ORGANISM: Artificial Sequence
<220> FEATURE:
<223> OTHER INFORMATION: >ispF (ACSP50_8046)

<400> SEQUENCE: 28

```
gtgatcattc cgcgggtggg tatcggcacg gacgtgcacg cattcgacgc tgaccgggcc       60
tgctgggtgg ccgggctgga gtggccgggg gagccggggc tggccgggca ctcggacgcg      120
gacgtggtgg cccacgcggc ctgtgacgcg ctgctgtcgg cggccgggct cggggatctg      180
gggggcaact tcgggacgag ccggccggag tgggccgggg cagccggggt cacgctgctc      240
gccgagacgg cgcggctggt ccgggcggcc gggttcgcga tcggcaacgt gtcggtgcag      300
gtgatcggga accggccgaa gatcgggaag cggcgggccg aggccgagaa ggtgctctcc      360
gcggcggtgg gggcgccggt caccgtgtcc gggaccacat ccgacgggct ggggctcacc      420
gggcgtggtg aggggctggc cggagtcgcg gtggcgatgg tctacacgga gaacgctctt      480
ccggcctga                                                             489
```

<210> SEQ ID NO 29
<211> LENGTH: 732
<212> TYPE: DNA
<213> ORGANISM: Artificial Sequence
<220> FEATURE:
<223> OTHER INFORMATION: >ispD (ACSP50_8047)

<400> SEQUENCE: 29

```
gtgatcgccg accgcgacgt gaccgcgcag ctcaatgctc gcggtgacgt cgcggtcgtc       60
gttccggcgc cggggcggg tctccggctc ggcccgggcg gccgaaagc tctgcgtctg       120 ctcgacggcg agccgctgct cgtgcacgcg gtccggcggt tggccgcggc cgcgccggtc      180
cgcatgatcg tggtggccgc tccgcccgcc gaggtcgacg cggtgtccgc gctcctcgcc      240
ccggtggccc cggtcaccgt cgtgcccggc ggcgccgaac gccaggaatc ggtcgccgcg      300
gcactcgcgg tcgttccgcc ggacgttccg atcgttctgg tccacgacgc ggctcgatgc      360 ctcacccccgc cctcggttac ggagcgtgtc gccgccgctg tccgggacgg tgccgacgcg      420
gtgatcccgg tcctgccggt cgtcgacacg atcaaagagg tcgcggccga tgccaccgtt      480
ctcggcacgg tcgaccgttc cgtgctgcgt cggtacagaa ctccgcaagg cttccgcgcc      540
tcggtgctgc gcgccgctca ccgggccgcc gccgactcac acaccgacga cgccggtgcc      600
gtcgagaagc tcggcatccc ggtcctgtgc gtcccgggct ccgacctcgc gctcaagatc      660
acccggccga tcgatctggc gctcgccacg cacctcctgg ccctgccgga ccggacgcc       720
```

```
cctaccgcct ga                                                    732
```

<210> SEQ ID NO 30
<211> LENGTH: 585
<212> TYPE: DNA
<213> ORGANISM: Artificial Sequence
<220> FEATURE:
<223> OTHER INFORMATION: >idi (ACSP50_0146)

<400> SEQUENCE: 30

```
atgagcagca tcggtcacct caaccgtgaa gatcatctcg tcgagctcgt caacgaggag    60
gggcagccgc tcgggtcggc caccgtctcc gacgcccacc tctcgccggg tgcgctgcac   120
cgggccttct cggtcttcct caccgacgat gagggccggg tgctgctcca gcagcgggcc   180
gcggccaaaa cccgcttccc gctccgctgg ggcaacacct gctgcggcca ccccgcgccc   240
ggcgagccgg tcacggtcgc cgcggcgcgg cgtctcaccg aggaattggc ggtacgtgac   300
gtcacgctga ccgagatcgg cgtgtacacc taccgcgcga ccgacccggt caccggccgg   360
gtggagcacg aatacgacca cgtgctgatc ggcgccctgc cggacggcgt cgtgccacac   420
cccgatccgg cggagatcgc cacgctgcgc tgggcctcgc tgcccgggct gcgcaccggg   480
ttgacggagt cccccgagct gtacgcgccc tggctccccg gggtgttcga gattctcacg   540
gagcggtcgg gtgtcctttc cacggagcgg tcgggtggcc ggtga                   585
```

<210> SEQ ID NO 31
<211> LENGTH: 1071
<212> TYPE: DNA
<213> ORGANISM: Artificial Sequence
<220> FEATURE:
<223> OTHER INFORMATION: >crtE ldsA (ACSP50_0148)

<400> SEQUENCE: 31

```
gtggccaatg acaccctcga gggaaatcgc cttgccgcga taccccggca gtccgtctct    60
cacactgggc tggtcggtgc agtcgagggg acgctcgccg acttcctcgc ctcccagatc   120
gcctctctcg acgccgtcga cccatcgctc ggtggcttcg ccgcaccgc ccgtgacctg    180
gtgatggccg gcggcaaacg gctgcggccg acgttcgcgt actggggctg gcgcggcgtc   240
gccgggccgg ccgcggacgc cgagacgctg ctgcccgcgc tcggcgcgct ggagctgatg   300
cacaccttcg cgctcgtcca cgacgacgtg atggacgact cgtccacccg ccgcggccgg   360
cccaccgccc accggatctt cgcggcccag cacggcggcc ggttcggcac gtcggccgcg   420
atcctggtcg cgaccctctg cctggtctgg ccgaccagc tgttggcccg caccccggtg    480
ccggcggcca ccctgcttgc agtccgcgcg cattacgacc ggatgcggat cgaggcggtc   540
gccgggcagt atctggacgt cctcggtgag accgatccgg cgtcctggtc ggtggagcgc   600
gcactgctgg tcgcccggca caagaccgcc agctacaccg tgcagcggcc gctcgacttc   660
ggcctggccc tggccggggt cgaggacgtg gaggtcgccg aggcgtaccg gacctacggc   720
atcgccgtcg gcgaggcctt ccagctgcgc gacgacctgc tcggtgtcta cggcgacccg   780
gcggtgaccg gcaaaccggt cagcgacgac ctgcgcaccg gcaaaccgac cgcactgctg   840
atgctggccc gtcggatggc cacccccggc cagctggccg agctggagtc ggcggagatc   900
gagcgcaagg cgcaggtcgt cgccgagacc ggcgcccgg cccgggtcga ggagatgatc    960
cgtgcccggg tcaccgaagg actgaccgcg ctggcctcgg cgccgatcga cgccgaggcc  1020
cgtgccaccc tgatcgagct ggccaccgtg gcgacgcagc gcccggcatg a            1071
```

```
<210> SEQ ID NO 32
<211> LENGTH: 888
<212> TYPE: DNA
<213> ORGANISM: Artificial Sequence
<220> FEATURE:
<223> OTHER INFORMATION: >crtB (ACSP50_0149)

<400> SEQUENCE: 32
atggaaaccg atctggccgc cgcctatgag cggtgccgtg agctacaccg agagcacgga      60
cgcacgtact acctggcgac ccggttacta ccggcctgga agcgccggca tgtgcacgct     120
ctgtatggat tcacccggtt cgccgacgag atcgtcgacc gcaccgaggc gcaaccaccc     180
gccgagcgcg ccgccgagct ggccacctgg tccgccggat tcctcgccgg actgcgcggc     240
gagccggtcg acgacccgct gctcccggcc gtgctgcaca ccatcgcggt cttcgggctc     300
gacctggagg acttcgcgaa gttcctgcgc agcatggaga tggacctcac cgtcaccggc     360
taccgcacct acgacgacct gctcgactac atggagggct cggccgccgt gatcggcacc     420
atgatgctgc cgatcctggg ctccaccgac ccggccgccg cccgcgaacc ggcccgccag     480
ctcggcttcg ccttccagct caccaacttc atccgggacg tcgccgagga cctcgcgcgg     540
gaccggatct acctgcccga ggagcacctc gccgagttcg tgtgacccccg cgccgacctg     600 gccgccggcg tcgccacccc ggcgatccgc gcgctcatcc gggccgaggt ggaccgcgcc     660
cgtgagcact acgcggccgc cgcccccggc atcccgctgc tcgaacgcac ctcgcaggcc     720
tgcatgcgga ccgccttcca gctgtacggc gggatcctgg acgagatcga ggcggccgac     780
tacgacgtgt cgcccggcg gtcacggtg ccgaaccggc gccggccgc ggtcgccgtc     840 cgcagcctgc tcacccggcc cggcaccccg gtcgaactgg cggcctga                 888

<210> SEQ ID NO 33
<211> LENGTH: 1311
<212> TYPE: DNA
<213> ORGANISM: Artificial Sequence
<220> FEATURE:
<223> OTHER INFORMATION: >ACSP50_0150

<400> SEQUENCE: 33
atgggcgccc gcgtcgcgct gttcacccgc gacctgcgga tccacgacaa cccgctgctc      60
agcgggcccg accggtggt gccgctgttc gtcctcgacc cacggctgag cggcctctcg     120
gccaaccgca gccgctttct ccaccagagc ctggccgacc tgcggaacag tctccgcgag     180
cgtggcgccg acctggtgat ccgggagggc gacccggtgg ccgagaccat cgcggtcgcc     240
tccgaggtgg acgcgtcgac gatcacggtg gccgccgacg tgaccggtta cgcccagcgg     300
cgcgagcggc ggctgcggga cgagcgattc cgggtgaaga cggtgccgag cgtcacggtg     360
ctgccgcccg gtacggtccg gccgggcggg ggaggcgagt cgtaccgcgt gttcacgccg     420
tacttcaaag cctgggagaa agctgggtgg cgcgcaccct ccgcaacgcc ggggaaggtc     480
gcgatgccgg ccggcatcgc gccgggaagg ctccccgaga tgcccgccgg cgactcaccg     540
gacgccgtcg ccggtggcga gaccgagggc gccgccggc tccaggcctg gcagaaagaa     600
atggcgcggt acgccgagga ccacgacgac atggccgccg acaacaccag ccggctcagc     660
gcctacctcc ggttcggctg cctgtcgccg ctcgaactgg cgctggccgc gaaagccgac     720
gactctcccg gcgcccaggc ctacctgcgg caactgtgct ggcgggactt ctactaccag     780
gtcaccgcga ccttcccgga gatctccacc cggccgctgc gggagaaggc ggaccagaac     840
tggcgatacg acgacgacgc gctgcgtcac tggcaggacg gcctgaccgg ggtgccgatc     900
```

| | | |
|---|---|---|
| gtcgacgccg gcatgcgcca gctccgcgcg gagggctgga tgcacaaccg ggcccggctg | 960 | |
| atcaccgccg cgttcctcac caaacacctg ggcatcgact ggcggcccgg gctgcaatgg | 1020 | |
| ttcttccgct ggctgctcga cggcgacgtg ccgaacaact ccggcaactg cagtggacc | 1080 | |
| gccggcaccg gcaacgacac ccggccctat cgcaggttca atcccattcg ccaagcgcag | 1140 | |
| cgattcgatg cgcagggcgt gtacgttcgg cgctacgtac cggagttgaa agacatcgac | 1200 | |
| ggtgtcacgg tgcatcagcc gtggcgactg ccggaatcgg tacgccgcgg gctcgactat | 1260 | |
| cccggaccgt tggagtcaca tcgggacgag gcggtctggc tgcgcgactg a | 1311 | |

<210> SEQ ID NO 34
<211> LENGTH: 1362
<212> TYPE: DNA
<213> ORGANISM: Artificial Sequence
<220> FEATURE:
<223> OTHER INFORMATION: >ACSP50_0151

<400> SEQUENCE: 34

| | | |
|---|---|---|
| atgtctgaag cgcggcaagt ggacgtggtg gtcgtcgggc tcggtgtcgg cggcgaggag | 60 | |
| gtcgccggtc gcctggccgc ggccggcctg agcgtgatcg gcgtcgaaca ccgactggtc | 120 | |
| ggtggcgaat gcccgtactg gggatgcatc cccaccaaga tcatggtccg cgccgggaac | 180 | |
| gcgctggccg aggcccgccg gatccccggc ctcgccggga cgtccacggt gcgggccgac | 240 | |
| tgggcgccgg tcgccaaacg gatccgcgac gaggccaccg acgactggaa cgacaaggtc | 300 | |
| gccgtcgagc ggttcaccgg taagggcgga acgttcgtcc ggggcacggc cgaactgacc | 360 | |
| ggtcccggtc aggtccgggt cggggaccag gaattcgccg cttcgcgcgg cgtggtcatc | 420 | |
| gccaccggca ccgccgctgt ggtcccaccc atcgagggcc tgtccggtac gccgttctgg | 480 | |
| acgaaccgtg aggccgtgga agcggcggcc ctgcccgcat cgatgctggt gctcggcggc | 540 | |
| ggggcgatcg ggtgcgagct ggcccaggcg tacgcccggt tcggcgtgca ggtgacggtc | 600 | |
| atcgagggct caccccgggt gctggccatg gaggaaccgg agtcgtccga ggtggcggcc | 660 | |
| gccgccctga ccgccgacgg ggtccggatc gtcaccgggg tgcgcgcgca gaaggtcgcc | 720 | |
| cacgacgacg ggttccacgt gaccctctcc gacggcagcg tgctggccgg cgagaagctg | 780 | |
| ctggtcgcga ccgggcgggc ggcccggctc ggcgggctcg ggctggaccg ggtggggctg | 840 | |
| gacccgtcgg ctcgattcct ggccaccgat gaccggctgc gcgccggcga gggcatctgg | 900 | |
| gcggtggggg acgtgaccgg gaacggggcg ttcacccaca tggcgatgta cgaggcggac | 960 | |
| atcgcggtgc gggacatcct ggggcagggc ggcccgggag ccgactaccg ggcgcggccg | 1020 | |
| cgggtgaccct tcctcgaccc ggagatcggg gcggtgggga tgaccgagca gcaggcccgg | 1080 | |
| gacgccggcc tcgaggtgcg ggtggggtac gtgccgctga accagacctc gcagggttc | 1140 | |
| atccacgggc cggggaacga gggattcctc aaacttgtcg cggacgggga gcgggagtg | 1200 | |
| ctggtcggcg ggacgaccgc cggcagtcc ggtggcgaga tgatcggggc ggtggcggtg | 1260 | |
| gcggtgcacg ccgaggtgcc ggtgtcgacg ttgctcagcc agatctgggc gtacccgacg | 1320 | |
| tttcatcggg ggctggggca ggcgcttcag tcgctggcct ga | 1362 | |

<210> SEQ ID NO 35
<211> LENGTH: 351
<212> TYPE: DNA
<213> ORGANISM: Artificial Sequence
<220> FEATURE:
<223> OTHER INFORMATION: >ACSP50_1631

<400> SEQUENCE: 35

```
gtgagcgaac ccgtcatcac cgaaccggct gcctggatca acctgcccga cctgtccgag    60
aggctggacg tgtcgatcag caaggtgcac cagatgatca gagacggcga cctgctcgcg   120
gtccgccgcg acggcatccg cgtggtgccc gccgaactgg tggccaacgc caccgtcctc   180
aagcatctgc ccggtgtgct gaacgtgctc cgcgacgccg gtacaacga cgaagaggcc   240 ttccggtggc tctacgccga ggacgccgag gtcggcggca cgccgcgat cgcgctcggc   300 ggtcagcagg cgcgcgagat caagcgccgc gcgcaggccc tcggcttctg a           351

<210> SEQ ID NO 36
<211> LENGTH: 327
<212> TYPE: DNA
<213> ORGANISM: Artificial Sequence
<220> FEATURE:
<223> OTHER INFORMATION: >ACSP50_1632

<400> SEQUENCE: 36
atgaggcatt tgtcgtacgt cgcggtgctg gccggatgcc tggccggggc gctgtggctg    60
gaaccgatcc tgcgggtcaa cgtgctgcgc cggtggcgtc ggctgctgct ggccgtgctg   120
ccgatggcgg tcgtcttcac cctgtgggac ctggcggcga tcgcggccgg ccactggcac   180
ttcgacccgg cccagatcac cggcgtctac ctcggcggcg gctgccct cgacgaggtg    240 ctgttcttcc tggtggtgcc ggtctgcgcg atcctcggct tcgaggccgt gcgggccgtg   300
ctgcgacgtc cggcggggga cgagtga                                      327

<210> SEQ ID NO 37
<211> LENGTH: 336
<212> TYPE: DNA
<213> ORGANISM: Artificial Sequence
<220> FEATURE:
<223> OTHER INFORMATION: >ACSP50_1633

<400> SEQUENCE: 37
gtgacctaca ccaccgctgc ggtgctcggc gtgctggccg ccctcacgct cgacgtgctg    60
atcctgcgga cccggctcgt cgggcgactg gtgttctggg ccacgtaccc catcatcttc   120
gtctttcagt tgatctcgaa cggcattctg accgggcgcg acatcgtgat gtacgacccg   180
gccgcgatcc tcggcccgcg gctcgtccac gccccggtcg aggacctgct gttcggtttc   240
gccctggtgc tcggcacgct gtcgctgtgg gtggcgctgg gccggcgcgg catccagcgc   300
accccgcgag ccgggtctag acggaccgac gagtag                            336

<210> SEQ ID NO 38
<211> LENGTH: 1071
<212> TYPE: DNA
<213> ORGANISM: Artificial Sequence
<220> FEATURE:
<223> OTHER INFORMATION: >crtE fps2(ACSP50_1634)

<400> SEQUENCE: 38
gtgacgaact ccccgctcga cgaggccggt ctgcggtcgc gtgtcgacaa ggcgctgacc    60
gtgttcctgg ccgggcagcg tgaccggctg ctggcgatcg acccggcgct ggccgagatg   120
tccgccacgg tctccgagtt cgtgctgggc ggcgggaagc ggctgcggcc ggcattcgcc   180
tactggggtt tccgcggggc cggcggcgcc gactcggacg ccgtggtggc ggccgtcgcc   240
gcgctggagc tggtgcaggc cagcgcgctg atccacgacg atctgatgga ccgctcggac   300
acccggcgcg gggtgccgtc ggtgcaccgt cggttcgaga aactgcacgc cggcgagggc   360
```

```
tggcggggca gcgcggccgg gttcggcgac tgcgccgcgg tgctgctcgg cgacctggcc    420
ctggtctggt cggacgagct gctgcacacc tcggggatgg cggtggccga cgtgcaacgg    480
gcccgcccga tcttcgacgg gatgcgcacc gaggtgaccg tcgggcagta cctggacgtg    540
ctcacccagg cgaccggcga cacgtcgctg gagcgggccg gcaaggtggc cgtctacaag    600
gccgcgaaat acaccgtgga gcgtccgctg ctgctgggcg cggcgctggc cggagcggcc    660
cccggggtgc acgcggcgta ctcggcgttc ggcctgccgc tgggcgaggc gttccagctg    720
cgcgacgacg tgctgggcgt gttcggcgac ccggagcgga ccggcaagcc ggccggcgac    780
gacctgcgcg agggcaagcg cacctatctg gtcgcggccg ccttcggcgc gctggacgcg    840
gccgggcggg ccgaactgga cgccgcgctc ggcgaccccg gcctggacga ggccggggtg    900
gcccggctgc gcacggtcat ccgggacagc ggtgcgctgg ccgcgaccga ggcccggatc    960
gacgagctga tgaccgcgtc gatcggcgcg ctggacgcgg caccgatcga tcaggacgcc   1020
cgggaggtgc tgcgccggct ggccgacgcg ctactcgtc ggtccgtcta g             1071
```

<210> SEQ ID NO 39
<211> LENGTH: 924
<212> TYPE: DNA
<213> ORGANISM: Artificial Sequence
<220> FEATURE:
<223> OTHER INFORMATION: >ACSP50_1635

<400> SEQUENCE: 39

```
gtgtctctcg gacttccctc ccggctgccc ggcaccccgt cgatcggcga cctggtccgc     60
ggcgcggcgc cgacgttctc cttcgagttc ttcccgccga agacaccgga cggggagcgg    120
ctgctctggc aggccatccg ggagctggag tcgctgcggc ccagcttcgt ctcgatcacc    180
tacggggccg cgcaccac ccgggagacc acgtcgcgg tcaccgagcg ggtcgccacc       240
gagaccacgc tgctgccgct ggcccacctc accgcggtcg accactcagt ggccgacctg    300
cgcaacgtga tcgccggct ggccggcgcc gggatccgca acgtgctggc gctgcgcggc     360
gacccgccgg gcgacccgat gggcgagtgg gtccggcacc cggacggcgt cggttacgcc    420
gacgagctgg tccggctgat ccgcgagtcc ggcgacttca gcgtcggggt ggccgccttc    480
ccgcacaaac accccggtc ggccggcgtc aaggacgaca cccgcaactt cgtccgcaag     540
tgccgggccg gtgccgacta cgcgatcacc cagatgttct cgacgccga cgaatatctg     600 cggctgcgcg accgggtggt ggccgccggc tgtcacaccc cgatcgtggc cggcgtgatg    660
ccggtgaccc ggatggccac catcgcgcgc tccacccagc tctccggcgc gcccttcccg    720
ccggcgctgc tgcgcgactt cgagcgggtc gccggcgacg acgcggcgcg tgcgcgagctg   780 ggcatcgaga cgtgcgcggc gatgtgcgcc cggttgctgc gggagggtgt gccgggcatc    840
cacttcatca ccatgaaccg gtccaccgcc acccgcgagg tctggcagcg gctggccccc    900
gcggaagtcg ccgcgtcggc gtga                                           924
```

<210> SEQ ID NO 40
<211> LENGTH: 933
<212> TYPE: DNA
<213> ORGANISM: Artificial Sequence
<220> FEATURE:
<223> OTHER INFORMATION: >ACSP50_1650

<400> SEQUENCE: 40

```
gtgcagctgc aacaactccg gtacttcctg gcggtggtgg agacccggca tttcacccaa     60
gcagcggaca ttctgggcgt ctcgcaacct accttgagta agcagattca caccccttgag   120
```

```
atgtcactcg gagccccgct gttcgagcgg atgcgcggtg cggtgaccct gaccgtcgcc    180
ggcgagacat tgctgccgat ggcccagcgg atcgtcgccg acgccgacgc ggcccgcgac    240
gccgtgcagg acatcgtcgg tctgcgccgc ggcgaggtgc gcctgggtgc caccccgagc    300
ctgtgctcct cgctggtccc ggccgtgttg cgcaccttcc gcgccgacca cccggggtc     360 aagctgcaca tcagtgaggg cagctcgcac gacctgaccg ccggcctgct ggcgcacacc    420
ctggatctgg ccctgatcgt gcagcccgag cacggcgtcg atccggccct ggtggccatc    480
gagctgctgc gcgagagcct ggtggtggcc tcggtcgcgg ccggcccgcc gcccaccgtg    540
ggccgccaac tggagctctc cgagctgcgc cacaccccga tggtgatgtt ccgcgagggc    600
tacgacatcc gtgaggtcac cctgcacgcc tgcgagcggg ccggcttcgc gccgaagttc    660
gcggtcgagg tggtgagat ggacgcgtg ctcgccttcg tcgaggccgg cctcggggtc      720
gccctggtgc ccagcatggt gctcgccaac cggccgctgc tgcgggccac cccgctcgcg    780
ccgccgggga tgcgccggac catcgcgctc gcccagcgcc gtgccgcggt gctgccgcat    840
gccgcggccg cgctgcgtga ggtggtgctc gaccacatcg gctcgggccg gctgccgttc    900
ggcgtgcgcg ccctggagag accgtccact tag                                 933

<210> SEQ ID NO 41
<211> LENGTH: 750
<212> TYPE: DNA
<213> ORGANISM: Artificial Sequence
<220> FEATURE:
<223> OTHER INFORMATION: >ACSP50_1651

<400> SEQUENCE: 41
atgggcgagt ccacgaccc gcgactcgtc gaggtctacg acgccgaatg tccctggggc      60
tgggacgacg acttcttcat ggccgtgctc gccgaacgct ccgcgcaccg ggtcgccgac    120
ctggggtgcg gcaccggccg gctggccatc gcgatggccg cggccgggca cgaggtgatc    180
gcgatcgacc cggcgccggc cgccctggcc gcggcccgcc gcaagccggg cggcacccgg    240
gtgcgctggc tgcagggctc ggccgagcgg ctcgccccgc gctcgctcga cgccgcgttc    300
atgaccggtc acgtcgccca gtccttcgtc gacgacgagg aatgggacac cgtgctccgc    360
gggctgcgcc gggcgctggt cccggaggga cggctggtct tcgacagccg ggacccggac    420
gaccggccgt ggcagcagtg gaacccgcag gattcgtggc gcaccgtggt gctcgacgac    480
gggagggtgg tggaggcgtg gagcgaggcc gagcaggtcg ggctgaacac cgtgcgcgtc    540
accgggcgct accggttcgc cgacggaggg gaactggcga actcggcgac cctgcgtttc    600
cggaccgagc cggagctgcg cgactcactg cgcgaggcgg gcttccgggt cgagcggatc    660
tacgccggct gggggcgcga gccggtgggt ctgagcggcg acggcgagtt catcgtgatc    720
gcggtcgcga cgccccggct gatgtcctga                                     750

<210> SEQ ID NO 42
<211> LENGTH: 1722
<212> TYPE: DNA
<213> ORGANISM: Artificial Sequence
<220> FEATURE:
<223> OTHER INFORMATION: >ACSP50_1652

<400> SEQUENCE: 42
atgcccgaga acgagtggcc cgacgacccc cgcccgcccg accagggcga gtggagccag     60
ccgcatcacg agccgccacc cggccgtggc cgcgccctgc tggccgccgc ggtggtggtg    120
```

| | |
|---|---|
| ctggtcctgc tggccgccgg cggcatcgcc tggcgtctga tgagcagccg cggcgctacg | 180 |
| ccggtggcgc agcccaccgc gcccgccccg acgccaccg cgcagaccgc gccaccctgc | 240 |
| ccacagccgc gcctgcgggt cgccgccgcg ccggagatcg ccccggtgat ccagcaggcc | 300 |
| gccgccgcac tcagccagcc cggccagcgc tgctccgagg tgctggtgca ggccgccgag | 360 |
| ccgggcgccg cgctgaccgg caagccggac gtctgggtgc cgtccagcag cgtgtggctg | 420 |
| gccctggcca aaagccgcgg cgacgtctac accacgcagg gcgcgtcgct ggcctggtcg | 480 |
| ccgctggtga tcgccgggcc ggagtcgatc gccagcctgt tcgcgccgaa cggggtcacc | 540 |
| tcctggtccg gcctggtcca gggcaccatc cagaaacggg tgccggcggt ccggatgccc | 600 |
| gatccgacgc tgaccacgac cggactgctc agcgtctacg cggtgggcca ggccacggtc | 660 |
| aaggccaacc cggacgccgg gatcgcccag ttgcaggcgc tcaccctgcg cagccggctg | 720 |
| gagaacgcgg ccgccgaccc ggcggaactg ttcgcgcaga tgggcaagca gaccgacgcg | 780 |
| gccacgcgca tctaccaggt cggggtcttc ccgaccaccg agcagcagct gctgaccctat | 840 |
| cagaagagtc agcacgacgt ccggctgtcc ggctcggcgc ccgccgacgg ccagatcgac | 900 |
| gccgactatc cgtacgcggt ccgcaagggc gccccggccg acctggtcga gagccttcgc | 960 |
| gaggcgatca ccccggacgc gctgacgacg gccggattcc gggccaccgc gaccaagaac | 1020 |
| gcgctgcgcc tgccggcccc ggccgtgctc gccggggcgg cccggcagtg gtcggcgtac | 1080 |
| aagtcggtgg ccttccaggt gctgctgctg atcgacgcgt ccggctcgat gaacgagaag | 1140 |
| atcaccgacc gggccggccg cagcgtcacc aaggccgcgc tgctgcgcga gtccgggacc | 1200 |
| agcgcggccc agctcttcgg tgacgacacc agcctcggcc tgtggttctt cggcaccccg | 1260 |
| acggcggaca gcccggcgca caccgaggag gtgccgttcg gcccggtcat cgccaccgtc | 1320 |
| gacggcaaga gccgccgtga cctgctggcc gccaagatcg gcgagtaccg gccggtggcg | 1380 |
| aacgccggga ccccgctcta ccagagcgtg ctggacggcg tcgccgagat gcgcggccgg | 1440 |
| gccaagccgg acacgcgcgac cgtggtggtg gtcctcaccg acggctcgga cggcggcacg | 1500 |
| aagtaccgga tgtccaacgc ggacttcctg aagaagctga ccgccggtgc cgaccccgcc | 1560 |
| aagccggtgc cggtgatcgc cgtcggttac ggccggccg cgaacgccac cgccctgcag | 1620 |
| gccatggcca aggccaccgg tggccaggcg gtcaccgtca agaacccggc cgacctggcc | 1680 |
| gccggcatcg cccaggcctt cctcgccgca cacacccact ag | 1722 |

<210> SEQ ID NO 43
<211> LENGTH: 1437
<212> TYPE: DNA
<213> ORGANISM: Artificial Sequence
<220> FEATURE:
<223> OTHER INFORMATION: >crtD (ACSP50_1653)

<400> SEQUENCE: 43

| | |
|---|---|
| atgagcgaca tcgtggtggt cggggctggg gtcggcgggc tggccgcggc gatccggctg | 60 |
| gccgaggcgg ggcatcgggt cagcatccat gagcggtccg gcgtggtcgg cggcaagctg | 120 |
| gcggcatacg agagggacgg ctaccggttc gacaccggcc cagcctgct caccctgccg | 180 |
| gacgtgttca ccggcctcgg tctggacctg cgcccggagc gctggacccc ggtggtgcgg | 240 |
| cacttcttcc cggacggcac ggtgctggac tcgtcgtcgg accacgagac cttcctggcc | 300 |
| cggatcaccg acgcgctggg cggtgccgcg gcgcgcgact gggaccggtt ctggcgccgt | 360 |
| gccgagcgga tctggcacgc ctcctgggag tcggtgctgc cgccccggt gaccgcggcg | 420 |
| tcgctggccc ggctgtcctg gcggctcggt gacctggccg cgatcgctcc cggccggtca | 480 |

```
ctgcggtcgc tgggccgccg ctatctgcgc gacccgcggc tgcggatgct gctggaccgc    540
tatgcgacgt attcgggcgc ggatccgcgg cgggcgccgg cggcgctggc cgcgatcccc    600
tacgccgagc tggcgttcgg cgggtggtat ctgccgggtg ggctggtcac cctcgcggag    660
gcgctgctcg cccgatgcga gaaactgggc gtacgggtgc atctgcactc accggtcgcc    720
tcgatcgcca cgaccggcgc ccgggtgtcc ggggtccggc tggggacgg acccgcctc     780 gcggcggacg tcgtcgtctc caacgtggac gccgtcacgc tctaccggga tctgctgccc    840
agtccgaaac cgctggcccg cctcgccgac cggagcctgg ccggattcgt gctgctgctc    900
gcggtgcggg gcgagactcc gcggctggcg caccacaacg tgttcttccc gcgggactac    960
gacgccgagt tcgacgcggt cttcgggggg ccggggcggc gggcgcggcc ggccggcgac   1020
ccgaccgtct tcgtcacccg ggccgcggat ccggcggtgc gcccggccgg cgacgaggcg   1080
tggttcgtgc tggtcaacgc ggcgccacac ggcacctcgt ggtccaccgt ggactggctg   1140
cgggcggggc tggccgacgc gtaccgggat cgggtcctcg aggtcctggc ggggcgcggt   1200
ctcgacgtac gcgatcggct gatcttcgcc gagacccgga ccccggcgga tctggcggcg   1260
tcggccgcag cgccgggcgg agcgatctac ggcaccgccg gcggcctggt ccggccggcg   1320
aaccgcgcgc cggtcgacgg gttgttcctg gtcggcggct cgacgcatcc cggcggcggg   1380
ctgccgatgg tcaccctctc cgccgagatc gtcgcgggca tgatcggatc gaactga      1437

<210> SEQ ID NO 44
<211> LENGTH: 1080
<212> TYPE: DNA
<213> ORGANISM: Artificial Sequence
<220> FEATURE:
<223> OTHER INFORMATION: >cruC (ACSP50_1654)

<400> SEQUENCE: 44
atgatcgtcg cctggctgat cctgccgccg ctgctgctga tcaccgcaca caccgccgtc     60
aacgcgctgc tgctgcgccg cccgcgccgg gcggcgacca gcaccgaacg ggtcgccgtc    120
ctgctcccgc tgcgcgacga ggccaccccg gtcaccccgt gcctgcgcgc cctgctcgcc    180
cagcgcggcg tcgccgatct caccgtgcac gtgctcgacg acggctccac cgacggcacc    240
gcggacgtgg tccgggcggt cgccggcgac cgggtccggc tgcacaccgg cactccgccg    300
ccgcccggct ggctcggcaa accggccgcc tgccaacggc tcgccgacct ggccggggac    360
gtggacgtgc tggtcttcgt cgacgccgac gtggtgctcg cgccggacgc ggtggccggg    420
gccgtcgatc tgctgcgccg ggccggagcg gacctgctca gcccgtaccc gaagatcgtc    480
ggtgccggcc ggctggtcca gccgctgctg cagtggtcct ggctgagttt cctgccactg    540
cgcgcgatgg aacgctcggc gcggccgtcg ctggccgccg ccgtggccca gtggctggtg    600
ctggaccggg ccggttaccg gcgagccggt ggccacgccg cggtgcgcgg cgagatcctg    660
gaggacatcg cgctggcccg cgcggtcaaa cgggccggcg gcggatcgc cctggccgac    720 ggttccggcc tggccacctg ccggatgtac gagtcctggg acgagctcgc cgacggatac    780
gccaaatcgc tgtgggcgtc attggggtcc gcggccggcg cgaccgccgt cacgctcctg    840
ctgattctgc tgtacgtggt gccacccctg ctggcgccct cgccccgct tccggcggtg    900 ctcggctacc tgctcggcgt gaccggccgc atgatcgccg ccagggccac cggcggccgc    960
gtcctgcccg gcacgctggc ccatccggtc tccatcgtcc tgttcggcta cctgatcgcc   1020
cgctccttcc ggctgcgccg ggccggccgc ctggcctggc gggccgcgcc ggtgccctga   1080
```

<210> SEQ ID NO 45
<211> LENGTH: 756
<212> TYPE: DNA
<213> ORGANISM: Artificial Sequence
<220> FEATURE:
<223> OTHER INFORMATION: >cruF (ACSP50_1655)

<400> SEQUENCE: 45

| | | | | | |
|---|---|---|---|---|---|
| gtgtctcccc | gtcatctgcc | ctggggcctg | ctcggggcgc | tcgtgctcgc | ccagatctgc | 60 |
| tatccgctca | ccgagggtga | cacccgggcc | gggctgaccg | tgctcaccgt | gctgctcggc | 120 |
| gtcgcgttct | cgctgagcca | cgcgctgctc | acccggggcc | ccggcgct | cacggcgctg | 180 |
| ctgtcgaccg | ccaccctggg | cgggttcgcg | gtggaggcga | tcggggtggc | caccggtttc | 240 |
| ccgttcggtt | cctacgagta | ctccgggcgt | ctcggtccgc | gcctgctcgg | cgtaccgctg | 300 |
| atcatcccgc | tggcctggac | ctggatggcc | tggccgccct | ggctcgccgc | gctgcgggtg | 360 |
| acccggcggc | ggctcccccg | gatcctggtc | gccggggccg | gcctggccgc | ctgggacgtc | 420 |
| ttcctcgacc | cgcagatggt | cgccgaggac | tactggcggt | ggcggcaccc | ggtgcccgcg | 480 |
| ctgcccggcg | tgcccggtgt | gccgctcggc | aactacctgg | gctggctcgg | cttcgcgctg | 540 |
| ctgctgatga | ccgcgctggc | cgccgtcgcc | ggccgggccg | ccgaccggcc | gctgtccgcc | 600 |
| gaccggccgg | cgctcgccct | gtggatctgg | acgtacgcct | cgtcggtgct | cgcccacgcc | 660 |
| gtcttcctgt | cgctgccggc | gtccgcgcg | tggggcgcgc | tgatcatggg | cgccgcggtc | 720 |
| ctcccgctgc | tcgcccggct | gcgcgcaccc | gcatga | | | 756 |

<210> SEQ ID NO 46
<211> LENGTH: 579
<212> TYPE: DNA
<213> ORGANISM: Artificial Sequence
<220> FEATURE:
<223> OTHER INFORMATION: >ACSP50_1656

<400> SEQUENCE: 46

| | | | | | |
|---|---|---|---|---|---|
| atgaggcttg | tggcgtggca | gccggacgac | ctgctgcggc | ggctcgacga | cgtggtcggg | 60 |
| gtctacggcg | aggcgatggg | ctaccgccag | gagctgctgc | agacccgccg | gggatacatc | 120 |
| gggtcgcacg | tgcgccggcc | cgggttccgg | gcggtggcca | cgctgaccac | cgagggccgg | 180 |
| ctgatgggct | tcggatacgg | ctacacctcc | gccgccggcc | agtggtggca | cgaccaggtc | 240 |
| cggttcgctc | tcggcgagga | cgaccgccgg | cagtggctga | ccgactgctt | cgaggtggtc | 300 |
| gagctgcacg | tgcgcccggc | cgcgcaggc | cacggggtgg | cgcccggca | gctgcgcgcg | 360 |
| ctgctggcca | tggccaaagg | ccgcaccgtg | ctgctgtcca | ctccggaggc | cgacgagcag | 420 |
| gcgtcccgcg | cctggcggct | gtaccggcgg | tacggcttcg | ccgacgtgct | gcggcacttc | 480 |
| tacttcccgg | gtgacgagcg | ggccttcgcg | gtcctcggcc | gcgagctgcc | gctggccgag | 540 |
| cgtccgctcg | aggacgcacc | gggcatcgcc | ggcgcctga | | | 579 |

<210> SEQ ID NO 47
<211> LENGTH: 675
<212> TYPE: DNA
<213> ORGANISM: Artificial Sequence
<220> FEATURE:
<223> OTHER INFORMATION: >ACSP50_1657

<400> SEQUENCE: 47

| | | | | | |
|---|---|---|---|---|---|
| atgacgcacg | tcgccctgca | cgtctggcgg | gtgccgcgca | gcgccgtcgg | ctcggccatg | 60 |
| ctgcgcatgg | ccttcgcgcg | gcgccatctg | gccggtctgc | ggttcggcaa | gttcctcggc | 120 |

-continued

| | |
|---|---|
| accggcaccg gcaccggctt cggtcccggc acaccgatc tcacccgtg ggcggcgatc | 180 |
| acggtcagtg atgcgccggt acgtttcccc gtctgggagc ggatcgccgt caacggcgcc | 240 |
| cggatcgatc tggagccact gatcagccgg ggcacctggg ccggccgtac cccgttcgag | 300 |
| cccaccggcc gccgccgga cggtccggtg ctcgcgctca cccgggcccg gctgcggccg | 360 |
| gctcgcgcgc tgaccttctg gcgggcggtc ccggcggtgg tgcgcgaggt gcaccgggcg | 420 |
| cccgggctgc tcgcccggtt cggcgtcggc gaggcgccga tcggctggca gggcaccgtc | 480 |
| accgtgtggc gggacgcggc ggatctcgtc gcgttcgcgt accgtcagcc ggagcatcgc | 540 |
| gcggcgatcg cccggacccc ggccgaccgc tggtacgccg aggagttgtt cgcccggttc | 600 |
| gcggtgctcg ggatcagcgg tgaccggtcc gtgctgggct ggaccgccga cgaaggggaa | 660 |
| cgggcggaag catga | 675 |

<210> SEQ ID NO 48
<211> LENGTH: 816
<212> TYPE: DNA
<213> ORGANISM: Artificial Sequence
<220> FEATURE:
<223> OTHER INFORMATION: >ACSP50_1658

<400> SEQUENCE: 48

| | |
|---|---|
| atgacacaga ccatcgtgat caccggggcc agctccgggg tcgggctggc cgccgccgag | 60 |
| cagctcgccg cccgcggtga cgaggtggtg ctggtcggcc gcgacccggg ccggctcgac | 120 |
| gcggccgtgc agcgggtccg ggaggccggc ggcggccgcg cgcccggca cttccgggcc | 180 |
| gacttcgaac ggctcgacga cgtgcgggag ctcgccgccg ggctgctggc cgagctgccc | 240 |
| cggatcgacg tgctggccaa caacgccggc gggatcatca gcggccccg gcagacggtg | 300 |
| gacggccacg aggccaccat ccagggcaac cacctggccc cgttcctgct cacccacctg | 360 |
| ctgcgggagc ggctgaccgg gggccgggtg gtgaacaccg cctcggcggc acacgtgcag | 420 |
| ggccggcccg gcacccggtt caccgacgac ccgaagtcgt acagtccgtg gcgctcctac | 480 |
| ggggcgagca aggcggccaa catcctgttc gccgccgagg ccgcccgccg ctggccggac | 540 |
| gtgtgcagcg tctcgttcca ccccggtgtg gtgcgcacca acttcgggga gggccggctg | 600 |
| atccggctgt tctaccggta cgcgcccggc ctggtcaccc cggaggccgc cggcgagctg | 660 |
| ctgacctggc tgtgcaccac cccggccggg gagctggaga acggcgccta ctacgtcaag | 720 |
| cgtcaggtga cccggccggc cgcgcacgcc cgcgacccgc ggctggccgc cgagttgtgg | 780 |
| gacgccagcc tgaccgcgac cggcctcgcc ggatga | 816 |

<210> SEQ ID NO 49
<211> LENGTH: 1020
<212> TYPE: DNA
<213> ORGANISM: Artificial Sequence
<220> FEATURE:
<223> OTHER INFORMATION: >crtE (ACSP50_3873)

<400> SEQUENCE: 49

| | |
|---|---|
| gtgatcgacg acttcctcag cgcgcaacgc gacgtgctgg ccgaggtcag cgacgactgc | 60 |
| gcgccgctgg aacgctacgt ggccgacctg atgggcggcg gcaaacgact ccggccggcg | 120 |
| ttctgctact gggcgtggcg ggcggccggc gccccgacg gcccgggcat cgtggcggcc | 180 |
| gcgacatccc tggagttcct gcaggccgcc gcgctgatcc acgacgacat catggacgat | 240 |
| tcggacaccc gtcgcggcgc cccggcggtg caccgcagac tggcggccct gcactccggc | 300 |

-continued

| | |
|---|---:|
| ggccgctggg ccggggacgc cgaccacttc gggctgtccg ccgccgtgct cgccggcgac | 360 |
| ctgtgcctga cctggagcga cgcgttgtat tcgggcagcg gcctgcaccc gtccgcgctg | 420 |
| gcccggggcc ggccggtctt cgaccggatg cgcacccagc tgatgggcgg ccagtatctg | 480 |
| gacctgctgg accaggcgcg gccgtcccgg ggcggcgtcg accggcgcg ccgggtggtg | 540 |
| cacttcaaga gcgccaagta caccgtcgaa catccgctgc tgctcggcgc ccggctcgcc | 600 |
| ggcgcggacg acgatctgct cgcccggttg tccgcgttcg gtctgccgct gggcgaggcg | 660 |
| ttccagctgc gcgacgacct gctcggggtc ttcggcgacg cggcgcagac cggcaaaccc | 720 |
| accggcgacg acctgcgcga gggaaagcgc accacgctgg tcatcctggc cgcggaccgc | 780 |
| gccaccgcac cccagcaggc cgccctcacc gcgctgctcg gcgatcgcgg cctgaccggg | 840 |
| gccggcgtcg acaccctccg gcagatcatc gtggacaccg gtgcccgggc cgaggtcgag | 900 |
| cggatgatcg agcaactgct ggcgacgagt ctcggcgtgc tcagcggcac gcccgtcgac | 960 |
| gaggcggccc gctcggtgct gctcgccctc gccgaggcgg cgaccgcccg cagctcctga | 1020 |

<210> SEQ ID NO 50
<211> LENGTH: 1029
<212> TYPE: DNA
<213> ORGANISM: Artificial Sequence
<220> FEATURE:
<223> OTHER INFORMATION: >ACSP50_1950

<400> SEQUENCE: 50

| | |
|---|---:|
| atggtgagca cagtgatcgc ctcggggccc accggcctgg gcacctccgc ggcccgtctc | 60 |
| ttcggtcggg tggaccggga cgagccggag ctcttctgcc cggcgccgct cgcgacgac | 120 |
| cgggcgctgg gggagcgggt caacgacgcc gtggtccagt gggccgagaa ggccggcatc | 180 |
| taccccggcc ggctggacaa gctgcgcggg gcgaacttcg gccgcttcat gatgctcgcc | 240 |
| cacccggcca ccagcgatcc cgaccggctg ctcgccgcga cgaagtgtct ggtcgccgag | 300 |
| tgggcggcg acgactacta cgtcgacgag gtgtccctgg gcgcggatcc gatggtggtc | 360 |
| ggctcgcggc tggccaacct ctactcggtg gtcgacccgg cctcgctgac cccgcgctat | 420 |
| caggccgact cgagaagca tcaccgcctg cagccgatct cggtggcgtt ccgcaccgcg | 480 |
| atggaacacc tggccgagta cgcctcggtc acccaactgg cccggttcca gcaccagatg | 540 |
| gcgatcctgt tcgtcgcctg gtcgcaggag gccgactggc acgccaaccg cgcacccccg | 600 |
| ccggtctggg agtatctggt gcagcggcac ctgaacagct atctgccgcc gatgatcctg | 660 |
| gtcgacgtgc tggccgggta cgagctgtcg ccggccgagt tcttcgatcc gcgggtccgc | 720 |
| gcggcgttca ccaccgcagg caacgccgcc gtgctggtca acgacctcta ctcgggcagg | 780 |
| aacgagtccg agaccgatca caacctgccg accgtgctgg tgtccggga gcggctcacg | 840 |
| ccgcgggccg cggtccggcg caccgtggag atccacaacg agttgatgca caccttcgtg | 900 |
| acctcggccg cgtcgttgag cgcgtccggc tcgccgcagc tgcgccggtt tctcgcggac | 960 |
| acctgggcct ggctgggcgg aagtcgcgag tggcacgcca cgagcggccg ctaccactca | 1020 |
| tccaactga | 1029 |

<210> SEQ ID NO 51
<211> LENGTH: 1344
<212> TYPE: DNA
<213> ORGANISM: Artificial Sequence
<220> FEATURE:
<223> OTHER INFORMATION: >ACSP50_5522

<400> SEQUENCE: 51

```
atgacgacca ccgcaccgac tcccgcccac ctcgccggca acttcgcgcc cgtcaccggg      60
gagaccacca cgctcgacct gccggtcacc ggcgccgtcc cggccgaact gaccgggtgg     120
tatctgcgca acgggcccaa ccccaccac gggacctcgg cgcactggtt tctcggcgac      180
ggcatggtgc acggcgtccg cctcgatcac ggccgggcca cctggtaccg caaccgctgg     240
gtgcggaccc gggtgctgac cgacgacgcc cgcgcctacg gcccggacgg cacccgcgac     300
ctcaccgccg gcccggcgaa caccaacgtc gtgcgccacg gcggacgact gctggcgctg     360
gtcgagtccg cgcttccgta cgagatcacc accgacctgg agaccgtcgg ccctacgac      420 ttcggcggcc gcctgcacac cccgatgacc gcccacccca aggtctgtcc caccaccggg     480
gagatgcact tcttcggcta cggcggactc gagccgccct acctcaccta ccaccgcgcc     540
ggcgcggacg gccggctgtc gctcagccgc ccgatcgacg tccccgcgca acgatgatg      600 cacgacttca gcctcaccgc ggcccacgtg atcttcatgg acctgccggt gctgttcagc     660
ctggacgggg cgcggaccgg cggcatgccg taccggtggg acgacaccta ccaggcgcgc     720
ctgggcgtgc tgcggcgcga cgccccgcag ggggaggtcc gctggtacac catcgatccc     780
ggatacgtct tccacaccct gaacgcccac gacgacggcg accggatcgt catgcacgtc     840
gtccgccacg agcacgcgta ccgcccgggg cagcccgccg ccgcaccgga cctctggcgc     900
tggaccatcg accagcgcac cggccgggtc gccgaggaac ggctggacga cgaagcggtc     960
gagttccccc gcatcgacga tcggcgcacc gggcagccgg cccgttacgg cttcgccgtg    1020
accgacaacg ttccccgccg gctcgccgac gtcagcgccg tcatccgcta cgacctgcac    1080
accggctcga ccacccggca ccgcctgccg accgggcagg tacccggga ggcggtcttc     1140 gtgccggccg gcggcgcccc cgccggatcg gccgacggct ggctgctgac gttcgcctac    1200
gacccggggc gcgacgccag cgatctgatc atcatcgacg ccaccgacct cgccgccccg    1260
ccgctggccc ggatccacct gccgcaccgg gtgccgttcg gcttccacgg caactggctg    1320
cccgaccacg accgcgcaga atag                                           1344
```

<210> SEQ ID NO 52
<211> LENGTH: 640
<212> TYPE: PRT
<213> ORGANISM: Artificial Sequence
<220> FEATURE:
<223> OTHER INFORMATION: >Dxs (ACSP50_7096)

<400> SEQUENCE: 52

```
Met Ser Asp Ser Pro Ser Thr Pro Ala Gly Leu Leu Ala Ser Val Thr
1               5                   10                  15

Gly Pro Gly Ala Leu Lys Arg Leu Ser Ala Glu Gln Leu Thr Leu Leu
            20                  25                  30

Ala Ala Glu Ile Arg Asp Phe Leu Val Ala Lys Val Ser Lys Thr Gly
        35                  40                  45

Gly His Leu Gly Pro Asn Leu Gly Val Val Glu Met Thr Leu Ala Met
    50                  55                  60

His Arg Val Phe Asp Ser Pro Arg Asp Lys Ile Leu Phe Asp Thr Gly
65                  70                  75                  80

His Gln Ala Tyr Val His Lys Ile Val Thr Gly Arg Gln Asp Gly Phe
                85                  90                  95

Asp Leu Leu Arg Gln Arg Gly Gly Leu Thr Gly Tyr Pro Ser Gln Ala
            100                 105                 110

Glu Ser Glu His Asp Leu Ile Glu Asn Ser His Ala Ser Thr Ala Leu
```

-continued

```
            115                 120                 125
Ser Tyr Ala Asp Gly Leu Ala Lys Ala Phe Ala Leu Arg Gly Glu Asp
        130                 135                 140
Arg His Val Val Ala Val Val Gly Asp Gly Ala Leu Thr Gly Gly Met
145                 150                 155                 160
Cys Trp Glu Ala Leu Asn Asn Ile Ala Ala Thr Lys Asn Arg Leu Val
                165                 170                 175
Ile Val Val Asn Asp Asn Gly Arg Ser Tyr Ala Pro Thr Ile Gly Gly
                180                 185                 190
Leu Ala Asp His Leu Ser Thr Leu Arg Leu Asn Pro Gly Tyr Glu Lys
                195                 200                 205
Val Leu Asp Leu Val Lys Asp Ala Leu Gly Ser Thr Pro Leu Val Gly
        210                 215                 220
Lys Pro Val Phe Glu Val Leu His Ala Val Lys Arg Gly Ile Lys Asp
225                 230                 235                 240
Ala Val Ser Pro Gln Pro Met Phe Glu Asp Leu Gly Leu Lys Tyr Ile
                245                 250                 255
Gly Pro Val Asp Gly His Asp Gln Gln Ala Met Glu Ser Ala Leu Arg
                260                 265                 270
Arg Ala Lys Gly Phe Asn Ala Pro Val Ile Val His Ala Val Thr Arg
                275                 280                 285
Lys Gly Tyr Gly Tyr Arg Pro Ala Glu Gln Asp Glu Ala Asp Cys Leu
        290                 295                 300
His Gly Pro Gly Ala Phe Asp Pro Gln Thr Gly Ala Leu Thr Ala Lys
305                 310                 315                 320
Pro Ser Leu Lys Trp Thr Lys Val Phe Ala Glu Leu Val Lys Ile
                325                 330                 335
Ala Asp Glu Arg Pro Asp Val Val Gly Ile Thr Ala Ala Met Ala Glu
                340                 345                 350
Pro Thr Gly Ile Ala Ala Leu Ala Lys Lys Tyr Pro Asp Arg Ala Tyr
                355                 360                 365
Asp Val Gly Ile Ala Glu Gln His Ala Ala Thr Ser Ala Ala Gly Leu
        370                 375                 380
Ala Met Gly Gly Leu His Pro Val Val Ala Val Tyr Ala Thr Phe Leu
385                 390                 395                 400
Asn Arg Ala Phe Asp Gln Val Leu Leu Asp Val Ala Met His Arg Leu
                405                 410                 415
Pro Val Thr Phe Val Leu Asp Arg Ala Gly Ile Thr Gly Pro Asp Gly
                420                 425                 430
Pro Ser His Tyr Gly Ile Trp Asp Met Ser Val Phe Gly Ala Val Pro
                435                 440                 445
Gly Leu Arg Ile Ala Ala Pro Arg Asp Ala Ala Thr Leu Arg Glu Glu
        450                 455                 460
Leu Arg Glu Ala Val Ala Val Asp Asp Gly Pro Thr Ile Val Arg Phe
465                 470                 475                 480
Pro Thr Gly Ala Val Ala Ala Asp Thr Pro Ala Val Arg Arg Val Gly
                485                 490                 495
Gln Val Asp Val Leu Arg Glu Ala Glu Lys Lys Asp Ile Leu Leu Val
                500                 505                 510
Ala Val Gly Ser Phe Val Gly Leu Gly Leu Asp Ala Ala Glu Arg Leu
                515                 520                 525
Ala Glu Gln Gly Tyr Gly Val Thr Val Val Asp Pro Arg Trp Val Arg
        530                 535                 540
```

-continued

```
Pro Val Pro Ile Glu Leu Thr Gly Leu Ala Ala Gln His Arg Leu Val
545                 550                 555                 560

Val Thr Leu Glu Asp Gly Ile Arg Ala Gly Val Gly Asp Ala Val
            565                 570                 575

Ala Ala Ala Leu Arg Asp Ala Gly Val His Val Pro Leu Arg Asp Phe
            580                 585                 590

Gly Val Pro Ala Gly Phe His Pro His Gly Thr Arg Ala Glu Ile Leu
            595                 600                 605

Ala Ser Leu Gly Leu Thr Ala Gln Asp Val Ala Arg Asp Val Thr Gly
            610                 615                 620

Trp Val Ser Gly Leu Asp Ala Gly Thr Ser Val Ala Ala Pro Ala Ile
625                 630                 635                 640

<210> SEQ ID NO 53
<211> LENGTH: 390
<212> TYPE: PRT
<213> ORGANISM: Artificial Sequence
<220> FEATURE:
<223> OTHER INFORMATION: >IspG (ACSP50_7248)

<400> SEQUENCE: 53

Met Thr Ala Ile Ser Leu Gly Met Pro Ala Val Pro Pro Pro Leu
1               5                   10                  15

Ala Pro Arg Arg Gln Ser Arg Gln Ile Asn Val Gly Gly Val Leu Val
            20                  25                  30

Gly Gly Gly Ala Pro Val Ser Val Gln Ser Met Thr Thr Thr Leu Thr
            35                  40                  45

Ser Asp Val Asn Ala Thr Leu Gln Gln Ile Ala Glu Leu Thr Ala Ala
50                  55                  60

Gly Cys Gln Ile Val Arg Val Ala Val Pro Ser Gln Asp Asp Val Glu
65                  70                  75                  80

Ala Leu Pro Ala Ile Ala Lys Lys Ser Gln Ile Pro Val Ile Ala Asp
            85                  90                  95

Ile His Phe Gln Pro Lys Tyr Val Phe Ala Ala Ile Asp Ala Gly Cys
            100                 105                 110

Ala Ala Val Arg Val Asn Pro Gly Asn Ile Arg Gln Phe Asp Asp Lys
            115                 120                 125

Val Lys Glu Ile Ala Arg Ala Ala Ser Asp Ala Gly Val Pro Ile Arg
            130                 135                 140

Ile Gly Val Asn Ala Gly Ser Leu Asp Lys Arg Leu Leu Glu Lys Tyr
145                 150                 155                 160

Gly Lys Ala Thr Ala Glu Ala Leu Val Glu Ser Ala Leu Trp Glu Cys
            165                 170                 175

Ser Leu Phe Glu Glu His Gly Phe Arg Asp Ile Lys Ile Ser Val Lys
            180                 185                 190

His Asn Asp Pro Val Val Met Ile Arg Ala Tyr Arg Gln Leu Ala Glu
            195                 200                 205

Gln Cys Asp Tyr Pro Leu His Leu Gly Val Thr Glu Ala Gly Pro Ala
            210                 215                 220

Phe Gln Gly Thr Ile Lys Ser Ala Val Ala Phe Gly Ala Leu Leu Ala
225                 230                 235                 240

Glu Gly Ile Gly Asp Thr Ile Arg Val Ser Leu Ser Ala Pro Pro Val
            245                 250                 255

Glu Glu Ile Lys Val Gly Gln Gln Ile Leu Glu Ser Leu Gly Leu Arg
            260                 265                 270
```

-continued

```
Glu Arg Gly Leu Glu Ile Val Ser Cys Pro Ser Cys Gly Arg Ala Gln
            275                 280                 285

Val Asp Val Tyr Thr Leu Ala Glu Gln Val Thr Ala Ala Leu Asp Gly
        290                 295                 300

Phe Pro Val Pro Leu Arg Val Ala Val Met Gly Cys Val Val Asn Gly
305                 310                 315                 320

Pro Gly Glu Ala Arg Glu Ala Asp Leu Gly Val Ala Ser Gly Asn Gly
                325                 330                 335

Lys Gly Gln Ile Phe Val Lys Gly Lys Val Ile Lys Thr Val Pro Glu
            340                 345                 350

Ala Val Ile Val Glu Thr Leu Val Glu Glu Ala Leu Arg Leu Ala Asp
        355                 360                 365

Glu Met Gly Ala Glu Leu Pro Asp Glu Leu Arg Glu Leu Leu Pro Gly
370                 375                 380

Pro Thr Val Thr Val His
385                 390

<210> SEQ ID NO 54
<211> LENGTH: 399
<212> TYPE: PRT
<213> ORGANISM: Artificial Sequence
<220> FEATURE:
<223> OTHER INFORMATION: >Dxr (ACSP50_7250)

<400> SEQUENCE: 54

Met Arg Glu Leu Val Leu Leu Gly Ser Thr Gly Ser Ile Gly Thr Gln
1               5                   10                  15

Ala Ile Asp Ile Val Arg Arg Asn Pro Glu Leu Phe Arg Val Val Ala
            20                  25                  30

Ile Gly Ala Gly Gly Asn Val Ala Leu Leu Ala Ala Gln Ala Leu
        35                  40                  45

Glu Leu Gly Val Glu Val Val Gly Val Ala Arg Ala Ser Val Val Gln
    50                  55                  60

Asp Leu Gln Leu Ala Phe Tyr Ala Glu Ala Gln Lys Arg Gly Trp Ser
65                  70                  75                  80

Ser Gly Asp Phe Lys Leu Pro Lys Ile Val Ala Gly Pro Asp Ala Met
            85                  90                  95

Thr Glu Leu Ala Arg Trp Pro Cys Asp Val Val Leu Asn Gly Val Val
            100                 105                 110

Gly Ser Leu Gly Leu Ala Pro Thr Leu Ala Ala Leu Glu Ser Gly Arg
        115                 120                 125

Ile Leu Ala Leu Ala Asn Lys Glu Ser Leu Val Ala Gly Gly Pro Leu
    130                 135                 140

Val Arg Arg Ile Ala Lys Asp Gly Gln Ile Val Pro Val Asp Ser Glu
145                 150                 155                 160

His Ser Ala Leu Ala Gln Cys Leu Arg Gly Gly Arg Ala Ala Glu Val
            165                 170                 175

Arg Arg Leu Val Leu Thr Ala Ser Gly Gly Ala Phe Arg Gly Arg Arg
        180                 185                 190

Arg Ala Glu Leu Thr Asn Val Thr Pro Glu Glu Ala Leu Lys His Pro
    195                 200                 205

Thr Trp Asp Met Gly Pro Val Val Thr Ile Asn Ser Ala Thr Met Val
210                 215                 220

Asn Lys Ala Leu Glu Val Ile Glu Ala His Glu Leu Phe Gly Val Pro
225                 230                 235                 240
```

```
Tyr Asp Asp Ile Ala Val Met Val His Pro Gln Ser Val Leu His Ser
                245                 250                 255

Leu Val Glu Phe Thr Asp Gly Ser Thr Leu Ala Gln Ala Ser Pro Pro
            260                 265                 270

Asp Met Arg Leu Pro Ile Ala Leu Ala Leu Ala Trp Pro Asp Arg Val
        275                 280                 285

Pro Gly Ala Ala Ala Val Asp Trp Thr Leu Ala His Asn Trp Glu
    290                 295                 300

Leu Arg Pro Leu Asp Asp Glu Ala Phe Pro Ala Val Glu Leu Ala Lys
305                 310                 315                 320

Ala Ala Gly Arg Tyr Gly Arg Cys Arg Pro Ala Ile Phe Asn Ala Ala
                325                 330                 335

Asn Glu Glu Cys Val Ala Ala Phe Ala Ala Gly Arg Leu Pro Phe Leu
                340                 345                 350

Gly Ile Val Asp Thr Leu Glu Arg Val Leu Ala Ala Pro Asp Phe
                355                 360                 365

Ala Glu Pro Ser Thr Val Asp Asp Val Leu Ala Ala Glu Ser Trp Ala
        370                 375                 380

Arg Ala Gln Ala Gln Arg Thr Ile Ala Thr Val Ala Glu Gly Ala
385                 390                 395

<210> SEQ ID NO 55
<211> LENGTH: 320
<212> TYPE: PRT
<213> ORGANISM: Artificial Sequence
<220> FEATURE:
<223> OTHER INFORMATION: >IspH (ACSP50_7707)

<400> SEQUENCE: 55

Met Leu Leu Ala Lys Pro Arg Gly Tyr Cys Ala Gly Val Asp Arg Ala
1               5                   10                  15

Val Gln Thr Val Glu Glu Ala Leu Lys Leu Tyr Gly Ala Pro Val Tyr
            20                  25                  30

Val Arg Lys Gln Ile Val His Asn Lys His Val Val Ser Thr Leu Glu
        35                  40                  45

Ala Arg Gly Ala Ile Phe Val Glu Glu Asn Tyr Glu Val Pro Glu Gly
    50                  55                  60

Ala Thr Val Val Phe Ser Ala His Gly Val Ala Pro Glu Val His Asp
65                  70                  75                  80

Gln Ala Arg Glu Arg Arg Leu Lys Ala Ile Asp Ala Thr Cys Pro Leu
                85                  90                  95

Val Thr Lys Val His His Glu Ala Lys Arg Phe Ala Ala Glu Asp Tyr
            100                 105                 110

Asp Ile Leu Leu Ile Gly His Glu Gly His Glu Glu Val Ile Gly Thr
        115                 120                 125

Ser Gly Glu Ala Pro Ala His Ile Gln Leu Val Asp Gly Pro Asp Asp
    130                 135                 140

Val Ala Asn Val Val Arg Asp Pro Ala Lys Val Val Trp Leu Ser
145                 150                 155                 160

Gln Thr Thr Leu Ser Val Asp Glu Thr Met Glu Thr Val Ala Arg Leu
                165                 170                 175

Lys Thr Arg Leu Pro Leu Leu Gln Ser Pro Pro Ser Asp Asp Ile Cys
            180                 185                 190

Tyr Ala Thr Ser Asn Arg Gln His Val Ile Lys Glu Ile Ala Pro Glu
        195                 200                 205
```

```
Cys Asp Val Val Ile Val Val Gly Ser Thr Asn Ser Ser Asn Ser Val
            210                 215                 220

Arg Leu Val Glu Val Ala Leu Gly Ala Gly Ala Arg Ala Gly His Leu
225                 230                 235                 240

Val Asp Tyr Ala Ala Glu Ile Gln Asp Glu Trp Leu Ala Gly Ala Thr
                245                 250                 255

Thr Val Gly Val Ser Ser Gly Ala Ser Val Pro Asp Glu Leu Val Met
            260                 265                 270

Glu Val Leu Ala His Leu Ala Glu Arg Gly Phe Gly Glu Val Thr Glu
        275                 280                 285

Phe Thr Thr Ala Glu Glu Arg Leu Thr Phe Ser Leu Pro Gln Glu Leu
    290                 295                 300

Arg Lys Asp Met Lys Ala Ala Glu Ala Ala Arg Ala Ala Ala Ala Gly
305                 310                 315                 320

<210> SEQ ID NO 56
<211> LENGTH: 315
<212> TYPE: PRT
<213> ORGANISM: Artificial Sequence
<220> FEATURE:
<223> OTHER INFORMATION: >IspE (ACSP50_7802)

<400> SEQUENCE: 56

Met Thr Glu Ala Trp Gly Pro Asp Asp Glu Pro Arg Pro Tyr Ser
1               5                   10                  15

Gly Pro Val Lys Val Arg Val Pro Ala Lys Ile Asn Leu His Leu Ala
            20                  25                  30

Val Gly Pro Leu Arg Pro Asp Gly Tyr His Glu Leu Asn Thr Val Tyr
        35                  40                  45

His Ala Ile Ser Leu Phe Asp Glu Ile Thr Ala Arg His Gly Asp Thr
    50                  55                  60

Leu Thr Leu Thr Met Glu Gly Glu Gly Thr Gly Asp Leu Ala Leu Asp
65                  70                  75                  80

Glu Thr Asn Leu Ile Ile Arg Ala Ala Arg Ala Leu Ala Ala Arg Ala
                85                  90                  95

Arg Val Pro Ala Tyr Ala Arg Leu His Leu Arg Lys Ser Ile Pro Leu
            100                 105                 110

Ala Gly Gly Leu Ala Gly Gly Ser Ala Asp Ala Ala Thr Leu Ile
        115                 120                 125

Ala Cys Asp Leu Leu Trp Gly Leu Gly Met Ser Arg Asp Glu Leu Ala
    130                 135                 140

Glu Val Gly Ala Gln Leu Gly Ser Asp Ile Pro Phe Leu Leu His Gly
145                 150                 155                 160

Gly Thr Ala Leu Gly Thr Gly His Gly Glu Ala Val Ser Pro Ile Leu
                165                 170                 175

Ala Arg Pro Thr Thr Trp His Trp Thr Val Ala Ile Ala Asp Gly Gly
            180                 185                 190

Leu Ala Thr Pro Ala Val Tyr Arg Glu Leu Asp Thr Leu Arg Ala Gly
        195                 200                 205

Thr Trp Pro Pro Thr Pro Leu Gly Ser Ala Asp Thr Leu Met Ala Ala
    210                 215                 220

Leu Arg Gln Arg Asn Pro Glu Ile Leu Gly Ala Ala Leu Gly Asn Asp
225                 230                 235                 240

Leu Gln Pro Ala Ala Leu Ala Leu Arg Pro Gln Leu Ala Asp Val Leu
                245                 250                 255
```

-continued

Lys Ala Gly Thr Glu Ala Gly Ala Leu Ala Gly Leu Val Ser Gly Ser
                260                 265                 270

Gly Pro Thr Cys Val Phe Leu Ala Ala Asp Ala Thr His Ala Gln Glu
            275                 280                 285

Ile Ala Asp Ser Leu Thr Glu Ala Gly Val Cys Arg Ala Ala Val Thr
290                 295                 300

Ala Arg Gly Pro Gln Pro Gly Ala Arg Val Ile
305                 310                 315

<210> SEQ ID NO 57
<211> LENGTH: 162
<212> TYPE: PRT
<213> ORGANISM: Artificial Sequence
<220> FEATURE:
<223> OTHER INFORMATION: >IspF (ACSP50_8046)

<400> SEQUENCE: 57

Met Ile Ile Pro Arg Val Gly Ile Gly Thr Asp Val His Ala Phe Asp
1               5                   10                  15

Ala Asp Arg Ala Cys Trp Val Ala Gly Leu Glu Trp Pro Gly Glu Pro
            20                  25                  30

Gly Leu Ala Gly His Ser Asp Ala Asp Val Val Ala His Ala Ala Cys
        35                  40                  45

Asp Ala Leu Leu Ser Ala Ala Gly Leu Gly Asp Leu Gly Gly Asn Phe
    50                  55                  60

Gly Thr Ser Arg Pro Glu Trp Ala Gly Ala Gly Val Thr Leu Leu
65                  70                  75                  80

Ala Glu Thr Ala Arg Leu Val Arg Ala Ala Gly Phe Ala Ile Gly Asn
                85                  90                  95

Val Ser Val Gln Val Ile Gly Asn Arg Pro Lys Ile Gly Lys Arg Arg
            100                 105                 110

Ala Glu Ala Glu Lys Val Leu Ser Ala Ala Val Gly Ala Pro Val Thr
        115                 120                 125

Val Ser Gly Thr Thr Ser Asp Gly Leu Gly Leu Thr Gly Arg Gly Glu
    130                 135                 140

Gly Leu Ala Gly Val Ala Val Ala Met Val Tyr Thr Glu Asn Ala Leu
145                 150                 155                 160

Pro Ala

<210> SEQ ID NO 58
<211> LENGTH: 243
<212> TYPE: PRT
<213> ORGANISM: Artificial Sequence
<220> FEATURE:
<223> OTHER INFORMATION: >IspD (ACSP50_8047)

<400> SEQUENCE: 58

Met Ile Ala Asp Arg Asp Val Thr Ala Gln Leu Asn Ala Arg Gly Asp
1               5                   10                  15

Val Ala Val Val Val Pro Ala Ala Gly Ala Gly Leu Arg Leu Gly Pro
            20                  25                  30

Gly Gly Pro Lys Ala Leu Arg Leu Leu Asp Gly Glu Pro Leu Leu Val
        35                  40                  45

His Ala Val Arg Arg Leu Ala Ala Ala Pro Val Arg Met Ile Val
    50                  55                  60

Val Ala Ala Pro Pro Ala Glu Val Asp Ala Val Ser Ala Leu Leu Ala
65                  70                  75                  80

```
Pro Val Ala Pro Val Thr Val Pro Gly Gly Ala Glu Arg Gln Glu
                85                  90                  95

Ser Val Ala Ala Ala Leu Ala Val Val Pro Pro Asp Val Pro Ile Val
            100                 105                 110

Leu Val His Asp Ala Ala Arg Cys Leu Thr Pro Pro Ser Val Thr Glu
            115                 120                 125

Arg Val Ala Ala Ala Val Arg Asp Gly Ala Asp Ala Val Ile Pro Val
130                 135                 140

Leu Pro Val Val Asp Thr Ile Lys Glu Val Ala Ala Asp Ala Thr Val
145                 150                 155                 160

Leu Gly Thr Val Asp Arg Ser Val Leu Arg Ala Val Gln Thr Pro Gln
                165                 170                 175

Gly Phe Arg Ala Ser Val Leu Arg Ala Ala His Arg Ala Ala Ala Asp
            180                 185                 190

Ser His Thr Asp Asp Ala Gly Ala Val Glu Lys Leu Gly Ile Pro Val
            195                 200                 205

Leu Cys Val Pro Gly Ser Asp Leu Ala Leu Lys Ile Thr Arg Pro Ile
210                 215                 220

Asp Leu Ala Leu Ala Thr His Leu Leu Ala Leu Pro Asp Pro Asp Ala
225                 230                 235                 240

Pro Thr Ala

<210> SEQ ID NO 59
<211> LENGTH: 194
<212> TYPE: PRT
<213> ORGANISM: Artificial Sequence
<220> FEATURE:
<223> OTHER INFORMATION: >Idi (ACSP50_0146)

<400> SEQUENCE: 59

Met Ser Ser Ile Gly His Leu Asn Arg Glu Asp His Leu Val Glu Leu
1               5                   10                  15

Val Asn Glu Glu Gly Gln Pro Leu Gly Ser Ala Thr Val Ser Asp Ala
                20                  25                  30

His Leu Ser Pro Gly Ala Leu His Arg Ala Phe Ser Val Phe Leu Thr
            35                  40                  45

Asp Asp Glu Gly Arg Val Leu Leu Gln Gln Arg Ala Ala Ala Lys Thr
50                  55                  60

Arg Phe Pro Leu Arg Trp Gly Asn Thr Cys Cys Gly His Pro Ala Pro
65                  70                  75                  80

Gly Glu Pro Val Thr Val Ala Ala Ala Arg Leu Thr Glu Glu Leu
                85                  90                  95

Ala Val Arg Asp Val Thr Leu Thr Glu Ile Gly Val Tyr Thr Tyr Arg
            100                 105                 110

Ala Thr Asp Pro Val Thr Gly Arg Val Glu His Glu Tyr Asp His Val
            115                 120                 125

Leu Ile Gly Ala Leu Pro Asp Gly Val Pro His Pro Asp Pro Ala
130                 135                 140

Glu Ile Ala Thr Leu Arg Trp Ala Ser Leu Pro Gly Leu Arg Thr Gly
145                 150                 155                 160

Leu Thr Glu Ser Pro Glu Leu Tyr Ala Pro Trp Leu Pro Gly Val Phe
                165                 170                 175

Glu Ile Leu Thr Glu Arg Ser Gly Val Leu Ser Thr Glu Arg Ser Gly
            180                 185                 190
```

Gly Arg

<210> SEQ ID NO 60
<211> LENGTH: 356
<212> TYPE: PRT
<213> ORGANISM: Artificial Sequence
<220> FEATURE:
<223> OTHER INFORMATION: >CrtE ldsA (ACSP50_0148)

<400> SEQUENCE: 60

Met Ala Asn Asp Thr Leu Glu Gly Asn Arg Leu Ala Ala Ile Pro Arg
1               5                   10                  15

Gln Ser Val Ser His Thr Gly Leu Val Gly Ala Val Glu Gly Thr Leu
            20                  25                  30

Ala Asp Phe Leu Ala Ser Gln Ile Ala Ser Leu Asp Ala Val Asp Pro
        35                  40                  45

Ser Leu Gly Gly Phe Gly Arg Thr Ala Arg Asp Leu Val Met Ala Gly
    50                  55                  60

Gly Lys Arg Leu Arg Pro Thr Phe Ala Tyr Trp Gly Trp Arg Gly Val
65                  70                  75                  80

Ala Gly Pro Ala Ala Asp Ala Glu Thr Leu Leu Pro Ala Leu Gly Ala
                85                  90                  95

Leu Glu Leu Met His Thr Phe Ala Leu Val His Asp Asp Val Met Asp
            100                 105                 110

Asp Ser Thr Arg Arg Gly Arg Pro Thr Ala His Arg Ile Phe Ala
            115                 120                 125

Ala Gln His Gly Gly Arg Phe Gly Thr Ser Ala Ala Ile Leu Val Gly
        130                 135                 140

Asp Leu Cys Leu Val Trp Ala Asp Gln Leu Leu Ala Arg Thr Pro Val
145                 150                 155                 160

Pro Ala Ala Thr Leu Leu Ala Val Arg Ala His Tyr Asp Arg Met Arg
                165                 170                 175

Ile Glu Ala Val Ala Gly Gln Tyr Leu Asp Val Leu Gly Glu Thr Asp
            180                 185                 190

Pro Ala Ser Trp Ser Val Glu Arg Ala Leu Leu Val Ala Arg His Lys
        195                 200                 205

Thr Ala Ser Tyr Thr Val Gln Arg Pro Leu Asp Phe Gly Leu Ala Leu
    210                 215                 220

Ala Gly Val Glu Asp Val Glu Val Ala Glu Ala Tyr Arg Thr Tyr Gly
225                 230                 235                 240

Ile Ala Val Gly Glu Ala Phe Gln Leu Arg Asp Asp Leu Leu Gly Val
                245                 250                 255

Tyr Gly Asp Pro Ala Val Thr Gly Lys Pro Val Ser Asp Asp Leu Arg
            260                 265                 270

Thr Gly Lys Pro Thr Ala Leu Leu Met Leu Ala Arg Arg Met Ala Thr
        275                 280                 285

Pro Gly Gln Leu Ala Glu Leu Glu Ser Ala Glu Ile Glu Arg Lys Ala
    290                 295                 300

Gln Val Val Ala Glu Thr Gly Ala Pro Ala Arg Val Glu Glu Met Ile
305                 310                 315                 320

Arg Ala Arg Val Thr Glu Gly Leu Thr Leu Ala Leu Ala Ser Ala Pro Ile
                325                 330                 335

Asp Ala Glu Ala Arg Ala Thr Leu Ile Glu Leu Ala Thr Val Ala Thr
            340                 345                 350

Gln Arg Pro Ala

```
<210> SEQ ID NO 61
<211> LENGTH: 295
<212> TYPE: PRT
<213> ORGANISM: Artificial Sequence
<220> FEATURE:
<223> OTHER INFORMATION: >CrtB (ACSP50_0149)

<400> SEQUENCE: 61
```

Met Glu Thr Asp Leu Ala Ala Tyr Glu Arg Cys Arg Glu Leu His
1               5                   10                  15

Arg Glu His Gly Arg Thr Tyr Tyr Leu Ala Thr Arg Leu Leu Pro Ala
            20                  25                  30

Trp Lys Arg Arg His Val His Ala Leu Tyr Gly Phe Thr Arg Phe Ala
        35                  40                  45

Asp Glu Ile Val Asp Arg Thr Glu Ala Gln Pro Pro Ala Glu Arg Ala
    50                  55                  60

Ala Glu Leu Ala Thr Trp Ser Ala Gly Phe Leu Ala Gly Leu Arg Gly
65                  70                  75                  80

Glu Pro Val Asp Asp Pro Leu Leu Pro Ala Val Leu His Thr Ile Ala
                85                  90                  95

Val Phe Gly Leu Asp Leu Glu Asp Phe Ala Lys Phe Leu Arg Ser Met
            100                 105                 110

Glu Met Asp Leu Thr Val Thr Gly Tyr Arg Thr Tyr Asp Asp Leu Leu
        115                 120                 125

Asp Tyr Met Glu Gly Ser Ala Ala Val Ile Gly Thr Met Met Leu Pro
    130                 135                 140

Ile Leu Gly Ser Thr Asp Pro Ala Ala Ala Arg Glu Pro Ala Arg Gln
145                 150                 155                 160

Leu Gly Phe Ala Phe Gln Leu Thr Asn Phe Ile Arg Asp Val Ala Glu
                165                 170                 175

Asp Leu Ala Arg Asp Arg Ile Tyr Leu Pro Glu Glu His Leu Ala Glu
            180                 185                 190

Phe Gly Val Thr Arg Ala Asp Leu Ala Ala Gly Val Ala Thr Pro Ala
        195                 200                 205

Ile Arg Ala Leu Ile Arg Ala Glu Val Asp Arg Ala Arg Glu His Tyr
    210                 215                 220

Ala Ala Ala Ala Pro Gly Ile Pro Leu Leu Glu Arg Thr Ser Gln Ala
225                 230                 235                 240

Cys Met Arg Thr Ala Phe Gln Leu Tyr Gly Gly Ile Leu Asp Glu Ile
                245                 250                 255

Glu Ala Ala Asp Tyr Asp Val Phe Ala Arg Arg Val Thr Val Pro Asn
            260                 265                 270

Arg Arg Arg Ala Ala Val Ala Val Arg Ser Leu Leu Thr Arg Pro Gly
        275                 280                 285

Thr Pro Val Glu Leu Ala Ala
    290                 295

```
<210> SEQ ID NO 62
<211> LENGTH: 436
<212> TYPE: PRT
<213> ORGANISM: Artificial Sequence
<220> FEATURE:
<223> OTHER INFORMATION: >ACSP50_0150

<400> SEQUENCE: 62
```

-continued

```
Met Gly Ala Arg Val Ala Leu Phe Thr Arg Asp Leu Arg Ile His Asp
1               5                   10                  15

Asn Pro Leu Leu Ser Gly Pro Asp Pro Val Val Pro Leu Phe Val Leu
            20                  25                  30

Asp Pro Arg Leu Ser Gly Leu Ser Ala Asn Arg Ser Arg Phe Leu His
            35                  40                  45

Gln Ser Leu Ala Asp Leu Arg Asn Ser Leu Arg Glu Arg Gly Ala Asp
        50                  55                  60

Leu Val Ile Arg Glu Gly Asp Pro Val Ala Glu Thr Ile Ala Val Ala
65                  70                  75                  80

Ser Glu Val Asp Ala Ser Thr Ile Thr Val Ala Ala Asp Val Thr Gly
                85                  90                  95

Tyr Ala Gln Arg Arg Glu Arg Arg Leu Arg Asp Glu Arg Phe Arg Val
                    100                 105                 110

Lys Thr Val Pro Ser Val Thr Val Leu Pro Pro Gly Thr Val Arg Pro
            115                 120                 125

Gly Gly Gly Gly Glu Ser Tyr Arg Val Phe Thr Pro Tyr Phe Lys Ala
        130                 135                 140

Trp Glu Lys Ala Gly Trp Arg Ala Pro Ser Ala Thr Pro Gly Lys Val
145                 150                 155                 160

Ala Met Pro Ala Gly Ile Ala Pro Gly Arg Leu Pro Glu Met Pro Ala
                165                 170                 175

Gly Asp Ser Pro Asp Ala Val Ala Gly Gly Glu Thr Glu Gly Arg Arg
                180                 185                 190

Arg Leu Gln Ala Trp Gln Lys Glu Met Ala Arg Tyr Ala Glu Asp His
            195                 200                 205

Asp Asp Met Ala Ala Asp Asn Thr Ser Arg Leu Ser Ala Tyr Leu Arg
        210                 215                 220

Phe Gly Cys Leu Ser Pro Leu Glu Leu Ala Leu Ala Ala Lys Ala Asp
225                 230                 235                 240

Asp Ser Pro Gly Ala Gln Ala Tyr Leu Arg Gln Leu Cys Trp Arg Asp
                245                 250                 255

Phe Tyr Tyr Gln Val Thr Ala Thr Phe Pro Glu Ile Ser Thr Arg Pro
                260                 265                 270

Leu Arg Glu Lys Ala Asp Gln Asn Trp Arg Tyr Asp Asp Asp Ala Leu
            275                 280                 285

Arg His Trp Gln Asp Gly Leu Thr Gly Val Pro Ile Val Asp Ala Gly
        290                 295                 300

Met Arg Gln Leu Arg Ala Glu Gly Trp Met His Asn Arg Ala Arg Leu
305                 310                 315                 320

Ile Thr Ala Ala Phe Leu Thr Lys His Leu Gly Ile Asp Trp Arg Pro
                325                 330                 335

Gly Leu Gln Trp Phe Phe Arg Trp Leu Leu Asp Gly Asp Val Pro Asn
                340                 345                 350

Asn Ser Gly Asn Trp Gln Trp Thr Ala Gly Thr Gly Asn Asp Thr Arg
            355                 360                 365

Pro Tyr Arg Arg Phe Asn Pro Ile Arg Gln Ala Gln Arg Phe Asp Ala
        370                 375                 380

Gln Gly Val Tyr Val Arg Arg Tyr Val Pro Glu Leu Lys Asp Ile Asp
385                 390                 395                 400

Gly Val Thr Val His Gln Pro Trp Arg Leu Pro Glu Ser Val Arg Arg
                405                 410                 415

Gly Leu Asp Tyr Pro Gly Pro Leu Glu Ser His Arg Asp Glu Ala Val
```

Trp Leu Arg Asp
        435

<210> SEQ ID NO 63
<211> LENGTH: 453
<212> TYPE: PRT
<213> ORGANISM: Artificial Sequence
<220> FEATURE:
<223> OTHER INFORMATION: >ACSP50_0151

<400> SEQUENCE: 63

Met Ser Glu Ala Arg Gln Val Asp Val Val Val Gly Leu Gly Val
1               5                   10                  15

Gly Gly Glu Glu Val Ala Gly Arg Leu Ala Ala Gly Leu Ser Val
                20                  25                  30

Ile Gly Val Glu His Arg Leu Val Gly Gly Glu Cys Pro Tyr Trp Gly
            35                  40                  45

Cys Ile Pro Thr Lys Ile Met Val Arg Ala Gly Asn Ala Leu Ala Glu
        50                  55                  60

Ala Arg Arg Ile Pro Gly Leu Ala Gly Thr Ser Thr Val Arg Ala Asp
65                  70                  75                  80

Trp Ala Pro Val Ala Lys Arg Ile Arg Asp Glu Ala Thr Asp Asp Trp
                85                  90                  95

Asn Asp Lys Val Ala Val Glu Arg Phe Thr Gly Lys Gly Gly Thr Phe
            100                 105                 110

Val Arg Gly Thr Ala Glu Leu Thr Gly Pro Gly Gln Val Arg Val Gly
        115                 120                 125

Asp Gln Glu Phe Ala Ala Ser Arg Gly Val Val Ile Ala Thr Gly Thr
    130                 135                 140

Ala Ala Val Val Pro Pro Ile Glu Gly Leu Ser Gly Thr Pro Phe Trp
145                 150                 155                 160

Thr Asn Arg Glu Ala Val Glu Ala Ala Ala Leu Pro Ala Ser Met Leu
                165                 170                 175

Val Leu Gly Gly Gly Ala Ile Gly Cys Glu Leu Ala Gln Ala Tyr Ala
            180                 185                 190

Arg Phe Gly Val Gln Val Thr Val Ile Glu Gly Ser Pro Arg Val Leu
        195                 200                 205

Ala Met Glu Glu Pro Glu Ser Ser Glu Val Ala Ala Ala Leu Thr
    210                 215                 220

Ala Asp Gly Val Arg Ile Val Thr Gly Val Arg Ala Gln Lys Val Ala
225                 230                 235                 240

His Asp Asp Gly Phe His Val Thr Leu Ser Asp Gly Ser Val Leu Ala
                245                 250                 255

Gly Glu Lys Leu Leu Val Ala Thr Gly Arg Ala Ala Arg Leu Gly Gly
            260                 265                 270

Leu Gly Leu Asp Arg Val Gly Leu Asp Pro Ser Ala Arg Phe Leu Ala
        275                 280                 285

Thr Asp Asp Arg Leu Arg Ala Gly Glu Gly Ile Trp Ala Val Gly Asp
    290                 295                 300

Val Thr Gly Asn Gly Ala Phe Thr His Met Ala Met Tyr Glu Ala Asp
305                 310                 315                 320

Ile Ala Val Arg Asp Ile Leu Gly Gln Gly Gly Pro Gly Ala Asp Tyr
                325                 330                 335

Arg Ala Arg Pro Arg Val Thr Phe Leu Asp Pro Glu Ile Gly Ala Val

```
                    340                 345                 350
Gly Met Thr Glu Gln Gln Ala Arg Asp Ala Gly Leu Glu Val Arg Val
            355                 360                 365
Gly Tyr Val Pro Leu Asn Gln Thr Ser Arg Gly Phe Ile His Gly Pro
        370                 375                 380
Gly Asn Glu Gly Phe Leu Lys Leu Val Ala Asp Gly Glu Arg Gly Val
385                 390                 395                 400
Leu Val Gly Gly Thr Thr Ala Gly Gln Ser Gly Gly Glu Met Ile Gly
                405                 410                 415
Ala Val Ala Val Ala Val His Ala Glu Val Pro Val Ser Thr Leu Leu
            420                 425                 430
Ser Gln Ile Trp Ala Tyr Pro Thr Phe His Arg Gly Leu Gly Gln Ala
        435                 440                 445
Leu Gln Ser Leu Ala
    450

<210> SEQ ID NO 64
<211> LENGTH: 116
<212> TYPE: PRT
<213> ORGANISM: Artificial Sequence
<220> FEATURE:
<223> OTHER INFORMATION: >ACSP50_1631

<400> SEQUENCE: 64

Met Ser Glu Pro Val Ile Thr Glu Pro Ala Ala Trp Ile Asn Leu Pro
1               5                   10                  15
Asp Leu Ser Glu Arg Leu Asp Val Ser Ile Ser Lys Val His Gln Met
            20                  25                  30
Ile Arg Asp Gly Asp Leu Leu Ala Val Arg Arg Asp Gly Ile Arg Val
        35                  40                  45
Val Pro Ala Glu Leu Val Ala Asn Ala Thr Val Leu Lys His Leu Pro
    50                  55                  60
Gly Val Leu Asn Val Leu Arg Asp Ala Gly Tyr Asn Asp Glu Glu Ala
65                  70                  75                  80
Phe Arg Trp Leu Tyr Ala Glu Asp Ala Glu Val Gly Gly Ser Ala Ala
                85                  90                  95
Ile Ala Leu Gly Gly Gln Gln Ala Arg Glu Ile Lys Arg Arg Ala Gln
            100                 105                 110
Ala Leu Gly Phe
    115

<210> SEQ ID NO 65
<211> LENGTH: 108
<212> TYPE: PRT
<213> ORGANISM: Artificial Sequence
<220> FEATURE:
<223> OTHER INFORMATION: >ACSP50_1632

<400> SEQUENCE: 65

Met Arg His Leu Ser Tyr Val Ala Val Leu Ala Gly Cys Leu Ala Gly
1               5                   10                  15
Ala Leu Trp Leu Glu Pro Ile Leu Arg Val Asn Val Leu Arg Arg Trp
            20                  25                  30
Arg Arg Leu Leu Leu Ala Val Leu Pro Met Ala Val Val Phe Thr Leu
        35                  40                  45
Trp Asp Leu Ala Ala Ile Ala Ala Gly His Trp His Phe Asp Pro Ala
    50                  55                  60
```

Gln Ile Thr Gly Val Tyr Leu Gly Gly Leu Pro Leu Asp Glu Val
65                  70                  75                  80

Leu Phe Phe Leu Val Val Pro Val Cys Ala Ile Leu Gly Phe Glu Ala
                85                  90                  95

Val Arg Ala Val Leu Arg Arg Pro Ala Gly Asp Glu
            100                 105

<210> SEQ ID NO 66
<211> LENGTH: 111
<212> TYPE: PRT
<213> ORGANISM: Artificial Sequence
<220> FEATURE:
<223> OTHER INFORMATION: >ACSP50_1633

<400> SEQUENCE: 66

Met Thr Tyr Thr Thr Ala Ala Val Leu Gly Val Leu Ala Ala Leu Thr
1               5                   10                  15

Leu Asp Val Leu Ile Leu Arg Thr Arg Leu Val Gly Arg Leu Val Phe
                20                  25                  30

Trp Ala Thr Tyr Pro Ile Ile Phe Val Phe Gln Leu Ile Ser Asn Gly
            35                  40                  45

Ile Leu Thr Gly Arg Asp Ile Val Met Tyr Asp Pro Ala Ala Ile Leu
50                  55                  60

Gly Pro Arg Leu Val His Ala Pro Val Glu Asp Leu Leu Phe Gly Phe
65                  70                  75                  80

Ala Leu Val Leu Gly Thr Leu Ser Leu Trp Val Ala Leu Gly Arg Arg
                85                  90                  95

Gly Ile Gln Arg Thr Pro Arg Ala Gly Ser Arg Arg Thr Asp Glu
            100                 105                 110

<210> SEQ ID NO 67
<211> LENGTH: 356
<212> TYPE: PRT
<213> ORGANISM: Artificial Sequence
<220> FEATURE:
<223> OTHER INFORMATION: >CrtE fps2(ACSP50_1634)

<400> SEQUENCE: 67

Met Thr Asn Ser Pro Leu Asp Glu Ala Gly Leu Arg Ser Arg Val Asp
1               5                   10                  15

Lys Ala Leu Thr Val Phe Leu Ala Gly Gln Arg Asp Arg Leu Leu Ala
                20                  25                  30

Ile Asp Pro Ala Leu Ala Glu Met Ser Ala Thr Val Ser Glu Phe Val
            35                  40                  45

Leu Gly Gly Gly Lys Arg Leu Arg Pro Ala Phe Ala Tyr Trp Gly Phe
50                  55                  60

Arg Gly Ala Gly Gly Ala Asp Ser Asp Ala Val Ala Ala Val Ala
65                  70                  75                  80

Ala Leu Glu Leu Val Gln Ala Ser Ala Leu Ile His Asp Asp Leu Met
                85                  90                  95

Asp Arg Ser Asp Thr Arg Arg Gly Val Pro Ser Val His Arg Arg Phe
            100                 105                 110

Glu Lys Leu His Ala Gly Glu Gly Trp Arg Gly Ser Ala Ala Gly Phe
            115                 120                 125

Gly Asp Cys Ala Ala Val Leu Leu Gly Asp Leu Ala Leu Val Trp Ser
        130                 135                 140

Asp Glu Leu Leu His Thr Ser Gly Met Ala Val Ala Asp Val Gln Arg
145                 150                 155                 160

```
Ala Arg Pro Ile Phe Asp Gly Met Arg Thr Glu Val Thr Val Gly Gln
            165                 170                 175

Tyr Leu Asp Val Leu Thr Gln Ala Thr Gly Asp Thr Ser Leu Glu Arg
        180                 185                 190

Ala Gly Lys Val Ala Val Tyr Lys Ala Ala Lys Tyr Thr Val Glu Arg
            195                 200                 205

Pro Leu Leu Gly Ala Ala Leu Ala Gly Ala Pro Gly Val His
210                 215                 220

Ala Ala Tyr Ser Ala Phe Gly Leu Pro Leu Gly Glu Ala Phe Gln Leu
225                 230                 235                 240

Arg Asp Asp Val Leu Gly Val Phe Gly Asp Pro Glu Arg Thr Gly Lys
                245                 250                 255

Pro Ala Gly Asp Asp Leu Arg Glu Gly Lys Arg Thr Tyr Leu Val Ala
                260                 265                 270

Ala Phe Gly Ala Leu Asp Ala Ala Gly Arg Ala Glu Leu Asp Ala
            275                 280                 285

Ala Leu Gly Asp Pro Gly Leu Asp Glu Ala Gly Val Ala Arg Leu Arg
        290                 295                 300

Thr Val Ile Arg Asp Ser Gly Ala Leu Ala Ala Thr Glu Ala Arg Ile
305                 310                 315                 320

Asp Glu Leu Met Thr Ala Ser Ile Gly Ala Leu Asp Ala Ala Pro Ile
                325                 330                 335

Asp Gln Asp Ala Arg Glu Val Leu Arg Arg Leu Ala Asp Ala Ala Thr
                340                 345                 350

Arg Arg Ser Val
        355

<210> SEQ ID NO 68
<211> LENGTH: 307
<212> TYPE: PRT
<213> ORGANISM: Artificial Sequence
<220> FEATURE:
<223> OTHER INFORMATION: >ACSP50_1635

<400> SEQUENCE: 68

Met Ser Leu Gly Leu Pro Ser Arg Leu Pro Gly Thr Pro Ser Ile Gly
1               5                   10                  15

Asp Leu Val Arg Gly Ala Ala Pro Thr Phe Ser Phe Glu Phe Phe Pro
            20                  25                  30

Pro Lys Thr Pro Asp Gly Glu Arg Leu Leu Trp Gln Ala Ile Arg Glu
        35                  40                  45

Leu Glu Ser Leu Arg Pro Ser Phe Val Ser Ile Thr Tyr Gly Ala Gly
50                  55                  60

Gly Thr Thr Arg Glu Thr Thr Val Ala Val Thr Glu Arg Val Ala Thr
65                  70                  75                  80

Glu Thr Thr Leu Leu Pro Leu Ala His Leu Thr Ala Val Asp His Ser
                85                  90                  95

Val Ala Asp Leu Arg Asn Val Ile Gly Arg Leu Ala Gly Ala Gly Ile
            100                 105                 110

Arg Asn Val Leu Ala Leu Arg Gly Asp Pro Gly Asp Pro Met Gly
        115                 120                 125

Glu Trp Val Arg His Pro Asp Gly Val Gly Tyr Ala Asp Glu Leu Val
    130                 135                 140

Arg Leu Ile Arg Glu Ser Gly Asp Phe Ser Val Gly Val Ala Ala Phe
145                 150                 155                 160
```

```
Pro His Lys His Pro Arg Ser Ala Gly Val Lys Asp Asp Thr Arg Asn
            165                 170                 175

Phe Val Arg Lys Cys Arg Ala Gly Ala Asp Tyr Ala Ile Thr Gln Met
        180                 185                 190

Phe Phe Asp Ala Asp Glu Tyr Leu Arg Leu Arg Asp Arg Val Val Ala
        195                 200                 205

Ala Gly Cys His Thr Pro Ile Val Ala Gly Val Met Pro Val Thr Arg
        210                 215                 220

Met Ala Thr Ile Ala Arg Ser Thr Gln Leu Ser Gly Ala Pro Phe Pro
225                 230                 235                 240

Pro Ala Leu Leu Arg Asp Phe Glu Arg Val Ala Gly Asp Ala Ala
                245                 250                 255

Val Arg Glu Leu Gly Ile Glu Thr Cys Ala Ala Met Cys Ala Arg Leu
                260                 265                 270

Leu Arg Glu Gly Val Pro Gly Ile His Phe Ile Thr Met Asn Arg Ser
            275                 280                 285

Thr Ala Thr Arg Glu Val Trp Gln Arg Leu Ala Pro Ala Glu Val Ala
        290                 295                 300

Ala Ser Ala
305

<210> SEQ ID NO 69
<211> LENGTH: 310
<212> TYPE: PRT
<213> ORGANISM: Artificial Sequence
<220> FEATURE:
<223> OTHER INFORMATION: >ACSP50_1650

<400> SEQUENCE: 69

Met Gln Leu Gln Gln Leu Arg Tyr Phe Leu Ala Val Val Glu Thr Arg
1               5                   10                  15

His Phe Thr Gln Ala Ala Asp Ile Leu Gly Val Ser Gln Pro Thr Leu
            20                  25                  30

Ser Lys Gln Ile His Thr Leu Glu Met Ser Leu Gly Ala Pro Leu Phe
        35                  40                  45

Glu Arg Met Arg Gly Ala Val Thr Leu Thr Val Ala Gly Glu Thr Leu
    50                  55                  60

Leu Pro Met Ala Gln Arg Ile Val Ala Asp Ala Asp Ala Ala Arg Asp
65                  70                  75                  80

Ala Val Gln Asp Ile Val Gly Leu Arg Arg Gly Glu Val Arg Leu Gly
                85                  90                  95

Ala Thr Pro Ser Leu Cys Ser Ser Leu Val Pro Ala Val Leu Arg Thr
            100                 105                 110

Phe Arg Ala Asp His Pro Gly Val Lys Leu His Ile Ser Glu Gly Ser
        115                 120                 125

Ser His Asp Leu Thr Ala Gly Leu Leu Ala His Thr Leu Asp Leu Ala
    130                 135                 140

Leu Ile Val Gln Pro Glu His Gly Val Asp Pro Ala Leu Val Ala Ile
145                 150                 155                 160

Glu Leu Leu Arg Glu Ser Leu Val Val Ala Ser Val Ala Ala Gly Pro
                165                 170                 175

Pro Pro Thr Val Gly Arg Gln Leu Glu Leu Ser Glu Leu Arg His Thr
            180                 185                 190

Pro Met Val Met Phe Arg Glu Gly Tyr Asp Ile Arg Glu Val Thr Leu
        195                 200                 205
```

His Ala Cys Glu Arg Ala Gly Phe Ala Pro Lys Phe Ala Val Glu Gly
        210                 215                 220

Gly Glu Met Asp Ala Val Leu Ala Phe Val Glu Ala Gly Leu Gly Val
225                 230                 235                 240

Ala Leu Val Pro Ser Met Val Leu Ala Asn Arg Pro Leu Leu Arg Ala
                245                 250                 255

Thr Pro Leu Ala Pro Pro Gly Met Arg Arg Thr Ile Ala Leu Ala Gln
            260                 265                 270

Arg Arg Ala Ala Val Leu Pro His Ala Ala Ala Leu Arg Glu Val
        275                 280                 285

Val Leu Asp His Ile Gly Ser Gly Arg Leu Pro Phe Gly Val Arg Ala
    290                 295                 300

Leu Glu Arg Pro Ser Thr
305                 310

<210> SEQ ID NO 70
<211> LENGTH: 249
<212> TYPE: PRT
<213> ORGANISM: Artificial Sequence
<220> FEATURE:
<223> OTHER INFORMATION: >ACSP50_1651

<400> SEQUENCE: 70

Met Gly Glu Phe His Asp Pro Arg Leu Val Glu Val Tyr Asp Ala Glu
1               5                   10                  15

Cys Pro Trp Gly Trp Asp Asp Phe Phe Met Ala Val Leu Ala Glu
                20                  25                  30

Arg Ser Ala His Arg Val Ala Asp Leu Gly Cys Gly Thr Gly Arg Leu
        35                  40                  45

Ala Ile Ala Met Ala Ala Gly His Glu Val Ile Ala Ile Asp Pro
    50                  55                  60

Ala Pro Ala Ala Leu Ala Ala Arg Arg Lys Pro Gly Gly Thr Arg
65                  70                  75                  80

Val Arg Trp Leu Gln Gly Ser Ala Glu Arg Leu Ala Pro Arg Ser Leu
                85                  90                  95

Asp Ala Ala Phe Met Thr Gly His Val Ala Gln Ser Phe Val Asp Asp
            100                 105                 110

Glu Glu Trp Asp Thr Val Leu Arg Gly Leu Arg Arg Ala Leu Val Pro
        115                 120                 125

Glu Gly Arg Leu Val Phe Asp Ser Arg Asp Pro Asp Asp Arg Pro Trp
    130                 135                 140

Gln Gln Trp Asn Pro Gln Asp Ser Trp Arg Thr Val Val Leu Asp Asp
145                 150                 155                 160

Gly Arg Val Val Glu Ala Trp Ser Glu Ala Glu Gln Val Gly Leu Asn
                165                 170                 175

Thr Val Arg Val Thr Gly Arg Tyr Arg Phe Ala Asp Gly Gly Glu Leu
            180                 185                 190

Ala Asn Ser Ala Thr Leu Arg Phe Arg Thr Glu Pro Glu Leu Arg Asp
        195                 200                 205

Ser Leu Arg Glu Ala Gly Phe Arg Val Glu Arg Ile Tyr Gly Gly Trp
    210                 215                 220

Gly Arg Glu Pro Val Gly Leu Ser Gly Asp Gly Glu Phe Ile Val Ile
225                 230                 235                 240

Ala Val Ala Thr Pro Arg Leu Met Ser
                245

<210> SEQ ID NO 71
<211> LENGTH: 573
<212> TYPE: PRT
<213> ORGANISM: Artificial Sequence
<220> FEATURE:
<223> OTHER INFORMATION: >ACSP50_1652

<400> SEQUENCE: 71

```
Met Pro Glu Asn Glu Trp Pro Asp Asp Pro Arg Pro Asp Gln Gly
1               5                   10                  15

Glu Trp Ser Gln Pro His His Glu Pro Pro Gly Arg Gly Arg Ala
                20                  25                  30

Leu Leu Ala Ala Val Val Val Leu Val Leu Leu Ala Ala Gly Gly
            35                  40                  45

Ile Ala Trp Arg Leu Met Ser Ser Arg Gly Ala Thr Pro Val Ala Gln
    50                  55                  60

Pro Thr Ala Pro Ala Pro Thr Pro Thr Ala Gln Thr Ala Pro Pro Cys
65                  70                  75                  80

Pro Gln Pro Arg Leu Arg Val Ala Ala Ala Pro Glu Ile Ala Pro Val
                85                  90                  95

Ile Gln Gln Ala Ala Ala Ala Leu Ser Gln Pro Gly Gln Arg Cys Ser
                100                 105                 110

Glu Val Leu Val Gln Ala Ala Glu Pro Gly Ala Ala Leu Thr Gly Lys
                115                 120                 125

Pro Asp Val Trp Val Pro Ser Ser Ser Val Trp Leu Ala Leu Ala Lys
            130                 135                 140

Ser Arg Gly Asp Val Tyr Thr Thr Gln Gly Ala Ser Leu Ala Trp Ser
145                 150                 155                 160

Pro Leu Val Ile Ala Gly Pro Glu Ser Ile Ala Ser Leu Phe Ala Pro
                165                 170                 175

Asn Gly Val Thr Ser Trp Ser Gly Leu Val Gln Gly Thr Ile Gln Lys
                180                 185                 190

Arg Val Pro Ala Val Arg Met Pro Asp Pro Thr Leu Thr Thr Thr Gly
            195                 200                 205

Leu Leu Ser Val Tyr Ala Val Gly Gln Ala Thr Val Lys Ala Asn Pro
    210                 215                 220

Asp Ala Gly Ile Ala Gln Leu Gln Ala Leu Thr Leu Arg Ser Arg Leu
225                 230                 235                 240

Glu Asn Ala Ala Ala Asp Pro Ala Glu Leu Phe Ala Gln Met Gly Lys
                245                 250                 255

Gln Thr Asp Ala Ala Thr Ala Ile Tyr Gln Val Gly Val Phe Pro Thr
                260                 265                 270

Thr Glu Gln Gln Leu Leu Thr Tyr Gln Lys Ser Gln His Asp Val Arg
            275                 280                 285

Leu Ser Gly Ser Ala Pro Ala Asp Gly Gln Ile Asp Ala Asp Tyr Pro
    290                 295                 300

Tyr Ala Val Arg Lys Gly Ala Pro Ala Asp Leu Val Glu Ser Leu Arg
305                 310                 315                 320

Glu Ala Ile Thr Pro Asp Ala Leu Thr Thr Ala Gly Phe Arg Ala Thr
                325                 330                 335

Ala Thr Lys Asn Ala Leu Arg Leu Pro Ala Pro Ala Val Leu Ala Gly
                340                 345                 350

Ala Ala Arg Gln Trp Ser Ala Tyr Lys Ser Val Ala Phe Gln Val Leu
            355                 360                 365
```

-continued

```
Leu Leu Ile Asp Ala Ser Gly Ser Met Asn Glu Lys Ile Thr Asp Arg
        370                 375                 380

Ala Gly Arg Ser Val Thr Lys Ala Ala Leu Leu Arg Glu Ser Gly Thr
385                 390                 395                 400

Ser Ala Ala Gln Leu Phe Gly Asp Asp Thr Ser Leu Gly Leu Trp Phe
                405                 410                 415

Phe Gly Thr Pro Thr Ala Asp Ser Pro Ala His Thr Glu Glu Val Pro
            420                 425                 430

Phe Gly Pro Val Ile Ala Thr Val Asp Gly Lys Ser Arg Arg Asp Leu
        435                 440                 445

Leu Ala Ala Lys Ile Gly Glu Tyr Arg Pro Val Ala Asn Ala Gly Thr
450                 455                 460

Pro Leu Tyr Gln Ser Val Leu Asp Gly Val Ala Glu Met Arg Gly Arg
465                 470                 475                 480

Ala Lys Pro Asp Thr Ala Thr Val Val Val Leu Thr Asp Gly Ser
                485                 490                 495

Asp Gly Gly Thr Lys Tyr Arg Met Ser Asn Ala Asp Phe Leu Lys Lys
                500                 505                 510

Leu Thr Ala Gly Ala Asp Pro Ala Lys Pro Val Pro Val Ile Ala Val
        515                 520                 525

Gly Tyr Gly Pro Ala Ala Asn Ala Thr Ala Leu Gln Ala Met Ala Lys
530                 535                 540

Ala Thr Gly Gly Gln Ala Val Thr Val Lys Asn Pro Ala Asp Leu Ala
545                 550                 555                 560

Ala Gly Ile Ala Gln Ala Phe Leu Ala Ala His Thr His
                565                 570

<210> SEQ ID NO 72
<211> LENGTH: 478
<212> TYPE: PRT
<213> ORGANISM: Artificial Sequence
<220> FEATURE:
<223> OTHER INFORMATION: >CrtD (ACSP50_1653)

<400> SEQUENCE: 72

Met Ser Asp Ile Val Val Gly Ala Gly Val Gly Gly Leu Ala Ala
1               5                   10                  15

Ala Ile Arg Leu Ala Glu Ala Gly His Arg Val Ser Ile His Glu Arg
                20                  25                  30

Ser Gly Val Val Gly Gly Lys Leu Ala Ala Tyr Glu Arg Asp Gly Tyr
            35                  40                  45

Arg Phe Asp Thr Gly Pro Ser Leu Leu Thr Leu Pro Asp Val Phe Thr
        50                  55                  60

Gly Leu Gly Leu Asp Leu Arg Pro Glu Pro Leu Asp Pro Val Val Arg
65                  70                  75                  80

His Phe Phe Pro Asp Gly Thr Val Leu Asp Ser Ser Asp His Glu
                85                  90                  95

Thr Phe Leu Ala Arg Ile Thr Asp Ala Leu Gly Gly Ala Ala Ala Arg
                100                 105                 110

Asp Trp Asp Arg Phe Trp Arg Ala Glu Arg Ile Trp His Ala Ser
            115                 120                 125

Trp Glu Ser Val Leu Arg Pro Val Thr Ala Ala Ser Leu Ala Arg
        130                 135                 140

Leu Ser Trp Arg Leu Gly Asp Leu Ala Ala Ile Ala Pro Gly Arg Ser
145                 150                 155                 160
```

Leu Arg Ser Leu Gly Arg Arg Tyr Leu Arg Asp Pro Arg Leu Arg Met
            165                 170                 175

Leu Leu Asp Arg Tyr Ala Thr Tyr Ser Gly Ala Asp Pro Arg Arg Ala
        180                 185                 190

Pro Ala Ala Leu Ala Ala Ile Pro Tyr Ala Glu Leu Ala Phe Gly Gly
            195                 200                 205

Trp Tyr Leu Pro Gly Gly Leu Val Thr Leu Ala Glu Ala Leu Leu Ala
        210                 215                 220

Arg Cys Glu Lys Leu Gly Val Arg Val His Leu His Ser Pro Val Ala
225                 230                 235                 240

Ser Ile Ala Thr Thr Gly Ala Arg Val Ser Gly Val Arg Leu Gly Asp
            245                 250                 255

Gly Thr Arg Leu Ala Ala Asp Val Val Val Ser Asn Val Asp Ala Val
        260                 265                 270

Thr Leu Tyr Arg Asp Leu Leu Pro Ser Pro Lys Pro Leu Ala Arg Leu
    275                 280                 285

Ala Asp Arg Ser Leu Ala Gly Phe Val Leu Leu Ala Val Arg Gly
        290                 295                 300

Glu Thr Pro Arg Leu Ala His His Asn Val Phe Phe Pro Arg Asp Tyr
305                 310                 315                 320

Asp Ala Glu Phe Asp Ala Val Phe Gly Gly Pro Gly Arg Arg Ala Arg
                325                 330                 335

Pro Ala Gly Asp Pro Thr Val Phe Val Thr Arg Ala Ala Asp Pro Ala
            340                 345                 350

Val Arg Pro Ala Gly Asp Glu Ala Trp Phe Val Leu Val Asn Ala Ala
        355                 360                 365

Pro His Gly Thr Ser Trp Ser Thr Val Asp Trp Leu Arg Ala Gly Leu
    370                 375                 380

Ala Asp Ala Tyr Arg Asp Arg Val Leu Glu Val Leu Ala Gly Arg Gly
385                 390                 395                 400

Leu Asp Val Arg Asp Arg Leu Ile Phe Ala Glu Thr Arg Thr Pro Ala
                405                 410                 415

Asp Leu Ala Ala Ser Ala Ala Pro Gly Gly Ala Ile Tyr Gly Thr
            420                 425                 430

Ala Gly Gly Leu Val Arg Pro Ala Asn Arg Ala Pro Val Asp Gly Leu
        435                 440                 445

Phe Leu Val Gly Gly Ser Thr His Pro Gly Gly Leu Pro Met Val
    450                 455                 460

Thr Leu Ser Ala Glu Ile Val Ala Gly Met Ile Gly Ser Asn
465                 470                 475

<210> SEQ ID NO 73
<211> LENGTH: 359
<212> TYPE: PRT
<213> ORGANISM: Artificial Sequence
<220> FEATURE:
<223> OTHER INFORMATION: >CruC (ACSP50_1654)

<400> SEQUENCE: 73

Met Ile Val Ala Trp Leu Ile Leu Pro Pro Leu Leu Leu Ile Thr Ala
1               5                   10                  15

His Thr Ala Val Asn Ala Leu Leu Leu Arg Arg Pro Arg Arg Ala Ala
            20                  25                  30

Thr Ser Thr Glu Arg Val Ala Val Leu Leu Pro Leu Arg Asp Glu Ala
        35                  40                  45

```
Thr Arg Val Thr Pro Cys Leu Arg Ala Leu Leu Ala Gln Arg Gly Val
     50                  55                  60

Ala Asp Leu Thr Val His Val Leu Asp Asp Gly Ser Thr Asp Gly Thr
 65                  70                  75                  80

Ala Asp Val Val Arg Ala Val Ala Gly Asp Arg Val Arg Leu His Thr
                 85                  90                  95

Gly Thr Pro Pro Pro Gly Trp Leu Gly Lys Pro Ala Ala Cys Gln
                100                 105                 110

Arg Leu Ala Asp Leu Ala Gly Asp Val Asp Val Leu Phe Val Asp
            115                 120                 125

Ala Asp Val Val Leu Ala Pro Asp Ala Val Ala Gly Ala Val Asp Leu
    130                 135                 140

Leu Arg Arg Ala Gly Ala Asp Leu Leu Ser Pro Tyr Pro Lys Ile Val
145                 150                 155                 160

Gly Ala Gly Arg Leu Val Gln Pro Leu Leu Gln Trp Ser Trp Leu Ser
                165                 170                 175

Phe Leu Pro Leu Arg Ala Met Glu Arg Ser Ala Arg Pro Ser Leu Ala
            180                 185                 190

Ala Ala Gly Gly Gln Trp Leu Val Leu Asp Arg Ala Gly Tyr Arg Arg
    195                 200                 205

Ala Gly Gly His Ala Ala Val Arg Gly Glu Ile Leu Glu Asp Ile Ala
210                 215                 220

Leu Ala Arg Ala Val Lys Arg Ala Gly Gly Arg Ile Ala Leu Ala Asp
225                 230                 235                 240

Gly Ser Gly Leu Ala Thr Cys Arg Met Tyr Glu Ser Trp Asp Glu Leu
                245                 250                 255

Ala Asp Gly Tyr Ala Lys Ser Leu Trp Ala Ser Leu Gly Ser Ala Ala
            260                 265                 270

Gly Ala Thr Ala Val Thr Leu Leu Ile Leu Leu Tyr Val Val Pro
    275                 280                 285

Pro Leu Leu Ala Pro Phe Ala Pro Leu Pro Ala Val Leu Gly Tyr Leu
290                 295                 300

Leu Gly Val Thr Gly Arg Met Ile Ala Ala Arg Ala Thr Gly Gly Arg
305                 310                 315                 320

Val Leu Pro Gly Thr Leu Ala His Pro Val Ser Ile Val Leu Phe Gly
                325                 330                 335

Tyr Leu Ile Ala Arg Ser Phe Arg Leu Arg Arg Ala Gly Arg Leu Ala
            340                 345                 350

Trp Arg Gly Arg Pro Val Pro
        355

<210> SEQ ID NO 74
<211> LENGTH: 251
<212> TYPE: PRT
<213> ORGANISM: Artificial Sequence
<220> FEATURE:
<223> OTHER INFORMATION: >CruF (ACSP50_1655)

<400> SEQUENCE: 74

Met Ser Pro Arg His Leu Pro Trp Gly Leu Leu Gly Ala Leu Val Leu
 1               5                  10                  15

Ala Gln Ile Cys Tyr Pro Leu Thr Glu Gly Asp Thr Arg Ala Gly Leu
                 20                  25                  30

Thr Val Leu Thr Val Leu Leu Gly Val Ala Phe Ser Leu Ser His Ala
             35                  40                  45
```

```
Leu Leu Thr Arg Gly Pro Arg Ala Leu Thr Ala Leu Leu Ser Thr Ala
    50                  55                  60

Thr Leu Gly Gly Phe Ala Val Glu Ala Ile Gly Val Ala Thr Gly Phe
 65                  70                  75                  80

Pro Phe Gly Ser Tyr Glu Tyr Ser Gly Arg Leu Gly Pro Arg Leu Leu
                 85                  90                  95

Gly Val Pro Leu Ile Ile Pro Leu Ala Trp Thr Trp Met Ala Trp Pro
             100                 105                 110

Ala Trp Leu Ala Ala Leu Arg Val Thr Arg Arg Leu Pro Arg Ile
         115                 120                 125

Leu Val Ala Gly Ala Gly Leu Ala Ala Trp Asp Val Phe Leu Asp Pro
    130                 135                 140

Gln Met Val Ala Glu Asp Tyr Trp Arg Trp Arg His Pro Val Pro Ala
145                 150                 155                 160

Leu Pro Gly Val Pro Gly Val Pro Leu Gly Asn Tyr Leu Gly Trp Leu
                165                 170                 175

Gly Phe Ala Leu Leu Met Thr Ala Leu Ala Ala Val Ala Gly Arg
             180                 185                 190

Ala Ala Asp Arg Pro Leu Ser Ala Asp Arg Pro Ala Leu Ala Leu Trp
        195                 200                 205

Ile Trp Thr Tyr Ala Ser Ser Val Leu Ala His Ala Val Phe Leu Ser
    210                 215                 220

Leu Pro Ala Ser Ala Ala Trp Gly Ala Leu Ile Met Gly Ala Ala Val
225                 230                 235                 240

Leu Pro Leu Leu Ala Arg Leu Arg Ala Pro Ala
                245                 250

<210> SEQ ID NO 75
<211> LENGTH: 192
<212> TYPE: PRT
<213> ORGANISM: Artificial Sequence
<220> FEATURE:
<223> OTHER INFORMATION: >ACSP50_1656

<400> SEQUENCE: 75

Met Arg Leu Val Ala Trp Gln Pro Asp Asp Leu Leu Arg Arg Leu Asp
  1               5                  10                  15

Asp Val Val Gly Val Tyr Gly Glu Ala Met Gly Tyr Arg Gln Glu Leu
                 20                  25                  30

Leu Gln Thr Arg Arg Gly Tyr Ile Gly Ser His Val Arg Arg Pro Gly
             35                  40                  45

Phe Arg Ala Val Ala Thr Leu Thr Thr Glu Gly Arg Leu Met Gly Phe
 50                  55                  60

Gly Tyr Gly Tyr Thr Ser Ala Ala Gly Gln Trp Trp His Asp Gln Val
 65                  70                  75                  80

Arg Phe Ala Leu Gly Glu Asp Asp Arg Arg Gln Trp Leu Thr Asp Cys
                 85                  90                  95

Phe Glu Val Val Glu Leu His Val Arg Pro Ala Ala Gln Gly His Gly
            100                 105                 110

Val Gly Ala Arg Gln Leu Arg Ala Leu Leu Ala Met Ala Lys Gly Arg
            115                 120                 125

Thr Val Leu Leu Ser Thr Pro Glu Ala Asp Glu Gln Ala Ser Arg Ala
    130                 135                 140

Trp Arg Leu Tyr Arg Arg Tyr Gly Phe Ala Asp Val Leu Arg His Phe
145                 150                 155                 160
```

Tyr Phe Pro Gly Asp Glu Arg Ala Phe Ala Val Leu Gly Arg Glu Leu
                165                 170                 175

Pro Leu Ala Glu Arg Pro Leu Glu Asp Ala Pro Gly Ile Ala Gly Ala
            180                 185                 190

<210> SEQ ID NO 76
<211> LENGTH: 224
<212> TYPE: PRT
<213> ORGANISM: Artificial Sequence
<220> FEATURE:
<223> OTHER INFORMATION: >ACSP50_1657

<400> SEQUENCE: 76

Met Thr His Val Ala Leu His Val Trp Arg Val Pro Arg Ser Ala Val
1               5                   10                  15

Gly Ser Ala Met Leu Arg Met Ala Phe Ala Arg Arg His Leu Ala Gly
            20                  25                  30

Leu Arg Phe Gly Lys Phe Leu Gly Thr Gly Thr Gly Thr Gly Phe Gly
        35                  40                  45

Pro Gly Asp Thr Asp Leu Thr Arg Trp Ala Ala Ile Thr Val Ser Asp
    50                  55                  60

Ala Pro Val Arg Phe Pro Val Trp Glu Arg Ile Ala Val Asn Gly Ala
65                  70                  75                  80

Arg Ile Asp Leu Glu Pro Leu Ile Ser Arg Gly Thr Trp Ala Gly Arg
                85                  90                  95

Thr Pro Phe Glu Pro Thr Gly Arg Arg Pro Asp Gly Pro Val Leu Ala
            100                 105                 110

Leu Thr Arg Ala Arg Leu Arg Pro Ala Arg Ala Leu Thr Phe Trp Arg
        115                 120                 125

Ala Val Pro Ala Val Val Arg Glu Val His Arg Ala Pro Gly Leu Leu
    130                 135                 140

Ala Arg Phe Gly Val Gly Glu Ala Pro Ile Gly Trp Gln Gly Thr Val
145                 150                 155                 160

Thr Val Trp Arg Asp Ala Ala Asp Leu Val Ala Phe Ala Tyr Arg Gln
                165                 170                 175

Pro Glu His Arg Ala Ala Ile Ala Arg Thr Pro Ala Asp Arg Trp Tyr
            180                 185                 190

Ala Glu Glu Leu Phe Ala Arg Phe Ala Val Leu Gly Ile Ser Gly Asp
        195                 200                 205

Arg Ser Val Leu Gly Trp Thr Ala Asp Glu Gly Glu Arg Ala Glu Ala
    210                 215                 220

<210> SEQ ID NO 77
<211> LENGTH: 271
<212> TYPE: PRT
<213> ORGANISM: Artificial Sequence
<220> FEATURE:
<223> OTHER INFORMATION: >ACSP50_1658

<400> SEQUENCE: 77

Met Thr Gln Thr Ile Val Ile Thr Gly Ala Ser Ser Gly Val Gly Leu
1               5                   10                  15

Ala Ala Ala Glu Gln Leu Ala Ala Arg Gly Asp Glu Val Leu Val
            20                  25                  30

Gly Arg Asp Pro Gly Arg Leu Asp Ala Ala Val Gln Arg Val Arg Glu
        35                  40                  45

Ala Gly Gly Gly Arg Ala Pro Arg His Phe Arg Ala Asp Phe Glu Arg

```
                50                  55                  60
Leu Asp Asp Val Arg Glu Leu Ala Ala Gly Leu Ala Glu Leu Pro
65                  70                  75                  80

Arg Ile Asp Val Leu Ala Asn Ala Gly Gly Ile Ile Lys Arg Pro
                85                  90                  95

Arg Gln Thr Val Asp Gly His Glu Ala Thr Ile Gln Gly Asn His Leu
                100                 105                 110

Ala Pro Phe Leu Leu Thr His Leu Leu Arg Glu Arg Leu Thr Gly Gly
            115                 120                 125

Arg Val Val Asn Thr Ala Ser Ala Ala His Val Gln Gly Arg Pro Gly
            130                 135                 140

Thr Arg Phe Thr Asp Asp Pro Lys Ser Tyr Ser Pro Trp Arg Ser Tyr
145                 150                 155                 160

Gly Ala Ser Lys Ala Ala Asn Ile Leu Phe Ala Ala Glu Ala Ala Arg
                165                 170                 175

Arg Trp Pro Asp Val Cys Ser Val Ser Phe His Pro Gly Val Val Arg
            180                 185                 190

Thr Asn Phe Gly Glu Gly Arg Leu Ile Arg Leu Phe Tyr Arg Tyr Ala
            195                 200                 205

Pro Gly Leu Val Thr Pro Glu Ala Ala Gly Glu Leu Leu Thr Trp Leu
210                 215                 220

Cys Thr Thr Pro Ala Gly Glu Leu Glu Asn Gly Ala Tyr Tyr Val Lys
225                 230                 235                 240

Arg Gln Val Thr Arg Pro Ala Ala His Ala Arg Asp Pro Arg Leu Ala
                245                 250                 255

Ala Glu Leu Trp Asp Ala Ser Leu Thr Ala Thr Gly Leu Ala Gly
            260                 265                 270

<210> SEQ ID NO 78
<211> LENGTH: 339
<212> TYPE: PRT
<213> ORGANISM: Artificial Sequence
<220> FEATURE:
<223> OTHER INFORMATION: >CrtE (ACSP50_3873)

<400> SEQUENCE: 78

Met Ile Asp Asp Phe Leu Ser Ala Gln Arg Asp Val Leu Ala Glu Val
1               5                   10                  15

Ser Asp Asp Cys Ala Pro Leu Glu Arg Tyr Val Ala Asp Leu Met Gly
                20                  25                  30

Gly Gly Lys Arg Leu Arg Pro Ala Phe Cys Tyr Trp Ala Trp Arg Ala
            35                  40                  45

Ala Gly Ala Pro Asp Gly Pro Gly Ile Val Ala Ala Thr Ser Leu
        50                  55                  60

Glu Phe Leu Gln Ala Ala Leu Ile His Asp Asp Ile Met Asp Asp
65                  70                  75                  80

Ser Asp Thr Arg Arg Gly Ala Pro Ala Val His Arg Arg Leu Ala Ala
                85                  90                  95

Leu His Ser Gly Gly Arg Trp Ala Gly Asp Ala Asp His Phe Gly Leu
            100                 105                 110

Ser Ala Ala Val Leu Ala Gly Asp Leu Cys Leu Thr Trp Ser Asp Ala
            115                 120                 125

Leu Tyr Ser Gly Ser Gly Leu His Pro Ser Ala Leu Ala Arg Gly Arg
        130                 135                 140

Pro Val Phe Asp Arg Met Arg Thr Gln Leu Met Gly Gly Gln Tyr Leu
```

```
                145                 150                 155                 160
Asp Leu Leu Asp Gln Ala Arg Pro Ser Arg Gly Gly Val Asp Arg Ala
                165                 170                 175

Arg Arg Val Val His Phe Lys Ser Ala Lys Tyr Thr Val Glu His Pro
            180                 185                 190

Leu Leu Leu Gly Ala Arg Leu Ala Gly Ala Asp Asp Leu Leu Ala
        195                 200                 205

Arg Leu Ser Ala Phe Gly Leu Pro Leu Gly Glu Ala Phe Gln Leu Arg
    210                 215                 220

Asp Asp Leu Leu Gly Val Phe Gly Asp Ala Ala Gln Thr Gly Lys Pro
225                 230                 235                 240

Thr Gly Asp Asp Leu Arg Glu Gly Lys Arg Thr Thr Leu Val Ile Leu
                245                 250                 255

Ala Ala Asp Arg Ala Thr Ala Pro Gln Gln Ala Ala Leu Thr Ala Leu
            260                 265                 270

Leu Gly Asp Arg Gly Leu Thr Gly Ala Gly Val Asp Thr Leu Arg Gln
        275                 280                 285

Ile Ile Val Asp Thr Gly Ala Arg Ala Glu Val Glu Arg Met Ile Glu
    290                 295                 300

Gln Leu Leu Ala Thr Ser Leu Gly Val Leu Ser Gly Thr Pro Val Asp
305                 310                 315                 320

Glu Ala Ala Arg Ser Val Leu Leu Ala Leu Ala Glu Ala Ala Thr Ala
                325                 330                 335

Arg Ser Ser

<210> SEQ ID NO 79
<211> LENGTH: 342
<212> TYPE: PRT
<213> ORGANISM: Artificial Sequence
<220> FEATURE:
<223> OTHER INFORMATION: >ACSP50_1950

<400> SEQUENCE: 79

Met Val Ser Thr Val Ile Ala Ser Gly Pro Thr Gly Leu Gly Thr Ser
1               5                   10                  15

Ala Ala Arg Leu Phe Gly Arg Val Asp Arg Asp Glu Pro Glu Leu Phe
            20                  25                  30

Cys Pro Ala Pro Leu Arg Asp Asp Arg Ala Leu Gly Glu Arg Val Asn
        35                  40                  45

Asp Ala Val Val Gln Trp Ala Glu Lys Ala Gly Ile Tyr Pro Gly Arg
    50                  55                  60

Leu Asp Lys Leu Arg Gly Ala Asn Phe Gly Arg Phe Met Met Leu Ala
65                  70                  75                  80

His Pro Ala Thr Ser Asp Pro Asp Arg Leu Leu Ala Ala Thr Lys Cys
                85                  90                  95

Leu Val Ala Glu Trp Ala Ala Asp Asp Tyr Tyr Val Asp Glu Val Ser
            100                 105                 110

Leu Gly Ala Asp Pro Met Val Val Gly Ser Arg Leu Ala Asn Leu Tyr
        115                 120                 125

Ser Val Val Asp Pro Ala Ser Leu Thr Pro Arg Tyr Gln Ala Asp Phe
    130                 135                 140

Glu Lys His His Arg Leu Gln Pro Ile Ser Val Ala Phe Arg Thr Ala
145                 150                 155                 160

Met Glu His Leu Ala Glu Tyr Ala Ser Val Thr Gln Leu Ala Arg Phe
                165                 170                 175
```

Gln His Gln Met Ala Ile Leu Phe Val Ala Trp Ser Gln Glu Ala Asp
            180                 185                 190

Trp His Ala Asn Arg Arg Thr Pro Pro Val Trp Glu Tyr Leu Val Gln
            195                 200                 205

Arg His Leu Asn Ser Tyr Leu Pro Pro Met Ile Leu Val Asp Val Leu
210                 215                 220

Ala Gly Tyr Glu Leu Ser Pro Ala Glu Phe Phe Asp Pro Arg Val Arg
225                 230                 235                 240

Ala Ala Phe Thr Thr Ala Gly Asn Ala Ala Val Leu Val Asn Asp Leu
            245                 250                 255

Tyr Ser Gly Arg Asn Glu Ser Glu Thr Asp His Asn Leu Pro Thr Val
            260                 265                 270

Leu Val Ser Gly Glu Arg Leu Thr Pro Arg Ala Ala Val Arg Arg Thr
            275                 280                 285

Val Glu Ile His Asn Glu Leu Met His Thr Phe Val Thr Ser Ala Ala
            290                 295                 300

Ser Leu Ser Ala Ser Gly Ser Pro Gln Leu Arg Arg Phe Leu Ala Asp
305                 310                 315                 320

Thr Trp Ala Trp Leu Gly Gly Ser Arg Glu Trp His Ala Thr Ser Gly
            325                 330                 335

Arg Tyr His Ser Ser Asn
            340

<210> SEQ ID NO 80
<211> LENGTH: 447
<212> TYPE: PRT
<213> ORGANISM: Artificial Sequence
<220> FEATURE:
<223> OTHER INFORMATION: >ACSP50_5522

<400> SEQUENCE: 80

Met Thr Thr Thr Ala Pro Thr Pro Ala His Leu Ala Gly Asn Phe Ala
1               5                   10                  15

Pro Val Thr Gly Glu Thr Thr Thr Leu Asp Leu Pro Val Thr Gly Ala
            20                  25                  30

Val Pro Ala Glu Leu Thr Gly Trp Tyr Leu Arg Asn Gly Pro Asn Pro
        35                  40                  45

His His Gly Thr Ser Ala His Trp Phe Leu Gly Asp Gly Met Val His
    50                  55                  60

Gly Val Arg Leu Asp His Gly Arg Ala Thr Trp Tyr Arg Asn Arg Trp
65                  70                  75                  80

Val Arg Thr Arg Val Leu Thr Asp Asp Ala Arg Ala Tyr Gly Pro Asp
                85                  90                  95

Gly Thr Arg Asp Leu Thr Ala Gly Pro Ala Asn Thr Asn Val Val Arg
            100                 105                 110

His Gly Gly Arg Leu Leu Ala Leu Val Glu Ser Ala Leu Pro Tyr Glu
        115                 120                 125

Ile Thr Thr Asp Leu Glu Thr Val Gly Pro Tyr Asp Phe Gly Gly Arg
    130                 135                 140

Leu His Thr Pro Met Thr Ala His Pro Lys Val Cys Pro Thr Thr Gly
145                 150                 155                 160

Glu Met His Phe Phe Gly Tyr Gly Gly Leu Glu Pro Pro Tyr Leu Thr
                165                 170                 175

Tyr His Arg Ala Gly Ala Asp Gly Arg Leu Ser Leu Ser Arg Pro Ile
            180                 185                 190

```
Asp Val Pro Ala His Thr Met Met His Asp Phe Ser Leu Thr Ala Ala
            195                 200                 205

His Val Ile Phe Met Asp Leu Pro Val Leu Phe Ser Leu Asp Gly Ala
        210                 215                 220

Arg Thr Gly Gly Met Pro Tyr Arg Trp Asp Asp Thr Tyr Gln Ala Arg
225                 230                 235                 240

Leu Gly Val Leu Arg Arg Asp Ala Pro Gln Gly Glu Val Arg Trp Tyr
                245                 250                 255

Thr Ile Asp Pro Gly Tyr Val Phe His Thr Leu Asn Ala His Asp Asp
                260                 265                 270

Gly Asp Arg Ile Val Met His Val Arg His Glu His Ala Tyr Arg
            275                 280                 285

Pro Gly Gln Pro Ala Ala Ala Pro Asp Leu Trp Arg Trp Thr Ile Asp
        290                 295                 300

Gln Arg Thr Gly Arg Val Ala Glu Glu Arg Leu Asp Asp Glu Ala Val
305                 310                 315                 320

Glu Phe Pro Arg Ile Asp Asp Arg Arg Thr Gly Gln Pro Ala Arg Tyr
                325                 330                 335

Gly Phe Ala Val Thr Asp Asn Val Pro Arg Arg Leu Ala Asp Val Ser
                340                 345                 350

Ala Val Ile Arg Tyr Asp Leu His Thr Gly Ser Thr Thr Arg His Arg
            355                 360                 365

Leu Pro Thr Gly Gln Val Pro Gly Glu Ala Val Phe Val Pro Ala Gly
        370                 375                 380

Gly Ala Pro Ala Gly Ser Ala Asp Gly Trp Leu Leu Thr Phe Ala Tyr
385                 390                 395                 400

Asp Pro Gly Arg Asp Ala Ser Asp Leu Ile Ile Ile Asp Ala Thr Asp
                405                 410                 415

Leu Ala Ala Pro Pro Leu Ala Arg Ile His Leu Pro His Arg Val Pro
                420                 425                 430

Phe Gly Phe His Gly Asn Trp Leu Pro Asp His Asp Arg Ala Glu
            435                 440                 445

<210> SEQ ID NO 81
<211> LENGTH: 103
<212> TYPE: DNA
<213> ORGANISM: Artificial Sequence
<220> FEATURE:
<223> OTHER INFORMATION: >tipA promoter

<400> SEQUENCE: 81
atccctagaa cgtccgggct tgcacctcac gtcacgtgag gaggcagcgt ggacggcgtg    60
gtaccaagct tattggcact agtcgagcaa cggaggtatt ccg                     103

<210> SEQ ID NO 82
<211> LENGTH: 209
<212> TYPE: DNA
<213> ORGANISM: Artificial Sequence
<220> FEATURE:
<223> OTHER INFORMATION: >gapDH promoter

<400> SEQUENCE: 82
gtactggccg atgctgggag aagcgcgctg ctgtacggcg cgcaccgggt gcggagcccc    60
tcggcgagcg gtgtgaaact tctgtgaatg gcctgttcgg ttgcttttt tatacggctg    120 ccagataagg cttgcagcat ctgggcgcct accgctatga tcggggcgtt cctgcaattc   180
```
ttagtgcgag tatctgaaag gggatacgc                                   209

<210> SEQ ID NO 83
<211> LENGTH: 460
<212> TYPE: DNA
<213> ORGANISM: Artificial Sequence
<220> FEATURE:
<223> OTHER INFORMATION: >lacZ? promoter and gene

<400> SEQUENCE: 83
taatgtgagt tagctcactc attaggcacc ccaggcttta cactttatgc ttccggctcg    60
tatgttgtgt ggaattgtga gcggataaca atttcacaca ggaaacagct atgacatgat   120
tacgaattcg atatcgcgcg cggccgcgga tcctctagag tcgacctgca gcccaagctt   180
ggcactggcc gtcgttttac aacgtcgtga ctgggaaaac cctggcgtta cccaacttaa   240
tcgccttgca gcacatcccc ctttcgccag ctggcgtaat agcgaagagg cccgcaccga   300
tcgcccttcc caacagttgc gcagcctgaa tggcgaatgg cgcctgatgc ggtattttct   360
ccttacgcat ctgtgcggta tttcacaccg cataaattcc ccaatgtcaa gcacttccgg   420
aatcgggagc gcggccgatg caaagtgccg atcaacataa                          460

<210> SEQ ID NO 84
<211> LENGTH: 117
<212> TYPE: DNA
<213> ORGANISM: Artificial Sequence
<220> FEATURE:
<223> OTHER INFORMATION: >T4 terminator

<400> SEQUENCE: 84
aagctttatg cttgtaaacc gttttgtgaa aaatttttta aaataaaaaa ggggacctct    60
agggtcccca attaattagt aatataatct attaaaggtc attcaaaagg tcatcca      117

<210> SEQ ID NO 85
<211> LENGTH: 1818
<212> TYPE: DNA
<213> ORGANISM: Artificial Sequence
<220> FEATURE:
<223> OTHER INFORMATION: >PhiC31 integrase gene

<400> SEQUENCE: 85
gtggacacgt acgcgggtgc ttacgaccgt cagtcgcgcg agcgcgagaa ttcgagcgca    60
gcaagcccag cgacacagcg tagcgccaac gaagacaagg cggccgacct tcagcgcgaa   120
gtcgagcgcg acgggggccg gttcaggttc gtcgggcatt tcagcgaagc gccgggcacg   180
tcggcgttcg ggacggcgga gcgccggagt tcgaacgca tcctgaacga atgccgcgcc   240
gggcggctca acatgatcat tgtctatgac gtgtcgcgct ctcgcgcct gaaggtcatg   300 gacgcgattc cgattgtctc ggaattgctc gccctgggcg tgacgattgt ttccactcag   360
gaaggcgtct tccggcaggg aaacgtcatg gacctgattc acctgattat gcggctcgac   420
gcgtcgcaca aagaatcttc gctgaagtcg gcgaagattc tcgacacgaa gaaccttcag   480
cgcgaattgg gcgggtacgt cggcgggaag gcgccttacg gcttcgagct tgtttcggag   540
acgaaggaga tcacgcgcaa cggccgaatg gtcaatgtcg tcatcaacaa gcttgcgcac   600
tcgaccactc cccttaccgg acccttcgag ttcgagcccg acgtaatccg gtggtggtgg   660
cgtgagatca gacgcacaa acaccttccc ttcaagccgg gcagtcaagc cgccattcac   720
ccgggcagca tcacggggct ttgtaagcgc atggacgctg acgccgtgcc gacccggggc   780
gagacgattg ggaagaagac cgcttcaagc gcctgggacc cggcaaccgt tatgcgaatc   840
cttcgggacc cgcgtattgc gggcttcgcc gctgaggtga tctacaagaa gaagccggac 900
ggcacgccga ccacgaagat tgagggttac cgcattcagc gcgacccgat cacgctccgg 960
ccggtcgagc ttgattgcgg accgatcatc gagcccgctg agtggtatga gcttcaggcg 1020
tggttggacg gcagggggcg cggcaagggg ctttcccggg ggcaagccat tctgtccgcc 1080
atggacaagc tgtactgcga gtgtggcgcc gtcatgactt cgaagcgcgg ggaagaatcg 1140
atcaaggact cttaccgctg ccgtcgccgg aaggtggtcg acccgtccgc acctgggcag 1200
cacgaaggca cgtgcaacgt cagcatggcg gcactcgaca agttcgttgc ggaacgcatc 1260
ttcaacaaga tcaggcacgc cgaaggcgac gaagagacgt tggcgcttct gtgggaagcc 1320
gcccgacgct tcggcaagct cactgaggcg cctgagaaga gcggcgaacg ggcgaacctt 1380
gttgcggagc gcgccgacgc cctgaacgcc cttgaagagc tgtacgaaga ccgcgcggca 1440
ggcgcgtacg acggacccgt tggcaggaag cacttccgga agcaacaggc agcgctgacg 1500
ctccggcagc aaggggcgga agagcggctt gccgaacttg aagccgccga agccccgaag 1560
cttccccttg accaatggtt ccccgaagac gccgacgctg acccgaccgg ccctaagtcg 1620
tggtgggggc gcgcgtcagt agacgacaag cgcgtgttcg tcgggctctt cgtagacaag 1680
atcgttgtca cgaagtcgac tacgggcagg gggcagggaa cgcccatcga gaagcgcgct 1740
tcgatcacgt gggcgaagcc gccgaccgac gacgacgaag acgacgccca ggacggcacg 1800
gaagacgtag cggcgtag 1818

<210> SEQ ID NO 86
<211> LENGTH: 100
<212> TYPE: DNA
<213> ORGANISM: Artificial Sequence
<220> FEATURE:
<223> OTHER INFORMATION: >PhiC31 attachment site

<400> SEQUENCE: 86
cccaggtcag aagcggtttt cgggagtagt gccccaactg gggtaacctt tgagttctct 60
cagttggggg cgtagggtcg ccgacatgac acaaggggtt 100

<210> SEQ ID NO 87
<211> LENGTH: 110
<212> TYPE: DNA
<213> ORGANISM: Artificial Sequence
<220> FEATURE:
<223> OTHER INFORMATION: >incP

<400> SEQUENCE: 87
ccggccagcc tcgcagagca ggattcccgt tgagcaccgc caggtgcgaa taagggacag 60
tgaagaagga acacccgctc gcgggtgggc ctacttcacc tatcctgccc 110

<210> SEQ ID NO 88
<211> LENGTH: 372
<212> TYPE: DNA
<213> ORGANISM: Artificial Sequence
<220> FEATURE:
<223> OTHER INFORMATION: >traJ

<400> SEQUENCE: 88
atggctgatg aaaccaagcc aaccaggaag ggcagcccac ctatcaaggt gtactgcctt 60
ccagacgaac gaagagcgat tgaggaaaag gcggcggcgg ccggcatgag cctgtcggcc 120
tacctgctgg ccgtcggcca gggctacaaa atcacgggcg tcgtggacta tgagcacgtc 180

```
cgcgagctgg cccgcatcaa tggcgacctg ggccgcctgg gcggcctgct gaaactctgg      240
ctcaccgacg acccgcgcac ggcgcggttc ggtgatgcca cgatcctcgc cctgctggcg      300
aagatcgaag agaagcagga cgagcttggc aaggtcatga tgggcgtggt ccgcccgagg      360
gcagagccat ga                                                         372
```

<210> SEQ ID NO 89
<211> LENGTH: 589
<212> TYPE: DNA
<213> ORGANISM: Artificial Sequence
<220> FEATURE:
<223> OTHER INFORMATION: >ColE1/pMB1/pBR322/pUC ori

<400> SEQUENCE: 89

```
ttgagatcct tttttctgc gcgtaatctg ctgcttgcaa acaaaaaaac caccgctacc       60
agcggtggtt tgtttgccgg atcaagagct accaactctt tttccgaagg taactggctt     120
cagcagagcg cagataccaa atactgttct ctagtgtag ccgtagttag gccaccactt      180
caagaactct gtagcaccgc ctacatacct cgctctgcta atcctgttac cagtggctgc     240
tgccagtggc gataagtcgt gtcttaccgg gttggactca agacgatagt taccggataa     300
ggcgcagcgg tcgggctgaa cggggggttc gtgcacacag cccagcttgg agcgaacgac     360
ctacaccgaa ctgagatacc tacagcgtga gctatgagaa agcgccacgc ttcccgaagg     420
gagaaaggcg gacaggtatc cggtaagcgg cagggtcgga acaggagagc gcacgaggga     480
gcttccaggg ggaaacgcct ggtatcttta tagtcctgtc gggtttcgcc acctctgact     540
tgagcgtcga ttttgtgat gctcgtcagg gggcggagc ctatggaaa                   589
```

<210> SEQ ID NO 90
<211> LENGTH: 777
<212> TYPE: DNA
<213> ORGANISM: Artificial Sequence
<220> FEATURE:
<223> OTHER INFORMATION: > aac(3)IV

<400> SEQUENCE: 90

```
gtgcaatacg aatggcgaaa agccgagctc atcggtcagc ttctcaacct tgggggttacc     60 cccggcggtg tgctgctggt ccacagctcc ttccgtagcg tccggcccct cgaagatggg    120
ccacttggac tgatcgaggc cctgcgtgct gcgctgggtc cgggagggac gctcgtcatg    180
ccctcgtggt caggtctgga cgacgagccg ttcgatcctg ccacgtcgcc cgttacaccg    240
gaccttggag ttgtctctga cacattctgg cgcctgccaa atgtaaagcg cagcgcccat    300
ccatttgcct ttgcggcagc ggggccacag gcagagcaga tcatctctga tccattgccc    360
ctgccacctc actcgcctgc aagcccggtc gcccgtgtcc atgaactcga tgggcaggta    420
cttctcctcg gcgtgggaca cgatgccaac acgacgctgc atcttgccga gttgatggca    480
aaggttccct atggggtgcc gagacactgc accattcttc aggatggcaa gttggtacgc    540
gtcgattatc tcgagaatga ccactgctgt gagcgctttg ccttggcgga caggtggctc    600
aaggagaaga gccttcagaa ggaaggtcca gtcggtcatg cctttgctcg gttgatccgc    660
tcccgcgaca ttgtggcgac agccctgggt caactgggcc gagatccgtt gatcttcctg    720
catccgccag aggcgggatg cgaagaatgc gatgccgctc gccagtcgat tggctga       777
```

<210> SEQ ID NO 91
<211> LENGTH: 582
<212> TYPE: DNA
<213> ORGANISM: Artificial Sequence
<220> FEATURE:
<223> OTHER INFORMATION: >cgt promoter

<400> SEQUENCE: 91

| | | | | | |
|---|---|---|---|---|---|
| gcccggccct | gtcgagctga | cggctgtccc | gcggcctcgt | catcggtgct | gtcgagcagg | 60 |
| ctgtcgcctg | gtaggaagat | tgccatggtc | cagatggacc | ccctcagcgc | acgtcccgat | 120 |
| ggacgacgtt | ccgtcttgtc | gacgactccg | agccgcccga | cccaccgggc | ctgagcgcgc | 180 |
| ccgatcacgg | ctccccggcc | tgacgggttc | tgcacctccg | gcggctttcc | cgaggacggc | 240 |
| gtggtggtcg | gtgacggctg | ctggacctcc | tccggtgggc | aagcgtttcg | gtgaggtggg | 300 |
| cagcccggct | gcgggcacat | cggggcgga | gagacgctta | ggtttattgc | aagttctttc | 360 |
| ttcggtggcg | cggcgtgtca | tcagcagccg | attgtggcat | tctggtgacg | cattgacgca | 420 |
| ggtcacagat | ttgttgggat | aggcaacgaa | caattcctaa | atcgcctatt | cggacaaata | 480 |
| ggcttgacct | gacgacgctg | tcccaccact | gtggatgacg | cctaccgcgc | aagttctgga | 540 |
| agtacttgca | atcagcggtg | aggatcatca | aaggggactg | tc | | 582 |

<210> SEQ ID NO 92
<211> LENGTH: 115
<212> TYPE: DNA
<213> ORGANISM: Artificial Sequence
<220> FEATURE:
<223> OTHER INFORMATION: >efp promoter

<400> SEQUENCE: 92

| | | | | | |
|---|---|---|---|---|---|
| tggagcacat | ctgccggtag | acccgattcg | ccctcaccag | cgaatcgccg | gtaaagtggt | 60 |
| tcggtcaacg | attcgagtca | agatcaaggc | aggacatggc | ttccaccaac | gacct | 115 |

<210> SEQ ID NO 93
<211> LENGTH: 372
<212> TYPE: DNA
<213> ORGANISM: Artificial Sequence
<220> FEATURE:
<223> OTHER INFORMATION: >rpsJ promoter

<400> SEQUENCE: 93

| | | | | | |
|---|---|---|---|---|---|
| attgcgggtt | gtcgccggtg | agagccggtg | acaaccccca | ccggtgaccc | cgattagcaa | 60 |
| tgctgcgttc | aatcgggcat | actagtcagg | ttgcgtccgc | gcggggtggg | tggctggcgt | 120 |
| tcgtcagccg | cccaccctcg | ccgggtgtcc | gggtgtgttt | ccagccgccc | ggcgccctca | 180 |
| gatccccgcg | atcgcgttcg | tccccggcaa | gatcggggat | ggaggccgaa | agctgagtgc | 240 |
| ccagcactct | gtgacgaggc | gcgacacgcc | cgaccgcggg | ggtcggacaa | cgcaggatca | 300 |
| acggtcctgc | gggcatgtgg | gggccaccgc | ctccgcacgt | agcggcatcg | agagaaggaa | 360 |
| acagaagcca | cc | | | | | 372 |

<210> SEQ ID NO 94
<211> LENGTH: 264
<212> TYPE: DNA
<213> ORGANISM: Artificial Sequence
<220> FEATURE:
<223> OTHER INFORMATION: >katE promoter

<400> SEQUENCE: 94

| | | | | | |
|---|---|---|---|---|---|
| atctcgggct | cggtaggcat | caggcactcg | tttcgtcggg | ctctcgtgac | agtgaccttg | 60 |
| atactggagg | ggtacgacaa | aaccgggacc | gccaccgacg | tccggaccga | cccgatcgtc | 120 |
| ggccacgaac | agggccggat | ggtcgtcgtg | acgcgtccgc | gagacgccgt | ccgggccggg | 180 |

```
ccgatgctcg gccggaccgt tgccgggggt tcatgcgggg tatccgccat ccgatcacat    240
acccttatcg aggagtttgt ccgg                                          264
```

<210> SEQ ID NO 95
<211> LENGTH: 470
<212> TYPE: DNA
<213> ORGANISM: Artificial Sequence
<220> FEATURE:
<223> OTHER INFORMATION: >moeE5 promoter

<400> SEQUENCE: 95

```
agggcgccac cagctggagc cccatccccg cggggaccag gagggcgagc agcgccacgg     60
cggtccgttc accgcgcagg tagcggacaa acgtggagag atgccgcaac ggactgtctg    120
ccaacgcgcc cctcccccgt tcgcccggcg gcgagcggcc agcataaagt cctgtgcgcc    180
tccttgtgaa tgacgcctcg tcaacggcgg ccggagcacg ccctttctgc gggaagccga    240
tagcggacgc cgctccggga gggggcgaag cacaccattg ctcgtgattg acgcatgctg    300
ttagactccc cacgtctctt ggtccggaca tgcgtttctc aacgccgaaa gcctggtcaa    360
ccgcactttc ggcaccgcac agtcccacgg cgtccgagcg gtcgcgcgag tcggcccggt    420
cgagccagag gcagccacac gaacgtgcac cgcaatgcac cgccttgatc              470
```

<210> SEQ ID NO 96
<211> LENGTH: 334
<212> TYPE: DNA
<213> ORGANISM: Artificial Sequence
<220> FEATURE:
<223> OTHER INFORMATION: >apm promoter

<400> SEQUENCE: 96

```
ctctgctgaa gccagttacc ttcggaaaaa gagttggtag ctcttgatcc ggcaaacaaa     60
ccaccgctgg tagcggtggt ttttttgttt gcaagcagca gattacgcgc agaaaaaaag    120
gatctcaaga agatcctttg atcttttcta cggggtctga cgctcagtgg aacgaaaact    180
cacgttaagg gattttggtc atgagattat caaaaaggat cttcacctag atccttttgg    240
ttcatgtgca gctccatcag caaaagggga tgataagttt atcaccaccg actatttgca    300
acagtgccgt tgatcgtgct atgatcgact gagc                               334
```

<210> SEQ ID NO 97
<211> LENGTH: 1094
<212> TYPE: DNA
<213> ORGANISM: Artificial Sequence
<220> FEATURE:
<223> OTHER INFORMATION: >cdaR promoter

<400> SEQUENCE: 97

```
gggccccccc tcgaggtcga cggtatcgat aagcttgatt tttctggaca acctggacgc     60
cgagacctcg gcggcgaccc tcgcgctgtt cctcacggcc ctgtgggcgc tggccgtcat    120
cgcccgcccc tacacctggt ggcgcgtgct gctggtgctg accatggcgg tgggcttcgc    180
cgtggtgctg gtggtgccct acctccagga gttcttccag ctgaagctgg tcggcgtcac    240
cgcgccgtgg gcggcggtcg cctgtgcggc ggtcgccggg ctggtgctgg agttggtgtg    300
ggcacgtatg cggcgtcgtc tcgacgccga ctgagcccac cgggcggtcg accccgtac    360 cgcccggtga agaggagggg acgccggtc cgtgccgggc gtcccctccg tctttgtgcg    420 cccccgccc accggaacgg cacgatccgg ccaaacctgc gcagcggtgc ggccggagga    480
gccgcttccg ggccgttcga cgggcggccc gccacgggac cggaacgagc cccggcatcc    540
```

```
gccgccacca gcggatttca cattccttac gcaatcggcg gcgagagcga ccggcaggta      600
acctcggggc tgaatccagg ccatcgggga atagcaaacg gcgcactgac gaaagcaagg      660
gcagagacct gccgaaagtt gagtgttgga ttcaaagaag atccgtatta ttccgactgc      720
aggcaggggg gagccggcta cgaaggaaaa gttccgcagg tcagattggg ccgggtcgca      780
ggcagcgccg caccggcaac cacgaccgcg actttcgtcg acgcacccc tcgcaccgcc       840 gcccggccac cggtccgggc gcacgacccg aagggaagtg aggctcacgc acggaccagc     900
agctcctgac gcagcgaccc ggacccggag gtgagtgaca tgacgacgag gccccgacca    960
gcggtgaacc ctgctgaccc ggccgtaacg aagtcttcat gcccgtggca cccgacggct   1020
tcggagagtt tcggcacgca gacatcagca caacttgacg cgggggtatc aagaggtcat   1080
ggatcttcgg tacc                                                      1094

<210> SEQ ID NO 98
<211> LENGTH: 145
<212> TYPE: DNA
<213> ORGANISM: Artificial Sequence
<220> FEATURE:
<223> OTHER INFORMATION: >ermE* promoter

<400> SEQUENCE: 98
gcggttgatc ggcgatcgca ggtgcacgcg gtcgatcttg acggctggcg agaggtgcgg       60
ggaggatctg accgacgcgg tccacacgtg gcaccgcgat gctgttgtgg gcacaatcgt      120
gccggttggt aggatccagc gagca                                           145

<210> SEQ ID NO 99
<211> LENGTH: 321
<212> TYPE: DNA
<213> ORGANISM: Artificial Sequence
<220> FEATURE:
<223> OTHER INFORMATION: >rpsL promoter

<400> SEQUENCE: 99
tgagcacgtc cgcgagctgg ccctgcaggc ggaagtcagg tagacacgac ttccgctagt       60
ccttgcaagg tctgctgacg tgaggcgggg cggtcgtttt tgaccgccct gccttcgtca      120
tgtaggctcg ctcgctgtgc ctggcgtgtc atcagacgcc caggtcccgg tgccgtgagg      180
cccgggccat cgagccggtg gtacgtggct gcggtcccct tgtgagggct gcgcgccgtg      240
tgctgtccgg cgcgcacagc cttgaatcca cccgcggggg ccggccggtc tccgtgagct      300
cgagtagacg acggagacgt a                                               321

<210> SEQ ID NO 100
<211> LENGTH: 1410
<212> TYPE: DNA
<213> ORGANISM: Artificial Sequence
<220> FEATURE:
<223> OTHER INFORMATION: >ACSP50_1949

<400> SEQUENCE: 100
gtggcgactc ccacgcagtc cgagatccgc gaggaagagc acgaagagca gcggcagagc       60
ctgagcacgg cggcggcccg caacctcacg accaccacca agaccgcgcc gcagatgcag      120
gagatcactt cgcgatggct gctccgtaag cttccctggg ttcaggtcgc cggtggggcg      180
tatcgggtga accggcggat gacttatcgg atcggcgacg gccggctgag cttcaccaac      240
gtcggtgcgc aggtccgggt cgtcccgccc gagctgcggg aactctcggt gctcagcgag      300
```

```
ttcgacgacg cggacgtgct ggccgccatg ccgacaagt tcgtgcagca ggagtaccag      360
cccggtcagg tgatcgtcga gttcggctcg gtcgccgacc acgtgtacgt gatcgcgcac      420
ggcaaggtga acaaggtcgg cgtcggcaac tacggcgacc cggtcaacct gggggtgctc      480
gccgacgggg aggcgttcgg cgagaagtcg ctcaccgacg aggagcggat ctgggactac      540
accgccaagg cgatgaccgc ggtgaccctg ctggccatgc cgcgctcggc gttcaccgcg      600
ctgctcggcc agagtgacca cctgcgcacg cacgtcgagc agttccgggc caagaaccgc      660
cggccgcaga acaagcacgg cgaggcggag atctcggtgg ccgccgggca caccggcgaa      720
ccgaagctgg acggcacgta cgtcgactac gagctgacgc cgcgcgaata cgagctgagc      780
gtcgcgcaga ccgtgctgcg cgtgcacacc cgggtcgccg acctctacaa cgagccgatg      840
aaccaggtgg agcagcagct ccggctgacc gtcgaggcgc tgcgcgagcg tcaggaatac      900
gaaatgatca caaccgcga gttcggcctg ctgcacaacg ccgacctgcg gcagcgcatc      960
cacacccggg gcggcccgcc caccccggac gacctcgacg agctgctcag catgcggcgc     1020
ggcaccagga tgttcgtggc ccaccgcag gcggtcgccg cgttcggccg ggagtgcacc     1080
aagcggggca tctatccacc gatgctggaa caggacggcg gcaccttcct gtcctggcgc     1140
ggggtcccga tcctgccgtg cggcaagatc ccggtgaccg agacgcacac cacctcgatc     1200
ctggcgatgc gcaccgggga gagcgaccag ggtgtggtcg ggctgcacca gaccgggatc     1260
ccggacgagt acgagccgag cctgtccgtg cggttcatgg ggatcagcga gcaggcgatc     1320
atgtcgtacc tggtgagcgc gtactactcg ccgcggtgc tggtgccgga cgcgctgggc     1380
atcctggacc acgtcgagct gtcccactga                                       1410

<210> SEQ ID NO 101
<211> LENGTH: 855
<212> TYPE: DNA
<213> ORGANISM: Artificial Sequence
<220> FEATURE:
<223> OTHER INFORMATION: >ACSP50_1951

<400> SEQUENCE: 101
atgacaagtg ctgttgcttc gccactgcgg accgacttcg agcgctcggt cgccagctac       60
tggaacacca accgggccga cccggtcaac ctgcgcctcg gcgaggtcga cgggctgtac      120
caccaccact acggcgtcgg cgagcccgac ctcagcgtgc tggacggccc ggccgacacc      180
cgcgagcagc ggatcatcgc cgagctgcac cggctggaga cgcccaggc cgacctgctg      240 ctcgaccacc tcggcccgat ccggccgggc gacgcgctgc tcgacggcgg gtccggccgc      300
ggcggcacca gcatcatggc caacgcgcgg ttcggctgcc gggtcgacgg ggtgtccatc      360
tcggaatacc aggtgggttt cgccaacgag caggccgctc agcgcggcgt cgccgacagg      420
gtgcgcttcc acttccgcaa catgctggac tccggattcg cgaccgggtc acggcaggcg      480
atctggacga acgagacgac gatgtacgtc gacctgttcg acctgtacgc ggagttcgcc      540
cggatgctcg gcttcggcgg ccgctacgtg tgcatcaccg gttgcgccaa cgacgtgacc      600
ggccggcgct ccaaggcggt caacaggatc aacgagcact acacctgtga catccacccg      660
cgcagcgact acttcaaggc gctcgccgcc acgatctcg tgccgatcgc cgtcaccgac      720
ctgaccgcgg ccaccatccc gtactgggag ctgcgcgccc ggtccgaggt ggcgaccggg      780
atcgaacagg ctttcctcac ggcgtactca gaaggcagtt ccactacct tctgatcgcc      840 gccgatcggg tctga                                                        855
```

<210> SEQ ID NO 102
<211> LENGTH: 1803
<212> TYPE: DNA
<213> ORGANISM: Artificial Sequence
<220> FEATURE:
<223> OTHER INFORMATION: >ACSP50_1952

<400> SEQUENCE: 102

```
atggccctgc cgatcgagga ctacgcgatc atcgccgaca cccagaccgc ggccctggtc    60
ggtcgcaacg gatcgatcga ctggctctgc gtgccccgct tcgactccgg cgcgatcttc   120
gcggcgctgc tcggcgaggc ggagaacggc cactggacca tcgcaccgtc cggcgaggtg   180
gtcaccaccc gccgccgcta ccgggacgac acgctggtgt ggagacggag gttcgagacg   240
gccggcggcg tcgcccggtt gatcgacttc atgccgccgc gcaccgactc gccgtccgtc   300
atccggatcg tcgagggcgt ccgcgggcag gtggacttcg gcatggagct gcggctgcgc   360
ttcgactatg gacacgtcgt gccatgggtc taccgcgagg gtggggcgct cgtcgcggtc   420
gccggtccgg acgcggcctg gttgcgcacc gacgtgccga cccggggcga gaatctgacc   480
accaaagccg atttccgggt acgggcgggg aacgcgccg ccttcaccct gacctggcgc   540
ccgtcgcatc tgccctcgcc cgccccgctg acccgccc acgagctcgg cgtgaccgag   600
ggttactggc gcggctgggt gtccgcctgc acgtacgagg gggagtggcg ggacgccgtc   660
gtccgatcgc tgctcactct gaaagccctc acctacgcac ccaccggcgg cattgtcgcg   720
gccgccacca ccagcctccc ggagaaactc ggcggcgtcc gcaactggga ctaccgcttc   780
tgctggctcc gcgacgccac catcaccctg cagtcgctgc tcttctccgg tttccagagt   840
gaggcgatcg cctggcgcaa atggctgctg cgcgcgatcg ccggcaaccc cgccgagctg   900
cagatcatgt acggcgtcgc cggcgaacgc cgcctcgacg agtatctggc cgactggctc   960
accggctacg acggcaaccc ggtccggatc ggcaacgccg ccgccgagca gttccagttg  1020
gacgtgtacg gcgaggtgat ggacgccctg catcagggcc gccgggcgg cctcaaagcc  1080
gacgacccgt cctgggggcct gcaggtcaaa ctgatggagt tcgtcgagga gcactggcag  1140
gacccggacg agggcatctg ggaggtccgc ggcggccccc gccagttcac ccactccaaa  1200
ctgatggcct gggtcgccgc cgaccgcgcc gtcaaggccg tcgaggagtt cggcctggac  1260
ggccccgccg accgctggcg ccgcctgcgc gacgagatcc gtcaggacat cctggacaag  1320
ggttacgacc cggtccgcaa gaccttcacc cagtactacg ctccgatga gctcgacgcc  1380
gcgatgctga tggtcccccct ggtcggcttc ctccccgggg atgacgaacg cgtcgccggc  1440
acggtcgccg ccatcgagca acacctgctg gtcgacggtt tcgtccagcg gtacacccaa  1500
catccggacg ccgacgtcga cggccttccc ccgggcgagg gcgcgttcct ggcctgcacg  1560
ttctggctgg ccgacaacta cgcgctgatg ggtcgccacg acgagcccg ggagacgttc  1620
gcccgcctgc tggccctgcg caacgacgtg ggtctgctcg ccgaggagta cgacaccacc  1680
accgccgcc tggtcggcaa cttccctcag gccttcagtc acgtcccgct gatcgacacg  1740
gcccggacct tgaccagcgc gctggcgccg accgaggccc gggcctcgga gggcctcagg  1800
tag                                                                1803
```

<210> SEQ ID NO 103
<211> LENGTH: 276
<212> TYPE: DNA
<213> ORGANISM: Artificial Sequence
<220> FEATURE:
<223> OTHER INFORMATION: >ACSP50_1953

-continued

<400> SEQUENCE: 103

```
atgcgtacgg tgattcgtgg gatcgtggtg ttggcgctgg tggccggggg tggcgccggc      60
atggtggggc cgccggagc ggcgccggcg gtgacgttca gaactgcac tgagctgaac      120 aagaagtaca agcacggggt cggcaagcgg ggcgccgagg acagggtgag cgggtccacc      180
aagccggtca ccaccttctc cgtgaacaac gatctctatg cggcgaacaa gaggctggac      240
cgtgacaagg acgggatcgc ctgcgagaag cggtga                               276
```

<210> SEQ ID NO 104
<211> LENGTH: 469
<212> TYPE: PRT
<213> ORGANISM: Artificial Sequence
<220> FEATURE:
<223> OTHER INFORMATION: >ACSP50_1949

<400> SEQUENCE: 104

```
Met Ala Thr Pro Thr Gln Ser Glu Ile Arg Glu Glu Glu His Glu Glu
1               5                   10                  15

Gln Arg Gln Ser Leu Ser Thr Ala Ala Ala Arg Asn Leu Thr Thr Thr
            20                  25                  30

Thr Lys Thr Ala Pro Gln Met Gln Glu Ile Thr Ser Arg Trp Leu Leu
        35                  40                  45

Arg Lys Leu Pro Trp Val Gln Val Ala Gly Ala Tyr Arg Val Asn
    50                  55                  60

Arg Arg Met Thr Tyr Arg Ile Gly Asp Gly Arg Leu Ser Phe Thr Asn
65                  70                  75                  80

Val Gly Ala Gln Val Arg Val Val Pro Ala Glu Leu Arg Glu Leu Ser
                85                  90                  95

Val Leu Ser Glu Phe Asp Asp Ala Asp Val Leu Ala Ala Met Ala Asp
            100                 105                 110

Lys Phe Val Gln Gln Glu Tyr Gln Pro Gly Gln Val Ile Val Glu Phe
        115                 120                 125

Gly Ser Val Ala Asp His Val Tyr Val Ile Ala His Gly Lys Val Asn
    130                 135                 140

Lys Val Gly Val Gly Asn Tyr Gly Asp Pro Val Asn Leu Gly Val Leu
145                 150                 155                 160

Ala Asp Gly Glu Ala Phe Gly Glu Lys Ser Leu Thr Asp Glu Arg
                165                 170                 175

Ile Trp Asp Tyr Thr Ala Lys Ala Met Thr Ala Val Thr Leu Leu Ala
            180                 185                 190

Met Pro Arg Ser Ala Phe Thr Ala Leu Leu Gly Gln Ser Asp His Leu
        195                 200                 205

Arg Thr His Val Glu Gln Phe Arg Ala Lys Asn Arg Arg Pro Gln Asn
    210                 215                 220

Lys His Gly Glu Ala Glu Ile Ser Val Ala Ala Gly His Thr Gly Glu
225                 230                 235                 240

Pro Lys Leu Asp Gly Thr Tyr Val Asp Tyr Glu Leu Thr Pro Arg Glu
                245                 250                 255

Tyr Glu Leu Ser Val Ala Gln Thr Val Leu Arg Val His Thr Arg Val
            260                 265                 270

Ala Asp Leu Tyr Asn Glu Pro Met Asn Gln Val Glu Gln Gln Leu Arg
        275                 280                 285

Leu Thr Val Glu Ala Leu Arg Glu Arg Gln Glu Tyr Glu Met Ile Asn
    290                 295                 300
```

Asn Arg Glu Phe Gly Leu Leu His Asn Ala Asp Leu Arg Gln Arg Ile
305                 310                 315                 320

His Thr Arg Gly Gly Pro Pro Thr Pro Asp Asp Leu Asp Glu Leu Leu
            325                 330                 335

Ser Met Arg Arg Gly Thr Arg Met Phe Val Ala His Pro Gln Ala Val
            340                 345                 350

Ala Ala Phe Gly Arg Glu Cys Thr Lys Arg Gly Ile Tyr Pro Pro Met
            355                 360                 365

Leu Glu Gln Asp Gly Gly Thr Phe Leu Ser Trp Arg Gly Val Pro Ile
    370                 375                 380

Leu Pro Cys Gly Lys Ile Pro Val Thr Glu Thr His Thr Thr Ser Ile
385                 390                 395                 400

Leu Ala Met Arg Thr Gly Glu Ser Asp Gln Gly Val Val Gly Leu His
            405                 410                 415

Gln Thr Gly Ile Pro Asp Glu Tyr Glu Pro Ser Leu Ser Val Arg Phe
            420                 425                 430

Met Gly Ile Ser Glu Gln Ala Ile Met Ser Tyr Leu Val Ser Ala Tyr
            435                 440                 445

Tyr Ser Ala Ala Val Leu Val Pro Asp Ala Leu Gly Ile Leu Asp His
450                 455                 460

Val Glu Leu Ser His
465

<210> SEQ ID NO 105
<211> LENGTH: 284
<212> TYPE: PRT
<213> ORGANISM: Artificial Sequence
<220> FEATURE:
<223> OTHER INFORMATION: >ACSP50_1951

<400> SEQUENCE: 105

Met Thr Ser Ala Val Ala Ser Pro Leu Arg Thr Asp Phe Glu Arg Ser
1               5                   10                  15

Val Ala Ser Tyr Trp Asn Thr Asn Arg Ala Asp Pro Val Asn Leu Arg
            20                  25                  30

Leu Gly Glu Val Asp Gly Leu Tyr His His Tyr Gly Val Gly Glu
        35                  40                  45

Pro Asp Leu Ser Val Leu Asp Gly Pro Ala Asp Thr Arg Glu Gln Arg
    50                  55                  60

Ile Ile Ala Glu Leu His Arg Leu Glu Asn Ala Gln Ala Asp Leu Leu
65                  70                  75                  80

Leu Asp His Leu Gly Pro Ile Arg Pro Gly Asp Ala Leu Leu Asp Gly
                85                  90                  95

Gly Ser Gly Arg Gly Gly Thr Ser Ile Met Ala Asn Ala Arg Phe Gly
            100                 105                 110

Cys Arg Val Asp Gly Val Ser Ile Ser Glu Tyr Gln Val Gly Phe Ala
        115                 120                 125

Asn Glu Gln Ala Ala Gln Arg Gly Val Ala Asp Arg Val Arg Phe His
    130                 135                 140

Phe Arg Asn Met Leu Asp Ser Gly Phe Ala Thr Gly Ser Arg Gln Ala
145                 150                 155                 160

Ile Trp Thr Asn Glu Thr Thr Met Tyr Val Asp Leu Phe Asp Leu Tyr
                165                 170                 175

Ala Glu Phe Ala Arg Met Leu Gly Phe Gly Arg Tyr Val Cys Ile
            180                 185                 190

-continued

```
Thr Gly Cys Ala Asn Asp Val Thr Gly Arg Arg Ser Lys Ala Val Asn
            195                 200                 205

Arg Ile Asn Glu His Tyr Thr Cys Asp Ile His Pro Arg Ser Asp Tyr
        210                 215                 220

Phe Lys Ala Leu Ala Ala His Asp Leu Val Pro Ile Ala Val Thr Asp
225                 230                 235                 240

Leu Thr Ala Ala Thr Ile Pro Tyr Trp Glu Leu Arg Ala Arg Ser Glu
                245                 250                 255

Val Ala Thr Gly Ile Glu Gln Ala Phe Leu Thr Ala Tyr Ser Glu Gly
            260                 265                 270

Ser Phe His Tyr Leu Leu Ile Ala Ala Asp Arg Val
        275                 280

<210> SEQ ID NO 106
<211> LENGTH: 600
<212> TYPE: PRT
<213> ORGANISM: Artificial Sequence
<220> FEATURE:
<223> OTHER INFORMATION: >ACSP50_1952

<400> SEQUENCE: 106

Met Ala Leu Pro Ile Glu Asp Tyr Ala Ile Ile Ala Asp Thr Gln Thr
1               5                   10                  15

Ala Ala Leu Val Gly Arg Asn Gly Ser Ile Asp Trp Leu Cys Val Pro
            20                  25                  30

Arg Phe Asp Ser Gly Ala Ile Phe Ala Ala Leu Leu Gly Glu Ala Glu
        35                  40                  45

Asn Gly His Trp Thr Ile Ala Pro Ser Gly Val Val Thr Thr Arg
    50                  55                  60

Arg Arg Tyr Arg Asp Asp Thr Leu Val Leu Glu Thr Glu Phe Glu Thr
65                  70                  75                  80

Ala Gly Gly Val Ala Arg Leu Ile Asp Phe Met Pro Pro Arg Thr Asp
                85                  90                  95

Ser Pro Ser Val Ile Arg Ile Val Glu Gly Val Arg Gly Gln Val Asp
            100                 105                 110

Phe Gly Met Glu Leu Arg Leu Arg Phe Asp Tyr Gly His Val Val Pro
        115                 120                 125

Trp Val Tyr Arg Glu Gly Gly Ala Leu Val Ala Val Ala Gly Pro Asp
    130                 135                 140

Ala Ala Trp Leu Arg Thr Asp Val Pro Thr Arg Gly Glu Asn Leu Thr
145                 150                 155                 160

Thr Lys Ala Asp Phe Arg Val Arg Ala Gly Glu Arg Ala Ala Phe Thr
                165                 170                 175

Leu Thr Trp Arg Pro Ser His Leu Pro Ser Pro Ala Pro Leu Asp Pro
            180                 185                 190

Ala His Glu Leu Gly Val Thr Glu Gly Tyr Trp Arg Gly Trp Val Ser
        195                 200                 205

Ala Cys Thr Tyr Glu Gly Glu Trp Arg Asp Ala Val Val Arg Ser Leu
    210                 215                 220

Leu Thr Leu Lys Ala Leu Thr Tyr Ala Pro Thr Gly Gly Ile Val Ala
225                 230                 235                 240

Ala Ala Thr Thr Ser Leu Pro Glu Lys Leu Gly Gly Val Arg Asn Trp
                245                 250                 255

Asp Tyr Arg Phe Cys Trp Leu Arg Asp Ala Thr Ile Thr Leu Gln Ser
            260                 265                 270
```

```
Leu Leu Phe Ser Gly Phe Gln Ser Glu Ala Ile Ala Trp Arg Lys Trp
        275                 280                 285

Leu Leu Arg Ala Ile Ala Gly Asn Pro Ala Glu Leu Gln Ile Met Tyr
        290                 295                 300

Gly Val Ala Gly Glu Arg Arg Leu Asp Glu Tyr Leu Ala Asp Trp Leu
305                 310                 315                 320

Thr Gly Tyr Asp Gly Asn Pro Val Arg Ile Gly Asn Ala Ala Ala Glu
                325                 330                 335

Gln Phe Gln Leu Asp Val Tyr Gly Glu Val Met Asp Ala Leu His Gln
            340                 345                 350

Gly Arg Arg Ala Gly Leu Lys Ala Asp Pro Ser Trp Gly Leu Gln
        355                 360                 365

Val Lys Leu Met Glu Phe Val Glu His Trp Gln Asp Pro Asp Glu
370                 375                 380

Gly Ile Trp Glu Val Arg Gly Gly Pro Arg Gln Phe Thr His Ser Lys
385                 390                 395                 400

Leu Met Ala Trp Val Ala Ala Asp Arg Ala Val Lys Ala Val Glu Glu
                405                 410                 415

Phe Gly Leu Asp Gly Pro Ala Asp Arg Trp Arg Leu Arg Asp Glu
            420                 425                 430

Ile Arg Gln Asp Ile Leu Asp Lys Gly Tyr Asp Pro Val Arg Lys Thr
        435                 440                 445

Phe Thr Gln Tyr Tyr Gly Ser Asp Glu Leu Asp Ala Ala Met Leu Met
        450                 455                 460

Val Pro Leu Val Gly Phe Leu Pro Gly Asp Asp Glu Arg Val Ala Gly
465                 470                 475                 480

Thr Val Ala Ala Ile Glu Gln His Leu Leu Val Asp Gly Phe Val Gln
                485                 490                 495

Arg Tyr Thr Gln His Pro Asp Ala Asp Val Asp Gly Leu Pro Pro Gly
            500                 505                 510

Glu Gly Ala Phe Leu Ala Cys Thr Phe Trp Leu Ala Asp Asn Tyr Ala
        515                 520                 525

Leu Met Gly Arg His Asp Glu Ala Arg Glu Thr Phe Ala Arg Leu Leu
530                 535                 540

Ala Leu Arg Asn Asp Val Gly Leu Leu Ala Glu Glu Tyr Asp Thr Thr
545                 550                 555                 560

Thr Gly Arg Leu Val Gly Asn Phe Pro Gln Ala Phe Ser His Val Pro
                565                 570                 575

Leu Ile Asp Thr Ala Arg Thr Leu Thr Ser Ala Leu Ala Pro Thr Glu
            580                 585                 590

Ala Arg Ala Ser Glu Gly Leu Arg
        595                 600

<210> SEQ ID NO 107
<211> LENGTH: 91
<212> TYPE: PRT
<213> ORGANISM: Artificial Sequence
<220> FEATURE:
<223> OTHER INFORMATION: >ACSP50_1953

<400> SEQUENCE: 107

Met Arg Thr Val Ile Arg Gly Ile Val Val Leu Ala Leu Val Ala Gly
1               5                   10                  15

Gly Gly Ala Gly Met Val Gly Pro Ala Gly Ala Ala Pro Ala Val Thr
            20                  25                  30
```

```
Phe Lys Asn Cys Thr Glu Leu Asn Lys Lys Tyr Lys His Gly Val Gly
             35                  40                  45

Lys Arg Gly Ala Glu Asp Arg Val Ser Gly Ser Thr Lys Pro Val Thr
 50                  55                  60

Thr Phe Ser Val Asn Asn Asp Leu Tyr Ala Ala Asn Lys Arg Leu Asp
 65                  70                  75                  80

Arg Asp Lys Asp Gly Ile Ala Cys Glu Lys Arg
                 85                  90
```

<210> SEQ ID NO 108
<211> LENGTH: 57
<212> TYPE: DNA
<213> ORGANISM: Artificial Sequence
<220> FEATURE:
<223> OTHER INFORMATION: >antisense 1 (putative antisense promoters)

<400> SEQUENCE: 108

```
cactcattag gcaccccagg ctttacactt tatgcttccg gctcgtatgt tgtgtgg       57
```

<210> SEQ ID NO 109
<211> LENGTH: 57
<212> TYPE: DNA
<213> ORGANISM: Artificial Sequence
<220> FEATURE:
<223> OTHER INFORMATION: >antisense 2 (putative antisense promoters)

<400> SEQUENCE: 109

```
acgcggtcga acacgcggtg gtacatgtcc agccacgcgc actggtactc ttcggac       57
```

<210> SEQ ID NO 110
<211> LENGTH: 6815
<212> TYPE: DNA
<213> ORGANISM: Artificial Sequence
<220> FEATURE:
<223> OTHER INFORMATION: >pSETT4gap

<400> SEQUENCE: 110

```
aagcgcgggg aagaatcgat caaggactct taccgctgcc gtcgccggaa ggtggtcgac      60
ccgtccgcac ctgggcagca cgaaggcacg tgcaacgtca gcatggcggc actcgacaag     120
ttcgttgcgg aacgcatctt caacaagatc aggcacgccg aaggcgacga agagacgttg     180
gcgcttctgt gggaagccgc ccgacgcttc ggcaagctca ctgaggcgcc tgagaagagc     240
ggcgaacggg cgaaccttgt tgcggagcgc gccgacgccc tgaacgccct tgaagagctg     300
tacgaagacc gcgcggcagg cgcgtacgac ggacccgttg gcaggaagca cttccggaag     360
caacaggcag cgctgacgct ccggcagcaa ggggcggaag agcggcttgc cgaacttgaa     420
gccgccgaag ccccgaagct tccccttgac caatggttcc ccgaagacgc cgacgctgac     480
ccgaccggcc ctaagtcgtg gtgggggcgc gcgtcagtag acgacaagcg cgtgttcgtc     540
gggctcttcg tagacaagat cgttgtcacg aagtcgacta cgggcagggg gcagggaacg     600
cccatcgaga agcgcgcttc gatcacgtgg gcgaagccgc cgaccgacga cgacgaagac     660
gacgcccagg acggcacgga agacgtagcg gcgtagcgag acacccggga agcctgatct     720
acgtctgtcg agaagtttct gatcgaaaag ttcgacagcg tctccgacct gatgcagctc     780
tcgcagggcg aagaatctcg tgctttcagc ttcgatgtag gagggcgtgg atatgtcctg     840 cgggtaaaata gctgcgccga tggttctctg tcgtcgctga cgtctgtagt ctagcctcat     900
tatgattgta cgctattcag ggattgactg ataccggaag acatctcaaa tgaagtggtc     960
aagctttatg cttgtaaacc gttttgtgaa aaaattttta aaataaaaaa ggggacctct    1020
```

```
agggtcccca attaattagt aatataatct attaaaggtc attcaaaagg tcatccaagc    1080
ttggctgttt tggcggatga gagaagattt tcagcctgat acagattaaa tcagaacgca    1140
gaagcggtct gataaaacag aatttgcctg gcggcagtag cgcggtggtc ccacctgacc    1200
ccatgccgaa ctcagaagtg aaacgccgta gcgccgatgg tagtgtggcc catgcgagag    1260
tacatatggt actggccgat gctgggagaa gcgcgctgct gtacggcgcg caccgggtgc    1320
ggagcccctc ggcgagcggt gtgaaacttc tgtgaatggc ctgttcggtt gcttttttta    1380
tacggctgcc agataaggct tgcagcatct gggcggctac cgctatgatc ggggcgttcc    1440
tgcaattctt agtgcgagta tctgaaaggg gatacgcatg gtaccgagac cttatgttga    1500
tcggcacttt gcatcggccg cgctcccgat tccgaagtg cttgacattg gggaatttat    1560
gcggtgtgaa ataccgcaca gatgcgtaag gagaaaatac cgcatcaggc gccattcgcc    1620
attcaggctg cgcaactgtt gggaagggcg atcggtgcgg gcctcttcgc tattacgcca    1680
gctggcgaaa gggggatgtg ctgcaaggcg attaagttgg gtaacgccag gttttccca    1740
gtcacgacgt tgtaaaacga cggccagtgc caagcttggg ctgcaggtcg actctagagg    1800
atccgcggcc gcgcgcgata tcgaattcgt aatcatgtca tagctgtttc ctgtgtgaaa    1860
ttgttatccg ctcacaattc cacacaacat acgagccgga agcataaagt gtaaagcctg    1920
gggtgcctaa tgagtgagct aactcacatt aattgcgttg cgcggtctcg cgtttcgtg    1980
ccgcgtgatt ttccgccaaa aactttaacg aacgttcgtt ataatggtgt catgaccttc    2040
acgacgaagt actaaaattg gcccgaatca tcagctaagc tttatgcttg taaaccgttt    2100
tgtgaaaaaa ttttttaaaat aaaaaagggg acctctaggg tccccaatta attagtaata    2160
taatctatta aaggtcattc aaaaggtcat ccacctcact tcggtgaatc gaagcgcggc    2220
atcagggtta cttttttggat acctgagaca ttcgtcgctt ccgggtatgc gctctatgtg    2280
acggtctttt ggcgcacaaa tgctcagcac catttaaatt agaccgactc cagatctgta    2340
aggtccaaca aaacccatcg tagtccttag acttggcaca cttacacctg cagtggatga    2400
cctttttgaat gaccttttaat agattatatt actaattaat tggggaccct agaggtcccc    2460
ttttttattt taaaaatttt ttcacaaaac ggtttacaag cataaagctt gccacgcaga    2520
cgacagccca cgctgaccga tctacctgaa cggcgaccat ctgtgtggta ctggggcgga    2580
gagataacta cggtgccgct taccgggctc actcaaaggc ggtaatacgg ttatccacag    2640
aatcagggga taacgcagga agaacatgt gagcaaaagg ccagcaaaag gccaggaacc    2700
gtaaaaaggc cgcgttgctg gcgttttcc ataggctccg ccccctgac gagcatcaca    2760
aaaatcgacg ctcaagtcag aggtggcgaa acccgacagg actataaaga taccaggcgt    2820
ttcccctgg aagctccctc gtgcgctctc ctgttccgac cctgccgctt accggatacc    2880
tgtccgcctt tctcccttcg ggaagcgtgg cgctttctca tagctcacgc tgtaggtatc    2940
tcagttcggt gtaggtcgtt cgctccaagc tgggctgtgt gcacgaaccc ccgttcagc    3000
ccgaccgctg cgccttatcc ggtaactatc gtcttgagtc caacccggta agacacgact    3060
tatcgccact ggcagcagcc actggtaaca ggattagcag agcgaggtat gtaggcggtg    3120
ctacagagtt cttgaagtgg tggcctaact acggctacac tagaagaaca gtatttggta    3180
tctgcgctct gctgaagcca gttaccttcg gaaaaagagt tggtagctct tgatccggca    3240
aacaaaccac cgctggtagc ggtggttttt tgtttgcaa gcagcagatt acgcgcagaa    3300
aaaaaggatc tcaagaagat cctttgatct tttctacggg gtctgacgct cagtggaacg    3360
```

```
aaaactcacg ttaagggatt tggtcatga gattatcaaa aaggatcttc acctagatcc    3420
ttttggttca tgtgcagctc catcagcaaa aggggatgat aagtttatca ccaccgacta    3480
tttgcaacag tgccgttgat cgtgctatga tcgactgatg tcatcagcgg tggagtgcaa    3540
tgtcgtgcaa tacgaatggc gaaaagccga gctcatcggt cagcttctca accttggggt    3600
tacccccggc ggtgtgctgc tggtccacag ctccttccgt agcgtccggc ccctcgaaga    3660
tgggccactt ggactgatcg aggccctgcg tgctgcgctg ggtccgggag ggacgctcgt    3720
catgccctcg tggtcaggtc tggacgacga gccgttcgat cctgccacgt cgcccgttac    3780
accggacctt ggagttgtct ctgacacatt ctggcgcctg ccaaatgtaa agcgcagcgc    3840
ccatccattt gcctttgcgg cagcggggcc acaggcagag cagatcatct ctgatccatt    3900
gcccctgcca cctcactcgc ctgcaagccc ggtcgcccgt gtccatgaac tcgatgggca    3960
ggtacttctc ctcggcgtgg gacacgatgc caacacgacg ctgcatcttg ccgagttgat    4020
ggcaaaggtt ccctatgggg tgccgagaca ctgcaccatt cttcaggatg gcaagttggt    4080
acgcgtcgat tatctcgaga atgaccactg ctgtgagcgc tttgccttgg cggacaggtg    4140
gctcaaggag aagagcgttc agaaggaagg tccagtcggt catgcctttg ctcggttgat    4200
ccgctcccgc gacattgtgg cgacagccct gggtcaactg gccgagatc cgttgatctt    4260
cctgcatccg ccagaggcgg gatgcgaaga atgcgatgcc gctcgccagt cgattggctg    4320
agctcatgag cggagaacga gatgacgttg gaggggcaag gtcgcgctga ttgctggggc    4380
aacacgtgga gcggatcggg gattgtcttt cttcagctcg ctgatgatat gctgacgctc    4440
aatgccgttt ggcctccgac taacgaaaat cccgcatttg gacggctgat ccgattggca    4500
cggcggacgg cgaatggcgg agcagacgct cgtccggggg caatgagata tgaaaaagcc    4560
tgaactcacc gcgacgtatc gggccctggc cagctagcta gagtcgacct gcaggtcccc    4620
ggggatcggt cttgccttgc tcgtcggtga tgtacttcac cagctccgcg aagtcgctct    4680
tcttgatgga gcgcatgggg acgtgcttgg caatcacgcg cacccccggg ccgttttagc    4740
ggctaaaaaa gtcatggctc tgccctcggg cggaccacgc ccatcatgac cttgccaagc    4800
tcgtcctgct tctcttcgat cttcgccagc agggcgagga tcgtggcatc accgaaccgc    4860
gccgtgcgcg ggtcgtcggt gagccagagt ttcagcaggc cgcccaggcg gcccaggtcg    4920
ccattgatgc gggccagctc gcggacgtgc tcatagtcca cgacgcccgt gattttgtag    4980
ccctggccga cggccagcag gtaggccgac aggctcatgc cggccgccgc cgccttttcc    5040
tcaatcgctc ttcgttcgtc tggaaggcag tacaccttga taggtgggct gcccttcctg    5100
gttggcttgg tttcatcagc catccgcttg ccctcatctg ttacgccggc ggtagccggc    5160
cagcctcgca gagcaggatt cccgttgagc accgccaggt gcgaataagg gacagtgaag    5220
aaggaacacc cgctcgcggg tgggcctact tcacctatcc tgcccggctg acgccgttgg    5280
atacaccaag gaaagtctac acgaaccctt ggcaaaatc ctgtatatcg tgcgaaaaag    5340
gatggatata ccgaaaaaat cgctataatg accccgaagc agggttatgc agcggaaaag    5400
atccgtcgac ctgcaggcat gcaagctcta gcgattccag acgtcccgaa ggcgtggcgc    5460
ggcttccccg tgccggagca atcgccctgg gtgggttaca cgacgcccct ctatggcccg    5520
tactgacgga cacaccgaag ccccggcggc aaccctcagc ggatgccccg ggcttcacg    5580
ttttcccagg tcagaagcgg ttttcggag tagtgcccca actgggtaa cctttgagtt    5640
ctctcagttg ggggcgtagg gtcgccgaca tgacacaagg ggttgtgacc ggggtggaca    5700
cgtacgcggg tgcttacgac cgtcagtcgc gcgagcgcga gaattcgagc gcagcaagcc    5760
```

```
cagcgacaca gcgtagcgcc aacgaagaca aggcggccga ccttcagcgc gaagtcgagc   5820
gcgacggggg ccggttcagg ttcgtcgggc atttcagcga agcgccgggc acgtcggcgt   5880
tcgggacggc ggagcgcccg gagttcgaac gcatcctgaa cgaatgccgc gccgggcggc   5940
tcaacatgat cattgtctat gacgtgtcgc gcttctcgcg cctgaaggtc atggacgcga   6000
ttccgattgt ctcggaattg ctcgccctgg gcgtgacgat tgtttccact caggaaggcg   6060
tcttccggca gggaaacgtc atggacctga ttcacctgat tatgcggctc gacgcgtcgc   6120
acaaagaatc ttcgctgaag tcggcgaaga ttctcgacac gaagaacctt cagcgcgaat   6180
tgggcgggta cgtcggcggg aaggcgcctt acggcttcga gcttgtttcg gagacgaagg   6240
agatcacgcg caacggccga atggtcaatg tcgtcatcaa caagcttgcg cactcgacca   6300
ctccccttac cggacccttc gagttcgagc ccgacgtaat ccggtggtgg tggcgtgaga   6360
tcaagacgca caaacacctt cccttcaagc cgggcagtca agccgccatt cacccgggca   6420
gcatcacggg gctttgtaag cgcatggacg ctgacgccgt gccgaccggg ggcgagacga   6480
ttgggaagaa gaccgcttca agcgcctggg acccggcaac cgttatgcga atccttcggg   6540
acccgcgtat tgcgggcttc gccgctgagg tgatctacaa gaagaagccg gacggcacgc   6600
cgaccacgaa gattgagggt taccgcattc agcgcgaccc gatcacgctc cggccggtcg   6660
agcttgattg cggaccgatc atcgagcccg ctgagtggta tgagcttcag gcgtggttgg   6720
acggcagggg gcgcggcaag gggctttccc gggggcaagc cattctgtcc gccatggaca   6780
agctgtactg cgagtgtggc gccgtcatga cttcg                               6815

<210> SEQ ID NO 111
<211> LENGTH: 6705
<212> TYPE: DNA
<213> ORGANISM: Artificial Sequence
<220> FEATURE:
<223> OTHER INFORMATION: >pSETT4tip

<400> SEQUENCE: 111
aagcgcgggg aagaatcgat caaggactct taccgctgcc gtcgccggaa ggtggtcgac     60
ccgtccgcac ctgggcagca cgaaggcacg tgcaacgtca gcatggcggc actcgacaag    120
ttcgttgcgg aacgcatctt caacaagatc aggcacgccg aaggcgacga agagacgttg    180
gcgcttctgt gggaagccgc ccgacgcttc ggcaagctca ctgaggcgcc tgagaagagc    240
ggcgaacggg cgaaccttgt tgcggagcgc gccgacgccc tgaacgccct tgaagagctg    300
tacgaagacc gcgcggcagg cgcgtacgac ggacccgttg gcaggaagca cttccggaag    360
caacaggcag cgctgacgct ccggcagcaa ggggcggaag agcggcttgc cgaacttgaa    420
gccgccgaag ccccgaagct tccccttgac caatggttcc ccgaagacgc cgacgctgac    480
ccgaccggcc ctaagtcgtg gtgggggcgc gcgtcagtag acgacaagcg cgtgttcgtc    540
gggctcttcg tagacaagat cgttgtcacg aagtcgacta cgggcagggg gcagggaacg    600
cccatcgaga agcgcgcttc gatcacgtgg gcgaagccgc cgaccgacga cgacgaagac    660
gacgcccagg acggcacgga agacgtagcg gcgtagcgag acacccggga agcctgatct    720
acgtctgtcg agaagtttct gatcgaaaag ttcgacagcg tctccgacct gatgcagctc    780
tcgcagggcg aagaatctcg tgctttcagc ttcgatgtag gagggcgtgg atatgtcctg    840
cgggtaaata gctgcgccga tggttctctg tcgtcgctga cgtctgtagt ctagcctcat    900
tatgattgta cgctattcag ggattgactg ataccggaag acatctcaaa tgaagtggtc    960
```

```
aagctttatg cttgtaaacc gttttgtgaa aaaattttta aaataaaaaa ggggacctct    1020
agggtcccca attaattagt aatataatct attaaaggtc attcaaaagg tcatccaagc    1080
ttggctgttt tggcggatga gagaagattt tcagcctgat acagattaaa tcagaacgca    1140
gaagcggtct gataaaacag aatttgcctg gcggcagtag cgcggtggtc ccacctgacc    1200
ccatgccgaa ctcagaagtg aaacgccgta gcgccgatgg tagtgtggcc catgcgagag    1260
tacaatccct agaacgtccg ggcttgcacc tcacgtcacg tgaggaggca gcgtggacgg    1320
cgtggtacca agcttattgg cactagtcga gcaacggagg tattccgatg gtaccgagac    1380
cttatgttga tcggcacttt gcatcggccg cgctcccgat tccggaagtg cttgacattg    1440
gggaatttat gcggtgtgaa ataccgcaca gatgcgtaag gagaaaatac cgcatcaggc    1500
gccattcgcc attcaggctg cgcaactgtt gggaagggcg atcggtgcgg gcctcttcgc    1560
tattacgcca gctggcgaaa ggggatgtg ctgcaaggcg attaagttgg gtaacgccag    1620
ggttttccca gtcacgacgt tgtaaaacga cggccagtgc caagcttggg ctgcaggtcg    1680
actctagagg atccgcggcc gcgcgcgata tcgaattcgt aatcatgtca tagctgtttc    1740
ctgtgtgaaa ttgttatccg ctcacaattc cacacaacat acgagccgga agcataaagt    1800
gtaaagcctg gggtgcctaa tgagtgagct aactcacatt aattgcgttg cgcggtctcg    1860
gcgtttcgtg ccgcgtgatt ttccgccaaa aactttaacg aacgttcgtt ataatggtgt    1920
catgaccttc acgacgaagt actaaaattg cccgaatca tcagctaagc tttatgcttg    1980
taaaccgttt tgtgaaaaaa tttttaaaat aaaaaggggg acctctaggg tccccaatta    2040
attagtaata taatctatta aaggtcattc aaaaggtcat ccacctcact tcggtgaatc    2100
gaagcgcggc atcagggtta cttttttggat acctgagaca ttcgtcgctt ccgggtatgc    2160
gctctatgtg acgtcttttt ggcgcacaaa tgctcagcac catttaaatt agaccgactc    2220
cagatctgta aggtccaaca aaacccatcg tagtccttag acttggcaca cttacacctg    2280
cagtggatga ccttttgaat gacctttaat agattatatt actaattaat tggggaccct    2340
agaggtcccc ttttttattt taaaatttt ttcacaaaac ggtttacaag cataaagctt    2400
gccacgcaga cgacagccca cgctgaccga tctacctgaa cggcgaccat ctgtgtggta    2460
ctggggcgga gagataacta cggtgccgct taccgggctc actcaaaggc ggtaatacgg    2520
ttatccacag aatcagggga taacgcagga aagaacatgt gagcaaaagg ccagcaaaag    2580
gccaggaacc gtaaaaaggc cgcgttgctg gcgttttttcc ataggctccg ccccccctgac    2640 gagcatcaca aaaatcgacg ctcaagtcag aggtggcgaa acccgacagg actataaaga    2700
taccaggcgt ttccccctgg aagctccctc gtgcgctctc ctgttccgac cctgccgctt    2760
accggatacc tgtccgcctt tctcccttcg ggaagcgtgg cgctttctca tagctcacgc    2820
tgtaggtatc tcagttcggt gtaggtcgtt cgctccaagc tgggctgtgt gcacgaaccc    2880
cccgttcagc ccgaccgctg cgccttatcc ggtaactatc gtcttgagtc caacccggta    2940
agacacgact tatcgccact ggcagcagcc actggtaaca ggattagcag agcgaggtat    3000
gtaggcggtg ctacagagtt cttgaagtgg tggcctaact acggctacac tagaagaaca    3060
gtatttggta tctgcgctct gctgaagcca gttaccttcg gaaaaagagt ggtagctct    3120 tgatccggca aacaaaccac cgctggtagc ggtggttttt tgtttgcaa gcagcagatt    3180 acgcgcagaa aaaaggatc tcaagaagat cctttgatct tttctacggg gtctgacgct    3240
cagtggaacg aaaactcacg ttaagggatt ttggtcatga gattatcaaa aaggatcttc    3300
acctagatcc ttttggttca tgtgcagctc catcagcaaa aggggatgat aagtttatca    3360
```

```
ccaccgacta tttgcaacag tgccgttgat cgtgctatga tcgactgatg tcatcagcgg   3420
tggagtgcaa tgtcgtgcaa tacgaatggc gaaaagccga gctcatcggt cagcttctca   3480
accttggggt tacccccggc ggtgtgctgc tggtccacag ctccttccgt agcgtccggc   3540
ccctcgaaga tgggccactt ggactgatcg aggccctgcg tgctgcgctg gtccggggag   3600
ggacgctcgt catgccctcg tggtcaggtc tggacgacga gccgttcgat cctgccacgt   3660
cgcccgttac accggacctt ggagttgtct ctgacacatt ctggcgcctg ccaaatgtaa   3720
agcgcagcgc ccatccattt gcctttgcgg cagcggggcc acaggcagag cagatcatct   3780
ctgatccatt gcccctgcca cctcactcgc ctgcaagccc ggtcgcccgt gtccatgaac   3840
tcgatgggca ggtacttctc ctcggcgtgg gacacgatgc caacacgacg ctgcatcttg   3900
ccgagttgat ggcaaaggtt ccctatgggg tgccgagaca ctgcaccatt cttcaggatg   3960
gcaagttggt acgcgtcgat tatctcgaga atgaccactg ctgtgagcgc tttgccttgg   4020
cggacaggtg gctcaaggag aagagccttc agaaggaagg tccagtcggt catgcctttg   4080
ctcggttgat ccgctcccgc gacattgtgg cgacagccct gggtcaactg gccgagatc    4140 cgttgatctt cctgcatccg ccagaggcgg atgcgaagaa atgcgatgcc gctcgccagt   4200
cgattggctg agctcatgag cggagaacga gatgacgttg gaggggcaag gtcgcgctga   4260
ttgctggggc aacacgtgga gcggatcggg gattgtcttt cttcagctcg ctgatgatat   4320
gctgacgctc aatgccgttt ggcctccgac taacgaaaat cccgcatttg gacggctgat   4380
ccgattggca cggcggacgg cgaatggcgg agcagacgct cgtccggggg caatgagata   4440
tgaaaaagcc tgaactcacc gcgacgtatc gggccctggc cagctagcta gagtcgacct   4500
gcaggtcccc ggggatcggt cttgccttgc tcgtcggtga tgtacttcac cagctccgcg   4560
aagtcgctct tcttgatgga gcgcatgggg acgtgcttgg caatcacgcg cacccccgg    4620 ccgttttagc ggctaaaaaa gtcatggctc tgccctcggg cggaccacgc ccatcatgac   4680
cttgccaagc tcgtcctgct tctcttcgat cttgccagc agggcgagga tcgtggcatc    4740
accgaaccgc gccgtgcgcg ggtcgtcggt gagccagagt tcagcaggc cgcccaggcg    4800 gcccaggtcg ccattgatgc gggccagctc gcggacgtgc tcatagtcca cgacgcccgt   4860
gattttgtag ccctggccga cggccagcag gtaggccgac aggctcatgc cggccgccgc   4920
cgccttttcc tcaatcgctc ttcgttcgtc tggaaggcag tacaccttga taggtgggct   4980
gcccttcctg gttggcttgg tttcatcagc catccgcttg ccctcatctg ttacgccggc   5040
ggtagccggc cagcctcgca gagcaggatt cccgttgagc accgcaggt gcgaataagg    5100 gacagtgaag aaggaacacc cgctcgcggg tgggcctact tcacctatcc tgcccggctg   5160
acgccgttgg atacaccaag gaaagtctac acgaaccctt tggcaaaatc ctgtatatcg   5220
tgcgaaaaag gatggatata ccgaaaaaat cgctataatg accccgaagc agggttatgc   5280
agcgaaaaag atccgtcgac ctgcaggcat gcaagctcta gcgattccag acgtccgaa    5340 ggcgtggcgc ggcttccccg tgccggagca atcgccctgg gtgggttaca cgacgcccct   5400
ctatggcccg tactgacgga cacaccgaag ccccggcggc aacctcagc ggatgccccg    5460 gggcttcacg ttttcccagg tcagaagcgg ttttcgggag tagtgcccca actggggtaa   5520
cctttgagtt ctctcagttg ggggcgtagg gtcgccgaca tgacacaagg ggttgtgacc   5580
ggggtggaca cgtacgcggg tgcttacgac cgtcagtcgc gcgagcgcga gaattcgagc   5640
gcagcaagcc cagcgacaca gcgtagcgcc aacgaagaca aggcggccga ccttcagcgc   5700
```

```
gaagtcgagc gcgacggggg ccggttcagg ttcgtcgggc atttcagcga agcgccgggc    5760
acgtcggcgt tcgggacggc ggagcgcccg gagttcgaac gcatcctgaa cgaatgccgc    5820
gccgggcggc tcaacatgat cattgtctat gacgtgtcgc gcttctcgcg cctgaaggtc    5880
atggacgcga ttccgattgt ctcggaattg ctcgccctgg gcgtgacgat tgtttccact    5940
caggaaggcg tcttccggca gggaaacgtc atggacctga ttcacctgat tatgcggctc    6000
gacgcgtcgc acaaagaatc ttcgctgaag tcggcgaaga ttctcgacac gaagaacctt    6060
cagcgcgaat tgggcgggta cgtcggcggg aaggcgcctt acggcttcga gcttgtttcg    6120
gagacgaagg agatcacgcg caacggccga atggtcaatg tcgtcatcaa caagcttgcg    6180
cactcgacca ctccccttac cggacccttc gagttcgagc ccgacgtaat ccggtggtgg    6240
tggcgtgaga tcaagacgca caaacaccct cccttcaagc cgggcagtca agccgccatt    6300
cacccgggca gcatcacggg gctttgtaag cgcatggacg ctgacgccgt gccgacccgg    6360
ggcgagacga ttgggaagaa gaccgcttca agcgcctggg acccggcaac cgttatgcga    6420
atccttcggg acccgcgtat tgcgggcttc gccgctgagg tgatctacaa gaagaagccg    6480
gacggcacgc cgaccacgaa gattgagggt taccgcattc agcgcgaccc gatcacgctc    6540
cggccggtcg agcttgattg cggaccgatc atcgagcccg ctgagtggta tgagcttcag    6600
gcgtggttgg acggcagggg gcgcggcaag gggctttccc gggggcaagc cattctgtcc    6660
gccatggaca agctgtactg cgagtgtggc gccgtcatga cttcg                    6705
```